(12) United States Patent
Choi et al.

(10) Patent No.: US 11,707,302 B2
(45) Date of Patent: Jul. 25, 2023

(54) INTERSPINOUS SPACERS AND ASSOCIATED METHODS OF USE AND MANUFACTURE

(71) Applicant: Howmedica Osteonics Corp., Mahwah, NJ (US)

(72) Inventors: Andy Wonyong Choi, Irvine, CA (US); Kim Thien Nguyen, Oceanside, CA (US); Robert Leslie Richards, Hamden, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 214 days.

(21) Appl. No.: 17/182,476

(22) Filed: Feb. 23, 2021

(65) Prior Publication Data
US 2021/0204985 A1 Jul. 8, 2021

Related U.S. Application Data

(63) Continuation of application No. 15/962,071, filed on Apr. 25, 2018, now Pat. No. 10,945,769, which is a continuation of application No. 13/679,986, filed on Nov. 16, 2012, now Pat. No. 9,956,007.

(60) Provisional application No. 61/561,204, filed on Nov. 17, 2011.

(51) Int. Cl.
*A61B 17/70* (2006.01)

(52) U.S. Cl.
CPC ...... *A61B 17/7047* (2013.01); *A61B 17/7065* (2013.01); *A61B 17/7074* (2013.01)

(58) Field of Classification Search
CPC .......................................... A61B 17/7062–707
See application file for complete search history.

(56) References Cited

U.S. PATENT DOCUMENTS

| 3,648,691 | A | 3/1972 | Lumb et al. |
| 4,448,191 | A | 5/1984 | Rodnyansky et al. |
| 4,554,914 | A | 11/1985 | Kapp et al. |
| 5,011,484 | A | 4/1991 | Breard |
| 5,059,193 | A | 10/1991 | Kuslich |
| 5,084,049 | A | 1/1992 | Asher et al. |

(Continued)

FOREIGN PATENT DOCUMENTS

| FR | 2681525 A1 | 3/1993 |
| FR | 2724554 A1 | 3/1996 |
| GB | 780652 A | 8/1957 |

OTHER PUBLICATIONS

Extended European Seach Report for Application No. 12850335.6 dated Jul. 29, 2015.

(Continued)

*Primary Examiner* — Eduardo C Robert
*Assistant Examiner* — Steven J Cotroneo
(74) *Attorney, Agent, or Firm* — Lerner David LLP

(57) ABSTRACT

Systems, devices, and methods for treating the spine are disclosed herein. Medical devices can be positioned along a subject's spine to treat various conditions and diseases. The medical device can include an actuator assembly and a clamp assembly. The actuator assembly can be positioned at an interspinous space between a superior spinous process and an inferior spinous process. The actuator assembly can be used to reconfigure the clamp assembly such that the clamp assembly clamps onto the superior and inferior spinous processes.

18 Claims, 92 Drawing Sheets

(56) References Cited

U.S. PATENT DOCUMENTS

| | | |
|---|---|---|
| 5,098,433 A | 3/1992 | Freedland |
| 5,395,370 A | 3/1995 | Muller et al. |
| 5,454,812 A | 10/1995 | Lin |
| 5,496,318 A | 3/1996 | Howland et al. |
| 5,609,634 A | 3/1997 | Voydeville et al. |
| 5,645,599 A | 7/1997 | Samani |
| 6,019,793 A | 2/2000 | Perren et al. |
| 6,048,342 A | 4/2000 | Zucherman et al. |
| 6,152,926 A | 11/2000 | Zucherman et al. |
| 6,156,038 A | 12/2000 | Zucherman et al. |
| 6,190,387 B1 | 2/2001 | Zucherman et al. |
| 6,235,030 B1 | 5/2001 | Zucherman et al. |
| 6,312,431 B1 | 11/2001 | Asfora |
| 6,332,883 B1 | 12/2001 | Zucherman et al. |
| 6,364,883 B1 | 4/2002 | Santilli |
| 6,419,676 B1 | 7/2002 | Zucherman et al. |
| 6,451,019 B1 | 9/2002 | Zucherman et al. |
| 6,626,944 B1 | 9/2003 | Taylor et al. |
| 6,695,842 B2 | 2/2004 | Zucherman et al. |
| 6,699,246 B2 | 3/2004 | Zucherman et al. |
| 6,733,534 B2 | 5/2004 | Sherman |
| 6,761,720 B1 | 7/2004 | Senegas |
| 6,796,983 B1 | 9/2004 | Zucherman et al. |
| 7,048,736 B2 | 5/2006 | Robinson et al. |
| 7,101,375 B2 | 9/2006 | Zucherman et al. |
| 7,201,751 B2 | 4/2007 | Zucherman et al. |
| 7,727,233 B2 | 6/2010 | Blackwell et al. |
| 7,749,252 B2 | 7/2010 | Zucherman et al. |
| 7,763,074 B2 | 7/2010 | Altarac et al. |
| 7,803,190 B2 | 9/2010 | Zucherman et al. |
| 7,918,877 B2 | 4/2011 | Zucherman et al. |
| 7,955,392 B2 | 6/2011 | Dewey et al. |
| 7,988,709 B2 | 8/2011 | Clark et al. |
| 7,993,342 B2 | 8/2011 | Malandain et al. |
| 8,002,802 B2 | 8/2011 | Abdou |
| 8,007,537 B2 | 8/2011 | Zucherman et al. |
| 8,012,207 B2 | 9/2011 | Kim |
| 8,123,782 B2 | 2/2012 | Altarac et al. |
| 8,123,807 B2 | 2/2012 | Kim |
| 8,128,661 B2 | 3/2012 | Zucherman et al. |
| 8,128,662 B2 | 3/2012 | Altarac et al. |
| 8,152,837 B2 | 4/2012 | Altarac et al. |
| 8,167,944 B2 | 5/2012 | Kim |
| 8,226,653 B2 | 7/2012 | Blackwell et al. |
| 8,273,107 B2 | 9/2012 | Zucherman et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,292,923 B1 | 10/2012 | Arnold et al. |
| 8,303,629 B1 | 11/2012 | Abdou |
| 8,317,864 B2 | 11/2012 | Kim |
| 8,425,559 B2 | 4/2013 | Tebbe et al. |
| 8,439,953 B2 | 5/2013 | Mitchell et al. |
| 2003/0040746 A1 | 2/2003 | Mitchell et al. |
| 2005/0245937 A1 | 11/2005 | Winslow |
| 2005/0256576 A1 | 11/2005 | Moskowitz et al. |
| 2006/0004447 A1 | 1/2006 | Mastrorio et al. |
| 2006/0085070 A1 | 4/2006 | Kim |
| 2006/0106381 A1* | 5/2006 | Ferree .................... A61F 2/4455 606/907 |
| 2006/0122620 A1 | 6/2006 | Kim |
| 2006/0264938 A1 | 11/2006 | Zucherman et al. |
| 2007/0032790 A1 | 2/2007 | Aschmann et al. |
| 2007/0173832 A1* | 7/2007 | Tebbe .................... A61B 17/56 606/279 |
| 2007/0276493 A1 | 11/2007 | Malandain et al. |
| 2007/0299526 A1* | 12/2007 | Malandain ......... A61B 17/7062 623/17.16 |
| 2008/0015700 A1 | 1/2008 | Zucherman et al. |
| 2008/0086212 A1* | 4/2008 | Zucherman ........ A61B 17/7068 606/90 |
| 2008/0177306 A1 | 7/2008 | Lamborne et al. |
| 2008/0177391 A1* | 7/2008 | Mitchell ............ A61B 17/7065 606/90 |
| 2008/0183211 A1* | 7/2008 | Lamborne .......... A61B 17/7061 606/248 |
| 2008/0183218 A1 | 7/2008 | Mueller et al. |
| 2008/0195152 A1 | 8/2008 | Altarac et al. |
| 2008/0319550 A1* | 12/2008 | Altarac .............. A61B 17/7065 606/90 |
| 2009/0125030 A1 | 5/2009 | Tebbe et al. |
| 2009/0138046 A1* | 5/2009 | Altarac .............. A61B 17/7076 623/17.11 |
| 2009/0138055 A1 | 5/2009 | Altarac et al. |
| 2009/0222043 A1* | 9/2009 | Altarac .............. A61B 17/7065 606/249 |
| 2009/0254185 A1* | 10/2009 | Dollinger ........... A61B 17/7065 623/17.16 |
| 2010/0070038 A1* | 3/2010 | Taylor ................ A61B 17/7062 623/17.16 |
| 2010/0087869 A1 | 4/2010 | Abdou |
| 2010/0152775 A1 | 6/2010 | Seifert et al. |
| 2010/0234889 A1* | 9/2010 | Hess ................ A61B 17/00234 606/279 |
| 2010/0318127 A1* | 12/2010 | Phan .................. A61B 17/7065 606/279 |
| 2011/0022090 A1 | 1/2011 | Gordon et al. |
| 2011/0066186 A1* | 3/2011 | Boyer, II ........... A61B 17/7065 606/249 |
| 2011/0106160 A1 | 5/2011 | Altarac et al. |
| 2011/0313457 A1 | 12/2011 | Reglos et al. |
| 2012/0130432 A1 | 5/2012 | Ferree et al. |
| 2012/0158063 A1 | 6/2012 | Altarac et al. |
| 2012/0226315 A1 | 9/2012 | Altarac et al. |

OTHER PUBLICATIONS

International Search Report for Application No. PCT/US2012/065715 dated Feb. 28, 2013.

\* cited by examiner

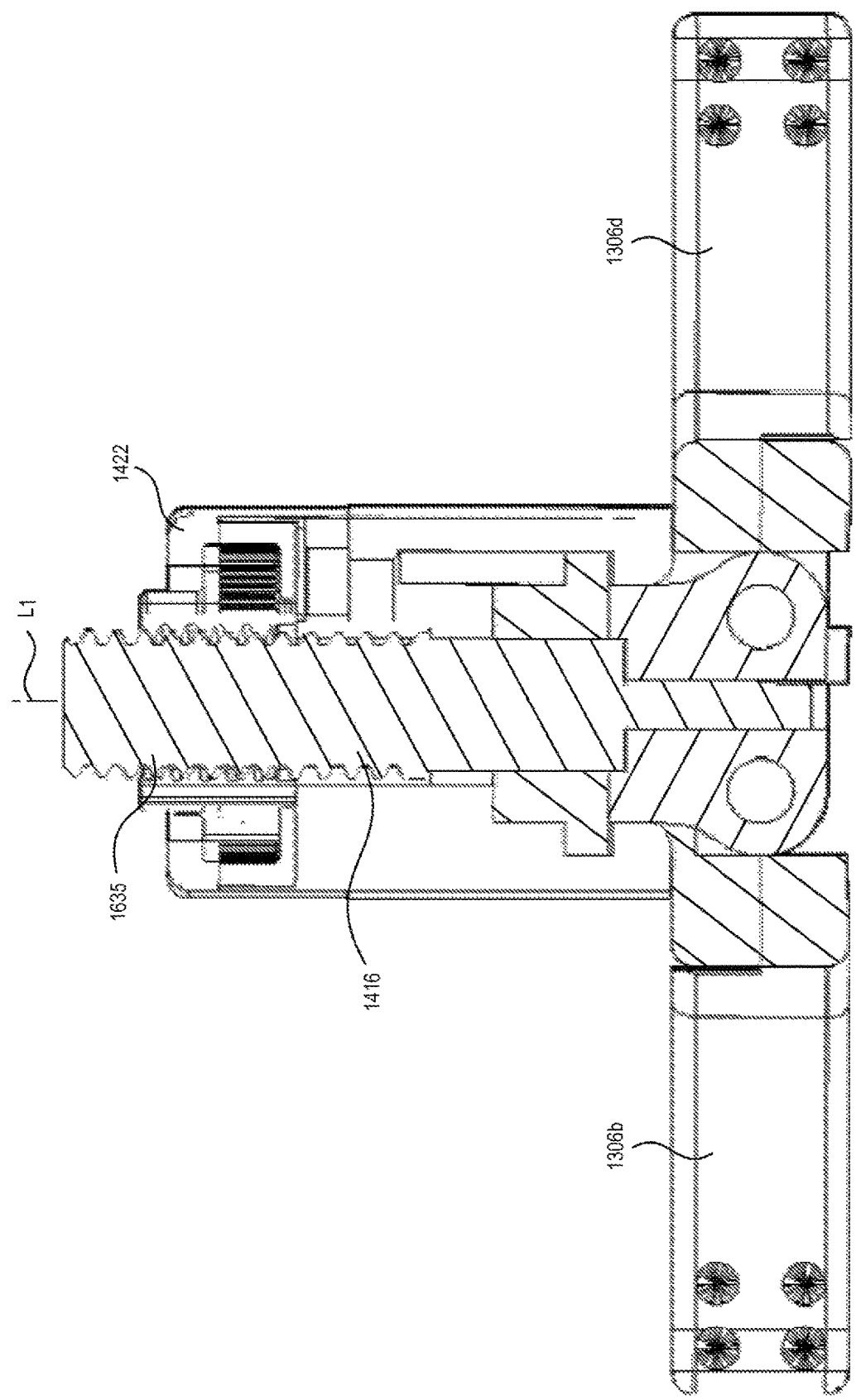

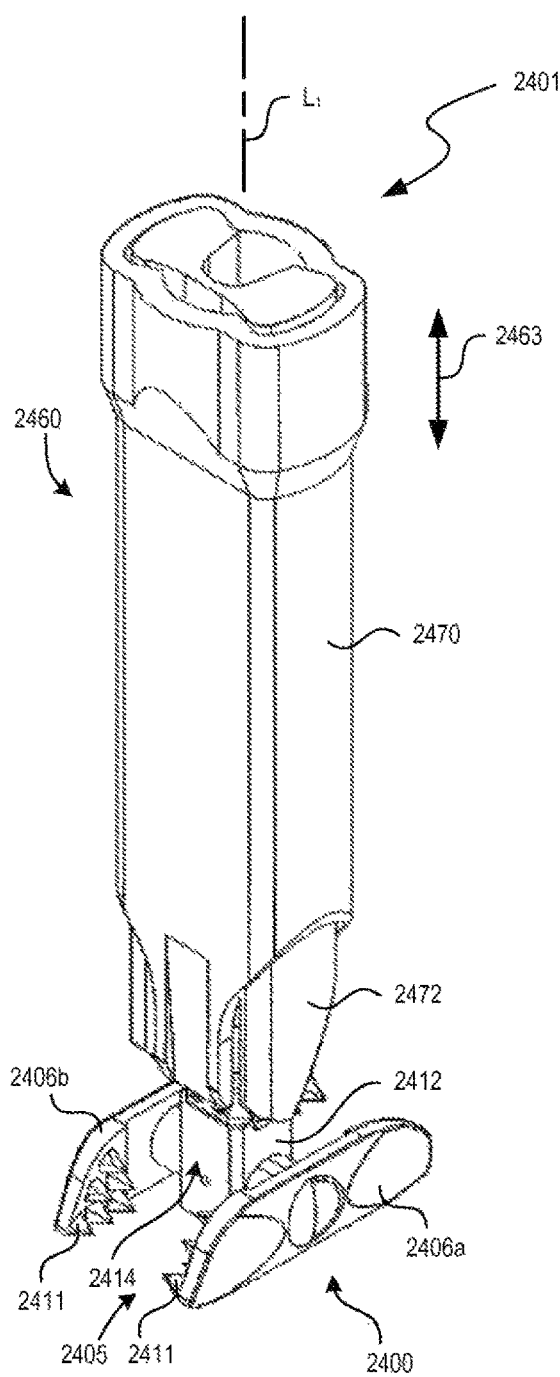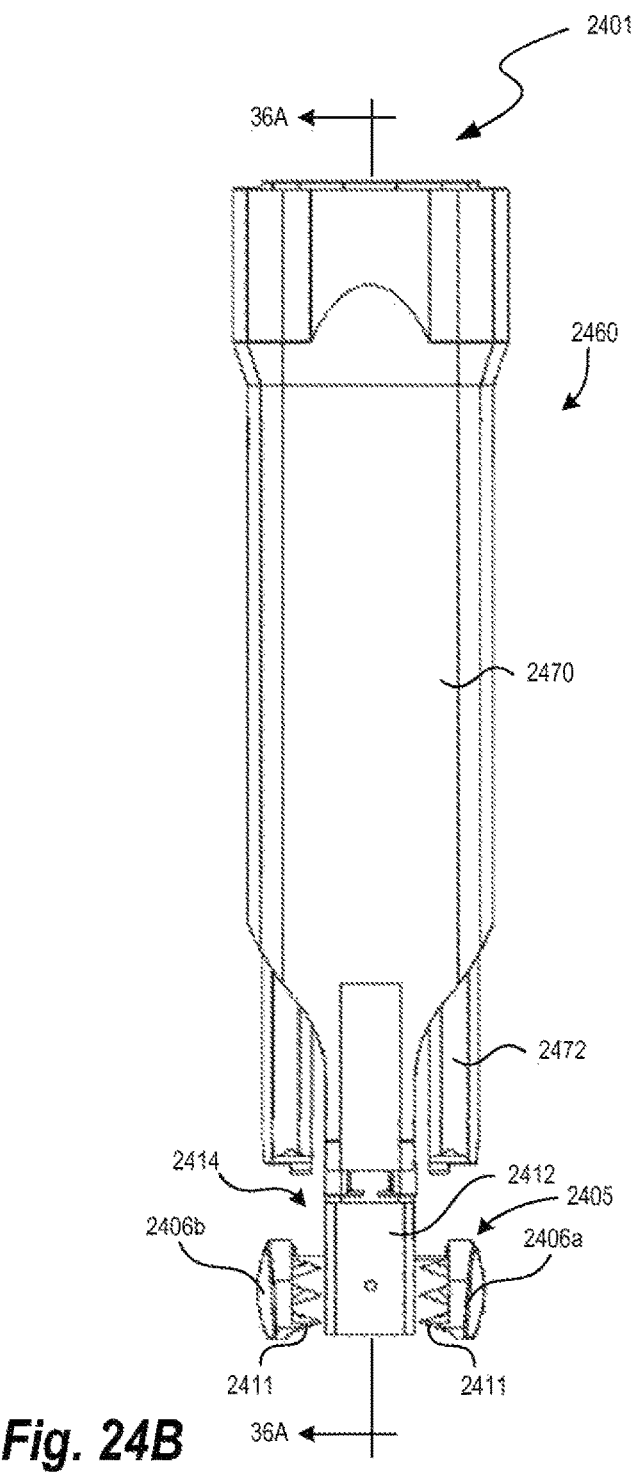
Fig. 24A
Fig. 24B

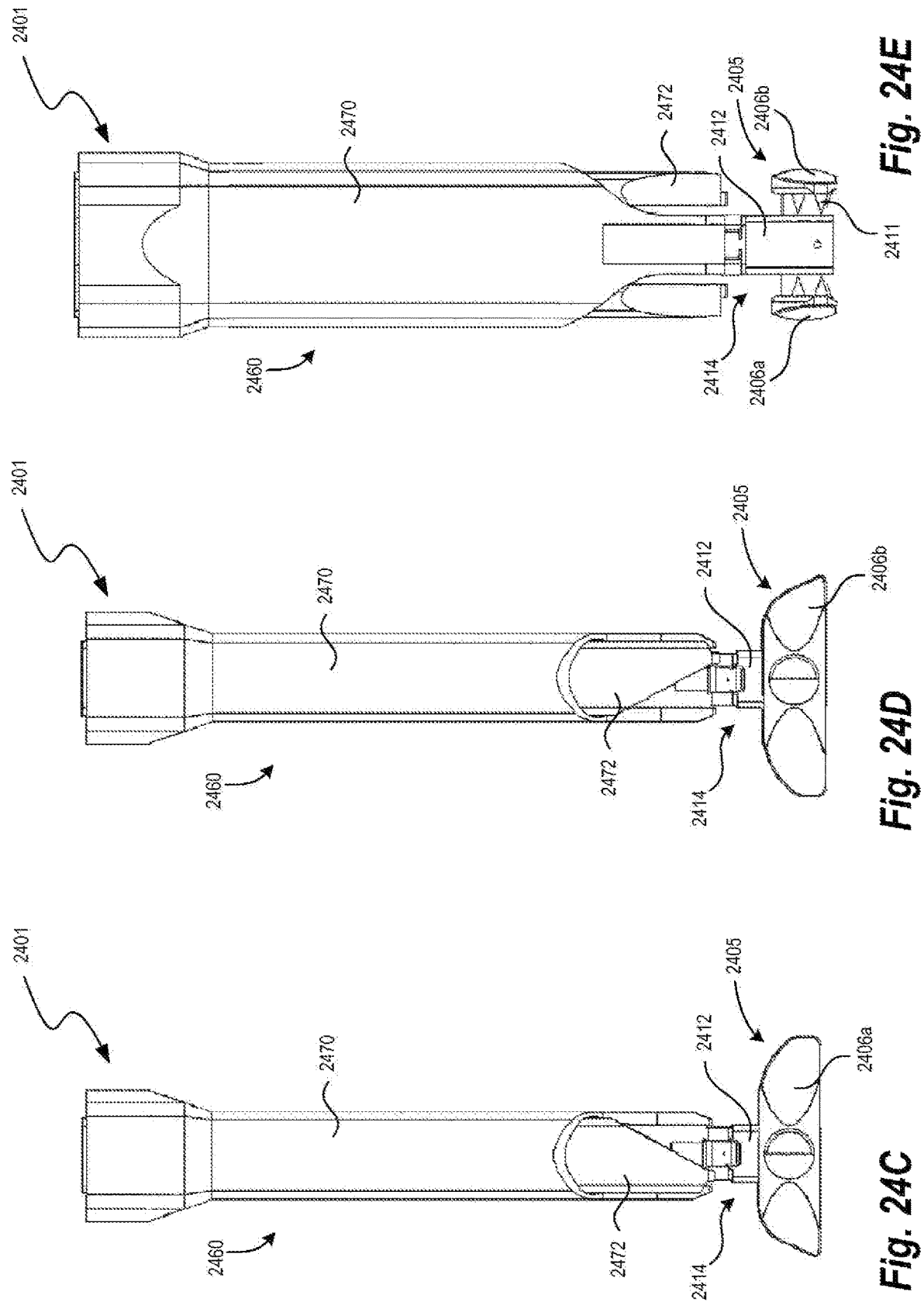

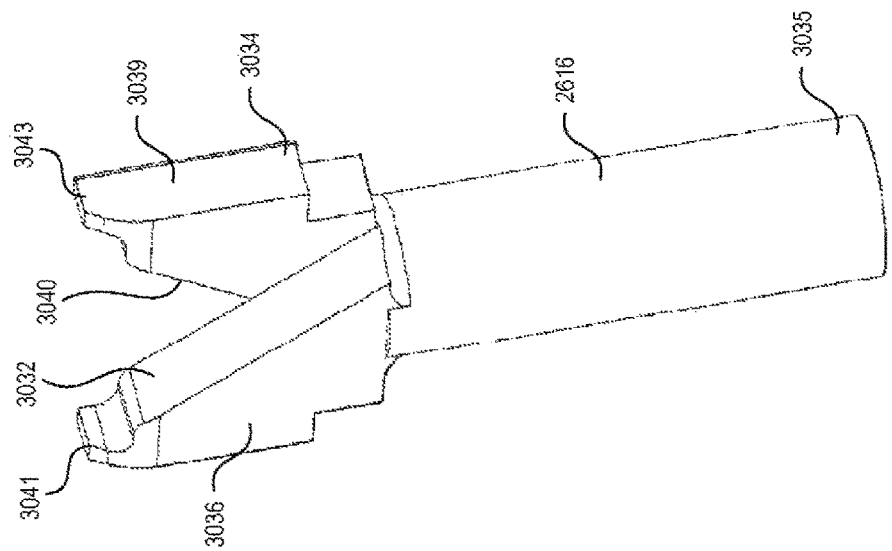
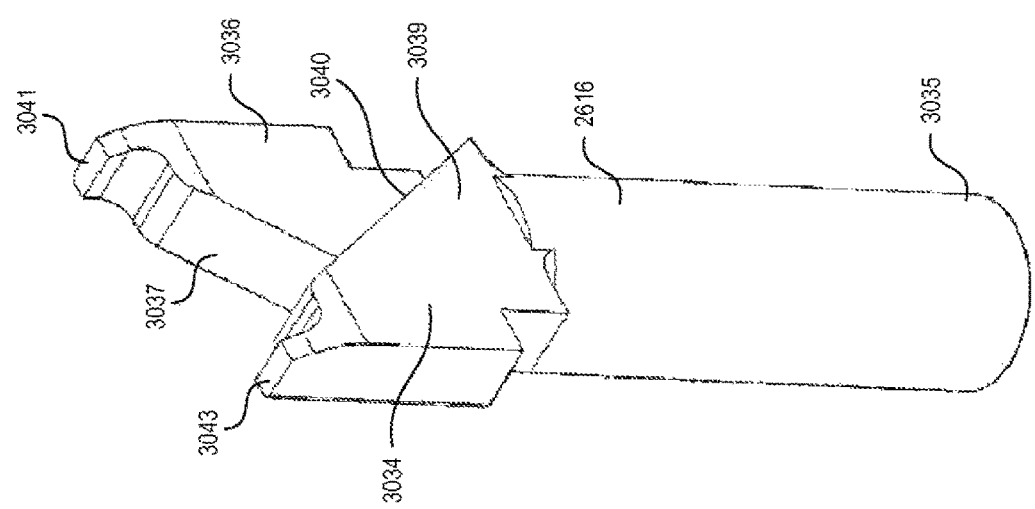
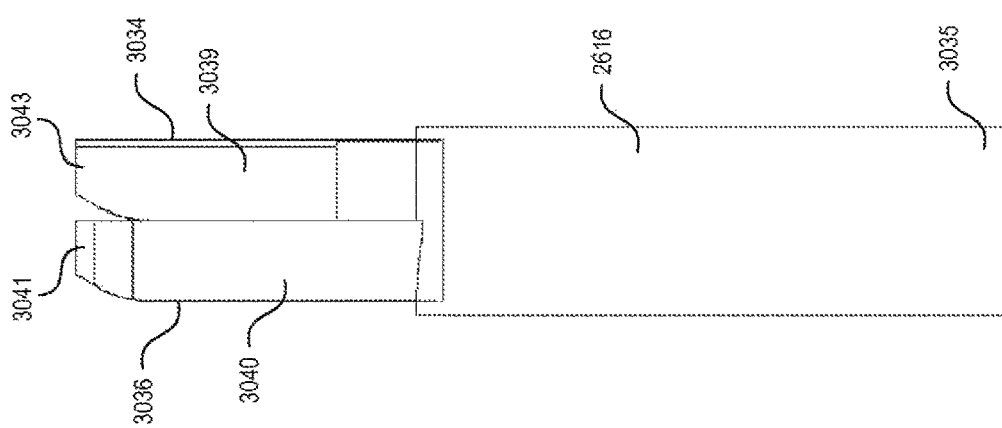

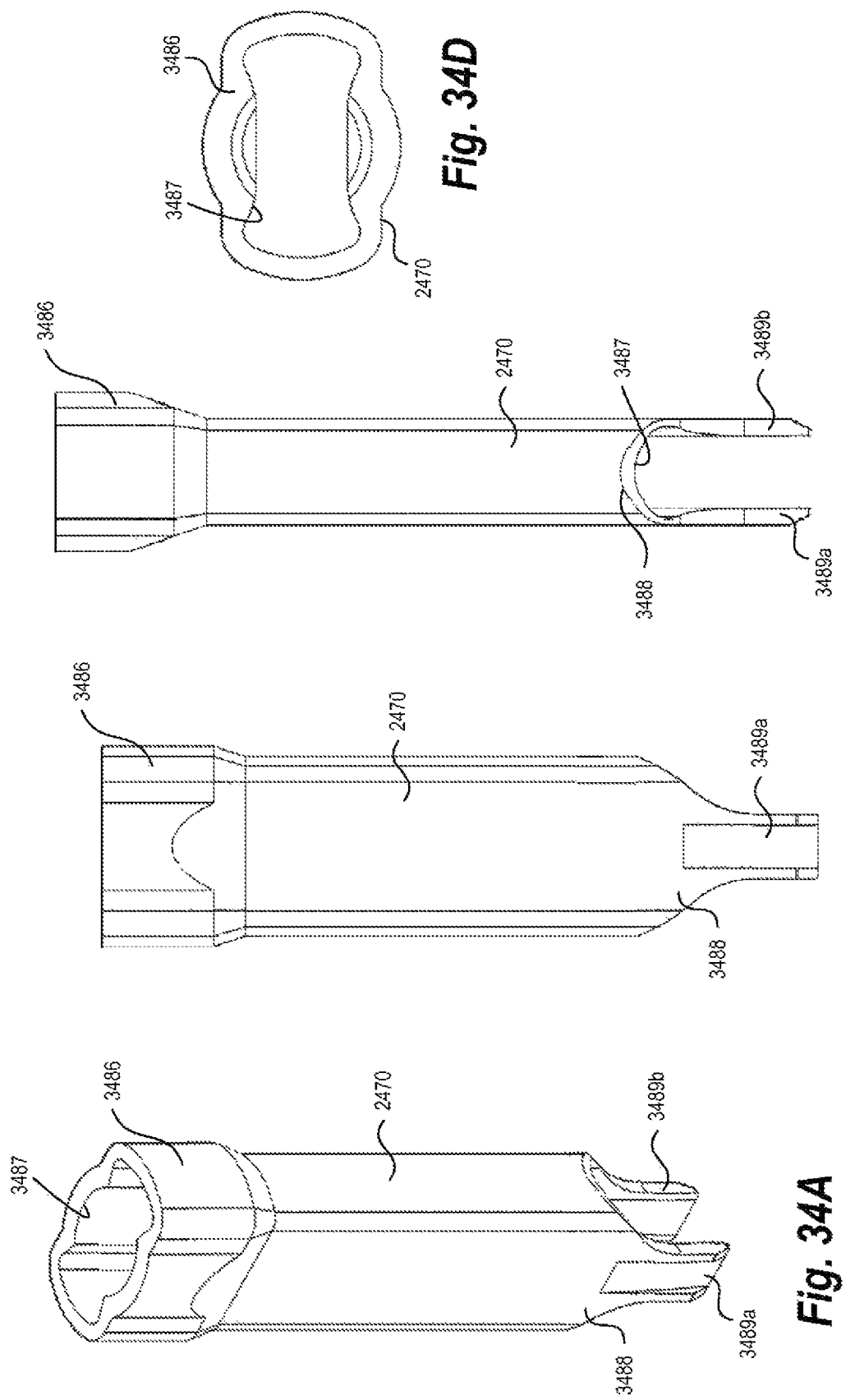

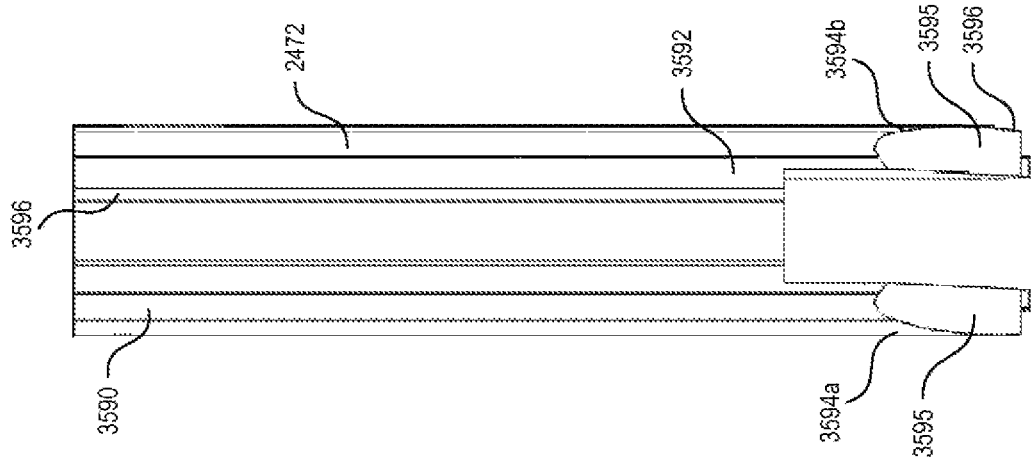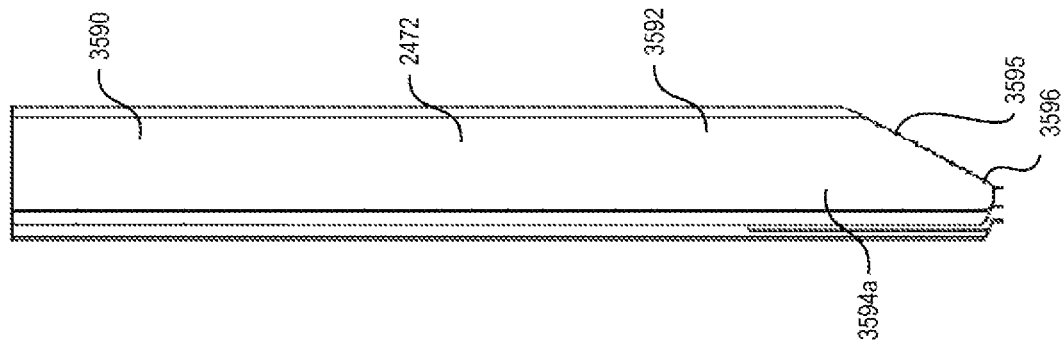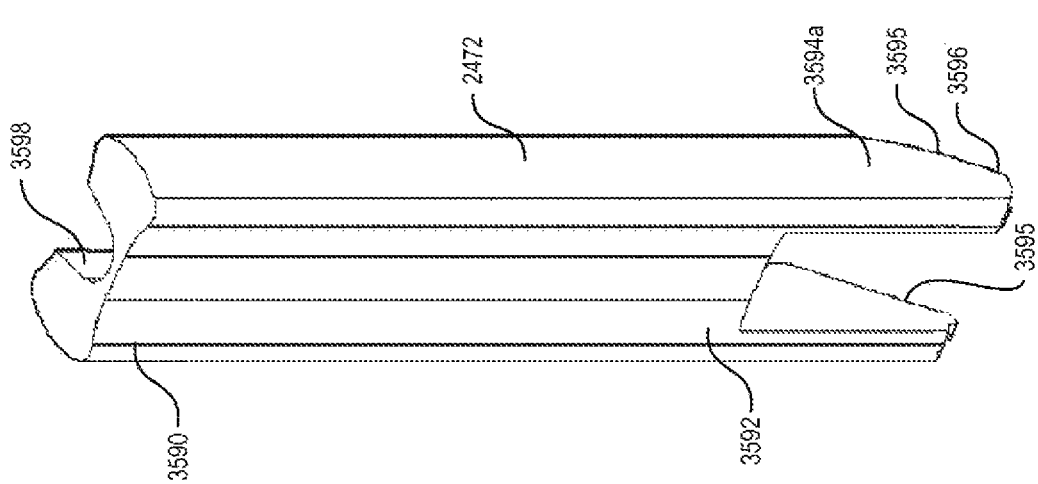

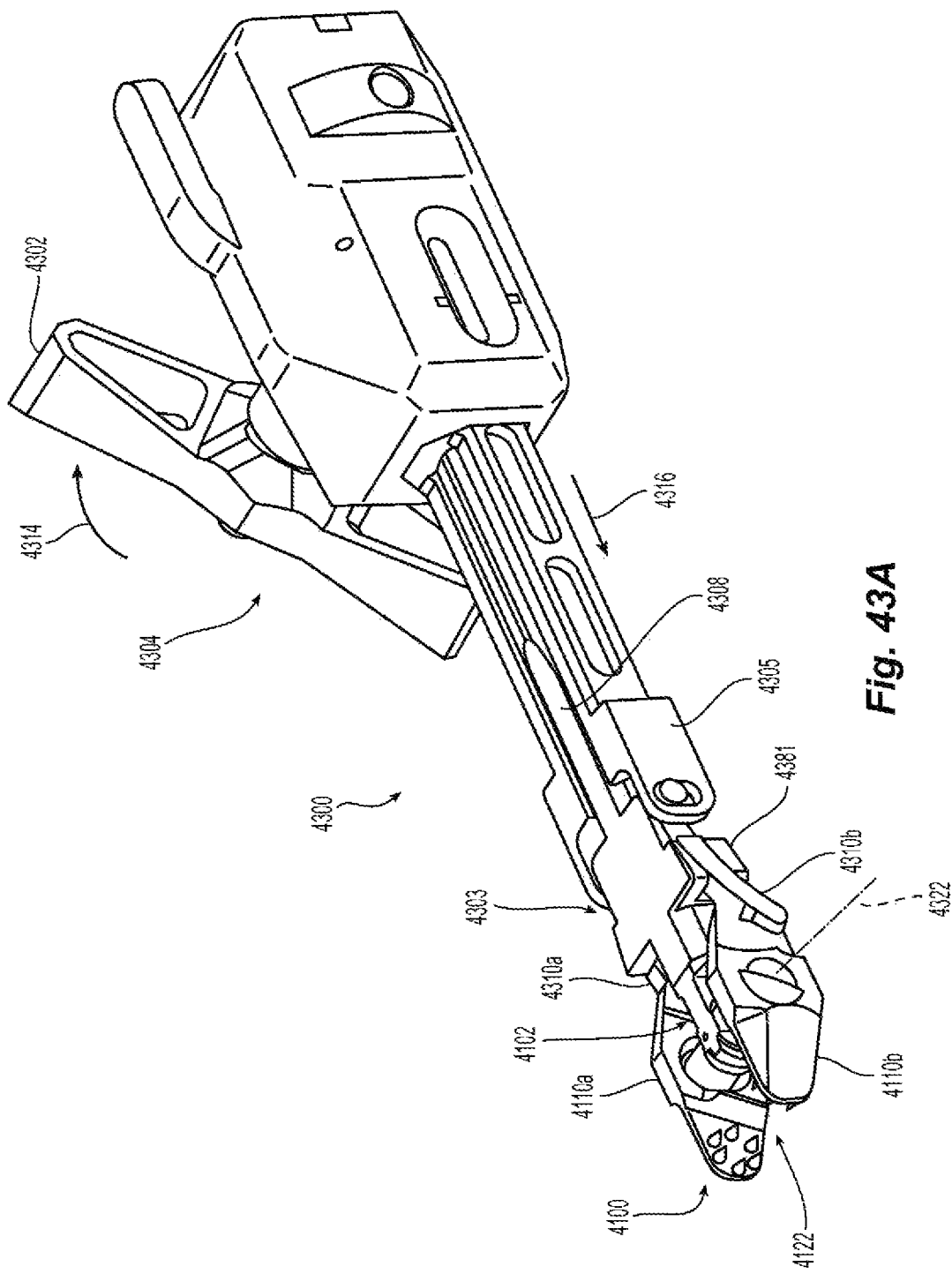

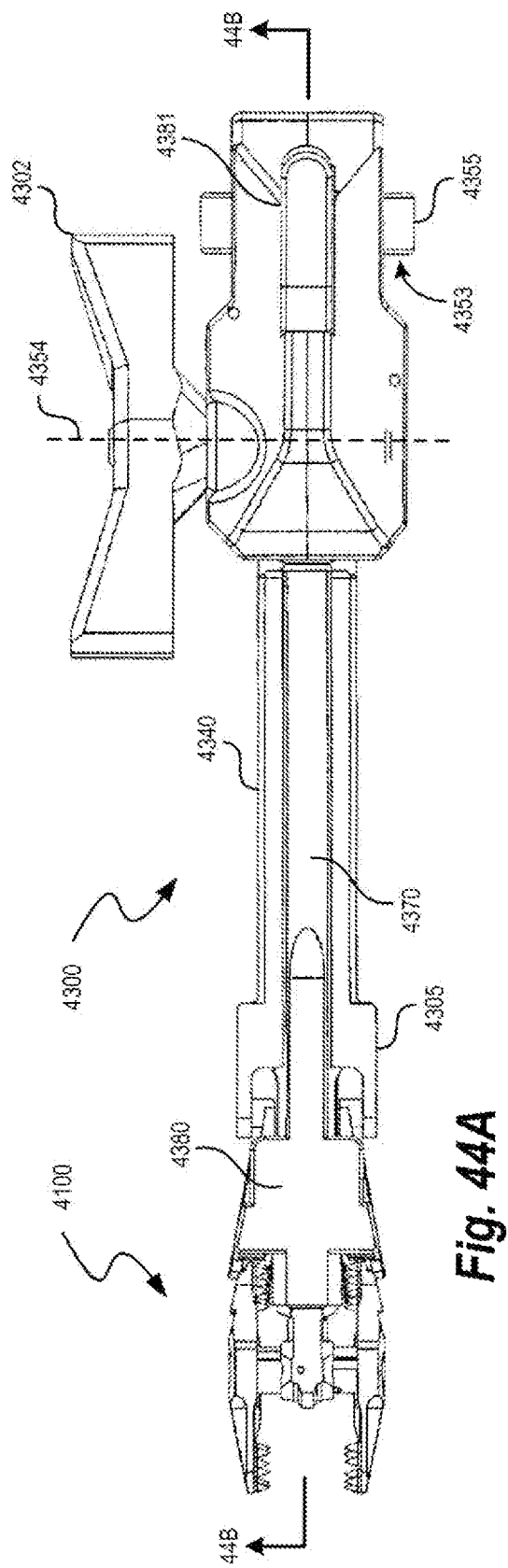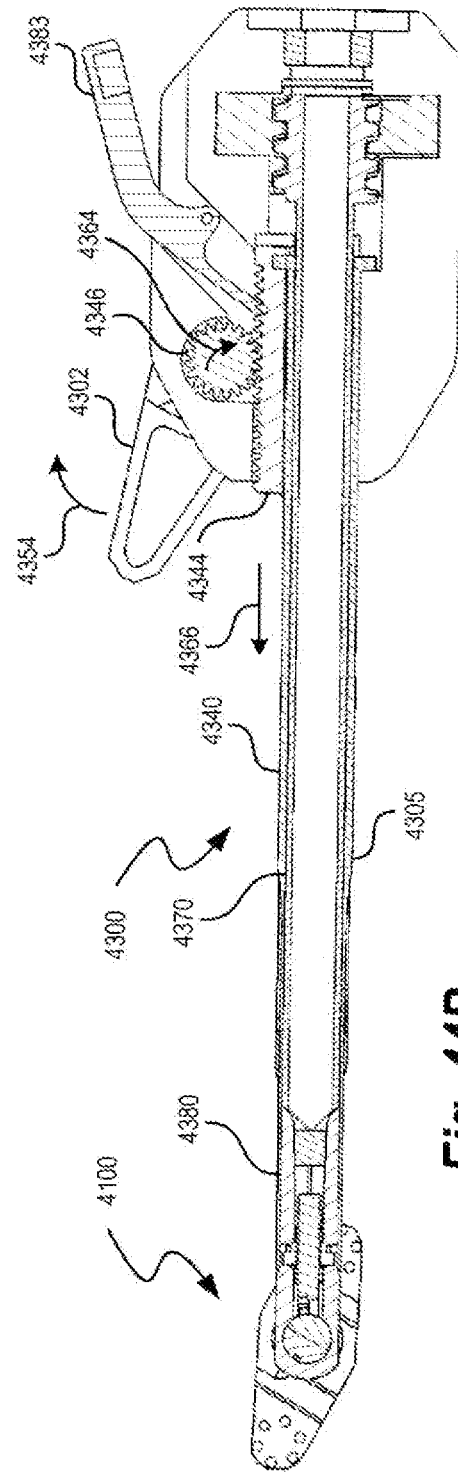

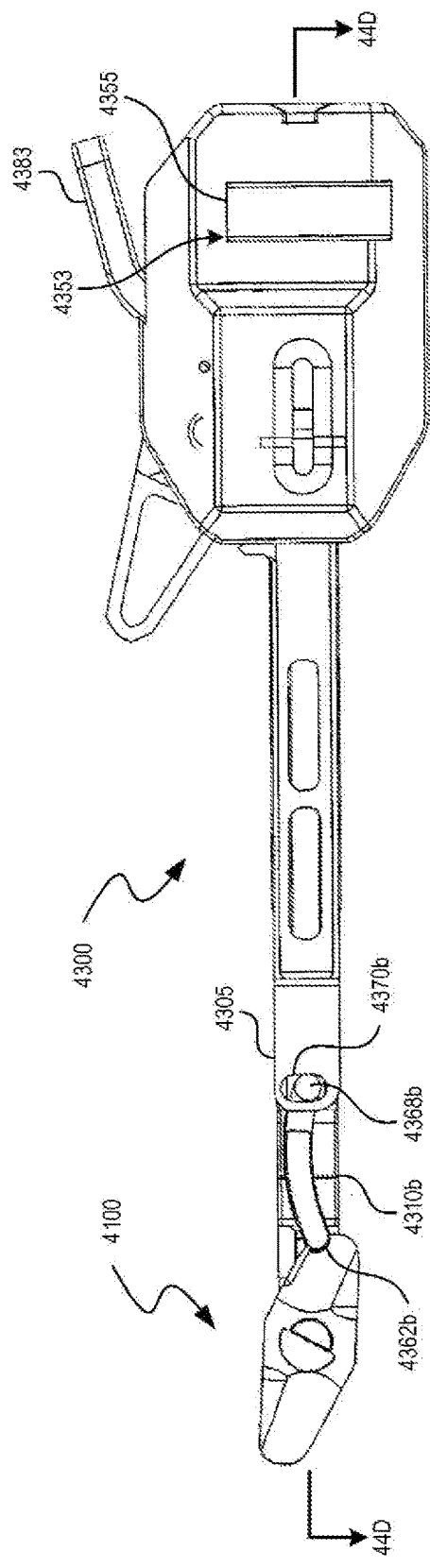
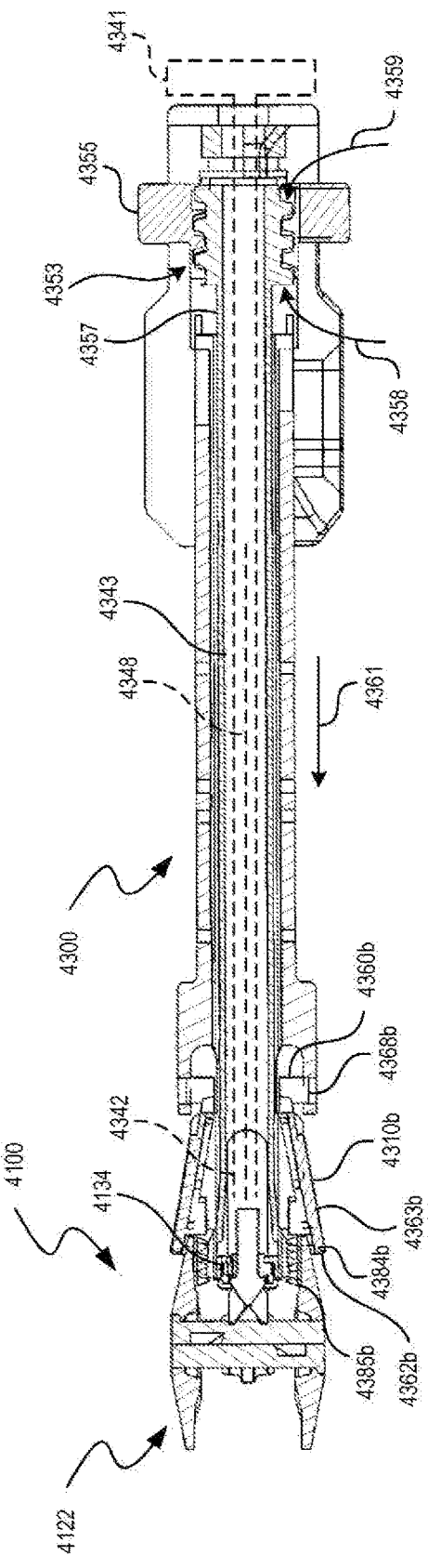
Fig. 44C
Fig. 44D

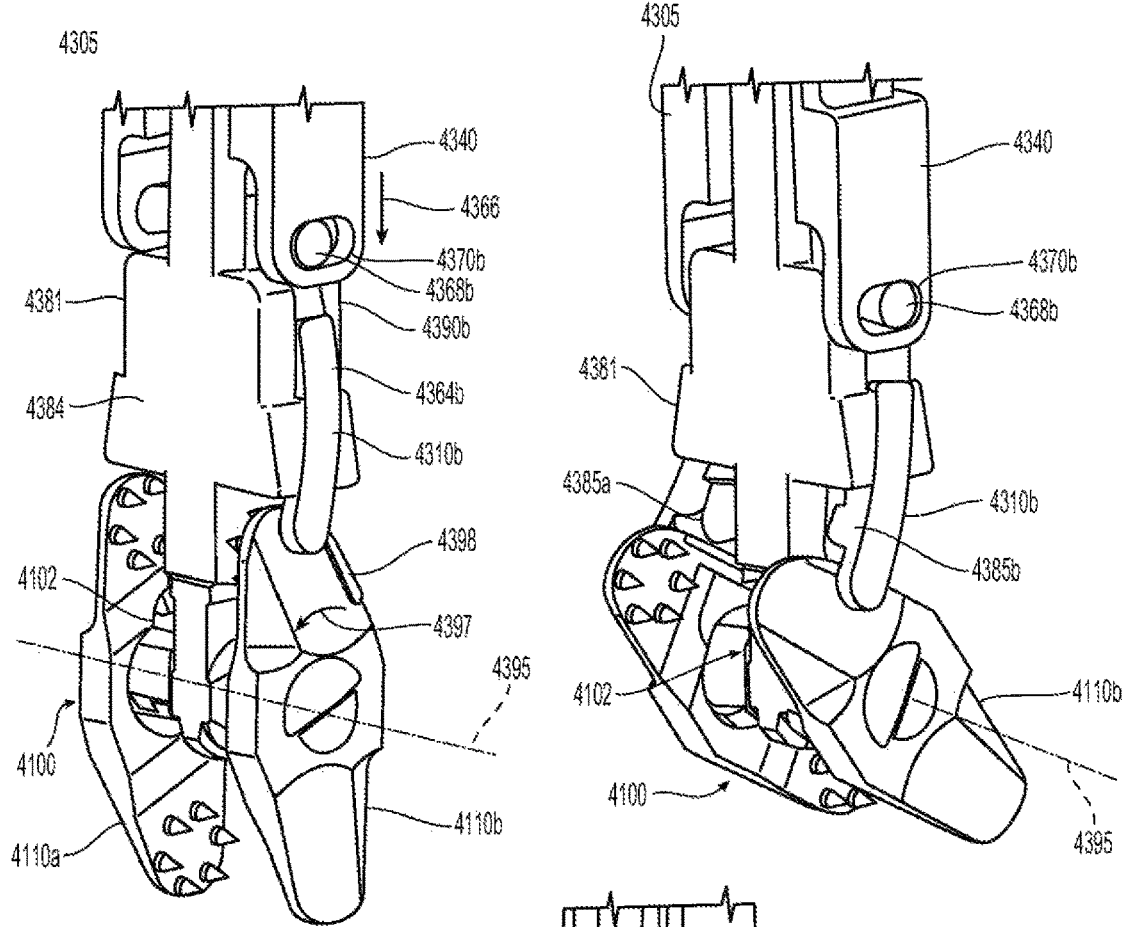
*Fig. 45A*
*Fig. 45B*
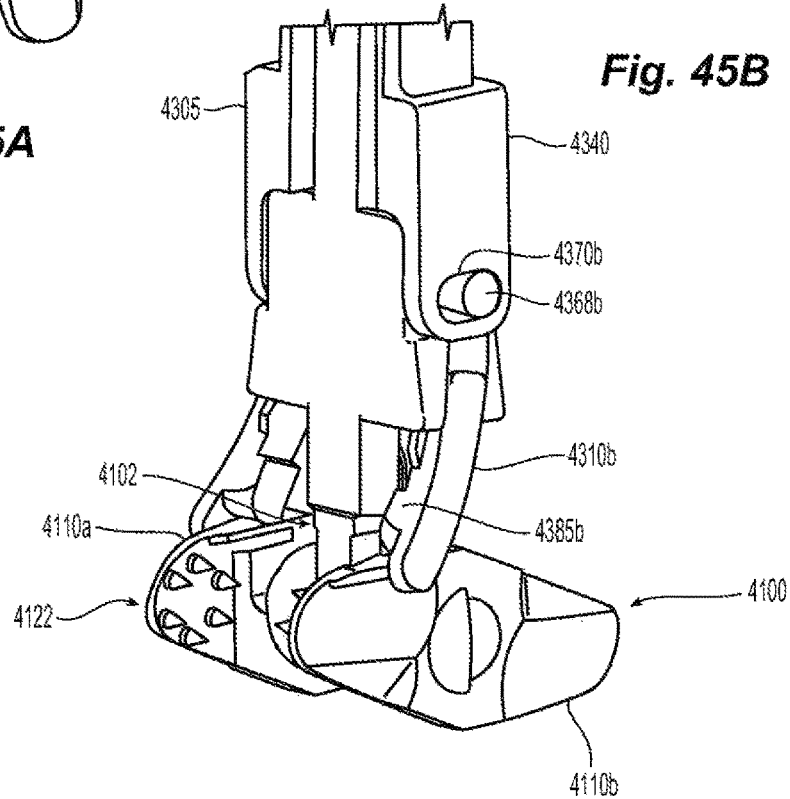
*Fig. 45C*

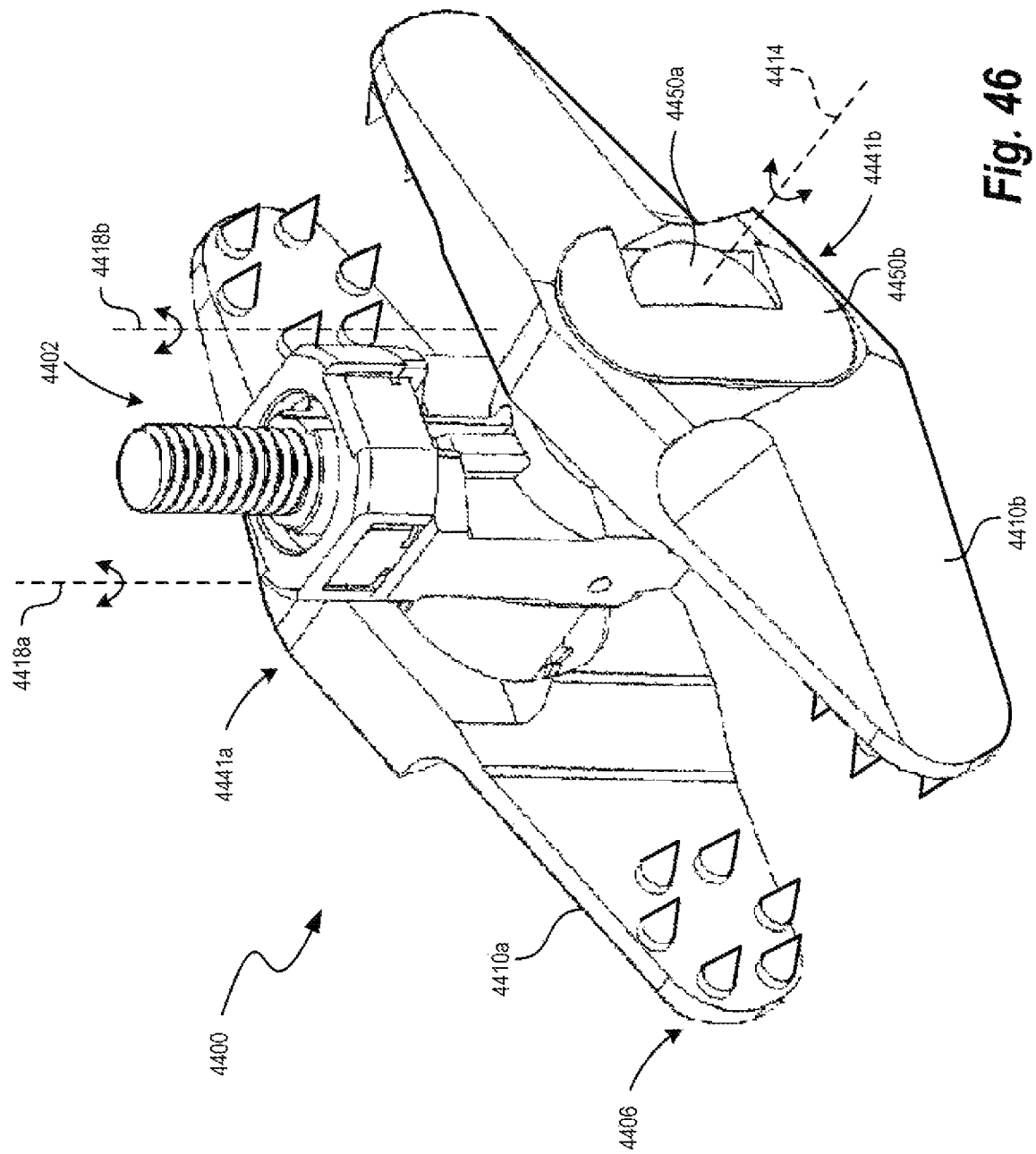

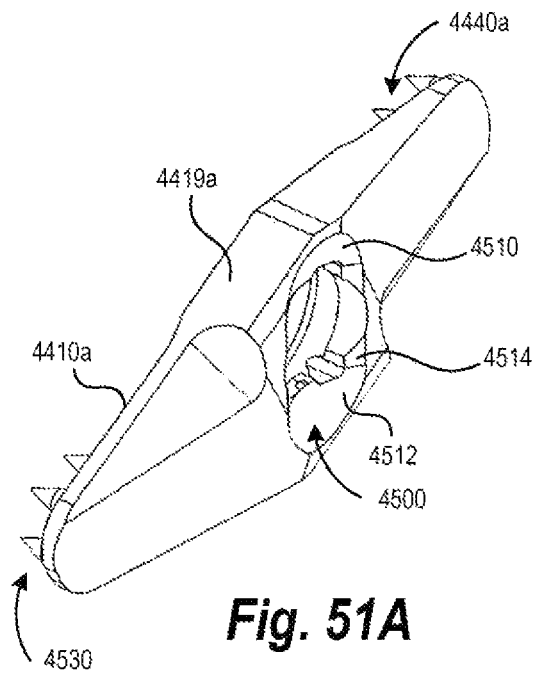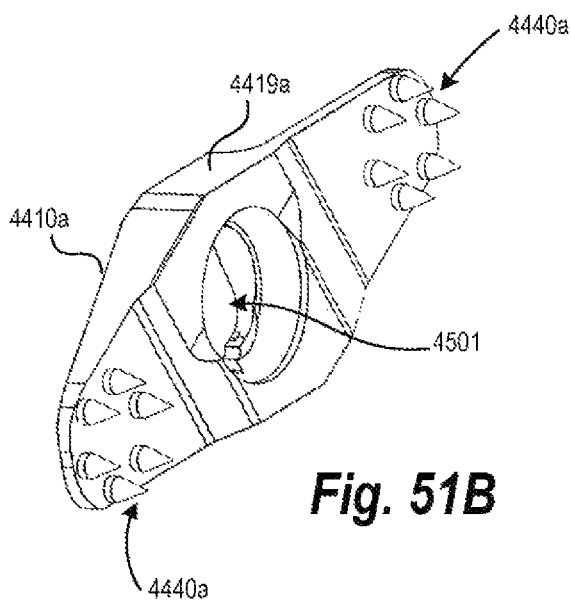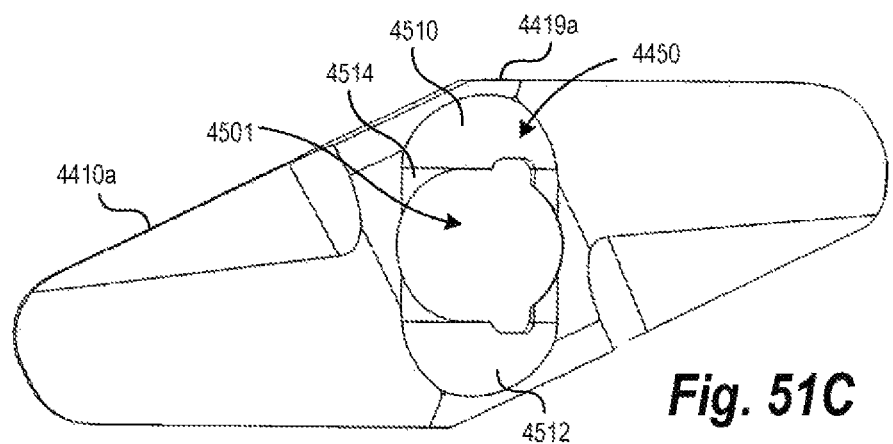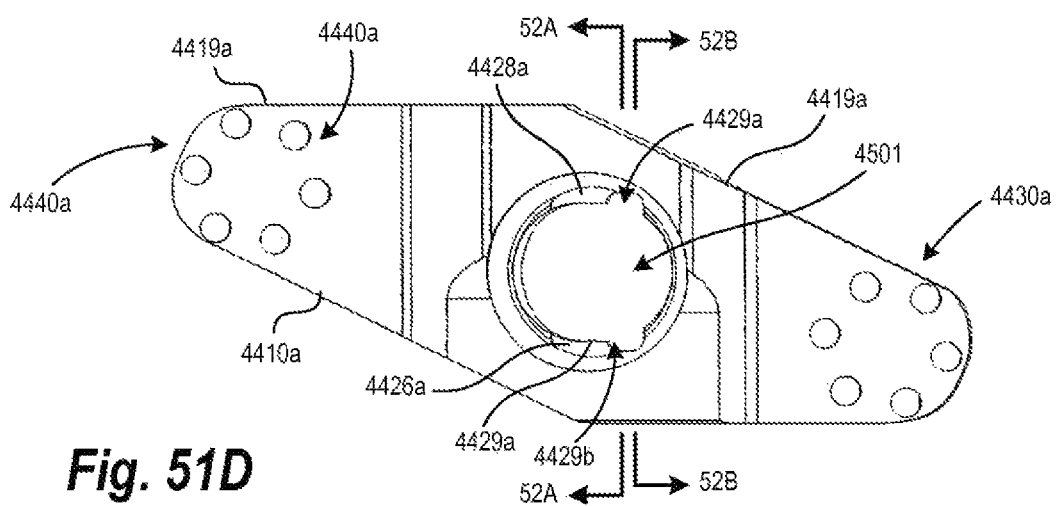

INTERSPINOUS SPACERS AND ASSOCIATED METHODS OF USE AND MANUFACTURE

CROSS-REFERENCE TO RELATED APPLICATIONS

This application is a continuation of U.S. application Ser. No. 15/962,071, filed Apr. 25, 2018, which is a continuation of U.S. application Ser. No. 13/679,986, filed on Nov. 16, 2012, now U.S. Pat. No. 9,956,007, and claims priority to U.S. Provisional Application No. 61/561,204, filed on Nov. 17, 2011, the disclosures of which are each incorporated herein by reference.

BACKGROUND OF THE INVENTION

The present disclosure relates generally to medical devices and, more particularly, to implants or spacers for placement between adjacent spinous processes. Spinal stenosis often involves narrowing of the spinal canal and pinching of the spinal cord and nerves, causing pain in the back and legs. Typically, with age, a person's ligaments may thicken, intervertebral discs may deteriorate, and facet joints may break down contributing to spinal stenosis. Injury, heredity, arthritis, changes in blood flow, and other causes may also contribute to spinal stenosis. Conventional spinal treatments often involve medications, surgical techniques, and implantable devices that alleviate debilitating pain associated with stenosis. Unfortunately, conventional treatments may not effectively treat spinal stenosis and may not alleviate pain.

BRIEF DESCRIPTION OF THE DRAWINGS

In the Figures, identical reference numbers identify identical or at least generally similar elements or acts.

FIG. 21B is a cross-sectional view taken substantially along lines 21B-21B in FIG. 13C.

FIG. 24A is an isometric view, FIG. 24B is an end view, FIGS. 24C and 24D are side views, and FIG. 24E is an end view of an assembly configured in accordance with another embodiment of the disclosure.

FIG. 30A is a side view, FIGS. 30B and 30C are isometric views.

FIG. 34A is an isometric view, FIGS. 34B and 34C are side views, and FIG. 34D is an end view of a cannula configured in accordance with an embodiment of the disclosure.

FIG. 35A is an isometric view and FIGS. 35B and 35C are side views of a plunger configured in accordance with an embodiment of the disclosure.

FIGS. 43A and 43B are isometric views of an instrument system coupled to a spacer in a delivery configuration and a partially deployed configuration in accordance with embodiments of the disclosure.

FIG. 44A is a top plan view of an instrument system coupled to a spacer. FIG. 44B is a cross-sectional view of the instrument system and the spacer taken along line 44B-44B of FIG. 44A. FIG. 44C is a side view of the instrument system coupled to the spacer.

FIG. 44D is a cross-sectional view of the instrument system and the spacer taken along line 44D-44D of FIG. 44C.

FIGS. 45A-45C are isometric views of a distal end of a delivery instrument reconfiguring a spacer in accordance with some embodiments of the disclosure.

FIG. 46 is an isometric view of a spacer in accordance with some embodiments of the disclosure.

FIGS. 51A and 51B are isometric views, FIG. 51C is a front view, and FIG. 51D is a back view of a wing in accordance with an embodiment of the disclosure.

DETAILED DESCRIPTION

Figure 59:
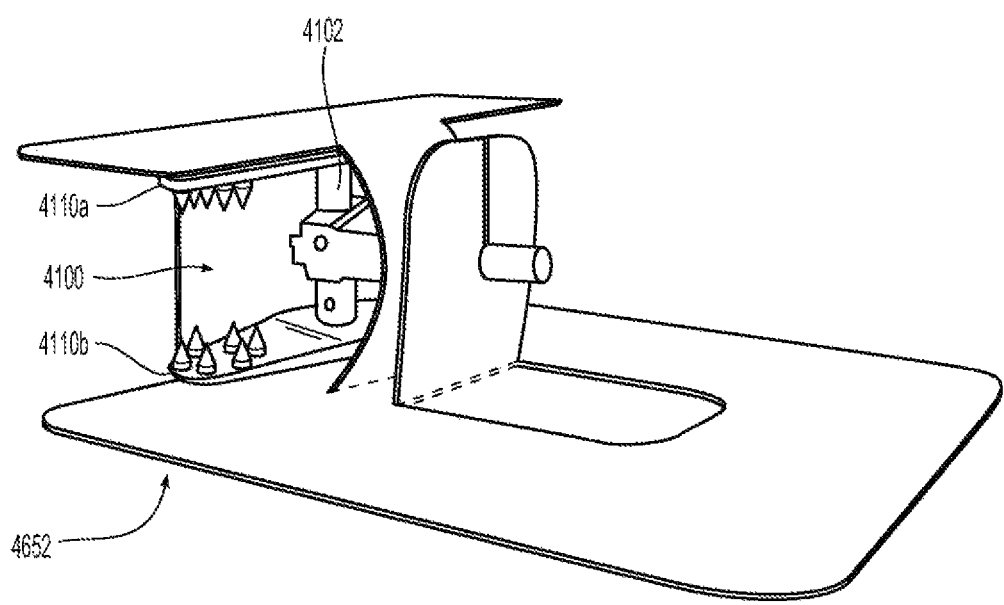
FIG. 59 is an isometric view of the foldable retainer holding a spacer in accordance with some embodiments of the disclosure.

The following disclosure describes various embodiments of medical devices, such as implants or spacers, and associated methods of manufacture and use. The medical devices can be delivered to interspinous spaces or other suitable location. For example, the medical devices can be implant along the spine to provide lateral stabilization, fixation (e.g., fusion), or positioning of anatomical structures to treat various diseases or conditions. Certain details are set forth in the following description and in FIGS. 1-59 to provide a thorough understanding of various embodiments of the disclosure. Other details describing well-known structures and systems often associated with interspinous implants, and methods for forming such parts, as well as other implants and assemblies, are not set forth in the following disclosure to avoid unnecessarily obscuring the description of the various embodiments of the disclosure.

At least some embodiments are directed to medical devices that can be positioned along a subject's spine to treat various conditions and diseases. The medical devices can include an actuator assembly and a clamp assembly. The actuator assembly can be positioned at an interspinous space between a superior spinous process and an inferior spinous process. The actuator assembly can be used to reconfigure the clamp assembly such that the clamp assembly clamps onto the superior and inferior spinous processes.

At least some embodiments include a spacer configured to be positioned at an interspinous space between the superior spinous process and the inferior spinous process. The spacer can be reconfigured to clamp onto the superior and inferior spinous processes. The spacer can be movable between different configurations.

In some embodiments, a spacer for holding a superior spinous process and an inferior spinous process comprises an actuator assembly and a clamp assembly. The actuator assembly is configured to be positioned at an interspinous space between the superior spinous process and the inferior spinous process. The clamp assembly includes a first wing and a second wing rotatably coupled to the actuator assembly. The actuator assembly is configured to move the clamp assembly from an open configuration for positioning at least one of the superior spinous process and the inferior spinous process between the first wing and the second wing and a clamping configuration for clamping onto the superior spinous process and the inferior spinous process.

In some further embodiments, an interspinous process spacer comprises a clamp assembly and an actuator assembly. The clamp assembly can include a pair of wings configured to clamp onto adjacent spinous processes of a subject. The actuator assembly can be configured to move the clamp assembly between different configurations. In some embodiments, the clamp assembly can be moved from an open configuration to a clamping configuration when the actuator assembly is at an interspinous space between the adjacent spinous processes.

The actuator assembly, in some embodiments, is coupled to the clamp assembly such that at least one of the wings is rotatable about two axes of rotation. In one embodiment, one of the wings is rotatable a first maximum angle (e.g., rotation about a first axis of rotation) in a range of about 75 degrees to 105 degrees and a second maximum angle (e.g., rotation about a second axis of rotation) equal to or less than about 20 degrees.

In some embodiments, an interspinous spacer includes means for clamping onto opposing sides of two adjacent spinous processes. The means for clamping can have an open configuration for receiving the adjacent spinous processes and a clamping configuration for holding the adjacent spinous processes. The spacer can further include mechanical means for actuating the means for clamping between multiple configurations (e.g., an open configuration to the clamping configuration, a delivery configuration for delivery to a treatment site, etc.). In one embodiment, the mechanical means for actuating is configured to be driven by an instrument releasably coupled to the spacer.

In yet further embodiments, a spacer for holding a first spinous process and a second spinous process comprises a clamp assembly and an actuator assembly. The clamp assembly is movable from an initial configuration to a rotated configuration and movable from the rotated configuration to a clamping configuration. The actuator assembly is configured to move the clamp assembly from the rotated configuration to the clamping configuration when at least a portion of the actuator assembly is positioned at an interspinous space between the first spinous process and the second spinous process.

In yet further embodiments, an interspinous system comprises a spacer and a retainer. The retainer can hold the spacer in a desired configuration. In some embodiments, the spacer includes a clamp assembly and an actuator assembly. The clamp assembly is movable between an open configuration for receiving two spinous processes and a clamping configuration for holding the spinous processes. The actuator assembly is coupleable to an instrument. In one embodiment, the instrument is capable of causing the actuator assembly to drive the clamp assembly between the open configuration and the clamping configuration. The retainer can be configured to hold the clamp assembly in the open configuration when the retainer is removably coupled to the spacer.

At least some embodiments are directed to an instrument system for reconfiguring a spacer. The instrument can reconfigure the spacer to facilitate delivery of the spacer and to deploy the spacer to engage one or more anatomical features.

In some embodiments, an instrument system includes a delivery instrument having a holder mechanism and a rotator device. The rotator device can be configured to cause rotation of a clamp assembly of an interspinous spacer held by the holder mechanism such that the clamp assembly moves between a delivery configuration for positioning at least a portion of the interspinous spacer between adjacent spinous processes and a rotated configuration. In some embodiments, the instrument system further includes one or more drivers, cannulas, or other delivery devices.

At least some embodiments are directed to a method for delivering a spacer into a subject. The method includes positioning a spacer at a treatment site. The spacer can be reconfigured to engage one or more anatomical features. In some embodiments, the method includes positioning a spacer between a superior spinous process and an inferior spinous process of a subject such that the superior and inferior spinous processes are received by a clamp assembly of the spacer. The clamp assembly can be moved between different configurations. In one embodiment, the clamp assembly can be moved from an open configuration to a clamping configuration. For example, an actuation assembly of the spacer can change the configuration of the spacer and can be driven by a delivery instrument (e.g., a delivery instrument removably coupled to the spacer). In some embodiments, the instrument can be separated from the spacer and removed from the subject.

Many of the details, dimensions, angles and/or other portions shown in the Figures are merely illustrative of particular embodiments of the disclosure. Accordingly, other embodiments can have other details, dimensions, angles and/or portions without departing from the spirit or scope of the present disclosure. In addition, further embodiments of the disclosure may be practiced without several of the details described below, while still other embodiments of the disclosure may be practiced with additional details and/or portions.

Treatment Systems

Figure 1:
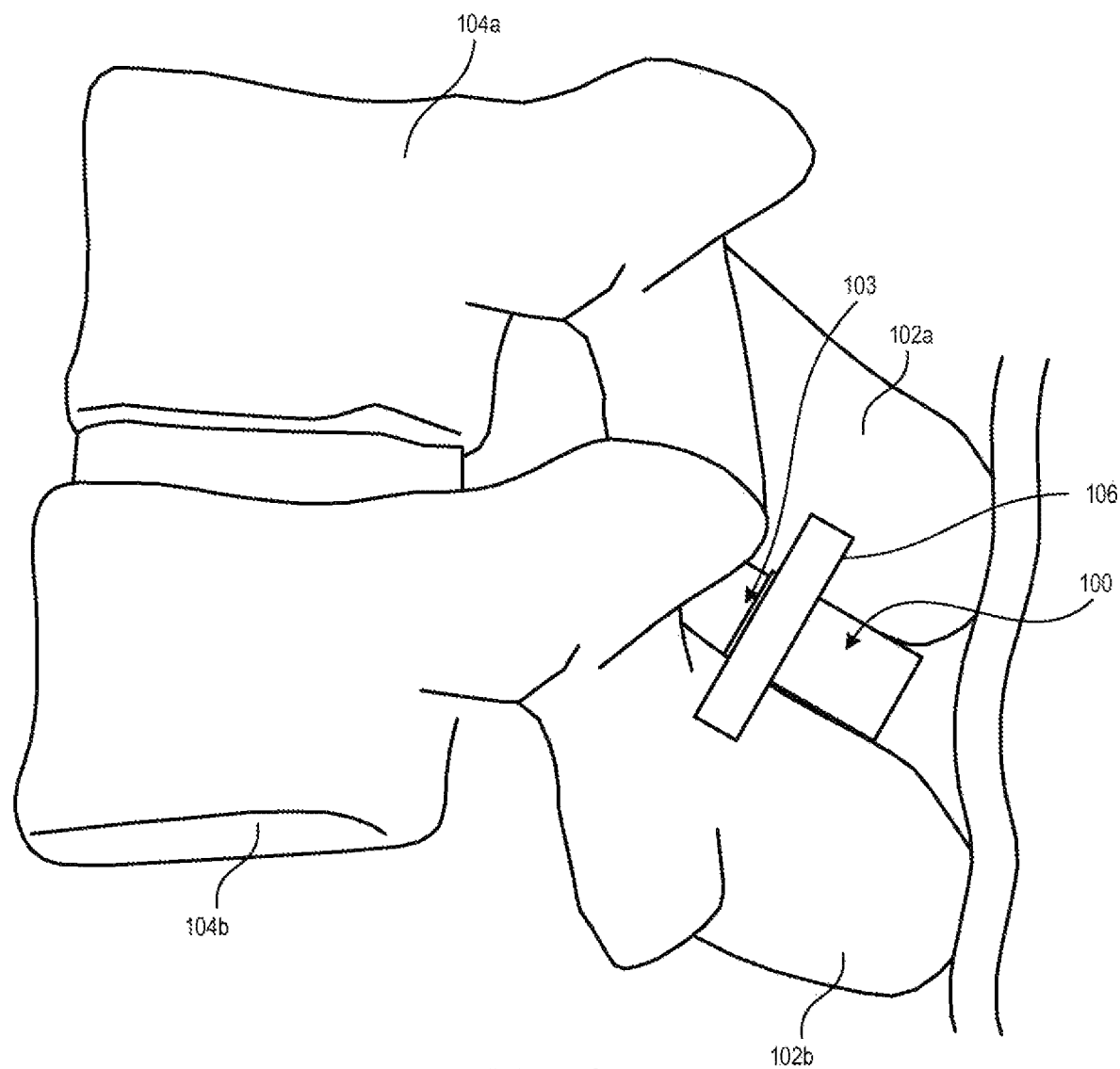
FIG. 1 is a partially schematic side view of a spacer configured in accordance with an embodiment of the disclosure.

FIG. 1 is a side partially schematic view of an implant or spacer 100 (shown schematically) configured in accordance with an embodiment of the disclosure. As shown in FIG. 1, the spacer 100 positioned between adjacent spinous processes 102 (identified individually as a first or superior spinous process 102a and a second or inferior spinous process 102b) associated with corresponding vertebral bodies 104 (identified individually as a first or superior vertebral body 104a and a second or inferior vertebral body 104b). The spacer 100 can be implant at an interspinous space 103 to provide lateral stabilization and/or fixation (e.g., fusion) to treat various diseases or conditions, such as degenerative disc disease (e.g., back pain of discogenic origin with degeneration of the disc confirmed by history and/or radiographic studies), spondylolisthesis, and/or trauma damage (e.g., fracture, dislocation, etc.). For example, the spacer 100 can be used for non-cervical fixation. In some procedures, the spacer 100 can be implanted at a non-cervical region of the spine (vertebrae T1-S1). Additionally, the spacer 100 can be used in conjunction with another procedure, such as a spinal fusion procedure (e.g., a spinal fusion procedure using a bone graft, a demineralized bone matrix, etc.).

The spacer 100 can inhibit, limit, or substantially prevent relative movement between the vertebral bodies 104 and/or the spinous processes 102 to facilitate the fusion process. In other procedures, the spacer 100 can be a stand-alone device that provides stabilization, fixation, etc. The spacer 100 can include individual opposing arms or wings 106 (only one of which is shown in FIG. 1) that engage each of the superior and inferior spinous processes 102a, 102b, to securely fuse or fix, as well as stabilize and align, the superior and inferior spinous processes 102a, 102b. Various additional features and details of spacers represented schematically by the spacer 100 of FIG. 1 are described in detail below with reference to FIGS. 2A-11E.

Figure 2A:
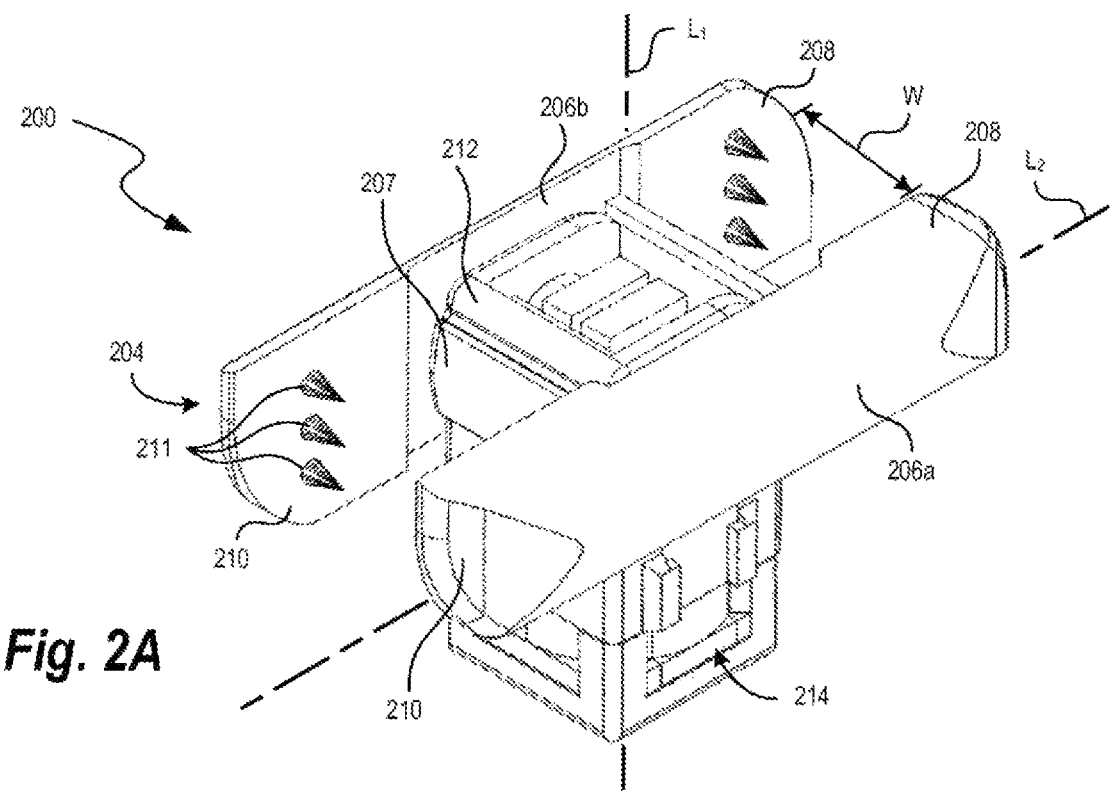
FIGS. 2A-2F are a series of views of a spacer configured in accordance with an embodiment of the disclosure.
Figure 2B:
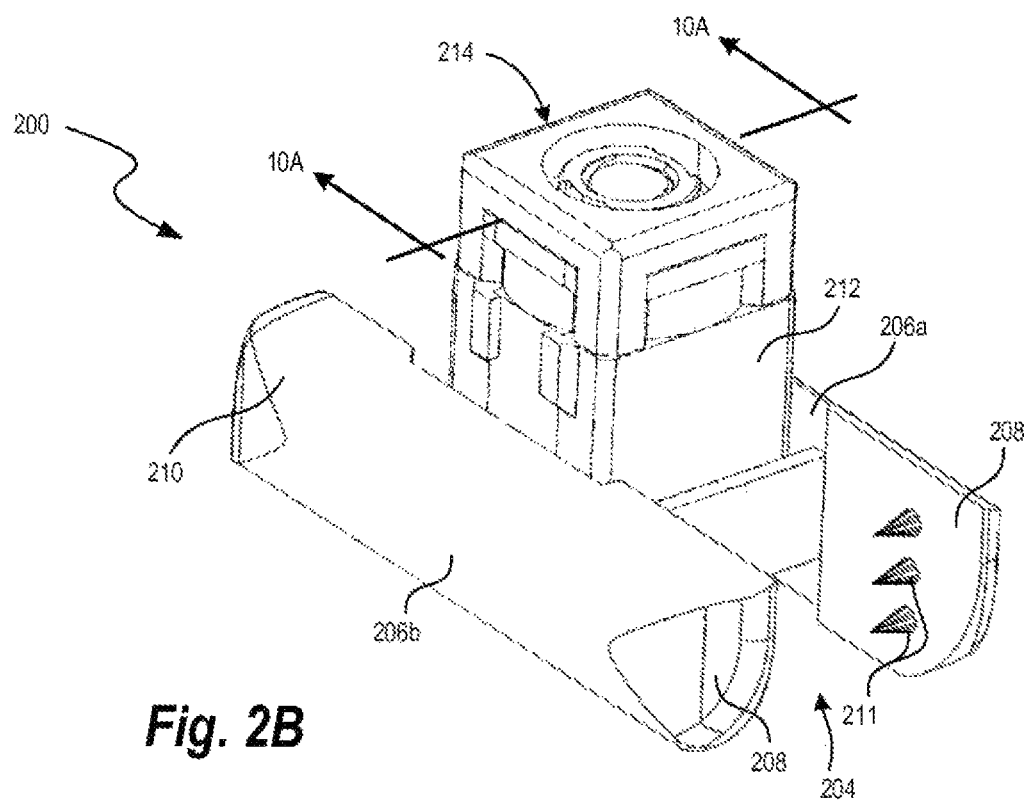
Figure 2C:
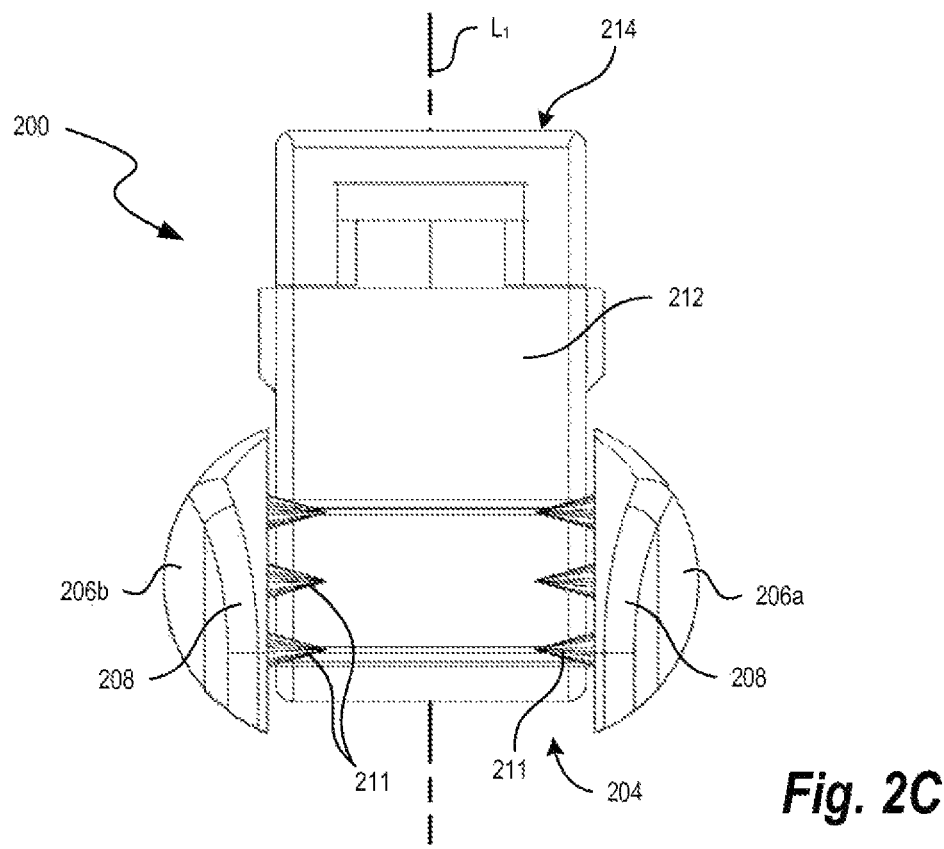
Figure 2D:
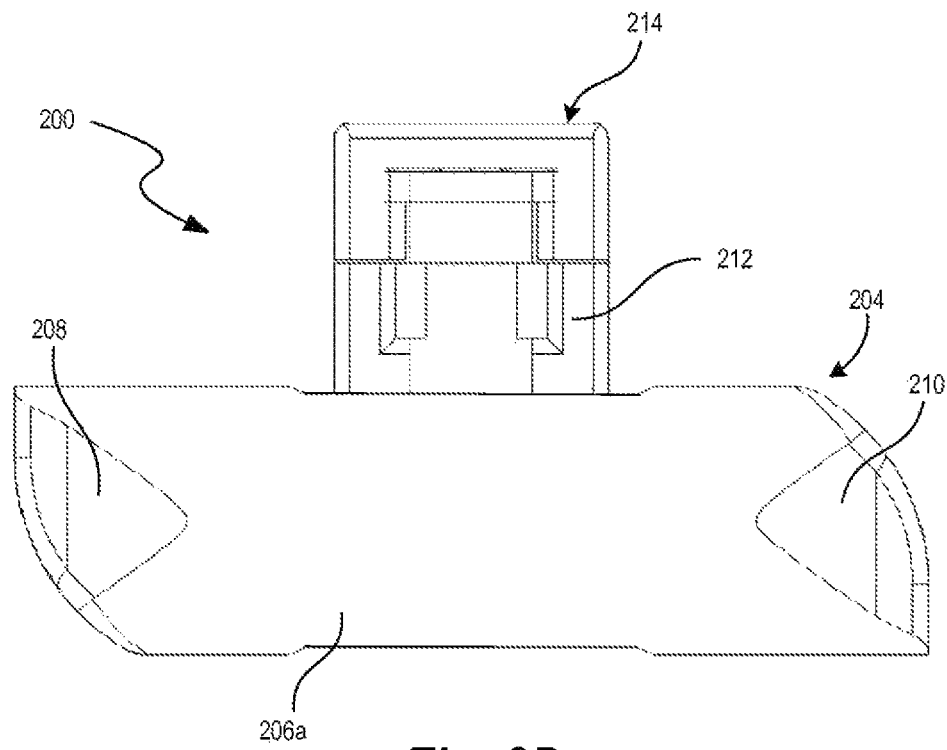
Figure 2E:
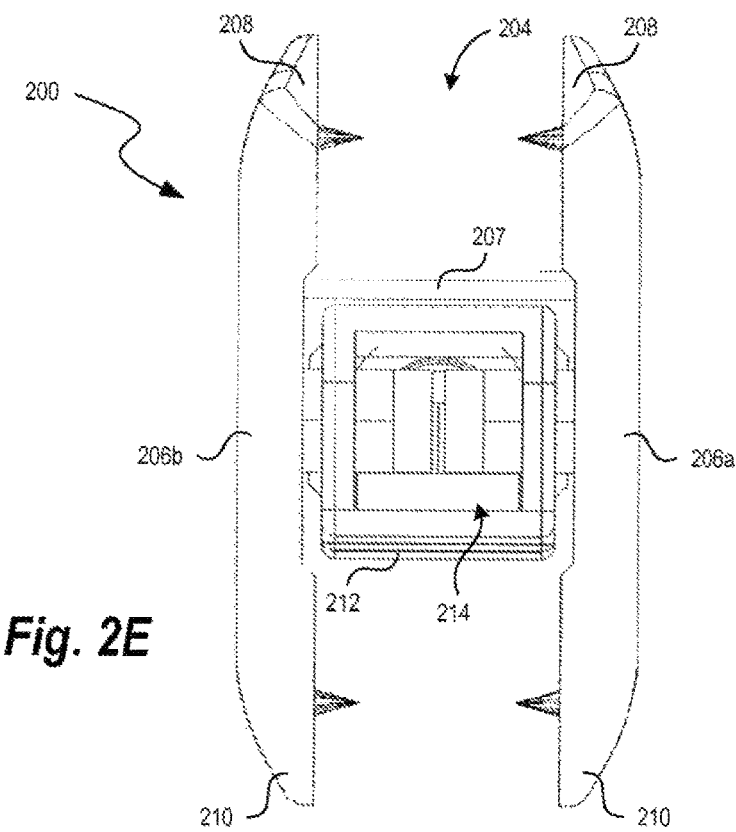
Figure 2F:
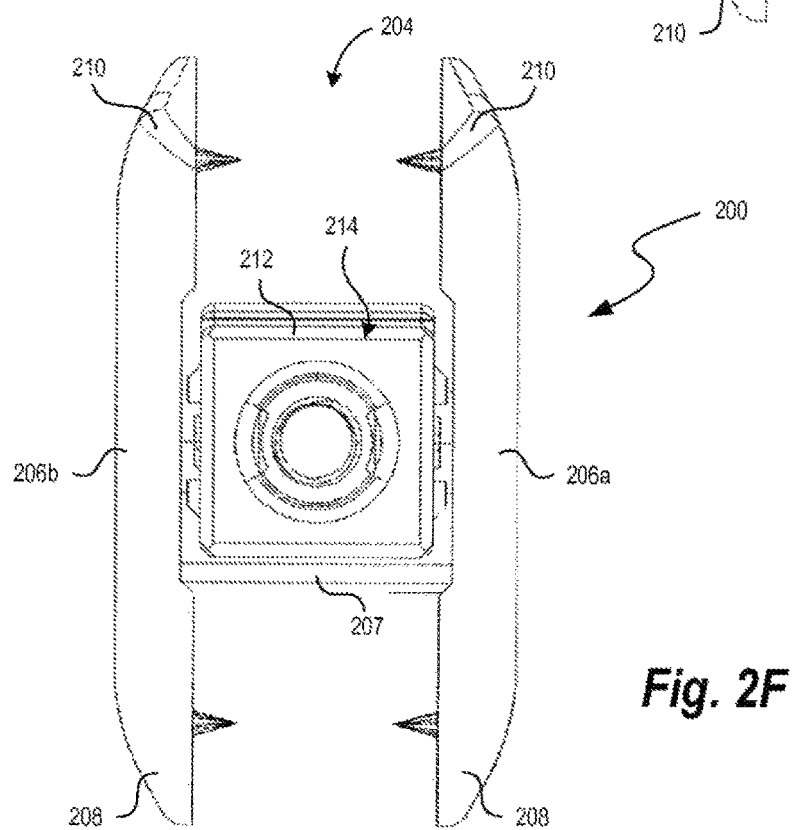

FIGS. 2A and 2B are isometric views, FIG. 2C is an end view, FIG. 2D is a side view, FIG. 2E is a bottom plan view, and FIG. 2F is a top view of a spacer 200 configured in accordance with embodiments of the disclosure. Referring to FIGS. 2A-2F together, the spacer 200 includes a clamp assembly 204, wings 206 (identified individually as a first wing 206a and a second wing 206b) movably coupled to a body 212. The wings 206 can be engaging extensions, rigid elongated members, arms, or the like. The spacer 200 also includes an actuator assembly 214 operably coupled to the body 212 and the wings 206. The actuator assembly 214 can convert a force or motion to another force or motion. For example, the actuator assembly 214 can convert rotational motion into linear motion.

Each wing 206 includes a first or proximal end portion 208 opposite a second or distal end portion 210. Each of the first and second end portions 208, 210 includes multiple engagement features 211 (e.g., spikes, barbs, etc.) that are configured to contact and engage corresponding spinous processes (e.g., spinous processes 102 illustrated in FIG. 1). Each wing 206 further includes a guide 207 (only one of which is visible in FIGS. 2A-2F) that facilitates alignment between the wings 206 as the wings 206 translate with reference to the body 212 between undeployed or partially deployed positions and a deployed position.

In FIGS. 2A-2F, the spacer 200 is shown in a fully deployed configuration. The fully deployed configuration can be a clamping configuration such that the spacer 200 is fixed to the spinous processes. More specifically, the body 212 includes a body longitudinal axis $L_1$ and each wing 206 includes a wing longitudinal axis $L_2$ (FIG. 2A). In the deployed position, the wings 206 can be oriented such that their corresponding wing longitudinal axes $L_2$ are at least generally perpendicular to the body longitudinal axis $L_1$. Moreover, in the fully deployed position, the wings 206 can be positioned adjacent to the body 212 thereby reducing a width W (FIG. 2A) between the wings 206. The width W can be configured to allow the wings 206 and engagement features 211 to engage corresponding spinous processes. As described in detail below with reference to 11A-11E, the wings 206 can rotate and slide or translate relative to the body 212 between at least a first or undeployed position (e.g., an initial position), a second or partially deployed position (e.g., a rotated position), and a third or fully deployed position (e.g., a clamped position).

Figure 3A:
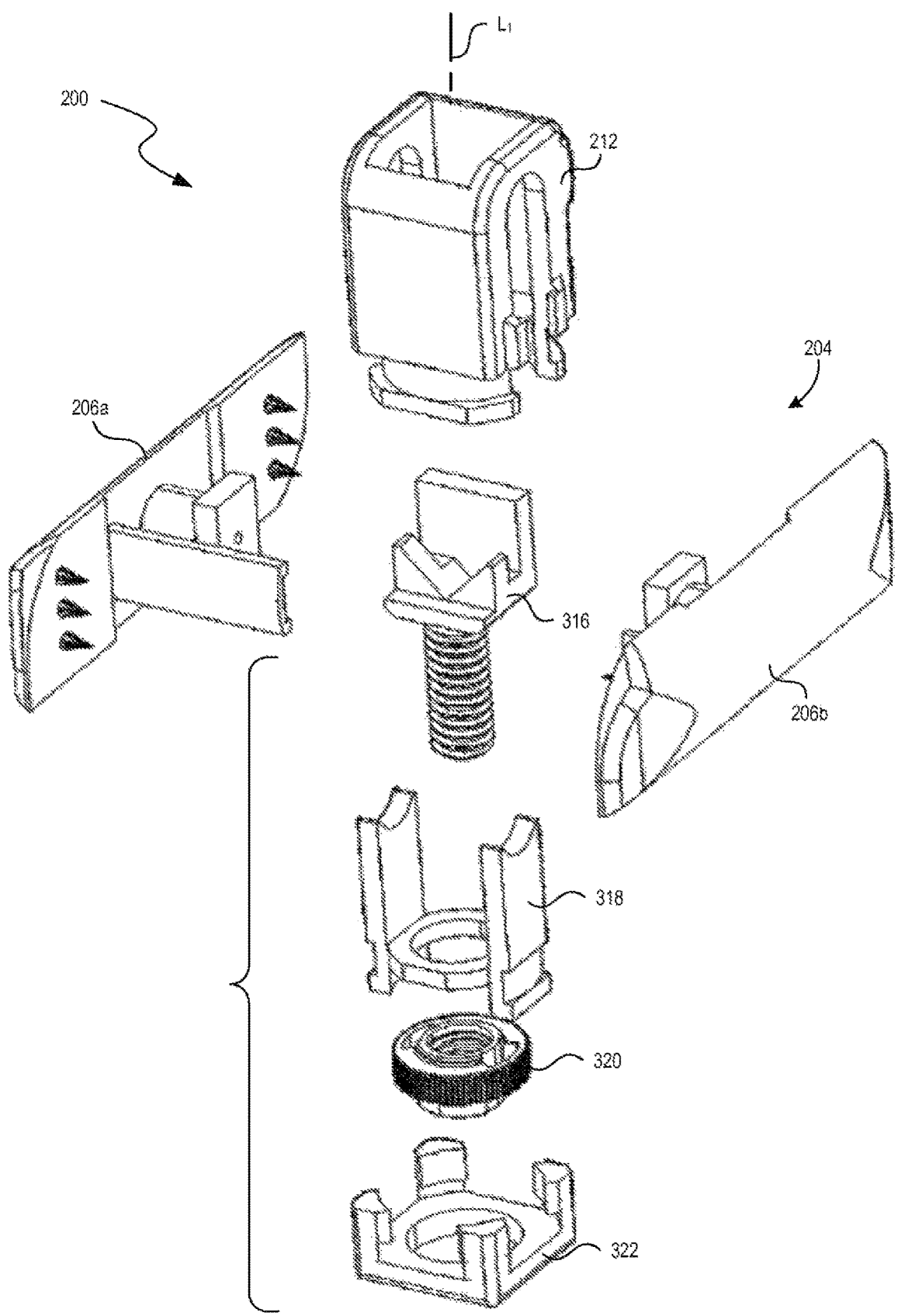
FIGS. 3A and 3B are exploded isometric views of the spacer illustrated in FIGS. 2A-2F.
Figure 3B:
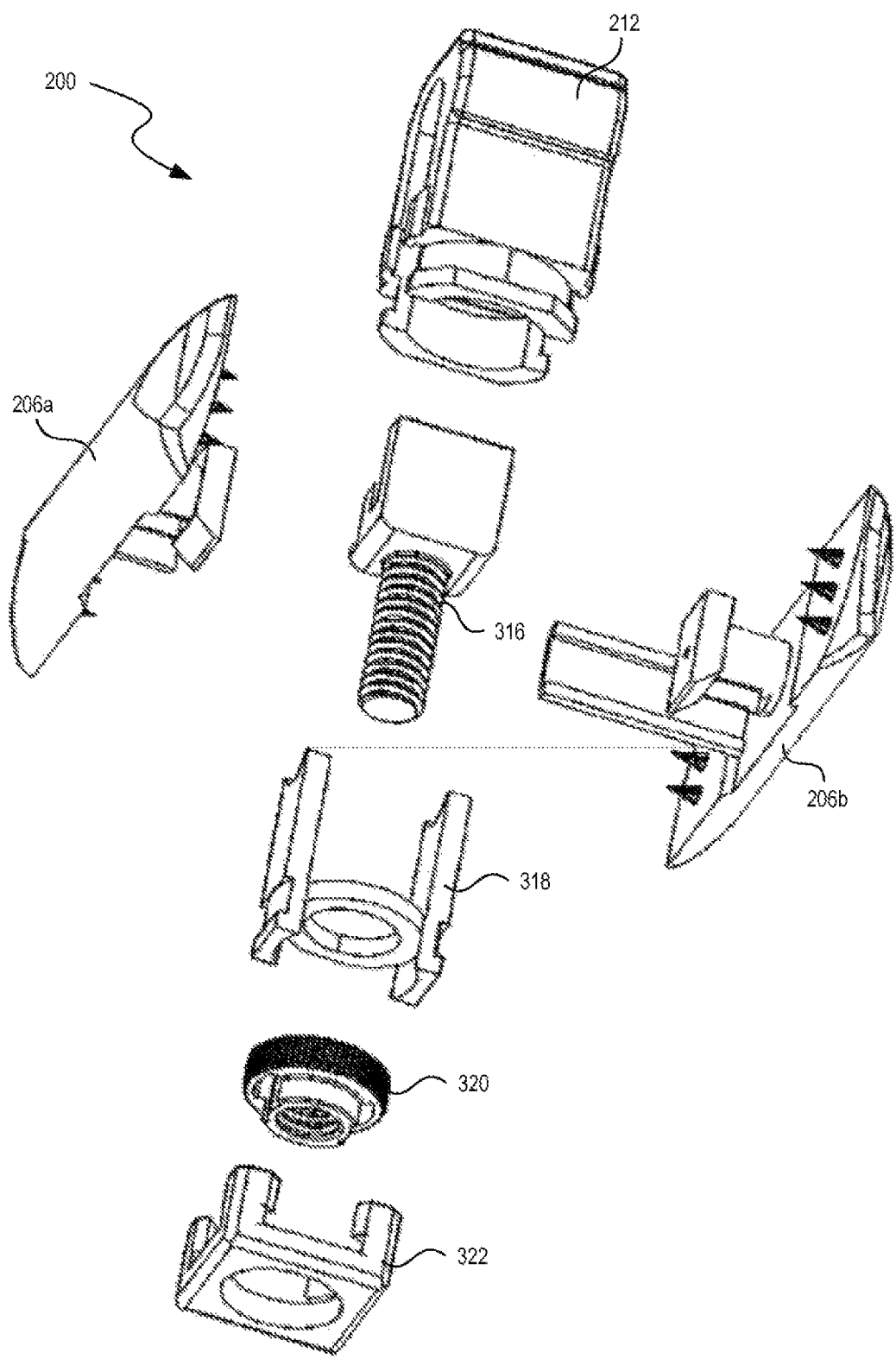

FIGS. 3A and 3B are exploded isometric views of the spacer 200 illustrated in FIGS. 2A-2F. Referring to FIGS. 3A and 3B together, the actuator assembly 214 includes an actuator 316, a guide 318, an actuator adjuster in the form of a wheel 320, and a cover 322. The actuator assembly 214 is operably coupled to the body 212 and the wings 206 to move the wings 206 between the undeployed configuration and the deployed configuration. More specifically, and as described in detail below, movement or rotation of the wheel 320 about the body longitudinal axis $L_1$ moves the actuator 316 within the body 212 in directions generally parallel to the body longitudinal axis $L_1$. As the actuator 316 moves within the body 212, the actuator 316 drives or urges the wings 206 to pivot or rotate, as well as slide or translate, about the body 212 and the guide 318 between the undeployed and deployed configurations. As such, the actuator 316 functions as a wing 206 rotational driver as well as a wing 206 sliding driver. Further details and features of the individual components illustrated in FIGS. 3A and 3B are described below with reference to FIGS. 4A-9B.

Figure 4A:
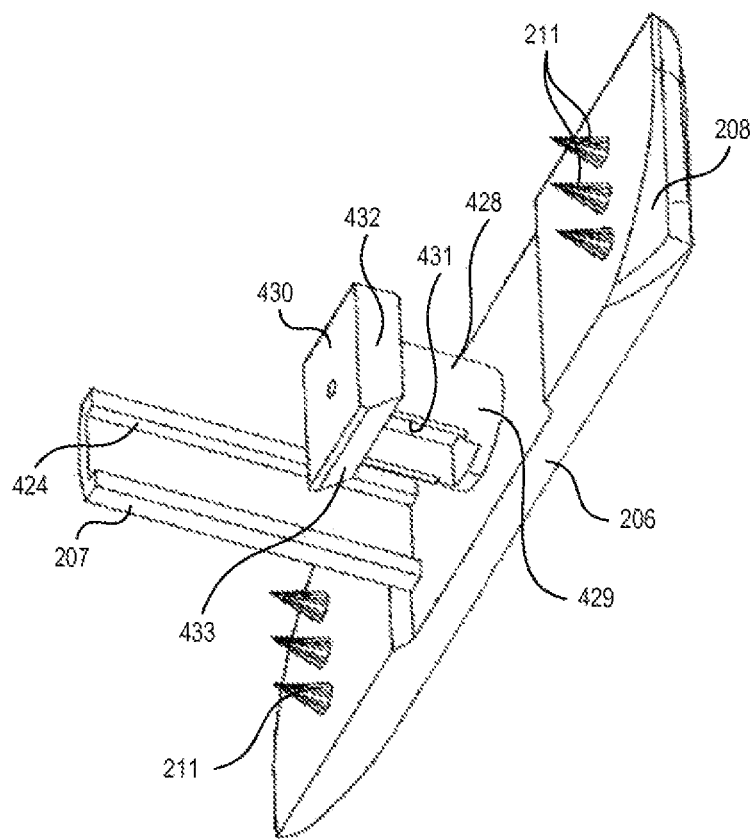
FIGS. 4A-4E are a series of views of an engaging extension or wing configured in accordance with an embodiment of the disclosure.
Figure 4B:
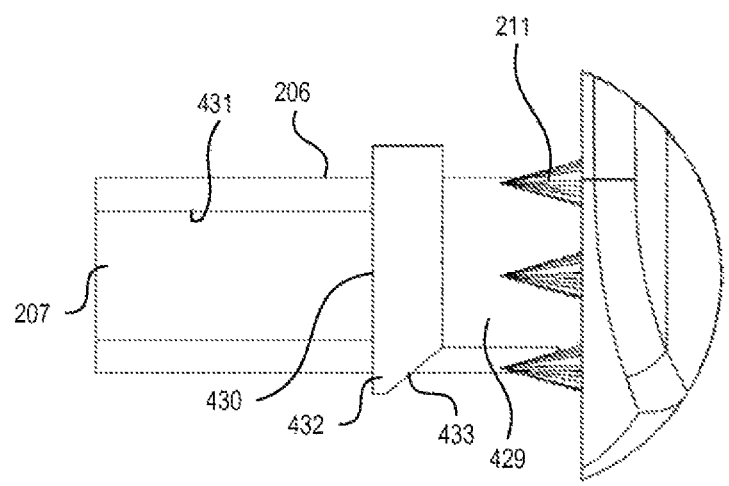
Figure 4C:
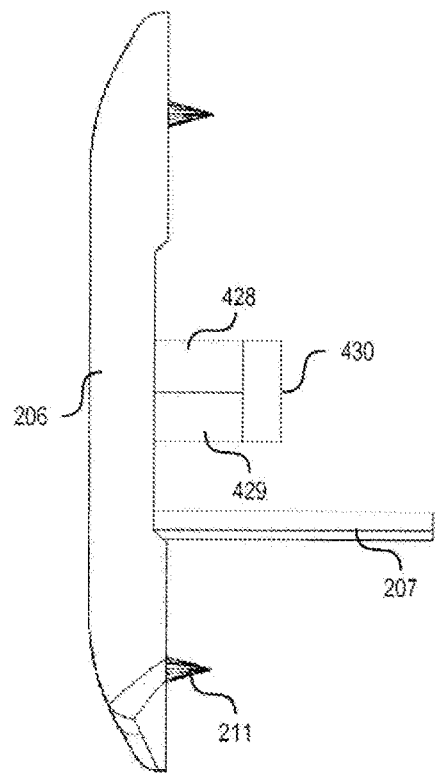
Figure 4D:
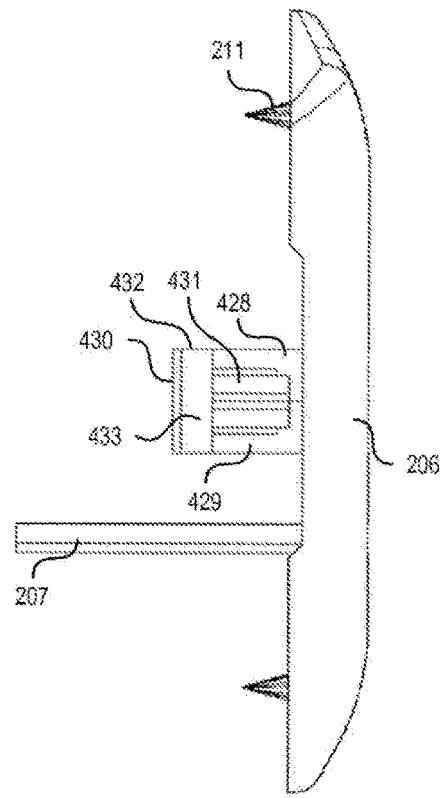
Figure 4E:
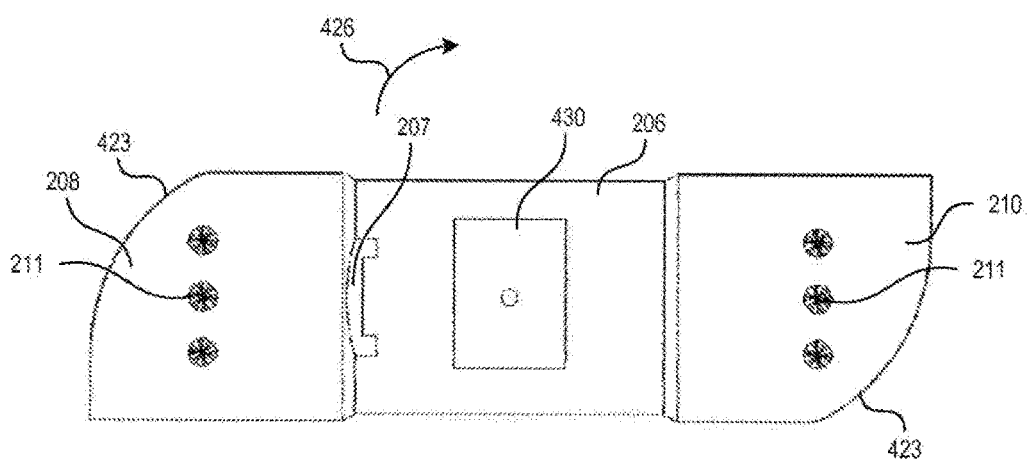

FIG. 4A is an isometric view, FIG. 4B is an end view, FIG. 4C is a bottom plan view, FIG. 4D is a top view, and FIG. 4E is a side view of the wing 206. The wing 206 represented in FIGS. 4A-4E is representative of each of the first and second wings 206a, 206b illustrated in FIGS. 2A-3B. Referring to FIGS. 4A-4E together, the wing 206 includes the first end portion 208 and the second end portion 210, each of which carries the engagement features 211. As shown in FIG. 4E, the first and second end portions 208, 210 can have a generally curved outer edge portion 423. The curved outer edge portions 423 are configured to facilitate or ease rotation of the wing 206 as the wing rotates into the deployed configuration (e.g., in a direction indicated by arrow 426). The wing 206 further includes the guide 207, which is configured to interact with or receive a corresponding guide from an opposing wing. In the illustrated embodiment, for example, the guide 207 includes an alignment feature or track 424 that at least partially receives a corresponding alignment feature to at least partially guide or align the wing 206 as the wing 206 slides or translates between undeployed and deployed configurations.

According to additional features of the illustrated embodiment, the wing 206 further includes a cross-member or deployment feature 428. The deployment feature 428 includes an end portion 430 carried by a shaft 429. The shaft 429 has a generally cylindrical shape that rotates about the spacer body 212 and spacer guide 318 (FIGS. 3A and 3B). The shaft 429 also includes a recess or channel 431 extending to the end portion 430. In the illustrated embodiment, the end portion 430 has a generally rectilinear shape including a first engagement surface 432 and a second engagement surface 433. The first engagement surface 432 is positioned in a plane that is generally perpendicular to the second engagement surface 433. As described in detail below, the first engagement surface 432, and more specifically a portion of the first engagement surface proximate to the second engagement surface 433, is configured to contact a first portion of the actuator 316 (FIGS. 3A and 3B) to pivot or rotate the wing 206 from the undeployed configuration to an intermediately or partially deployed configuration. The second engagement surface 433 is a ramped or angled inclined angled surface that is configured to contact a second portion of the actuator 316 (FIGS. 3A and 3B) to slide or translate the wing 306 from an intermediately deployed configuration to a fully deployed configuration.

Figure 5A:
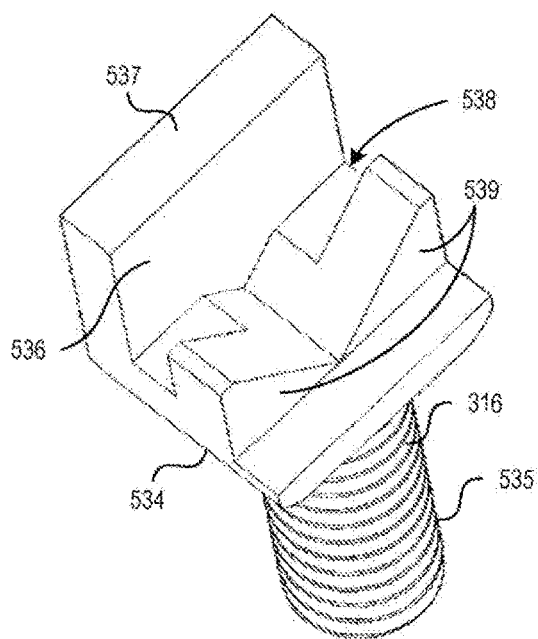
FIGS. 5A-5C are a series of views of an actuator configured in accordance with embodiments of the disclosure.
Figure 5B:
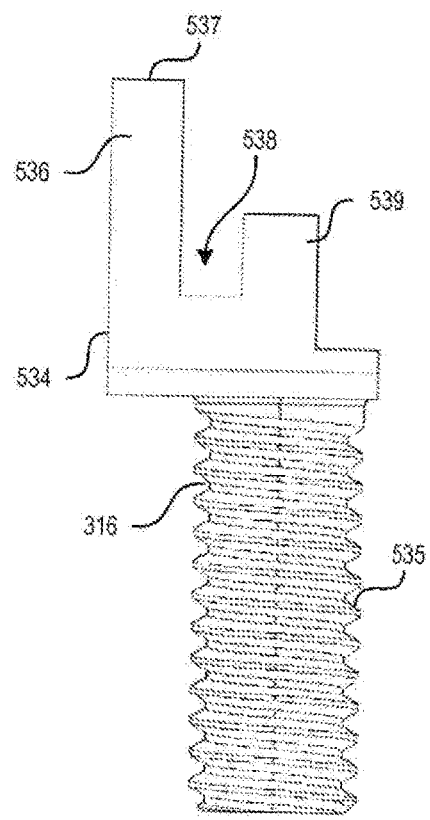
Figure 5C:
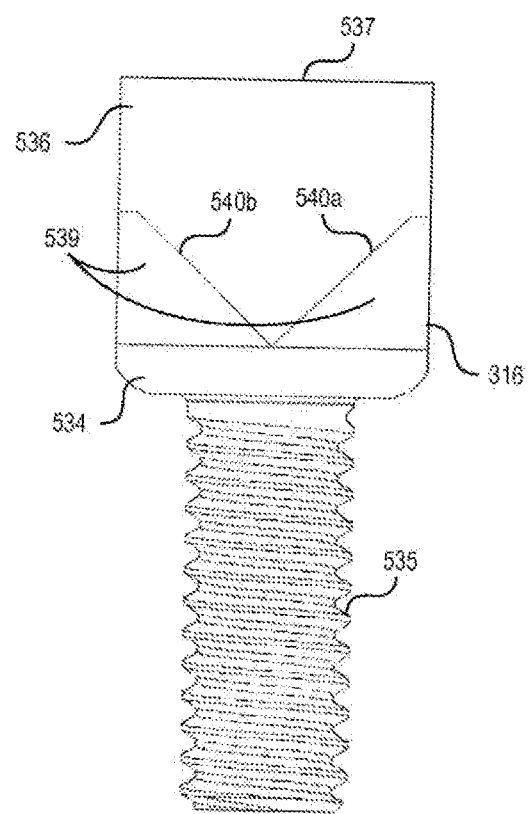

FIG. 5A is an isometric view, FIG. 5B is a side view, and FIG. 5C is an end view of the actuator 316. Referring to FIGS. 5A-5C together, the actuator 316 includes a proximal end portion 534 opposite a distal end portion 535. The distal end portion 535 is a threaded shaft that threadably engages the actuator adjustor or wheel 320 (FIGS. 3A and 3B). The proximal end portion 534 includes separate features for moving the wing 206 between distinct or separate deployment configurations. For example, the proximal end portion 534 includes a first camming feature 536 and a second camming feature 539. A channel 538 spaces the first camming feature 536 apart from the second camming feature 539. The first camming feature 536 includes a first camming surface 537 that is configured to contact the first engagement surface 432 of the wing 206 (FIGS. 4A, 4B, and 4D) to pivot or rotate the wing 206 from the undeployed configuration to an intermediately deployed configuration. As such, the first camming feature 536 and/or the first camming surface 537 act as a rotation driver of the wing 206. The second camming feature 539 includes a V-shaped groove or channel defined by converging ramped second camming surfaces 540 (identified individually as a first ramped surface 540a and a second ramped surface 540b). The second camming surfaces 540 are configured to contact the second engagement surface 433 of the actuator 316 to slide or translate the wing 206 from the intermediately deployed configuration to the fully deployed configuration. As such, the second camming feature 539 and/or the second camming surfaces 540 act as a translation or sliding driver to clamp or otherwise draw the wings 206 together.

Figure 6A:
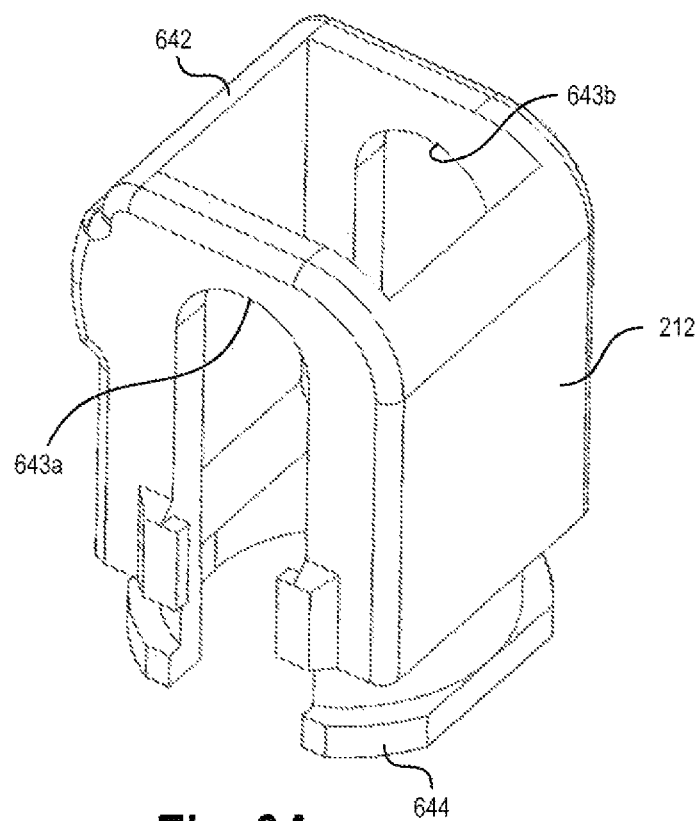
FIGS. 6A and 6B are isometric views of a body configured in accordance with embodiments of the disclosure.
Figure 6B:
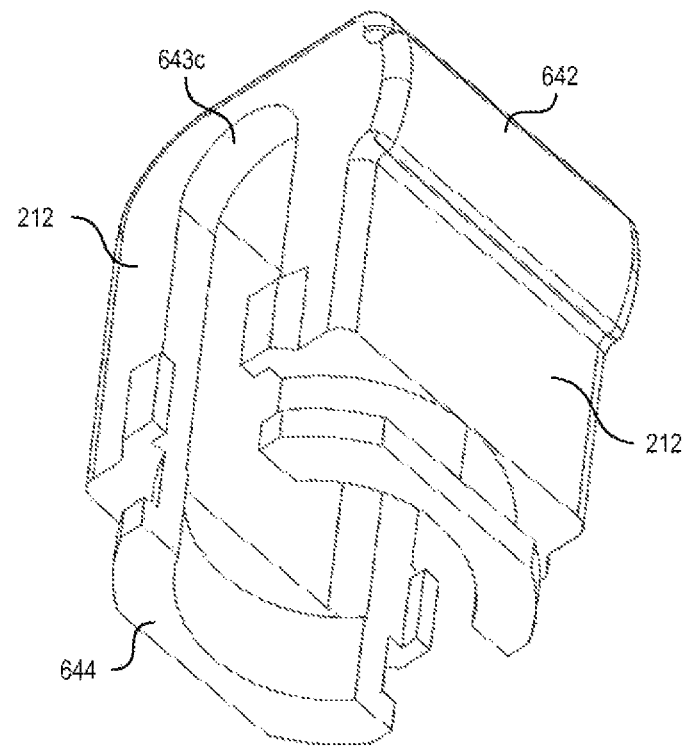

FIGS. 6A and 6B are isometric views of the body 212. Referring to FIGS. 6A and 6B together, the body 212 is generally configured to fit between adjacent spinous processes and to at least partially receive portions of the wings 206, actuator 316, guide 318, wheel 320 and cover 322 (FIGS. 3A and 3B) in a central portion thereof. The body 212 includes a proximal end portion 642 opposite a distal end portion 644. The proximal end portion 642 includes curved or semicircular rotation surfaces 643 (identified individually as a first rotation surface 643a and a second rotation surface 643b) configured to contact the shaft 429 of each wing deployment feature 428 on the corresponding wings 206 (FIGS. 4A and 4B). The distal end portion 644 is configured to engage the cover 322 and at least partially retain and position the wheel 320 between the cover 322 and the guide 318 (FIGS. 3A and 3B). The cover 322 can be a one-piece cap, a multi-piece cap, or other suitable structure for covering and/or protecting internal components of the spacer 200.

Figure 7A:
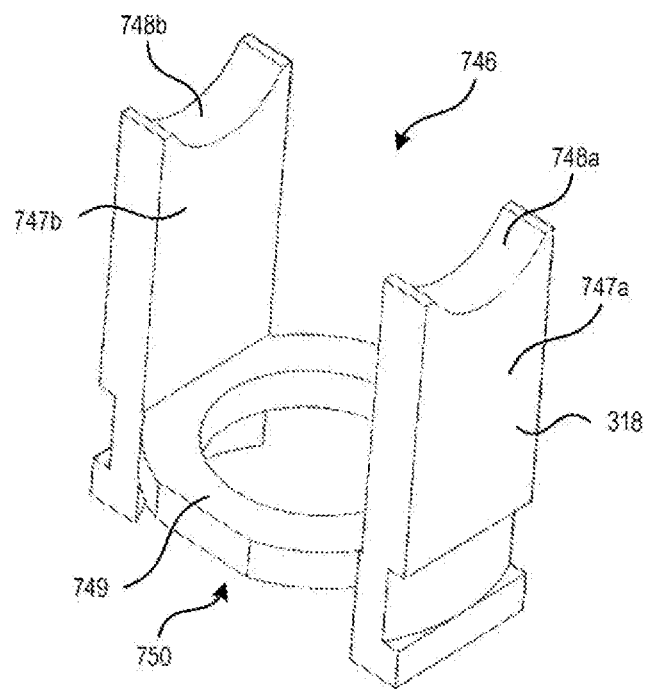
FIGS. 7A and 7B are isometric views of a guide configured in accordance with embodiments of the disclosure.
Figure 7B:
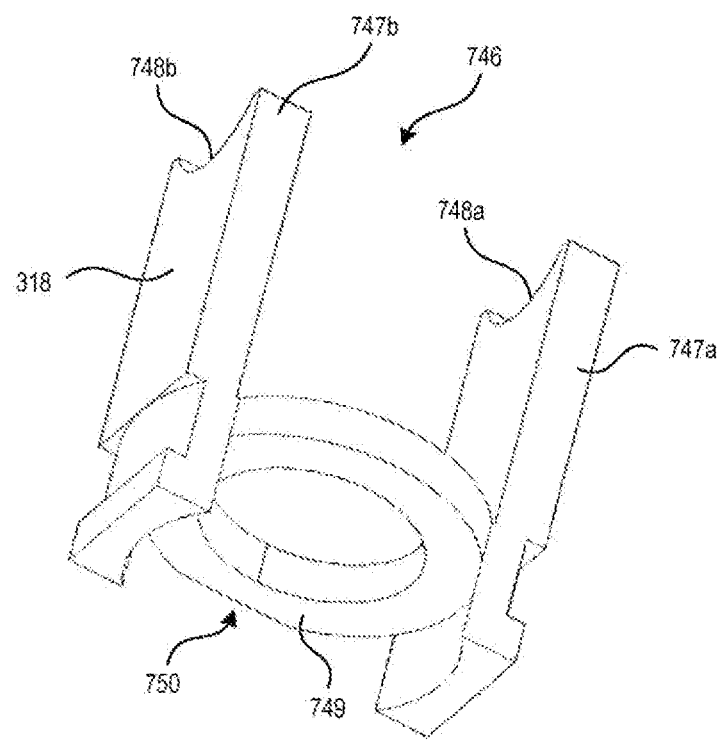

FIGS. 7A and 7B are isometric view of the guide 318. Referring to FIGS. 7A and 7B together, the guide 318 is configured to be positioned at least partially within the body 212 (FIGS. 6A and 6B) and includes a proximal end portion 746 opposite a distal end portion 550. Extension arms 747 (identified individually as a first extension arm 747a and a second extension arm 747b) project from the distal end portion 750 to the proximal end portion 747. At the proximal end portion, each extension arm 747 includes a corresponding curved or semicircular rotation surface 748 (identified individually as a first rotation surface 748a and a second rotation surface 748b). The rotation surfaces 548 are configured to be positioned proximate to the rotation surfaces 643 of the body (FIGS. 6A and 6B) to generally surround and contact the shaft 429 of each wing deployment feature 428 on the corresponding wings 206 (FIGS. 4A and 4B) to allow the wings 206 to rotate or pivot. The distal end portion 750 includes a ring or hoop portion 749 that is configured to mate with or contact a proximal surface of the wheel 320 (FIGS. 3A and 3B).

Figure 8A:
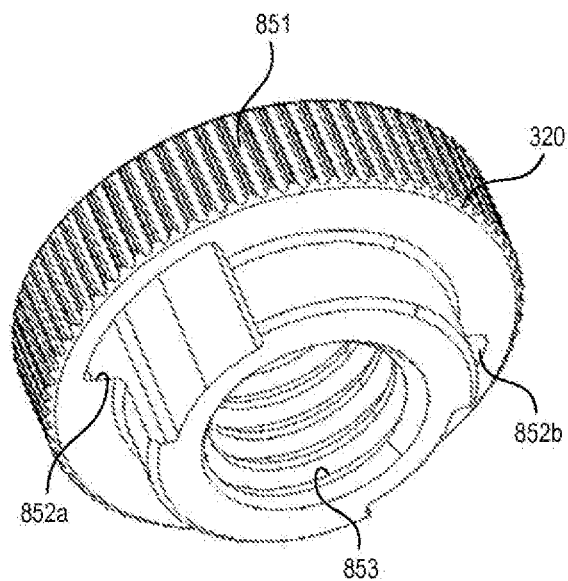
FIGS. 8A and 8B are isometric views of an actuator adjuster configured in accordance with an embodiment of the disclosure.
Figure 8B:
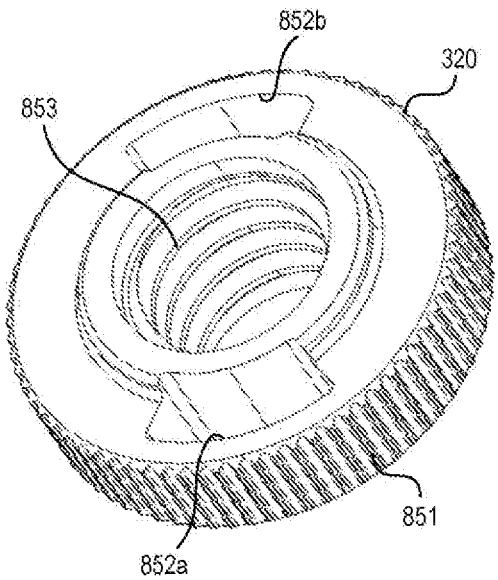

FIGS. 8A and 8B are isometric views of the actuator adjuster or wheel 320.

Referring to FIGS. 8A and 8B together, the wheel 320 includes a textured outer surface 851 as well as a central threaded bore 853. The threaded bore 853 is configured to correspond to the thread pitch of the threaded distal end portion 535 of the actuator 316 (FIGS. 5A-5C). Accordingly, rotating the wheel 320 threadably engages the actuator 316 to linearly move the actuator 316. The wheel 320 further includes opposing engagement openings or slots 852 (identified individually as a first engagement slot 852a and a second engagement slot 852b). The engagement slots 852 are configured to receive corresponding extensions from an actuation tool to allow rotation of the wheel 320.

Figure 9A:
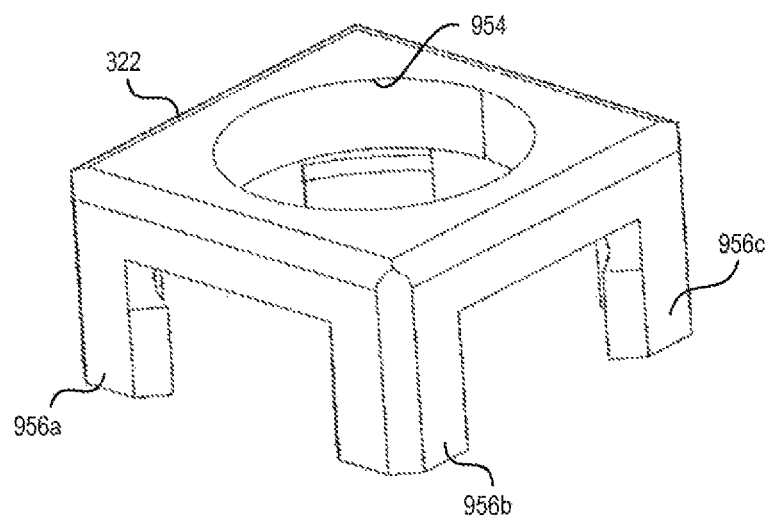
FIGS. 9A and 9B are isometric views of a cover configured in accordance with an embodiment of the disclosure.
Figure 9B:
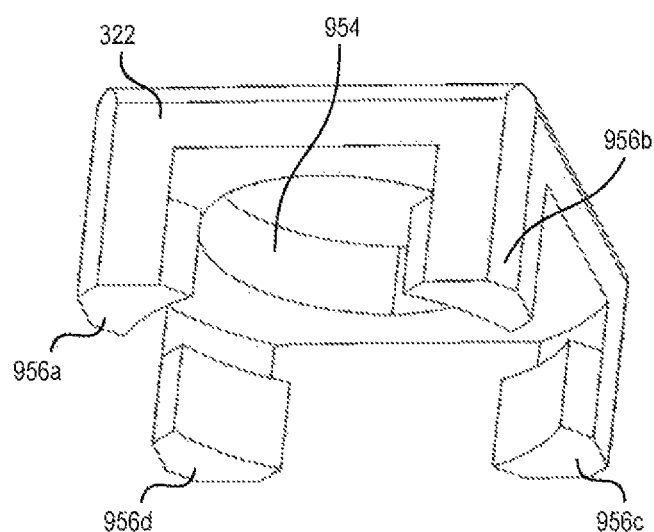

FIGS. 9A and 9B are isometric views of the cap or cover 322. Referring to FIGS. 9A and 9B together, the cover 322 includes a central bore 954 configured to partially receive the wheel 320 (FIGS. 8A and 8B) and to allow access to the wheel 320 for an actuation tool. The cover further includes extensions or legs 956 (identified individually as first through fourth legs 956a-956d) configured to engage or mate with the body 212 (FIGS. 3A and 3B).

Figure 10A:
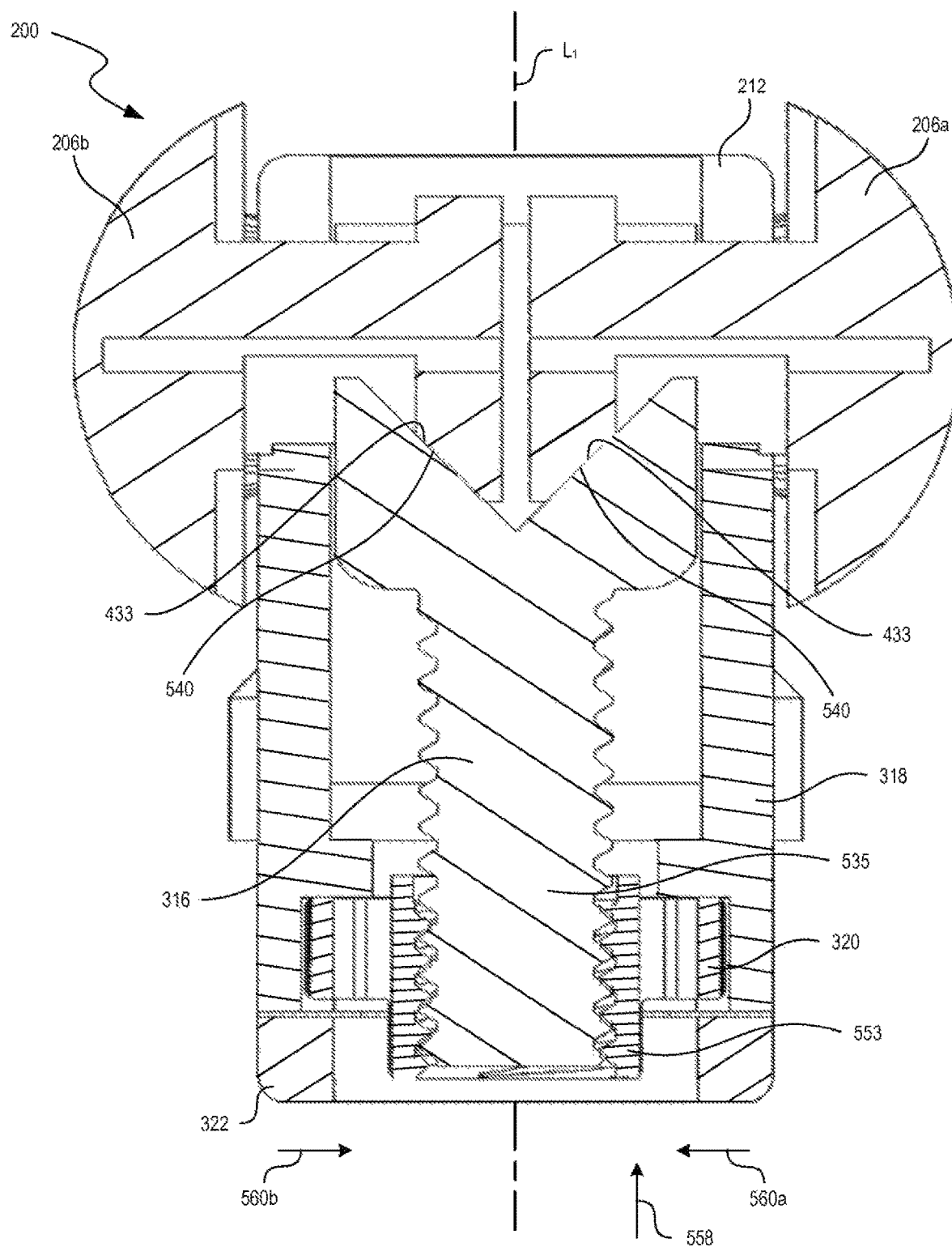
FIG. 10A is a cross-sectional end view of the spacer taken substantially along lines 10A-10A in FIG. 2B.

FIG. 10A is a cross-sectional view of the spacer 200 view taken substantially along lines 10A-10A in FIG. 2B. The cross-sectional view shown in FIG. 10A illustrates the relative positions of several components of the spacer 200 when the spacer 200 is in a deployed or fully deployed configuration. For example, FIG. 10A illustrates the wheel 320 positioned between the cover 322 and the guide 318, as well as the bore 553 of the wheel 320 threadably engaged with the distal end portion 535 of the actuator 316. Moreover, in the deployed configuration, each wing 206 is positioned and secured proximate or adjacent to corresponding sides of the body 212. More specifically, as the wheel 320 rotates it moves the actuator 316 in a proximal direction or in the direction of arrow 558 (which is in a direction at least generally parallel to the body longitudinal axis $L_1$), the second camming surfaces 540 of the actuator 316 contact the corresponding second engagement surfaces 433 of the individual wings 206. As such, the actuator 316 urges or drives the wings 206 toward the body 212 and also toward each other (i.e., by driving the first wing 206a in a first direction indicated by arrow 560a and by driving the second wing 206b in a second direction indicated by arrow 560b). More specifically, as the actuator 316 moves in the direction of arrow 558, the second engagement surfaces 433 slide along the corresponding second camming surfaces 540 to draw the wings 206 toward each other in the fully deployed configuration.

Figure 10B:
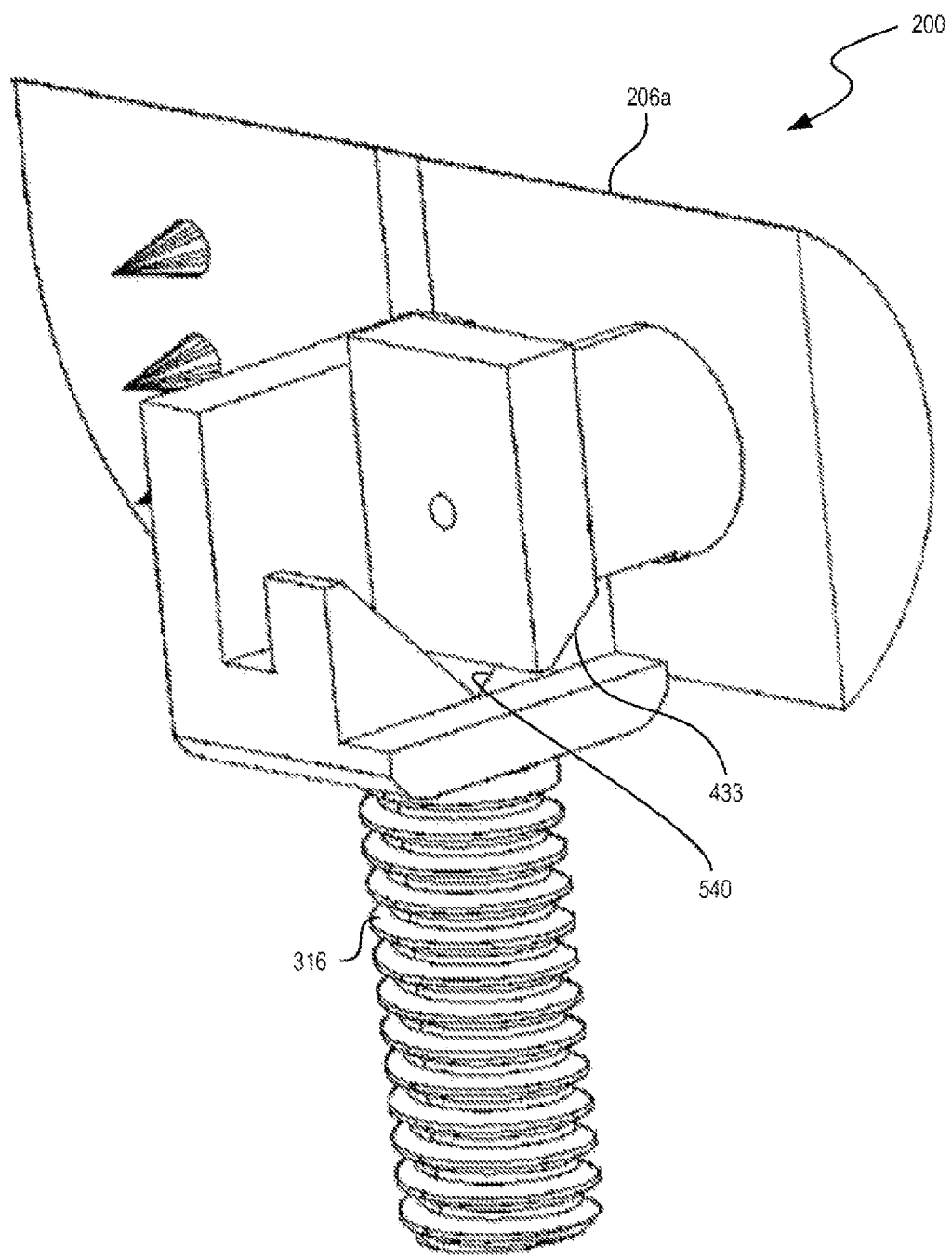
FIG. 10B is an isometric partial view of the spacer of FIG. 10A.

FIG. 10B is an isometric partial view of the spacer 200 in the fully deployed position showing only the first wing 206a and the actuator with the remainder of the components of the spacer 200 removed. As shown in FIG. 10B, the second engagement surface of the first wing 206a is mated with and retained in the deployed configuration by the second camming surface 540 of the actuator 316.

Figure 11A:
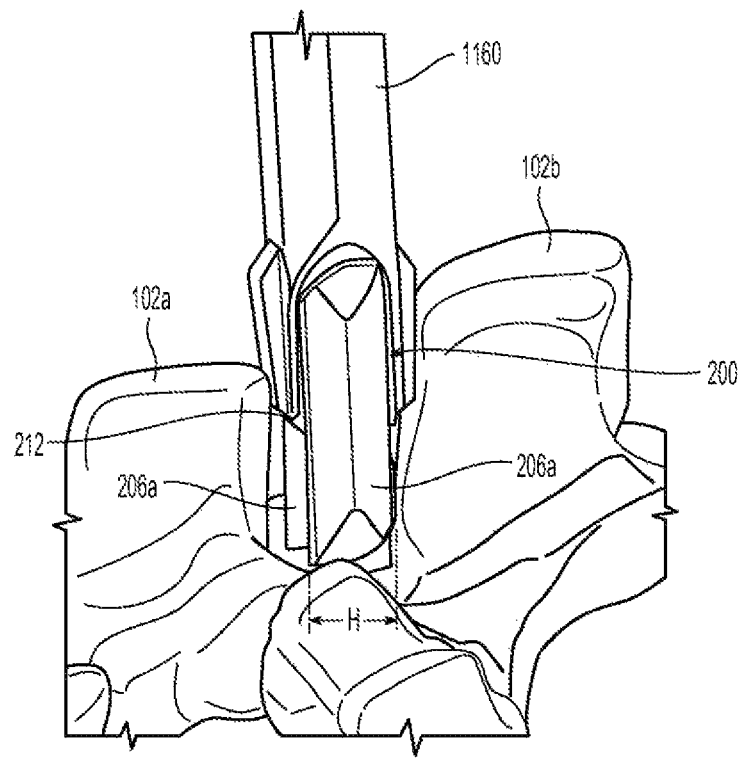
FIGS. 11A-11E are a series of views illustrating several configurations of a spacer configured in accordance with an embodiment of the disclosure.

FIGS. 11A-11E are a series of views illustrating several deployment configurations of the spacer 200. FIG. 11A, for example, is an isometric view illustrating the spacer 200 in an undeployed configuration (e.g., a delivery configuration) during insertion between a superior spinous process 102a and an inferior spinous process 102b. During insertion and deployment, the spacer 200 is coupled to a delivery instrument 1160. In the undeployed configuration as illustrated in FIG. 11A, the longitudinal axis of each wing 206 (e.g., wing longitudinal axis $L_2$ in FIG. 2A) is generally parallel to or aligned with the longitudinal axis of the spacer 200 (e.g., body longitudinal axis $L_1$ in FIG. 2A). The delivery instrument 1160 and the wing 206 can be at an anterior-posterior orientation (e.g., the longitudinal axes of the wings 206 and/or longitudinal axis of the body 212 can be in the anterior-posterior direction. The spacer 200 can have a low profile in the deployed configuration. Moreover, at least a portion of each wing 206 can overlap or share a length of the body 212, thereby reducing the overall length and/or height of the spacer 200 in the undeployed configuration. In the undeployed configuration and attached to the delivery instrument 1160, the spacer 200 can be inserted into a port or cannula that has been operatively positioned to provide access to an interspinous space via a minimally invasive incision. In other embodiments where a cannula may not be necessary, the spacer 200 may be inserted through an incision. Where a cannula is used, the spacer 200 can be advanced through the cannula within the targeted interspinous space and advanced beyond the end of the cannula, or alternatively, the cannula can be retracted to uncover the spacer. The wings 206 in the delivery positions can be rotated from the anterior-posterior orientation (FIG. 11A) towards a superior-inferior orientation (FIG. 1).

Figure 11B:
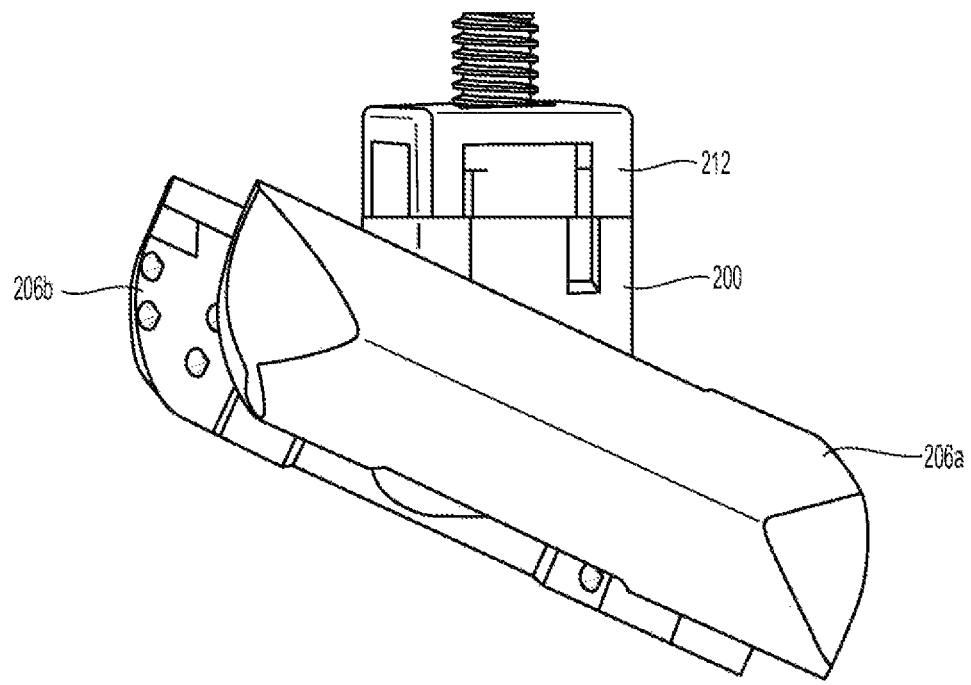

Referring next to FIG. 11B, the spacer 200 is in an intermediately deployed configuration with the wings 206 partially rotated relative to the body 212. More specifically, the longitudinal axis of each wing is rotated or pivoted relative to the longitudinal axis of the body 212. As described above, the actuator 316 (FIGS. 10A and 10B) moves a first distance longitudinally within the body 212 to rotate the wings 206.

Figure 11C:
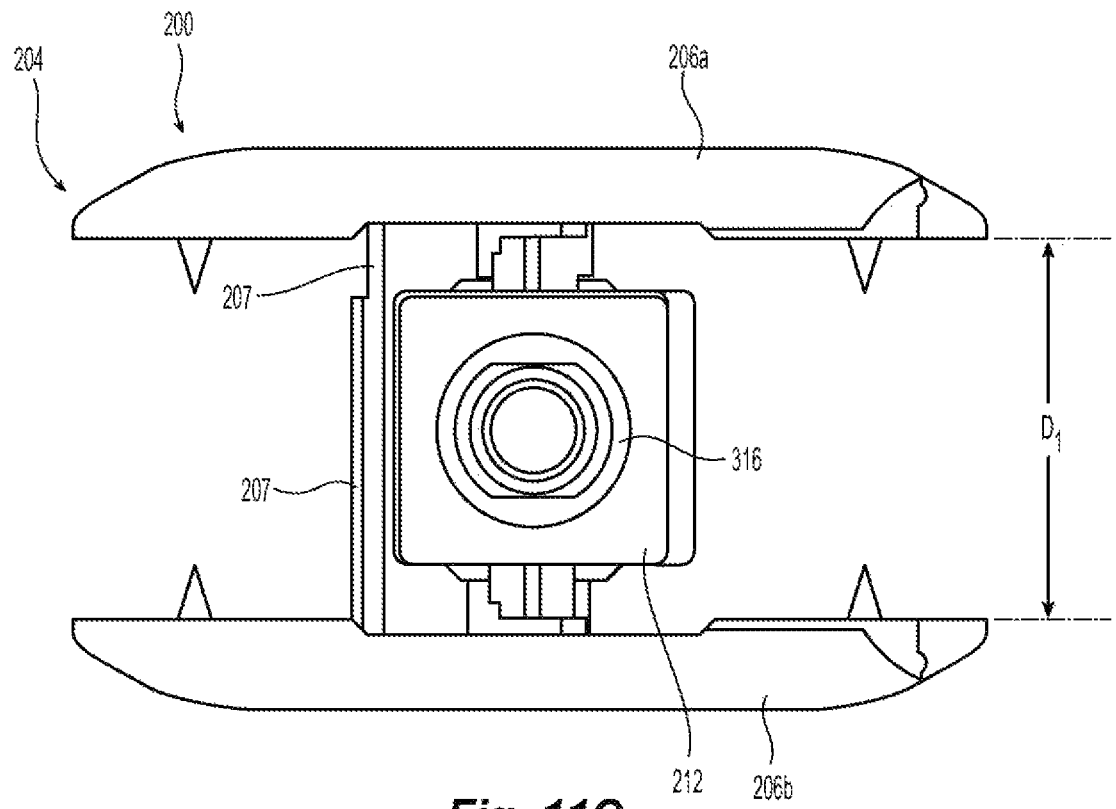

FIG. 11C is a top view of the spacer 200 in an intermediately deployed configuration with the clamp assembly 204 fully rotated or pivoted relative to the body 212. More specifically, in the intermediately deployed and rotated configuration, the longitudinal axis of each wing 206 of the clamp assembly 204 is rotated or pivoted generally perpendicularly to the longitudinal axis of the body 212. In other embodiments, however, the wings 206 can be positioned at an angle that is greater than or less than 90 degrees relative to the longitudinal axis of the body 212. According to an additional feature of the spacer 200 in the partially deployed configuration shown in FIG. 11C, the first wing 206a is spaced apart from the second wing 206b by a first distance $D_1$. To rotate the wings as shown in FIG. 11C, the actuator 316 has moved longitudinally within the body 212 a first predetermined distance to drive the wings 206 to the fully rotated position.

Figure 11D:
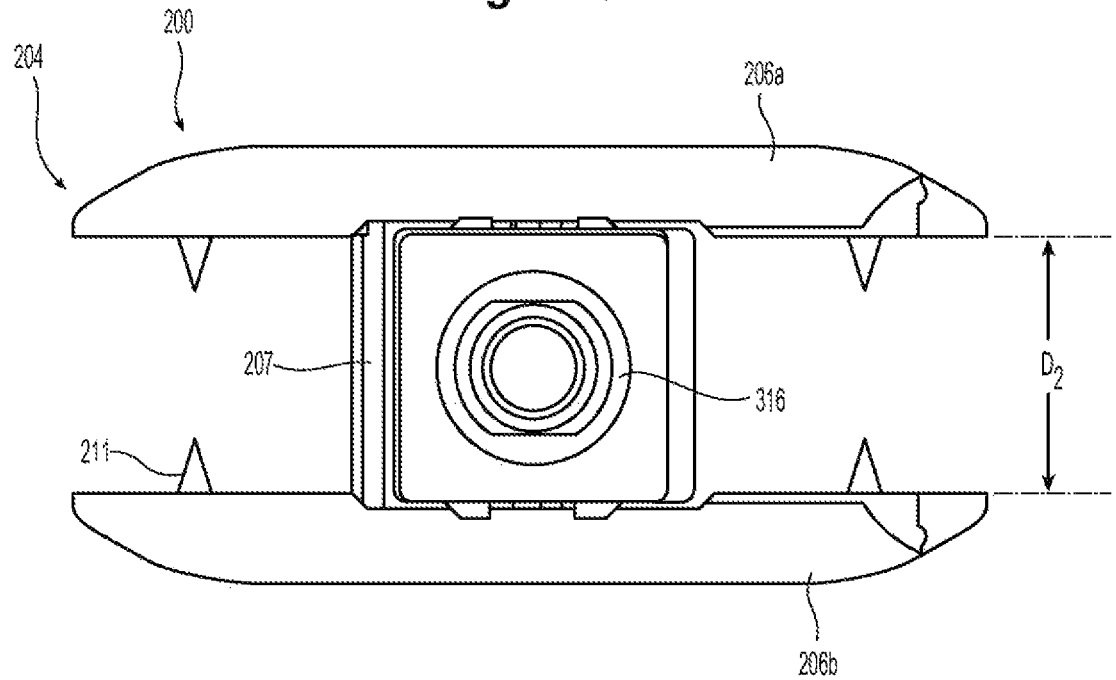

FIG. 11D is a top view of the spacer 200 with the clamp assembly 204 in a fully deployed or rotated and fully closed or clamping configuration with the wings 206 fully rotated and the wings 206 drawn proximate or adjacent to the body 212. More specifically, in the fully deployed position, the longitudinal axis of each wing 206 remains generally perpendicular to the longitudinal axis of the body 212. In other embodiments, however, the wings 206 can be positioned at an angle that is greater than or less than 90 degrees relative to the longitudinal axis of the body 212. According to an additional feature of the spacer 200 in the fully deployed configuration shown in FIG. 11D, the first wing 206a is spaced apart from the second wing 206b by a second distance $D_2$, which is less than the first distance $D_1$. The second distance $D_2$ is configured to allow the engagement features 211 of each wing 206 to at least partially embed or otherwise engage the corresponding spinous processes. To slide or translate the wings 206 to the positions shown in FIG. 11D, the actuator 316 has moved longitudinally within the body 212 a second predetermined distance, in addition to the first predetermined distance, to drive the wings 206 to the fully deployed position.

Figure 11E:
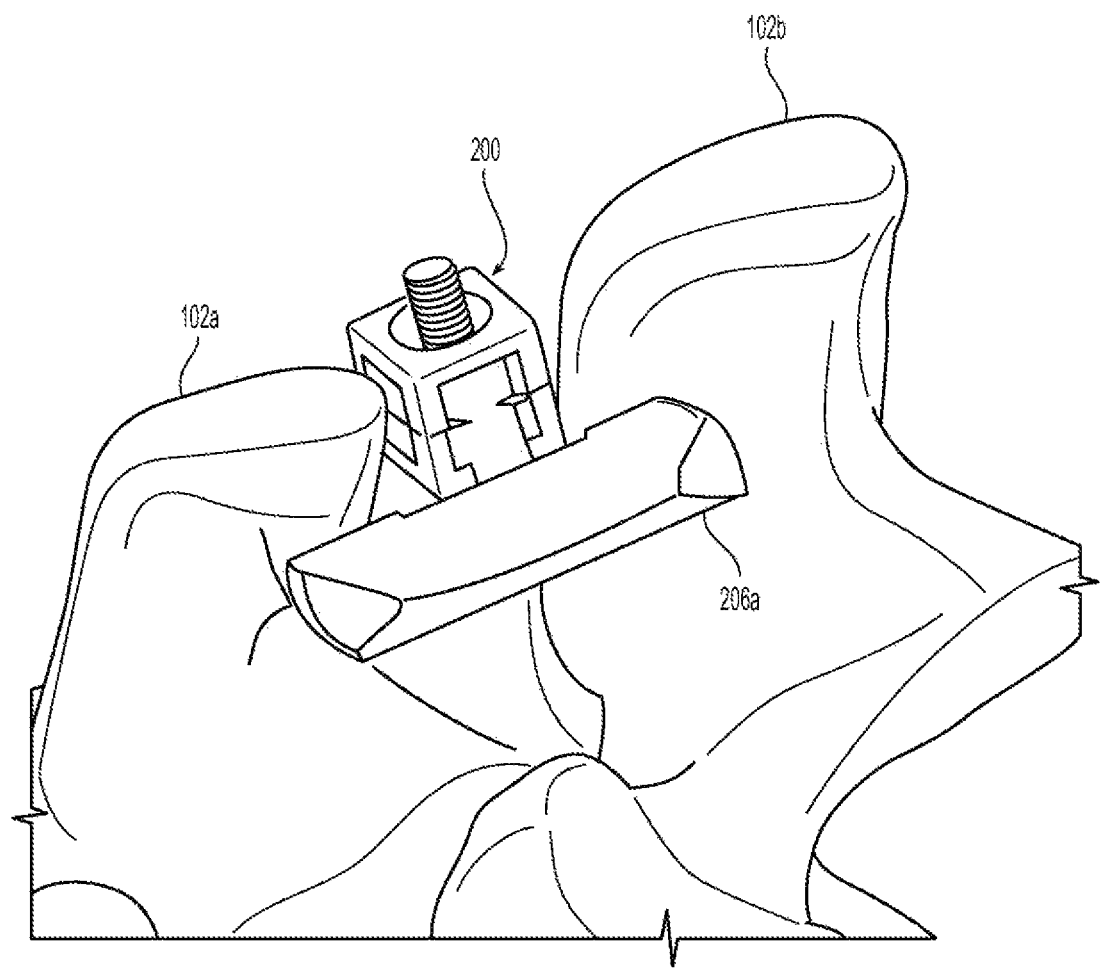

FIG. 11E is an isometric view illustrating the spacer 200 in the fully deployed configuration fusing the superior spinous process 102a relative to the inferior spinous process 102b.

Figure 12:
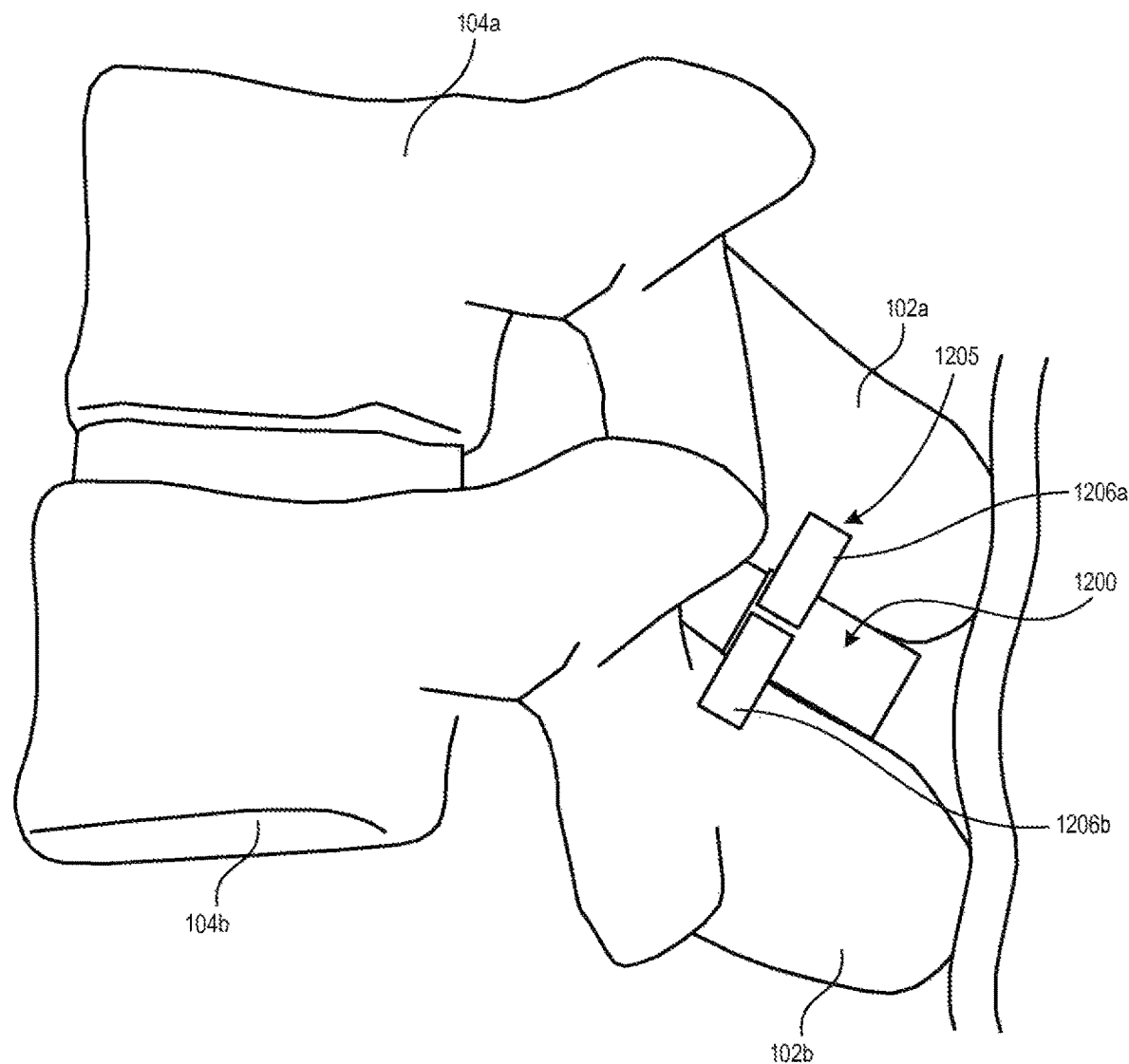
FIG. 12 is a partially schematic side view of an implant or spacer configured in accordance with an embodiment of the disclosure.

FIG. 12 is a partially schematic side view of an implant or spacer 1200 (shown schematically) configured in accordance with another embodiment of the disclosure. The spacer 1200 includes several features that are generally similar in structure and function to the spacers described above with reference to FIGS. 1-11E. For example, as shown in FIG. 12, the spacer 1200 positioned between adjacent spinous processes 102 (identified individually as a first or superior spinous process 102a and a second or inferior spinous process 102b) associated with corresponding vertebral bodies 104 (identified individually as a first or superior vertebral body 104a and a second or inferior vertebral body 104b). As described in detail below, the spacer 1200 includes a clamp assembly 1205, four individual opposing arms or wings 1206 (only a first wing 1206a and a second wing 1206b are visible in FIG. 12) that engage the corresponding superior and inferior spinous processes 102a, 102b, to securely fuse or fix, as well as stabilize and align, the superior and inferior spinous processes 102a, 102b. Various additional features and details of spacers represented schematically by the spacer 1200 of FIG. 12 are described in detail below with reference to FIGS. 13A-22E.

Figure 13A:
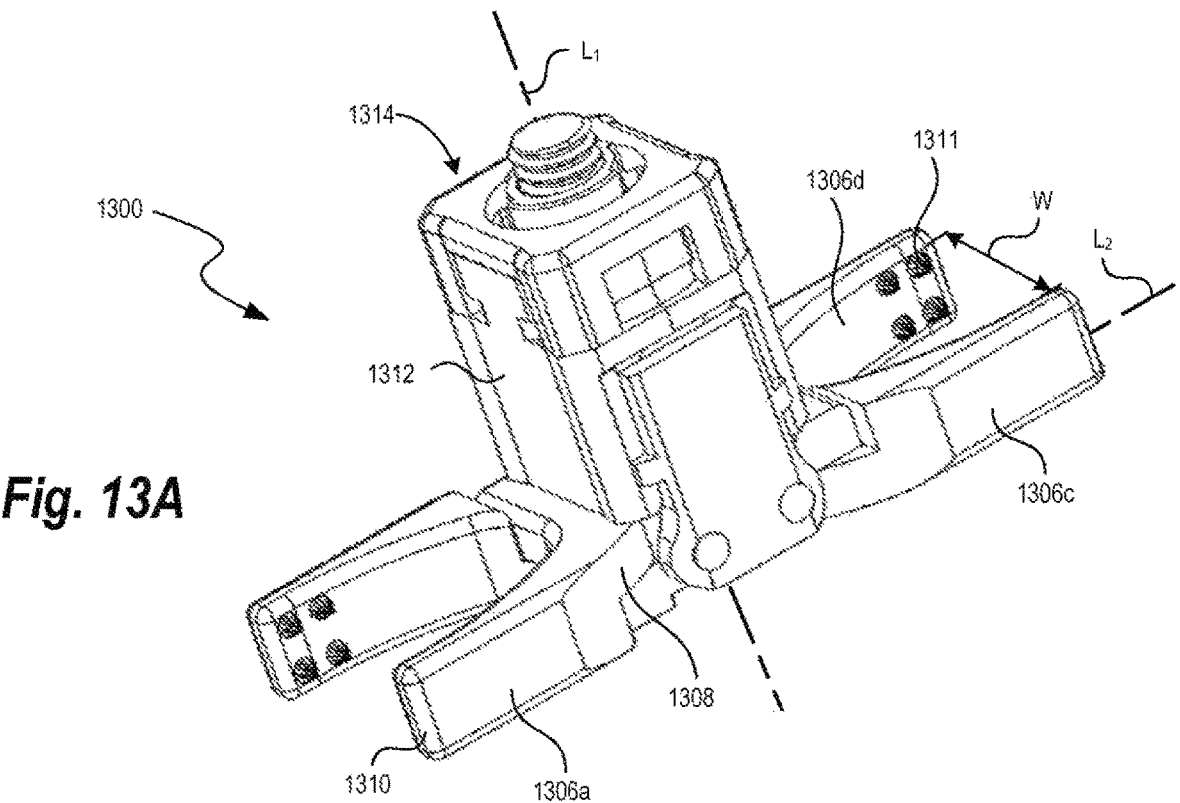
FIGS. 13A-13F are a series of views of a spacer configured in accordance with yet another embodiment of the disclosure.
Figure 13B:
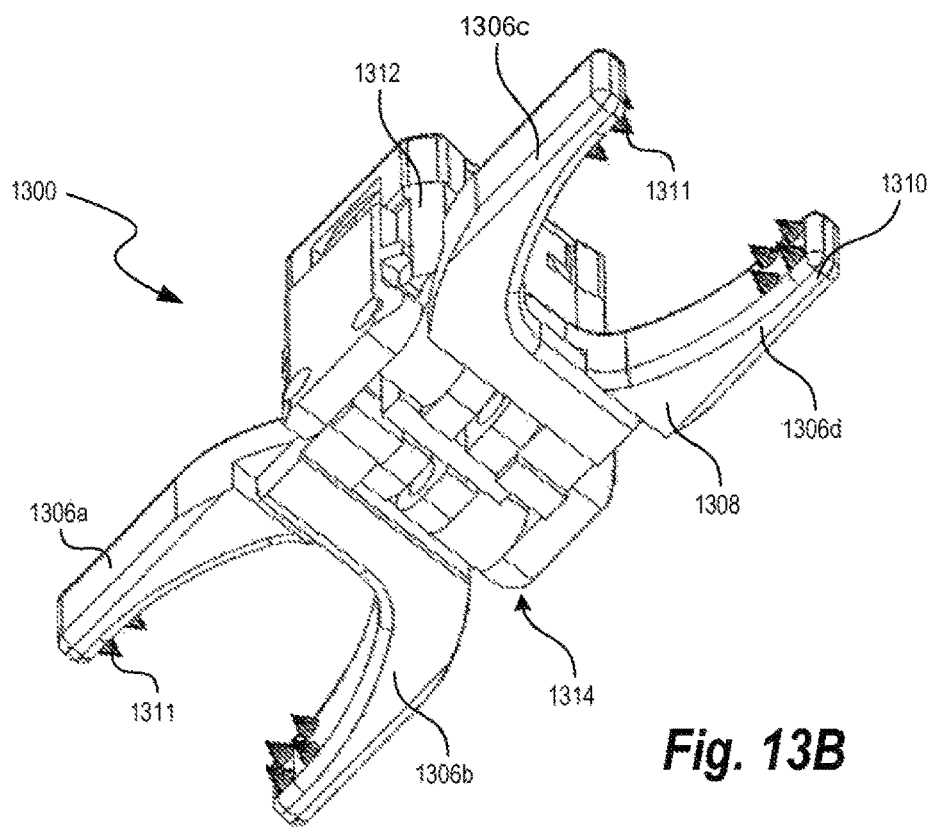
Figure 13C:
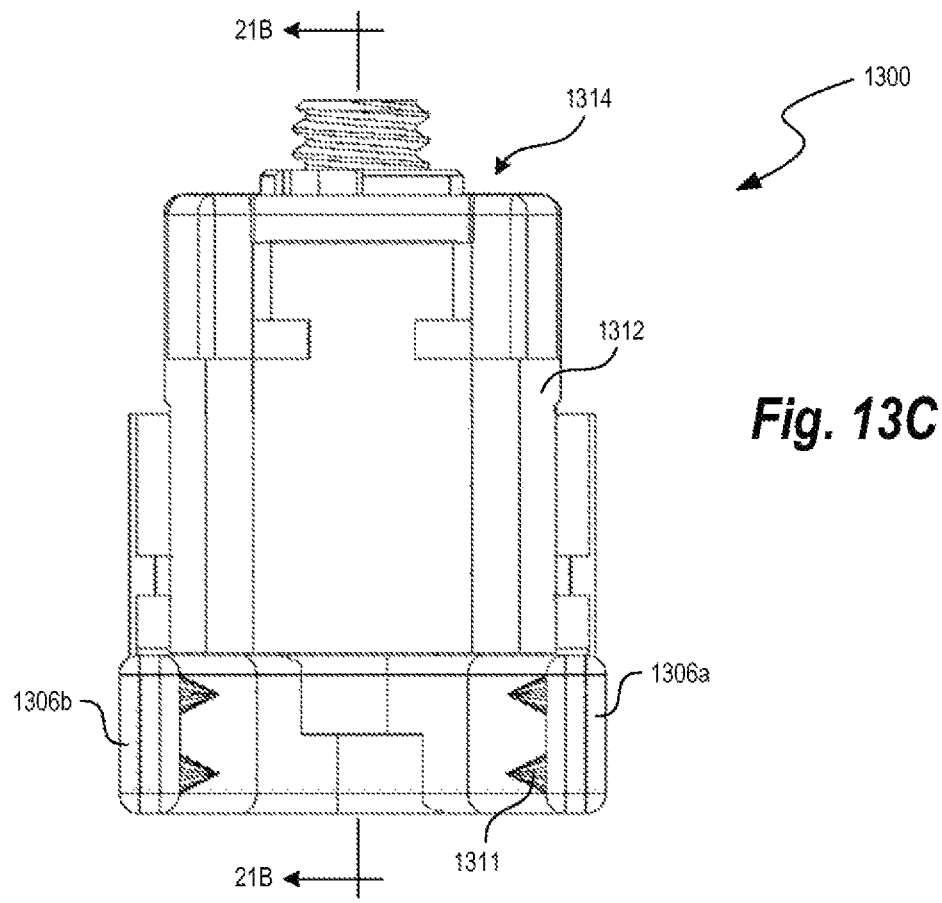
Figure 13D:
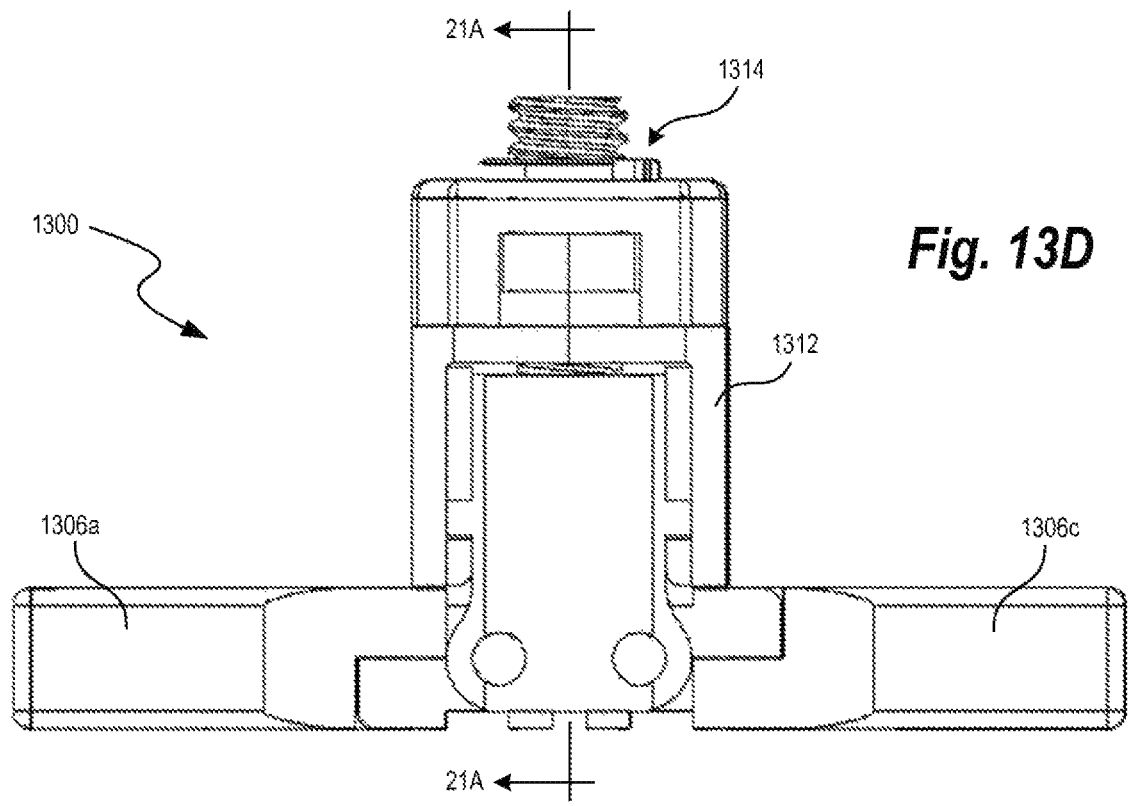
Figure 13E:
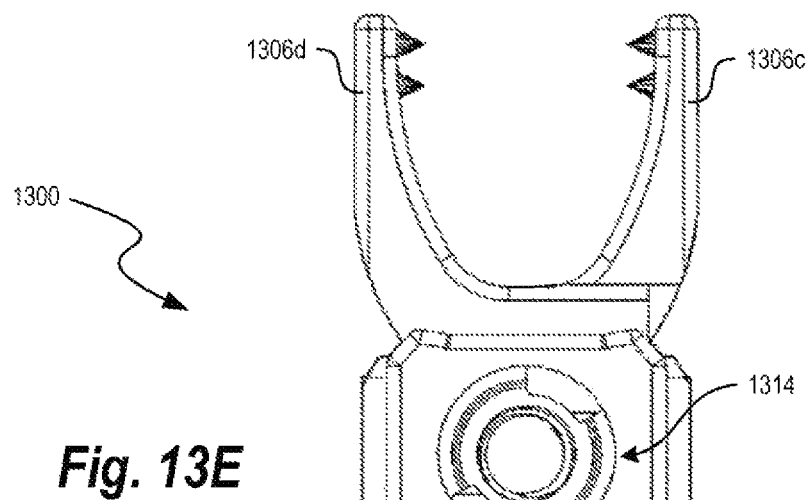
Figure 13F:
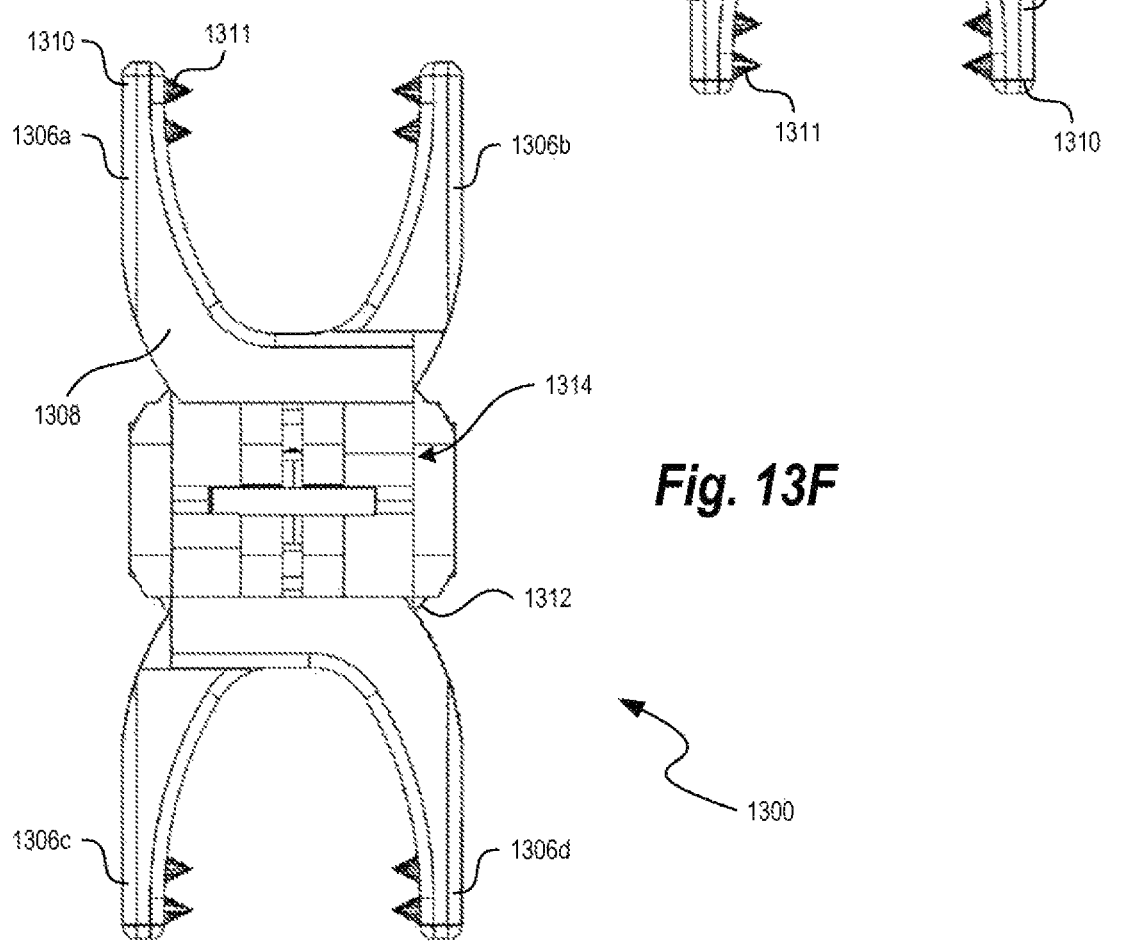

FIGS. 13A and 13B are isometric views, FIG. 13C is an end view, FIG. 13D is a side view, FIG. 13E is a top view, and FIG. 13F is a bottom plan view of a spacer 1300 configured in accordance with embodiments of the disclosure. Referring to FIGS. 13A-13F together, the spacer 1300 includes wings 1306 (identified individually as a first through fourth wings 1306a-1306d) movably coupled to a body 1312 and actuator assembly 1314. Each wing 1306 includes a first or proximal end portion 1308 opposite a second or distal end portion 1310. The distal end portion 1310 of each wing 1306 includes multiple engaging features 211 that are configured to contact and engage corresponding spinous processes (e.g., spinous processes 102 illustrated in FIG. 12). As described in detail below, each wing 1306 is configured to rotate or pivot as well as slide or translate with reference to the body 1312 between a first position (e.g., an undeployed or partially deployed position) and a second position (e.g., a deployed position, a clamped position, etc.).

The body 1312 includes a body longitudinal axis $L_1$ (FIG. 13A) and each wing 1306 includes a wing longitudinal axis $L_2$ (e.g., shown with reference to the third wing 1306c in FIG. 13). In FIGS. 13A-13F, the spacer 1300 is shown in a fully deployed configuration. More specifically, in the deployed position each wing 1306 is oriented such that their corresponding wing longitudinal axes $L_2$ are at least generally perpendicular to the body longitudinal axis $L_1$. Moreover, in the fully deployed position, the wings 1306 are positioned adjacent to the body 1312 thereby reducing a width W (FIG. 2A) between the wings 1306. The width W can be configured to allow the wings 1306 and engagement features 1311 to engage corresponding spinous processes. As described in detail below with reference to FIGS. 22A-22E, the wings 1306 can rotate or pivot as well as slide or translate relative to the body 1312 between at least a first or undeployed position, a second or partially deployed position, and a third or fully deployed position.

Figure 14A:
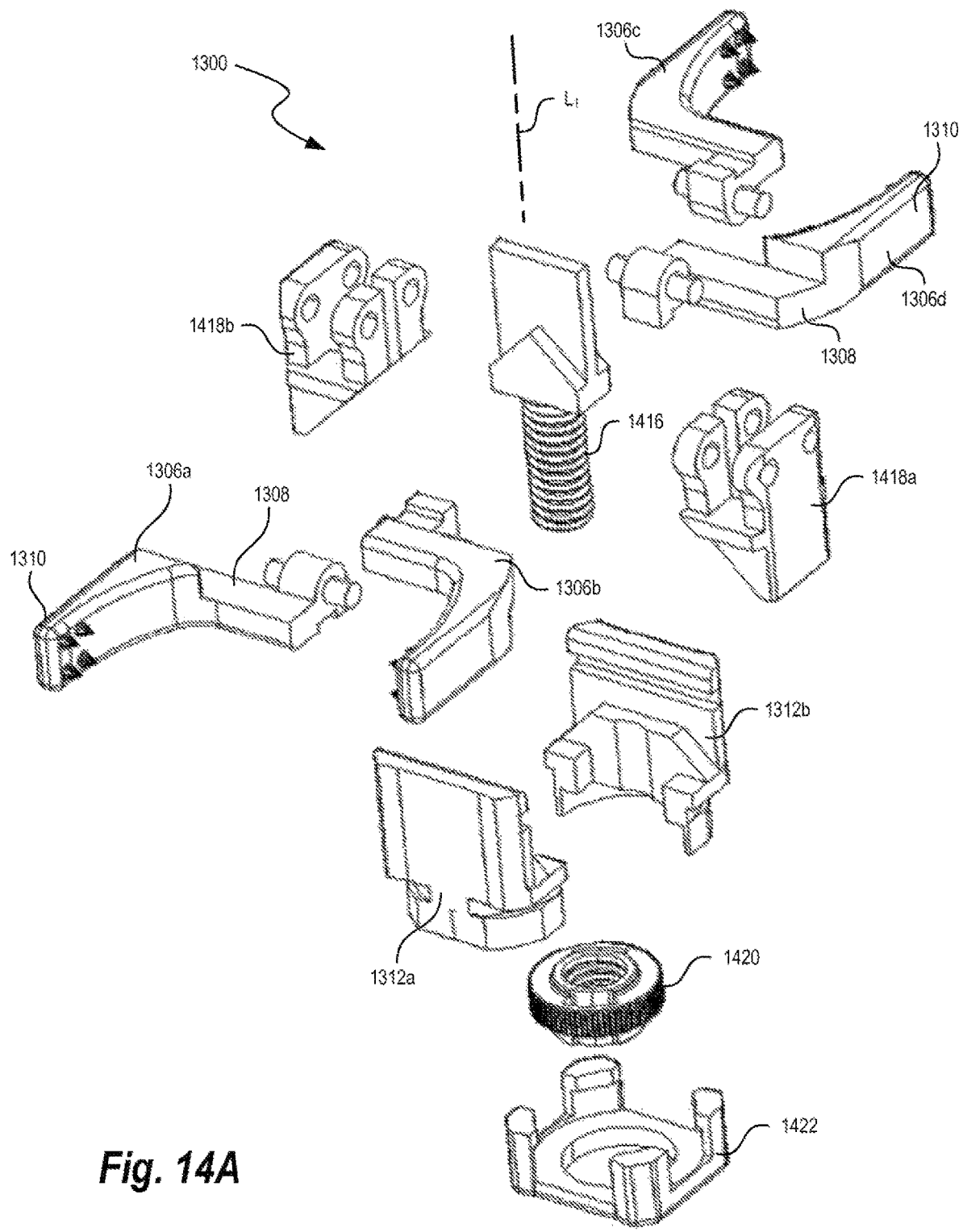
FIGS. 14A and 14B are exploded isometric views of the spacer illustrated in FIGS. 13A-13F.
Figure 14B:
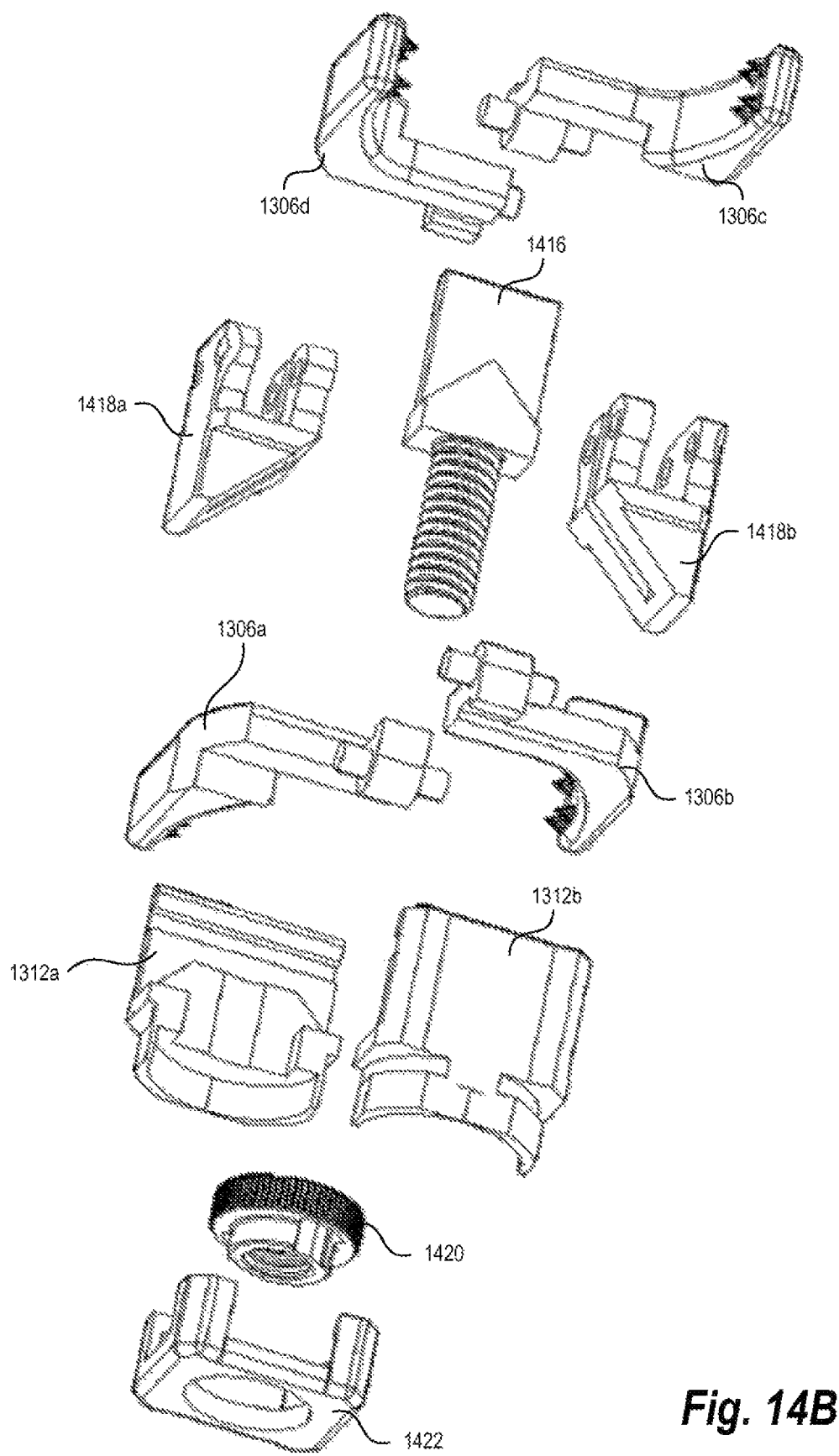

FIGS. 14A and 14B are exploded isometric views of the spacer 1300 illustrated in FIGS. 13A-13F. Referring to FIGS. 14A and 14B together, the actuator assembly 1314 includes an actuator 1416, a first guide 1418a and a second guide 1418b (collectively referred to as a guide 1418), an actuator adjuster or wheel 1420, and a cover 1422. Moreover, a first body 1312a and a second body 1312b are configured to mate and are referred to collectively as the body 1312. The actuator assembly 1314 is operably coupled to the body 1312 and the wings 1306 to move the wings 1306 between the undeployed and deployed configurations. More specifically, and as described in detail below, movement or rotation of the actuator adjuster 1420 about the body longitudinal axis $L_1$ moves the actuator 1416 within the body 1312 in directions parallel to the body longitudinal axis $L_1$. As the actuator 1416 moves within the body 1312, the actuator 1416 drives or urges the wings 1306 to pivot or rotate, as well as drives or urges the guides 1418 to slide or translate the corresponding wings 1306, relative to the body 1312 between the undeployed and deployed configurations. Further details and features of the individual components illustrated in FIGS. 14A and 14B are described below with reference to FIGS. 15A-20B.

Figures 15A, 15B:
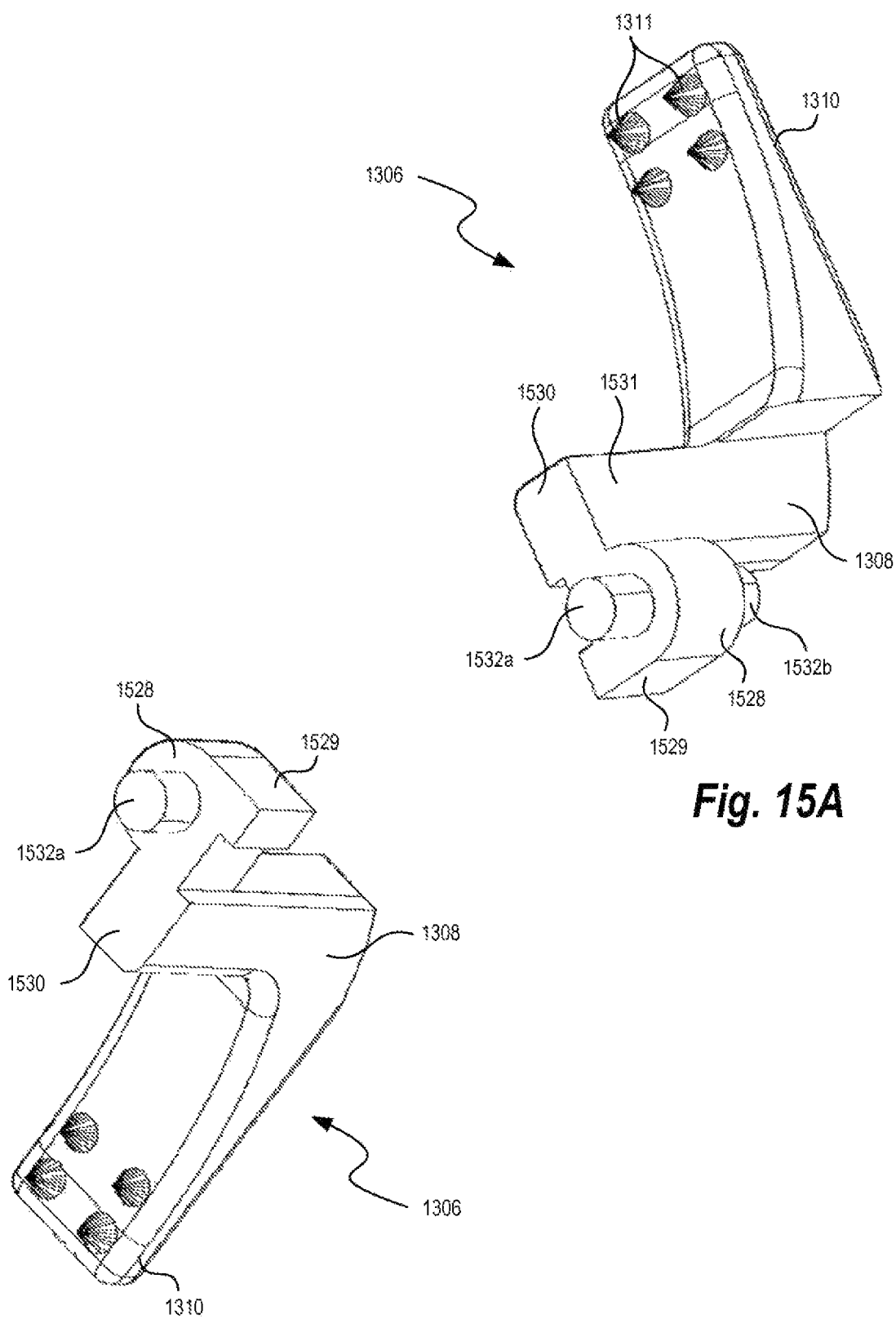
FIGS. 15A-15N are a series of views of an engaging extension or wing configured in accordance with an embodiment of the disclosure.
Figures 15C, 15D:
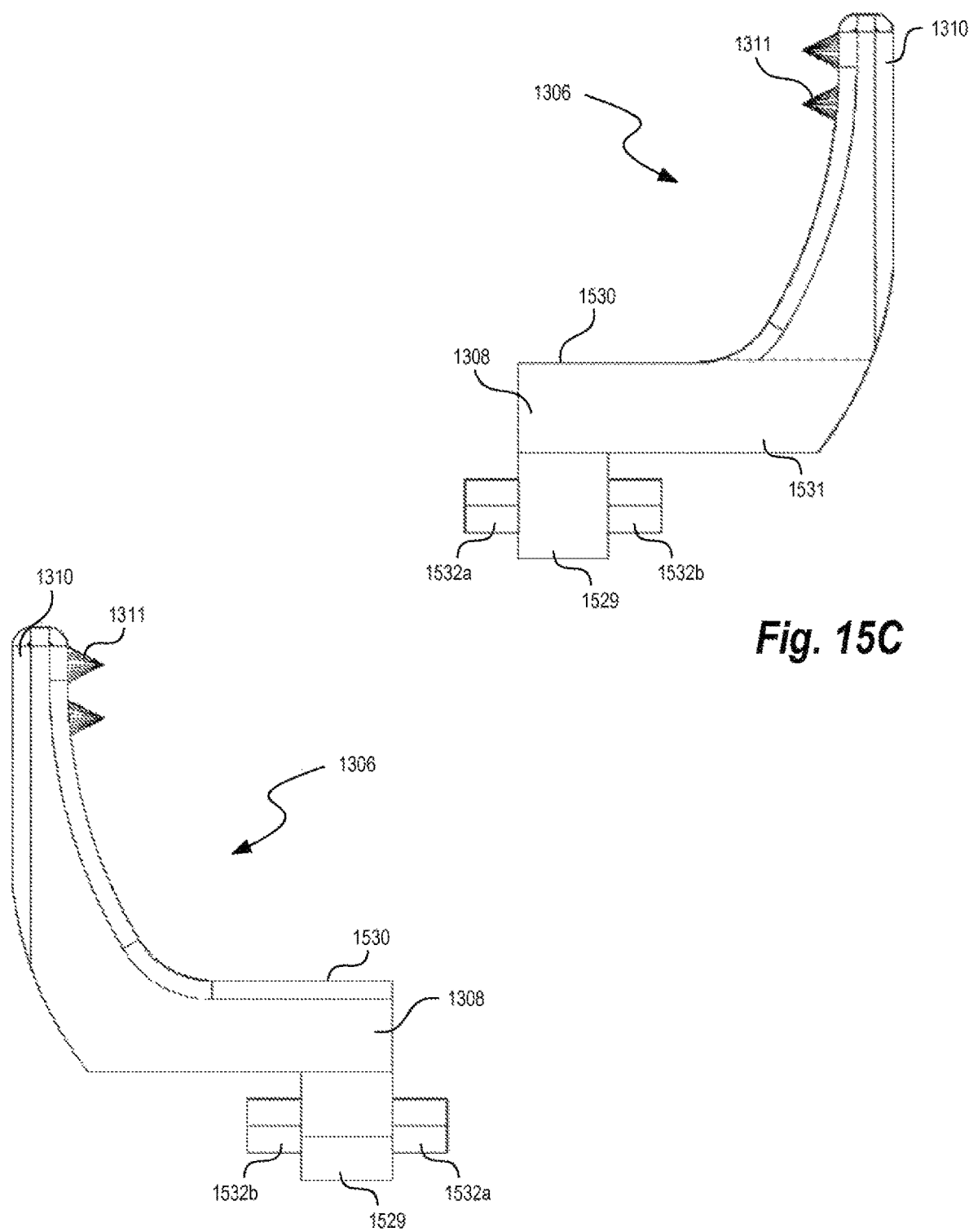
Figure 15E:
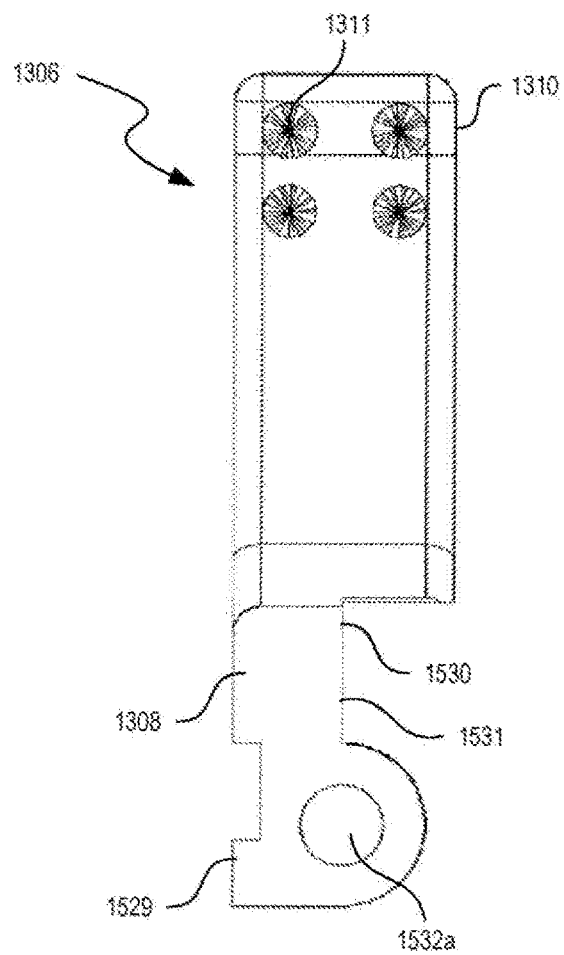
Figure 15F:
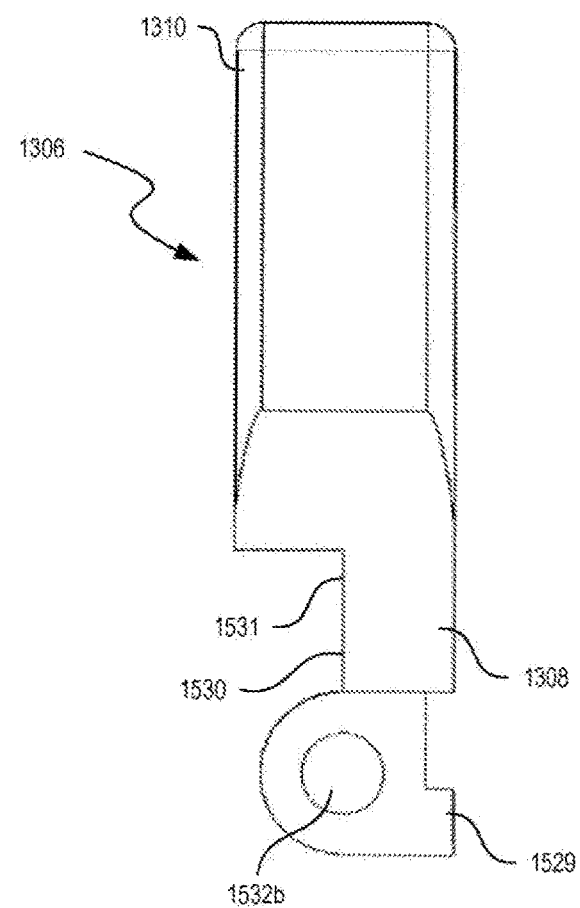
Figure 15G:
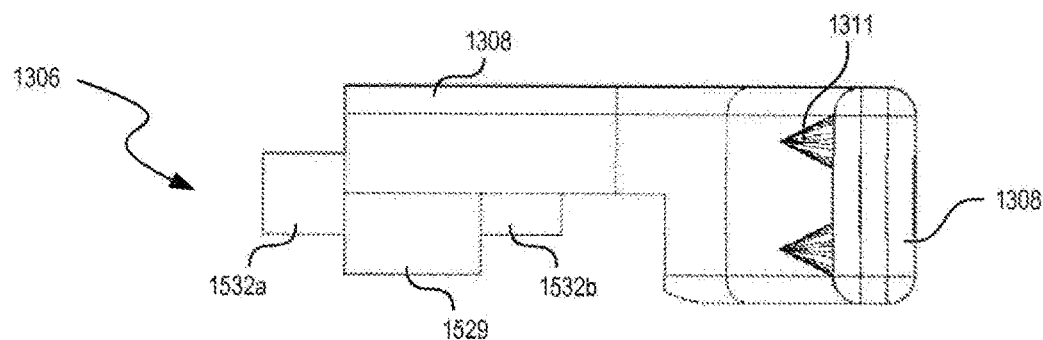

FIGS. 15A and 15B are isometric views, FIG. 15C is a bottom plan view, FIG. 15D is a top view, FIGS. 15E and 15F are side views, and FIG. 15G is an end view of one of the wings 1306. The wing 1306 represented in FIGS. 15A-15G is representative of each of the first and fourth wings 1306a, 1306d illustrated in FIGS. 13A-14B. Referring to FIGS. 15A-15G together, the wing 1306 includes the first end portion 1308 and the second end portion 1310 that carries the engagement features 1311. The first end portion 1308 is configured to contact or engage the actuator 1416 (FIG. 14A) to rotate the wing 1306. More specifically, the first end portion 1308 includes a laterally projecting extension portion 1530 including a mating surface 1531. The mating surface is configured to contact and slide against a corresponding mating surface of an adjacent wing 1306 (e.g., the second wing 1306b). In the illustrated embodiment, the wing 1306 further includes a deployment feature 1528 projecting from the extension portion 1530. The deployment feature 1528 includes a deployment surface 1529 that is configured to contact or engage the actuator 1416 (FIG. 14A) such that the actuator 1416 can pivot or rotate the wing 1306. The deployment feature 1528 further includes rotation features or pins 1532 (identified individually as a first rotation feature 1532a and a second rotation feature 1532b) that are configured to be inserted in openings in the guide 1418 (FIG. 14A). The pins 1532 allow the wing 1306 to pivot or rotate. As described in detail below, the pins 1532 also couple the wing 1306 to the corresponding guide 1418 to allow the wing to slide or translate with the guide 1418 as the actuator urges the guide 1418.

Figure 15H:
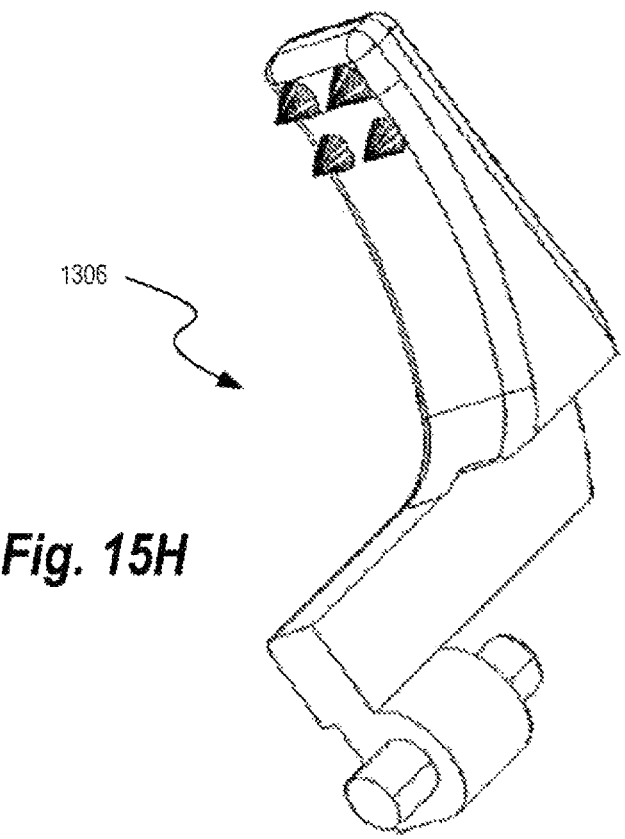
Figure 15I:
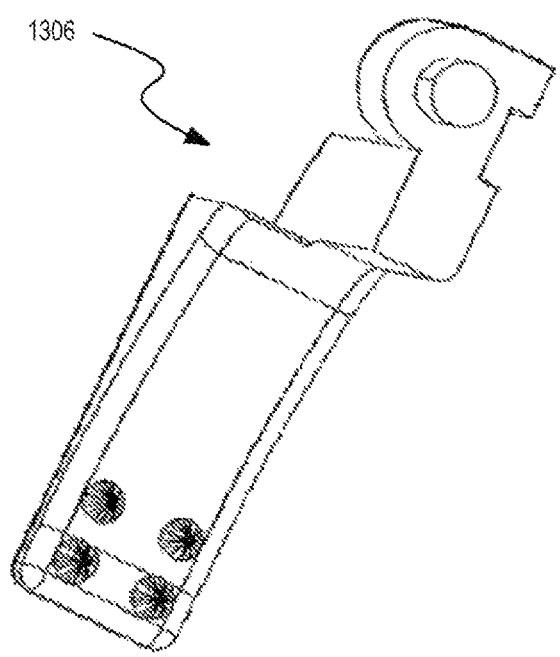
Figure 15J:
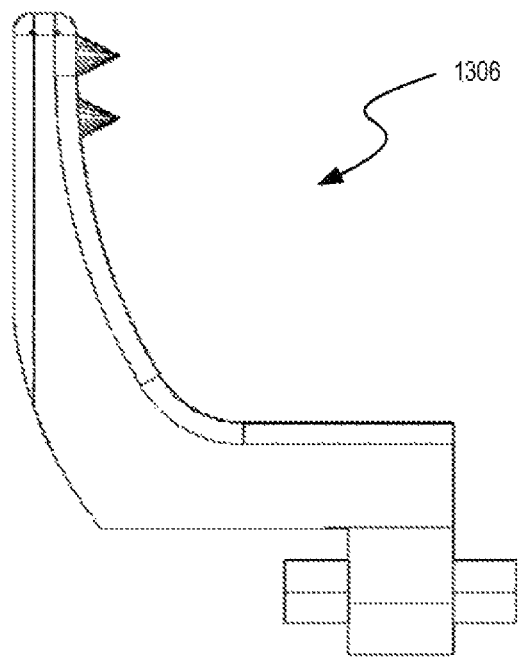
Figure 15K:
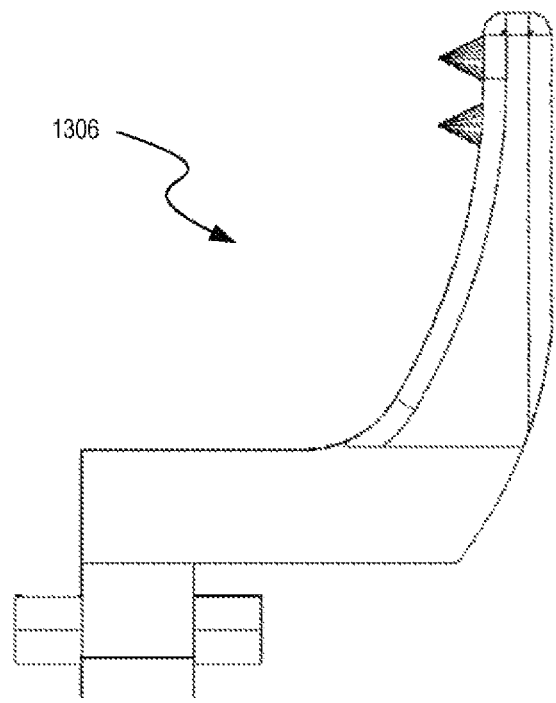
Figure 15L:
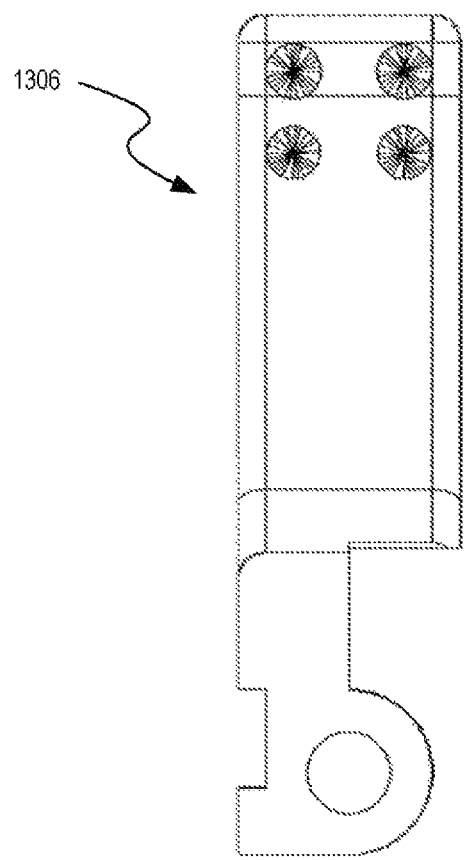
Figure 15M:
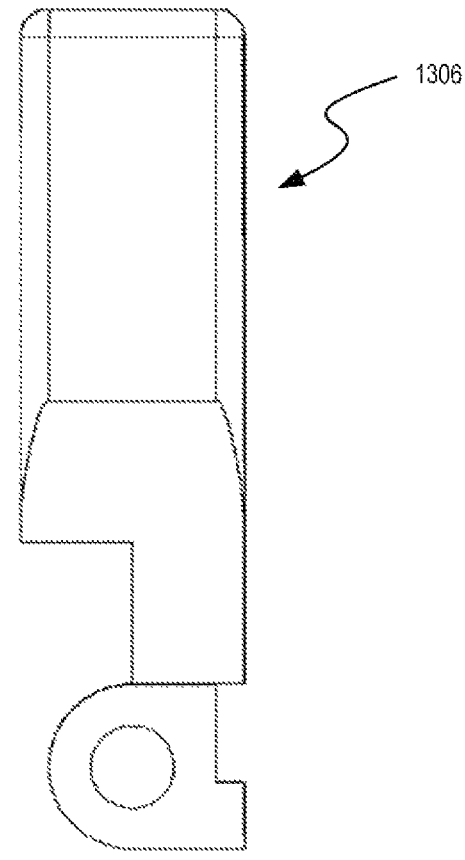
Figure 15N:
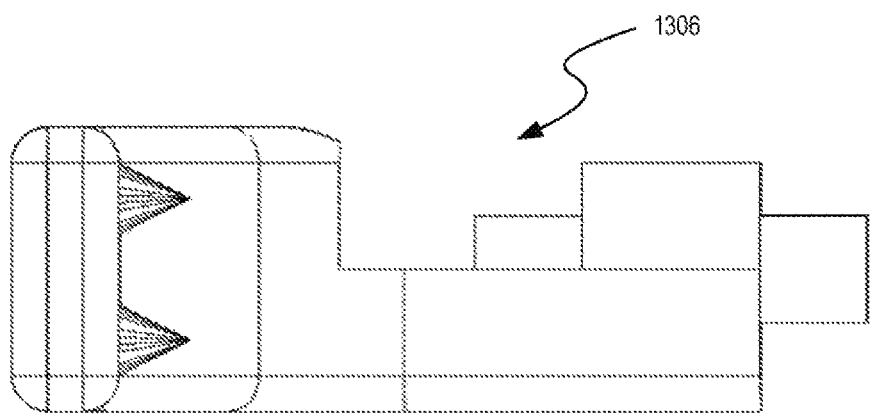

FIGS. 15H and 15I are isometric views, FIG. 15J is a bottom plan view, FIG. 15K is a top view, FIGS. 15L and 15M are side views, and FIG. 15N is an end view of one of the second and third wings 3106b, 1306c illustrated in FIGS. 13A-14B. The wing 1306 illustrated in FIGS. 15H-15N includes features that are generally similar in structure and function to the wing 1306 illustrated in FIGS. 15A-15G.

Figure 16A:
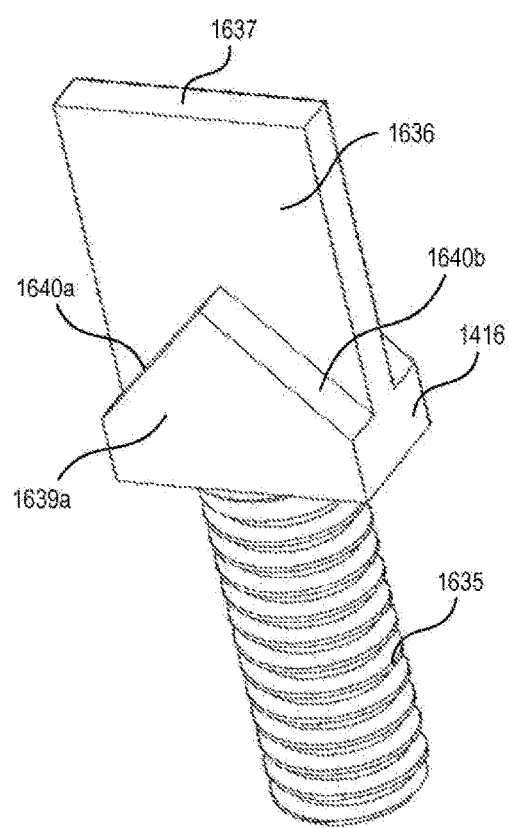
FIGS. 16A-16C are a series of various views of an actuator configured in accordance with embodiments of the disclosure.
Figure 16B:
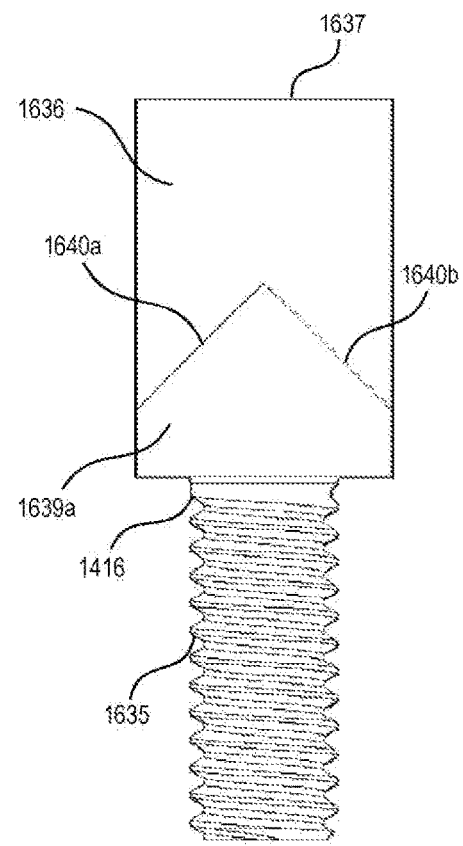
Figure 16C:
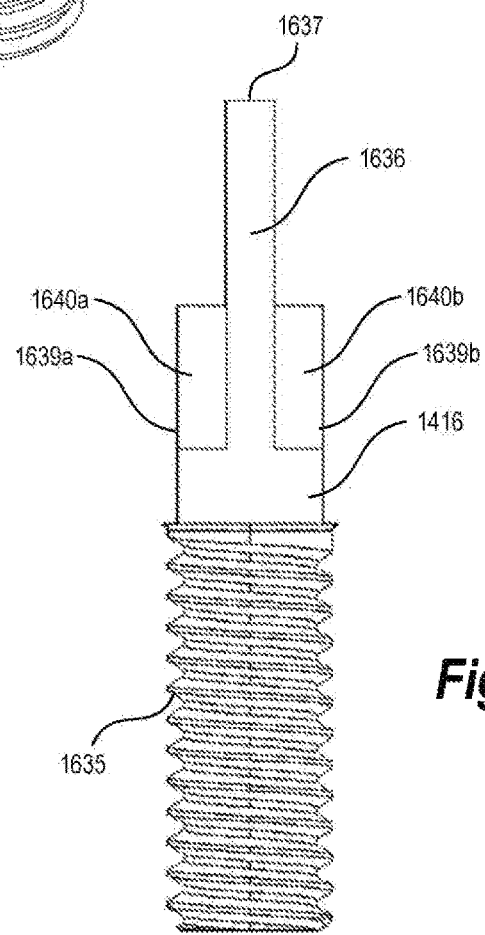

FIG. 16A is an isometric view, FIG. 16B is a side view, and FIG. 16C is an end view of the actuator 1416. Referring to FIGS. 16A-16C together, the actuator 1416 includes a proximal end portion 1634 opposite a distal end portion 1635. The distal end portion 1635 includes a threaded shaft that threadably engages the actuator adjustor or wheel 1420 (FIGS. 14A and 14B). The proximal end portion 1634 includes different features for moving the wings 1306 between distinct or separate deployment configurations. For example, the proximal end portion 1634 includes a first camming feature 1636 and second camming features 1639 (identified individually as 1639a and 1639b). The first camming feature 1636 includes a first camming surface 1637 that is configured to contact the deployment surface 1529 of each wing 1306 to pivot or rotate the wing 1306 from the undeployed configuration to an intermediately deployed configuration. As such, the first camming feature 1636 and/or the first camming surface 1637 act as a rotation driver of the wing 1306. Each second camming feature 1639 includes a inverted V-shaped protrusion extending from the first camming feature 1636 defined by converging ramped second camming surfaces 1640 (identified individually as a first ramped surface 1640a and a second ramped surface 1640b). The second camming surfaces 1640 are configured to contact the guide portions 1418 (FIGS. 14A and 14B) to slide or translate the wings 1306 from the intermediately deployed configuration to the fully deployed configuration. As such, each second camming feature 1639 and/or the second camming surfaces 1640 act as a translation or sliding driver to clamp or otherwise draw the opposing wings 1306 together.

Figure 17A:
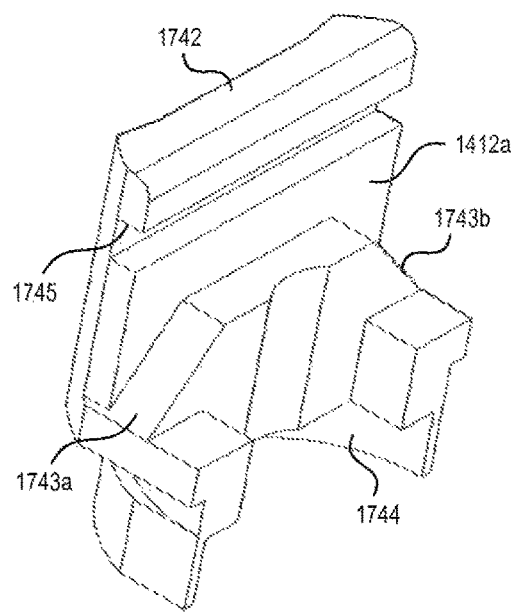
FIGS. 17A-17C are isometric views of a body configured in accordance with embodiments of the disclosure.
Figure 17B:
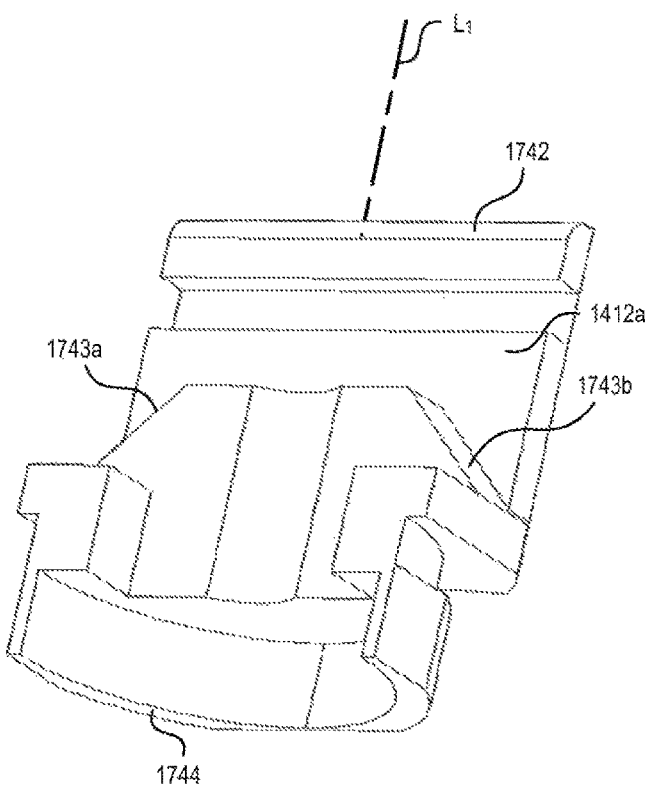
Figure 17C:
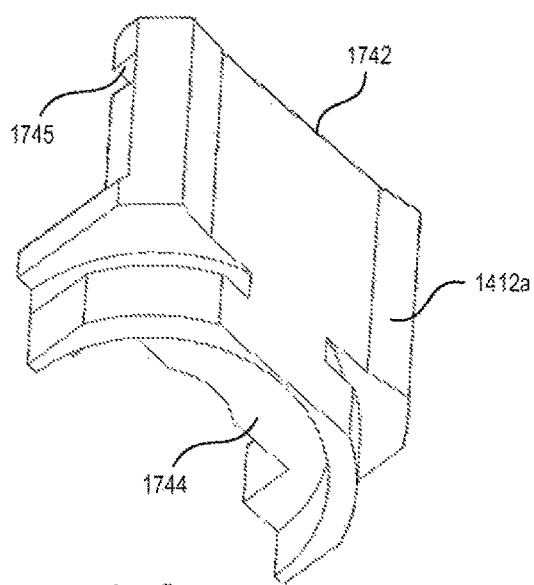

FIGS. 17A-17C are isometric views of the first body 1312a, which is a mirror image of the second body 1312b. Referring to FIGS. 17A-17C together, the body 1312 is generally configured to fit between adjacent spinous processes and to at least partially receive portions of the wings 1306, actuator 1416, guide 1418, wheel 1420 and cover 1422 (FIGS. 14A and 14B) in a central portion thereof. The first body 1312 includes a proximal end portion 1742 opposite a distal end portion 1744. The proximal end portion 1742 includes an alignment channel 1745 configured to receive an extension or ledge from the corresponding guide 1418. A mid portion between the proximal end portion 1742 and the distal end portion 1744 is configured to engage corresponding guide 1418 to move or drive the corresponding guide 1418 laterally with reference to the body 1312 (e.g., in a direction generally perpendicular to the body longitudinal axis $L_1$). More specifically, the body first 1412a includes deployment surfaces 1743 (identified individually as a first deployment surface 1743a and a second deployment surface 1743b) that are angled or ramped and configured to contact corresponding angled surfaces of the guides 1418 to cause the corresponding guides 1418 to translate or slide lateral with reference to the first body 1412a.

Figure 18A:
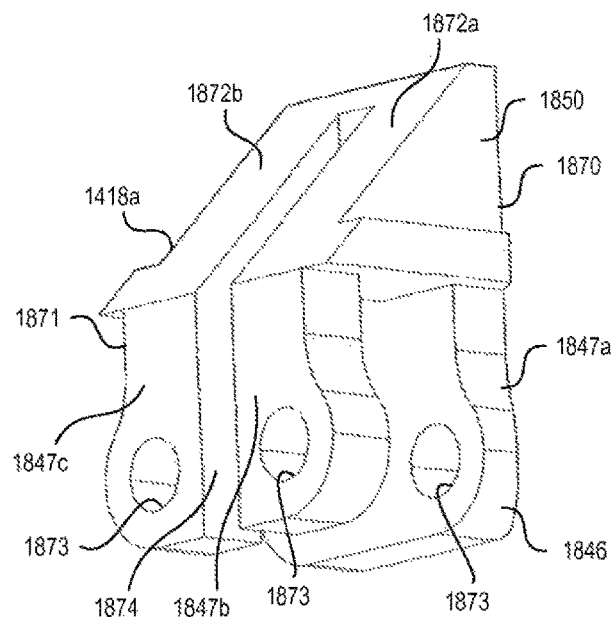
FIGS. 18A-18C are isometric views of a guide configured in accordance with embodiments of the disclosure.
Figure 18B:
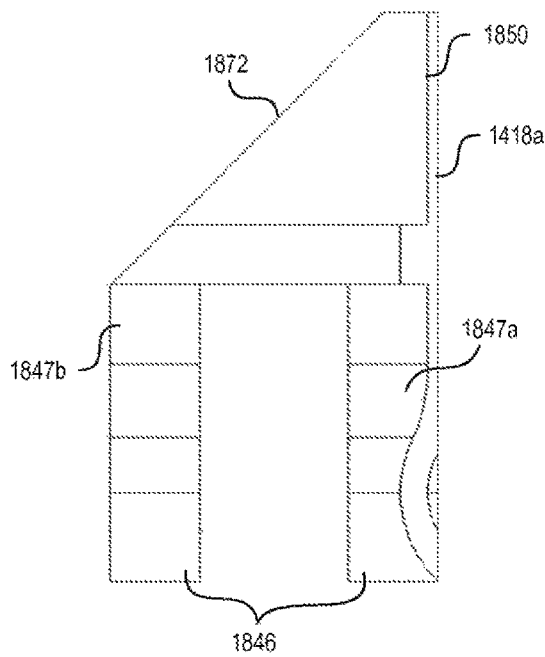
Figure 18C:
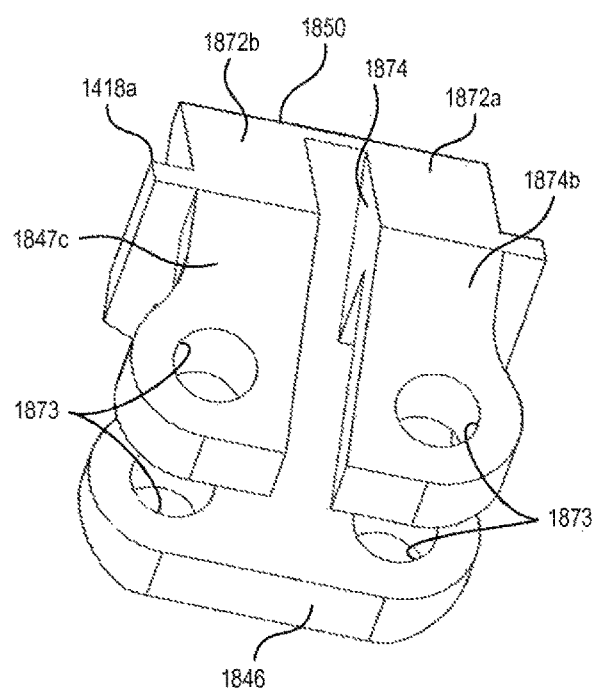

FIG. 18A is an isometric view, FIG. 18B is a side view, and FIG. 18C is an isometric view of the first guide 1418a, which is a mirror image of the second guide 1418b. Referring to FIGS. 18A-18C together, the first guide 1418 is configured to be positioned at least partially within the bodies 1312 (FIGS. 14A and 14B) and includes a proximal end portion 1846 opposite a distal end portion 1850. Extension arms 1847 (identified individually as a first through third extension arms 1847a-1847c) project toward the proximal end portion 1846. More specifically, the first extension arm 1847a is positioned at an exterior side 1870 of the first guide 1418a, and the second and third extension arms 1847b, 1847c are positioned at an interior side 1871 of the first guide 1418a. Each extension arm 1847 includes an opening 1873 configured to receive the corresponding rotation features 1532 of the wings 1206 (FIGS. 15A-15N) to allow the wings 1306 to pivot or rotate. The first guide 1418a further includes a camming feature channel or slot 1847 extending between the second and third extension arms 1847b, 1847c. The camming feature slot 1849 is configured to allow the first camming feature 1636 of the actuator 1416 to pass through the first guide 1418a.

According to additional features of the embodiment illustrated in FIGS. 18A-18C, the first guide 1418a includes first and second engagement or deployment or camming surfaces 1872a, 1872b that are configured to contact the corresponding first and second camming surfaces 1640a, 1640b of the actuator 1416 (FIGS. 16A-16C). As explained below, as the actuator 1416 moves a first distance relative to the first guide 1418a, the first camming feature 1636 passes through the camming feature slot 1874. As the actuator 1416 continues to move, the second camming feature 1639 of the actuator 1416 (FIGS. 16A-16C) contacts the first and second camming surfaces 1872a, 1872b of the first guide 1418a to slide, drive, or otherwise urge the first guide 1418*a* and corresponding wings 1306 laterally with reference to the bodies 1312.

Figure 19A:
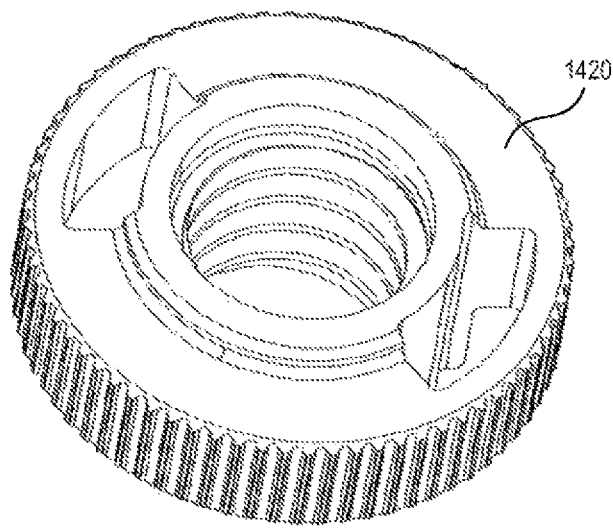
FIGS. 19A and 19B are isometric views of an actuator adjuster configured in accordance with an embodiment of the disclosure.
Figure 19B:
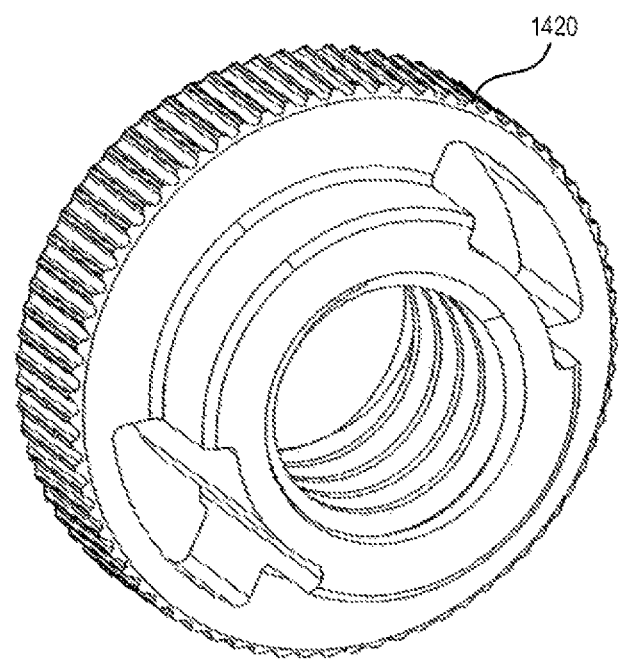

FIGS. 19A and 19B are isometric views of the actuator adjuster in the form of a wheel 1420, which is generally similar in structure and function to the actuator adjuster 320 described above with reference to FIGS. 8A and 8B.

Figure 20A:
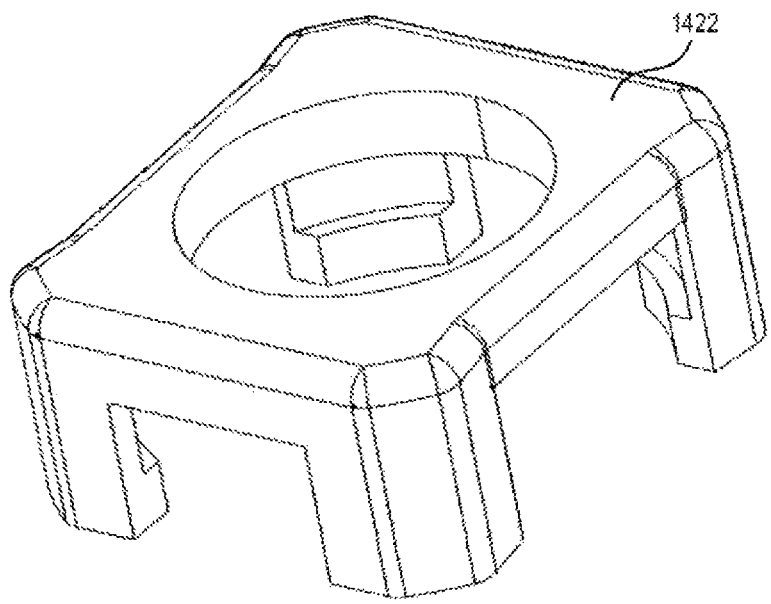
FIGS. 20A and 20B are isometric views of a cap configured in accordance with an embodiment of the disclosure.
Figure 20B:
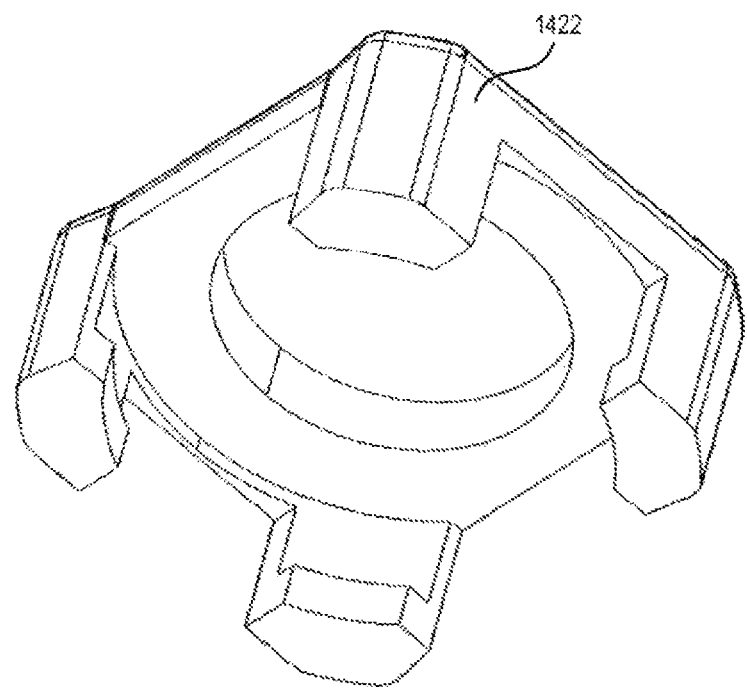

FIGS. 20A and 20B are isometric views of the cap or cover 1422, which is generally similar in structure and function to the cap or cover 322 described above with reference to FIGS. 9A and 9B.

Figure 21A:
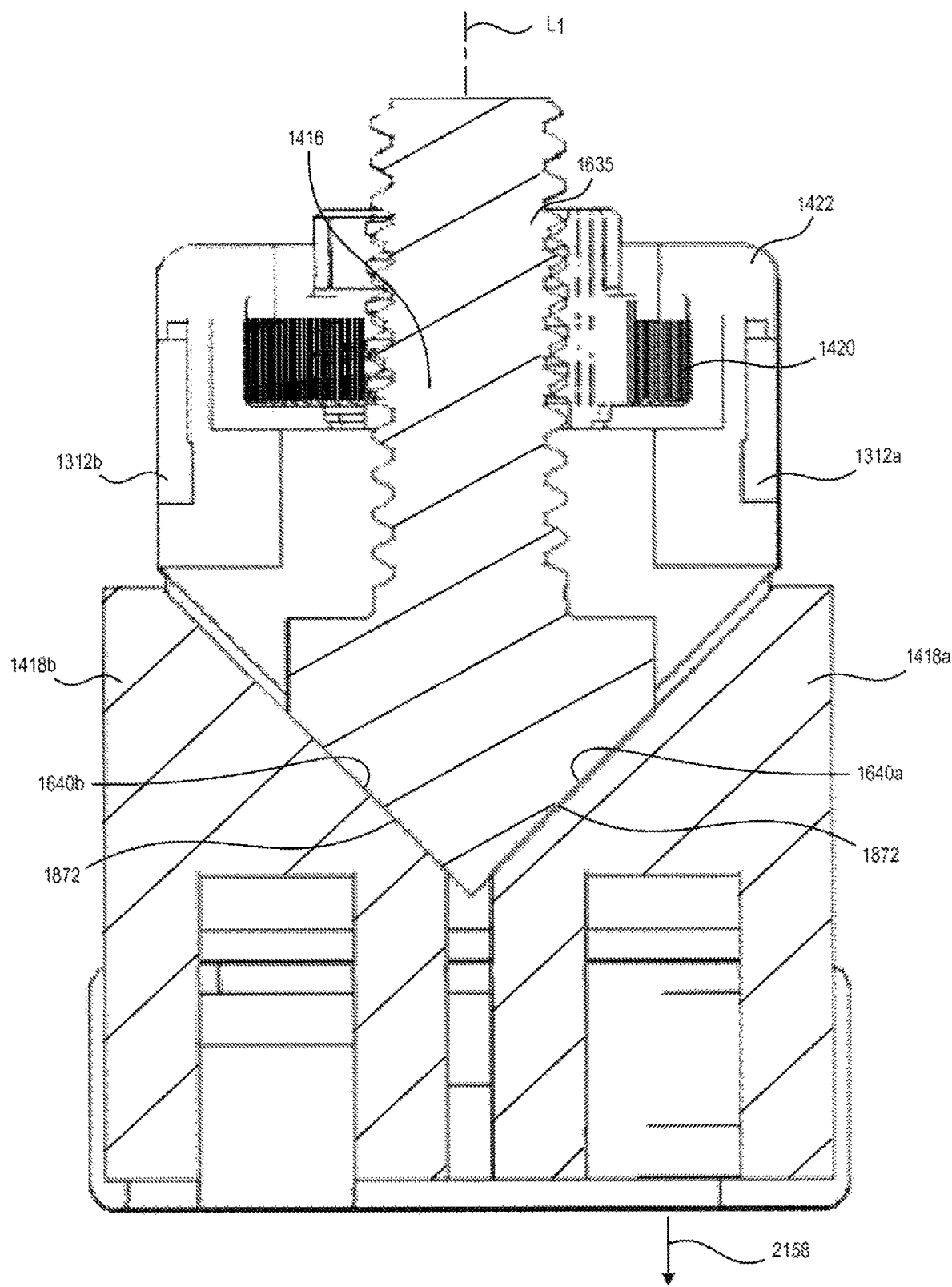
FIG. 21A is a cross-sectional view taken substantially along lines 21A-21A in FIG. 13D.

FIG. 21A is a cross-sectional view of the spacer 1300 view taken substantially along lines 21A-21A in FIG. 13D, and FIG. 21B is a cross-sectional view of the spacer 1300 taken substantially along lines 21B-21B in FIG. 13C. The cross-sectional views shown in FIGS. 21A and 21B illustrate the relative positions of several components of the spacer 1300 when the spacer 1300 is in deployed or fully deployed configuration. For example, FIGS. 21A and 21B illustrate the wheel 1420 positioned between the cover 1422 and the bodies 1312, as well as the wheel 1420 threadably engaged with the distal end portion 1635 of the actuator 1416. Moreover, in the deployed configuration, each wing 1306 is positioned and secured proximate or adjacent to corresponding bodies 1312. More specifically, as the wheel 1420 rotates it moves the actuator 1416 in a proximal direction or in the direction of arrow 2158 (which is in a direction at least generally parallel to the body longitudinal axis $L_1$), the second camming surfaces 1640 of the actuator 1416 contact the corresponding second engagement surfaces 1872 of the individual guides 1418. As such, the actuator 1416 urges or drives the guides 1418 away from the bodies 1312 and also urges or drive the corresponding opposing pairs of wings 1306 toward each other (e.g., the first wing 1306*a* and the second wing 1306*b*, as well as the third wing 1306*c* and the fourth wing 1306*d*). More specifically, as the actuator 1416 moves in the direction of arrow 2158, the second engagement surfaces 1872 slide along the corresponding second camming surfaces 1640 to draw the wings 1306 toward each other in the fully deployed configuration.

Figure 21C:
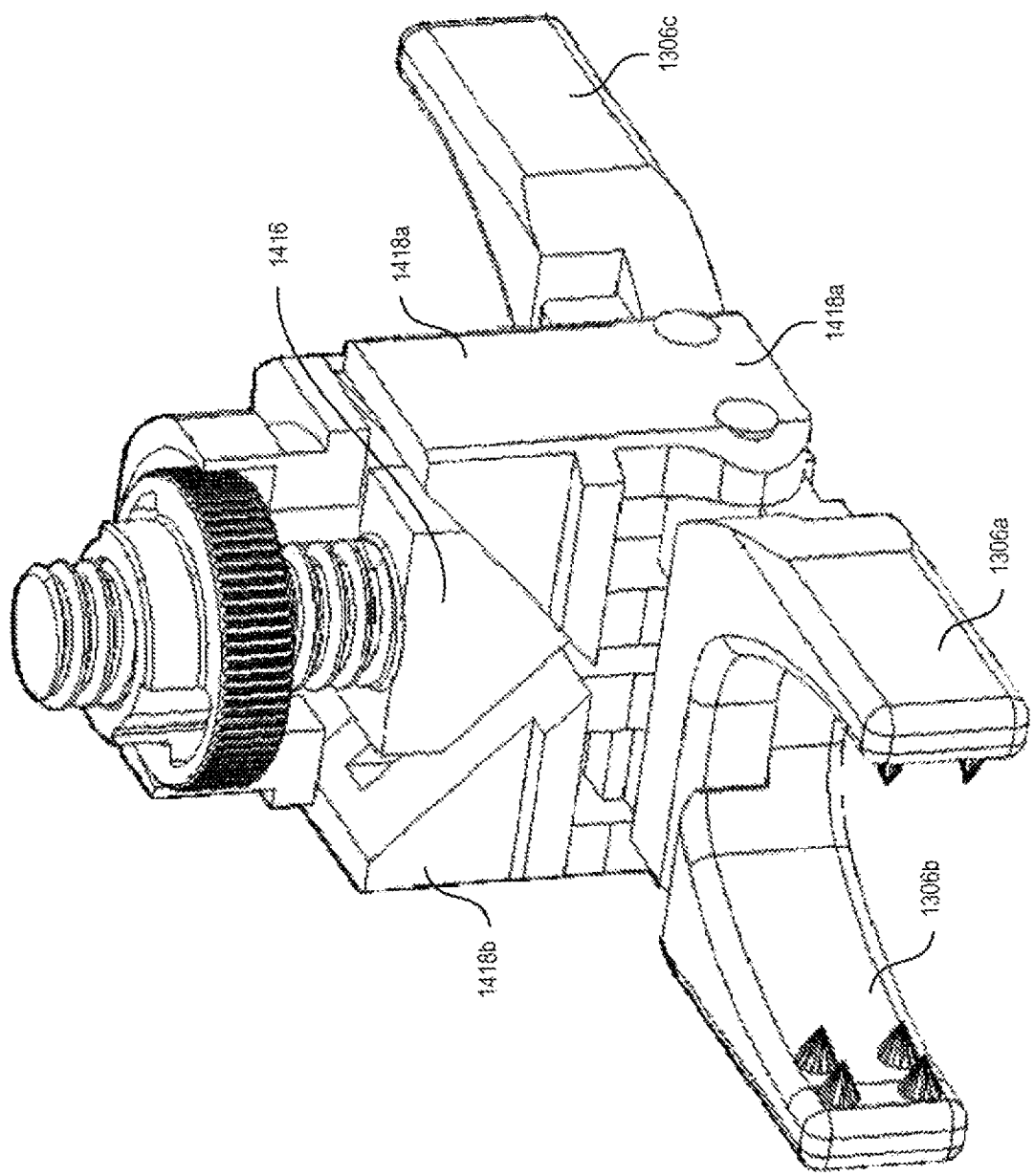
FIG. 21C is an isometric partial view of the spacer of FIG. 21A.

FIG. 21C is an isometric partial view of the spacer 1300 in the fully deployed position showing the positional relationship of the actuator 1416 relative to the guides 1418. FIG. 21C also illustrates that the guides 1418 protrude laterally from the body when the spacer 1300 is in the fully deployed position.

FIGS. 22A-22E are a series of views illustrating several deployment configurations of the spacer 1300. FIG. 21A, for example, is an isometric view illustrating the spacer 1300 in an undeployed configuration during insertion between a superior spinous process 102*a* and an inferior spinous process 102*b*. During insertion and deployment, the spacer 1300 is coupled to a delivery instrument 2160. In the undeployed configuration as illustrated in FIG. 21A, the longitudinal axis of each wing 1306 (e.g., wing longitudinal axis $L_2$ in FIG. 13A) can be generally parallel to or aligned with the longitudinal axis of the spacer (e.g., body longitudinal axis $L_1$ in FIG. 13A). As such, the spacer 1300 has a low profile in the deployed configuration. In the undeployed configuration and attached to the delivery instrument 1160, the spacer 1300 can be inserted into a port or cannula that has been operatively positioned in an interspinous space via a minimally invasive incision. In other embodiments where a cannula may not be necessary, the spacer 1300 may be inserted through an incision. Where a cannula is used, the spacer 1300 can be advanced through the cannula to within the targeted interspinous spacer and advanced beyond the end of the cannula, or alternatively, the cannula is retracted to uncover the spacer.

Figure 22A:
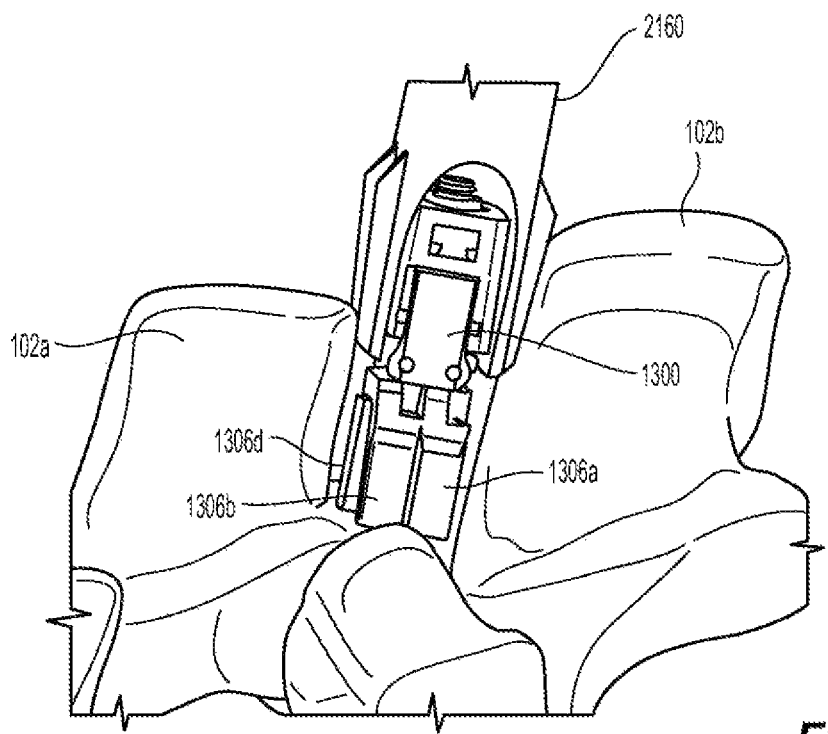
FIGS. 22A-22E are a series of views illustrating several configurations of a spacer configured in accordance with an embodiment of the disclosure.
Figure 22B:
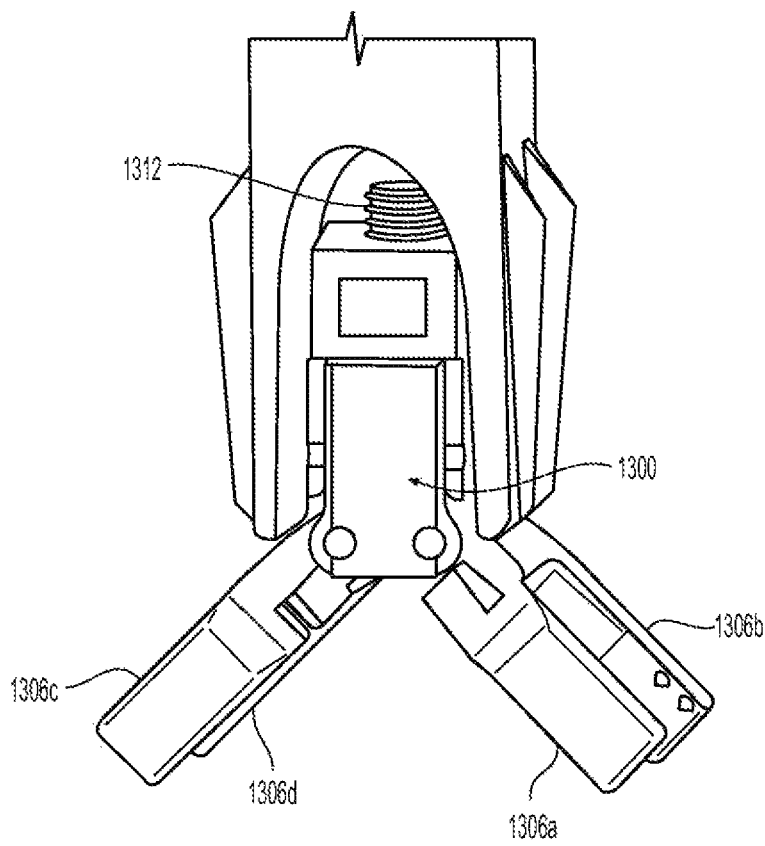

Referring next to FIG. 22B, the spacer 1300 is in an intermediately deployed configuration with the wings 1306 partially rotated relative to the body 1312. More specifically, the longitudinal axis of each wing is rotated or pivoted relative to the longitudinal axis of the body 1312. As described above, the actuator 1416 moves a first distance longitudinally within the body 1312 to rotate the wings 1306.

Figure 22C:
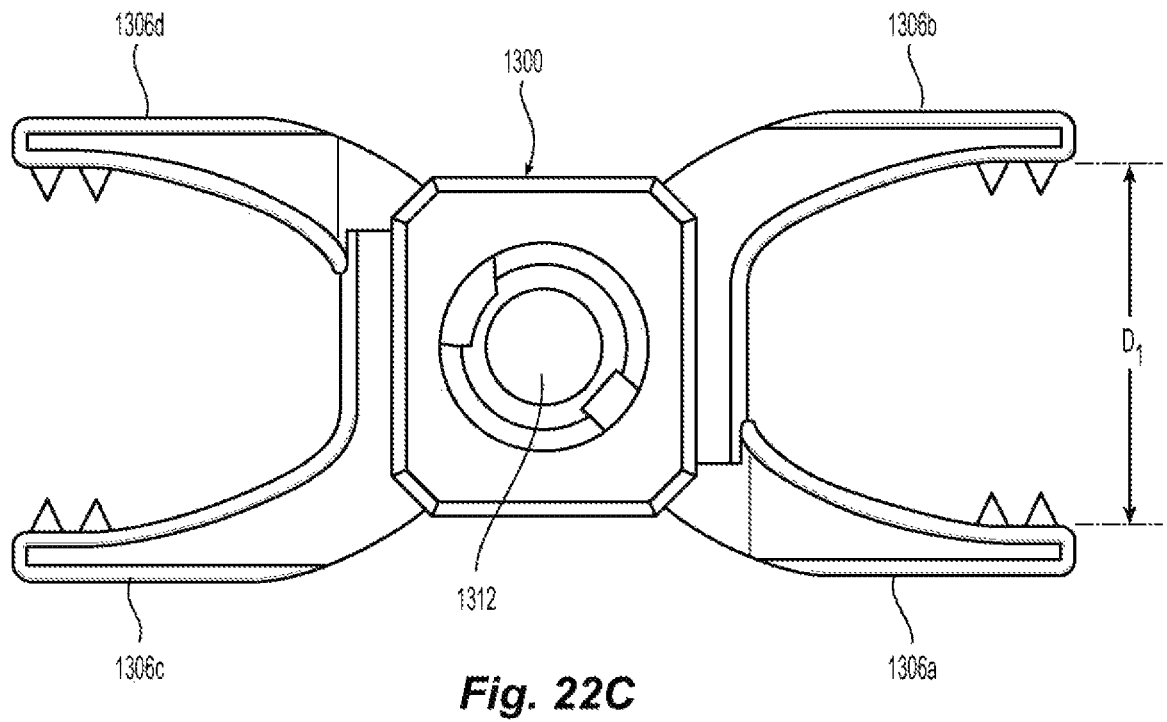

FIG. 22C is a top view of the spacer 1300 in an intermediately deployed configuration with the wings 1306 fully rotated or pivoted relative to the body 1312. More specifically, in the intermediately deployed and fully rotated configuration, the longitudinal axis of each wing 1306 is rotated or pivoted generally perpendicularly to the longitudinal axis of the body 1312. In other embodiments, however, the wings 1306 can be positioned at an angle that is greater than or less than 90 degrees (e.g., an angle in a range of about 75 degrees to 105 degrees) relative to the longitudinal axis of the body 1312. According to an additional feature of the spacer 1300 in the partially deployed configuration shown in FIG. 22C, the first wing 1306*a* is spaced apart from the second wing 1306*b* by a first distance $D_1$, and the third wing 1306*c* is also spaced apart from the fourth wing 1306*d* by the first distance $D_1$. To rotate the wings 1306 to the position shown in FIG. 22C, the actuator 1416 has moved longitudinally within the body 1312 a first predetermined distance to drive the wings 1306 to the fully rotated position.

Figure 22D:
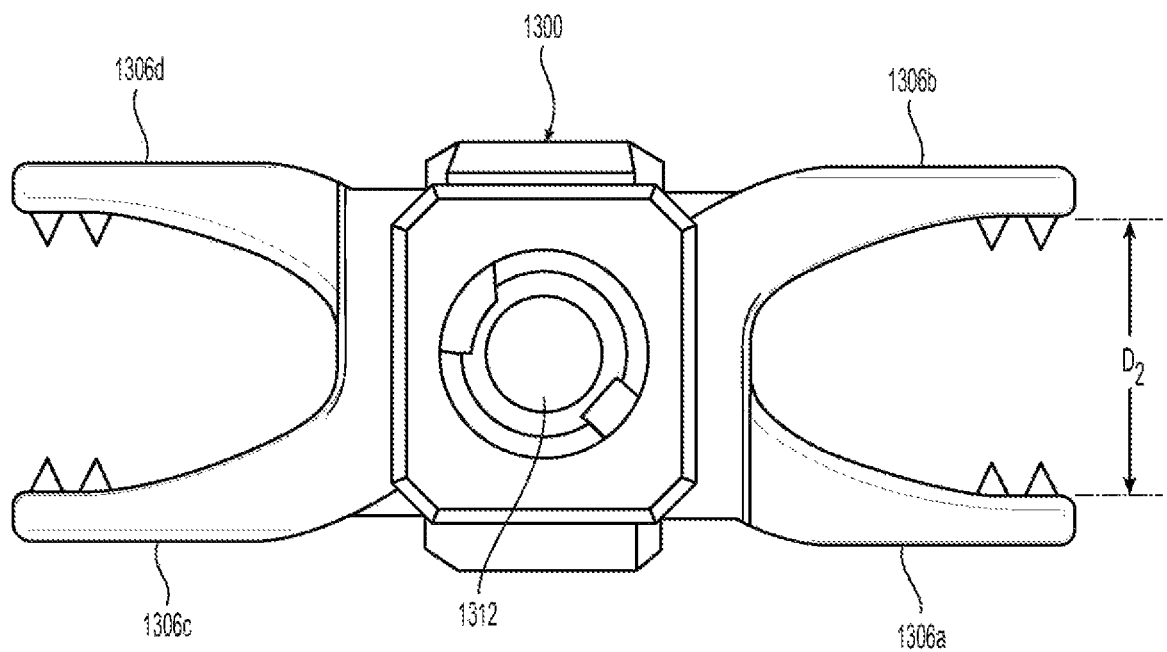

FIG. 22D is a top view of the spacer 1300 in a fully deployed or rotated and clamping configuration with the wings 1306 fully rotated and the wings 1306 drawn proximate or adjacent to the body 1312. More specifically, in the fully deployed position, the longitudinal axis of each wing 1306 remains generally perpendicular to the longitudinal axis of the body 1312. In other embodiments, however, the wings 1306 can be positioned at an angle that is greater than or less than 90 degrees relative to the longitudinal axis of the body 1312. According to an additional feature of the spacer 1300 in the fully deployed configuration shown in FIG. 22D, the first wing 1306*a* is spaced apart from the second wing 1306*b* by a second distance $D_2$, which is less than the first distance $D_1$. Moreover, the third wing 1306*c* is spaced apart from the fourth wing 1306*d* by the second distance $D_2$. The second distance $D_2$ is configured to allow the engagement features 1311 of each wing 1306 to at least partially embed or otherwise engage the corresponding spinous processes. To slide or translate the wings as shown in FIG. 22D, the actuator 1416 has moved longitudinally within the body 1312 a second predetermined distance, in addition to the first predetermined distance, to drive the guides 1418 away from each other to draw the corresponding wings 1306 to the fully deployed position.

Figure 22E:
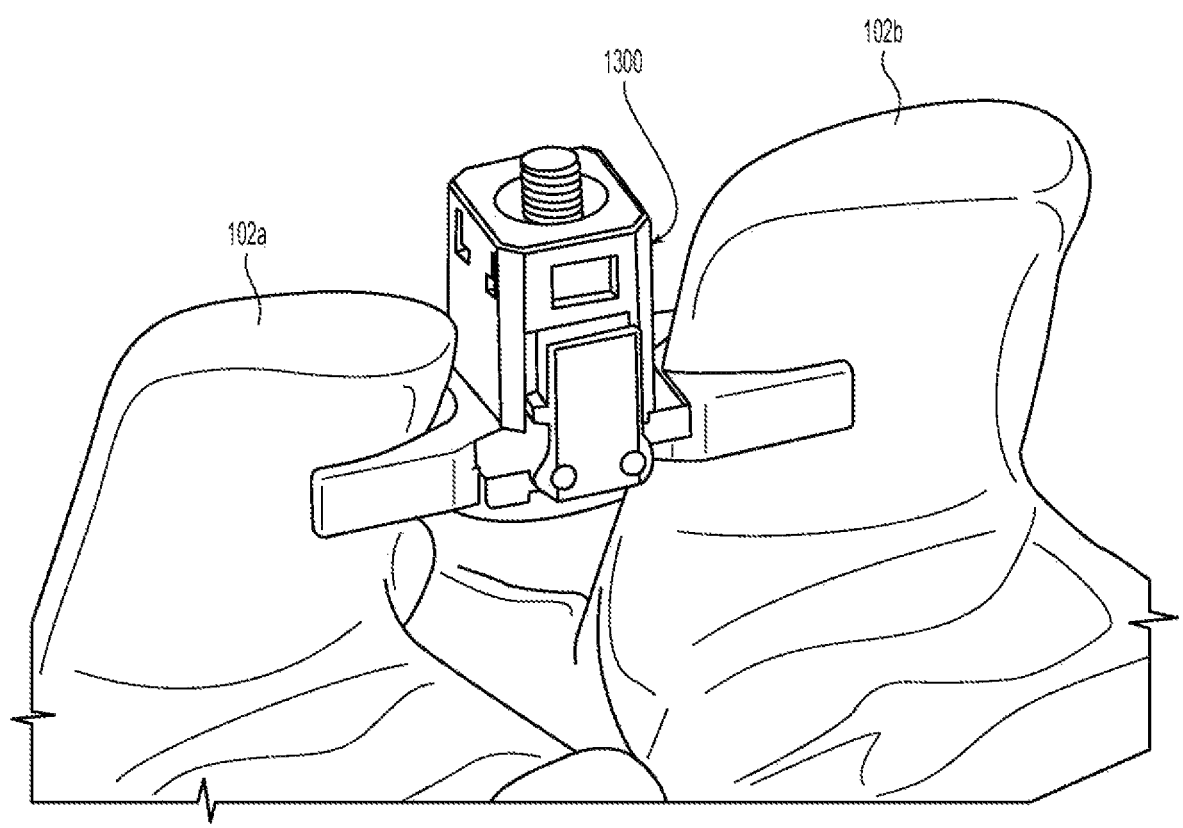

FIG. 22E is an isometric view illustrating the spacer 1300 in the fully deployed configuration fusing the superior spinous process 102*a* relative to the inferior spinous process 102*b*.

Figure 23A:
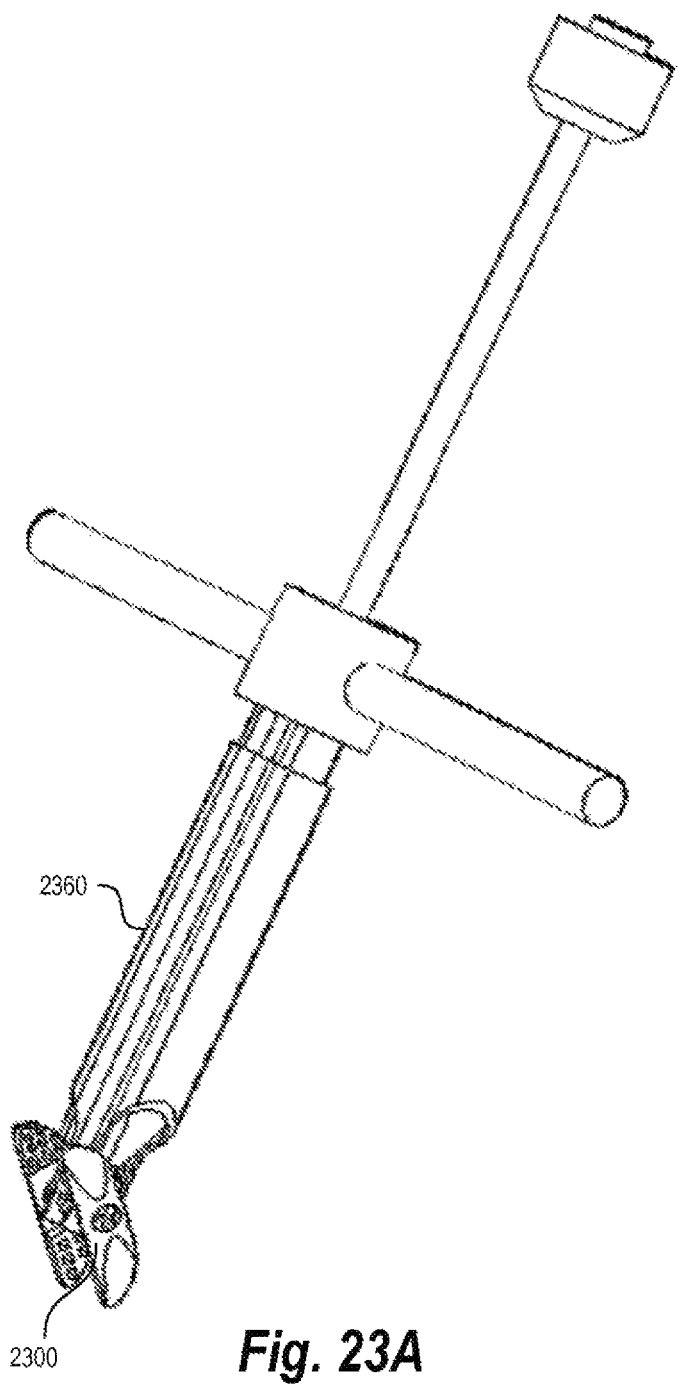
FIG. 23A is an isometric view of a spacer operably coupled to a delivery instrument configured in accordance with an embodiment of the disclosure.
Figure 23B:
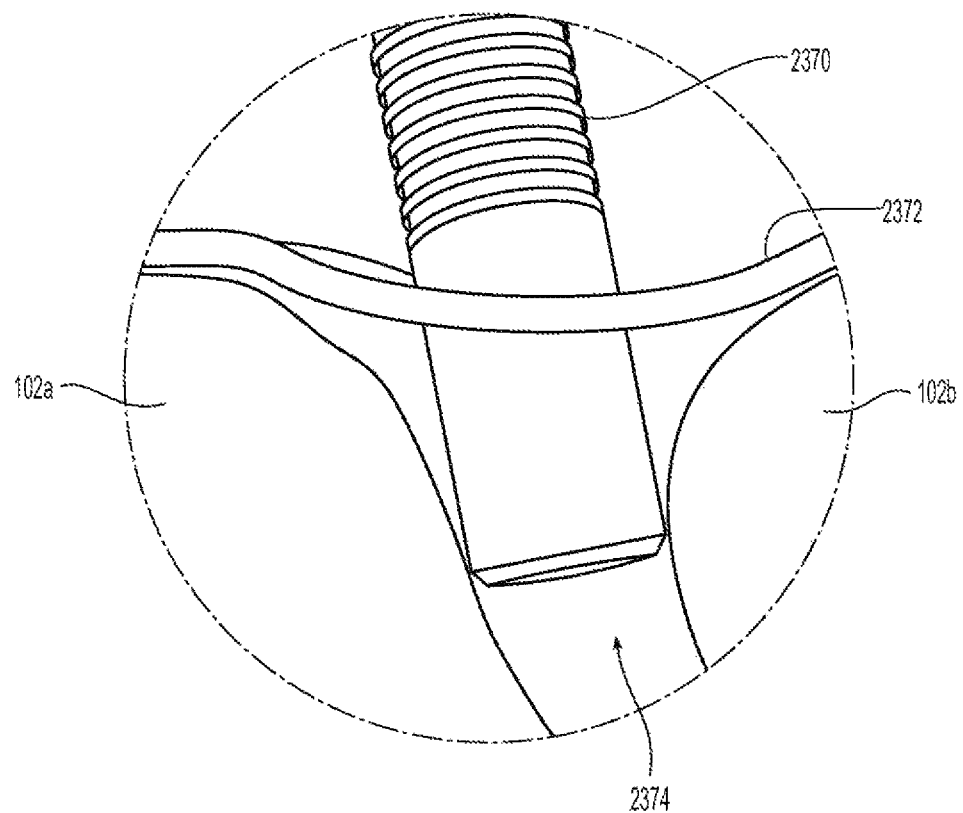
FIG. 23B is an isometric partial view of a cannula extending through a supraspinous ligament for positioning a spacer in accordance with embodiments of the disclosure.

FIG. 23A is an isometric view of a spacer 2300 operably coupled to a delivery instrument 2360. In the embodiment illustrated in FIG. 23A, a clamp assembly with wings is partially rotated relative to a longitudinal axis of the delivery instrument 2360. During insertion or initial delivery, however, the wings of the spacer 2300 are oriented such that their individual longitudinal axes are generally parallel to or otherwise aligned with a longitudinal axis of the delivery instrument 2360. After the spacer 2300 is inserted and positioned adjacent to the corresponding spinous processes, the clamp assembly can be rotated and clamped as described in detail herein. The delivery instrument 2360 is configured to be operably coupled to the spacer 2300 to deliver the spacer 2300 in a minimally invasive manner. For example, the delivery instrument 2360 can be configured to be used with a cannula. For example, FIG. 23B is an isometric view of a cannula 2370 extending through a supraspinous ligament 2372 and positioned at or adjacent to an interspinous process space 2374 between a superior spinous process 102a and an inferior spinous process 102b. At least a portion of the delivery instrument 2360 of FIG. 23A can be advanced through the cannula 2370 to allow placement of the spacer 2300 between the spinous process 102.

FIG. 24A is an isometric view, FIG. 24B is an end view, FIGS. 24C and 24D are side views, and FIG. 24E is an end view of an assembly 2401 configured in accordance with another embodiment of the disclosure. Referring to FIGS. 24A-24E together, the assembly 2401 includes a spacer 2400 operably coupled to a delivery instrument 2460. As described in detail below, the spacer 2400 includes several features that are generally similar in structure and function to the spacers described above. For example, the spacer 2400 includes a clamp assembly 2405 with opposing extensions, arms, or wings 2406 (identified individually as a first spacer 2406a and a second wing 2406b) that are rotatably or pivotally coupled to a body 2412. The body 2412 is configured to be positioned between adjacent spinous processes and each wing 2406 includes engagement features 2411 that are configured to engage or grip corresponding spinous processes when the wings 2406 are urged toward the body 2412. The spacer 2400 further includes an actuator assembly 2414 operably coupled to the body 2412 and the wings 2406. The delivery instrument 2460 includes a cannula 2470 at least partially disposed over or around a rotator device the form of a first actuator or plunger 2472. The plunger 2472 is coaxially aligned with the cannula 2470 (e.g., along longitudinal axis L of the delivery instrument 2460) and movable within the cannula 2470 in directions generally parallel to a longitudinal axis L of the cannula 2470 (e.g., in directions indicated by double headed arrow 2463). For example, the plunger 2472 is configured to move distally or out of the cannula 2470 to contact the wings 2406 to rotate the wings 2406 to an intermediately deployed position in which the wings 2406 are rotated at least approximately 90 degrees relative to the longitudinal axis L. In other embodiments, however, the wings 2406 can rotate to an angle that is greater than or less than 90 degrees relative to the longitudinal axis L As described in detail below, the assembly 2401 is configured to position the spacer 2400 between adjacent spinous processes and actuate the spacer 2400 from an undeployed or low profile configuration to a deployed configuration. More specifically, the assembly 2401 is configured to rotate the wings 2406 from a first or undeployed configuration to a second or intermediately or partially deployed configuration, and to further clamp or urge the wings 2406 toward each other from the partially deployed configuration to a third or fully deployed configuration. In the embodiment illustrated in FIGS. 24A-24E, the spacer 2400 is shown in the partially deployed configuration with the wings 2406 fully rotated but still fully spaced apart, or at least partially spaced apart, from each other and/or from the body 2412. As described in detail below, the plunger 2472 descends or otherwise moves within the cannula 2470 to contact and rotate each wing 2406. As such, although the wings 2406 are illustrated in the fully rotated configuration in FIGS. 24A-24E after contacting the plunger 2472, the plunger 2472 illustrated in FIGS. 24A-24E is shown as partially retracted or spaced apart from the wings 2406 after contacting and rotating the wings 2406.

Figure 25A:
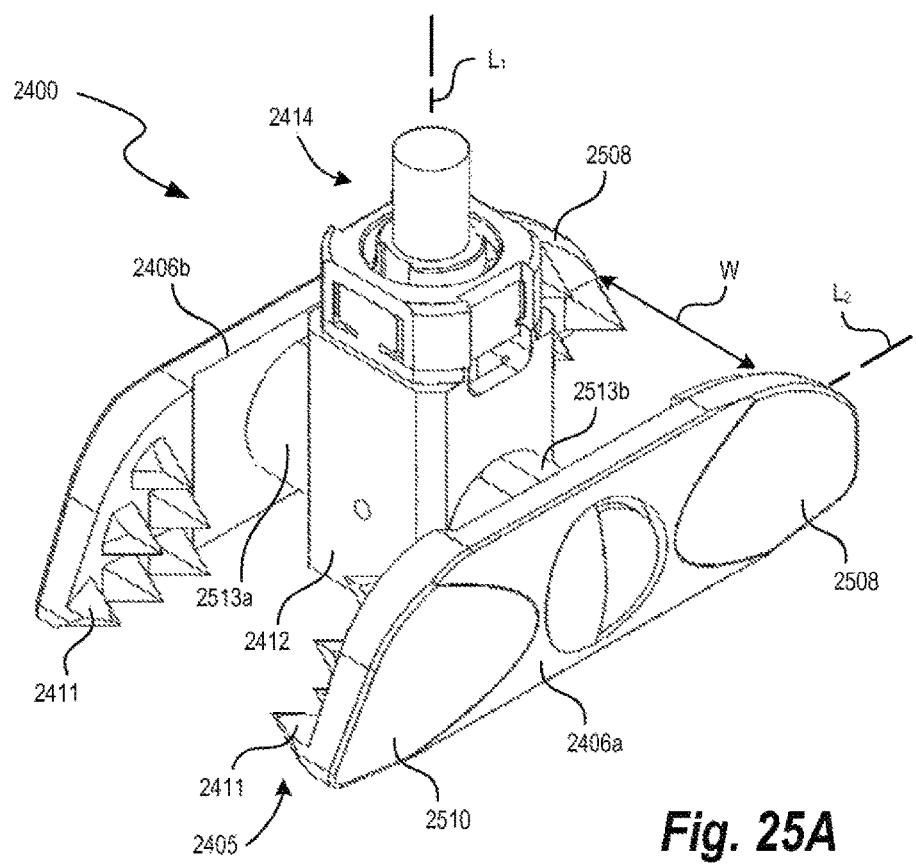
FIGS. 25A and 25B are isometric views.
Figure 25B:
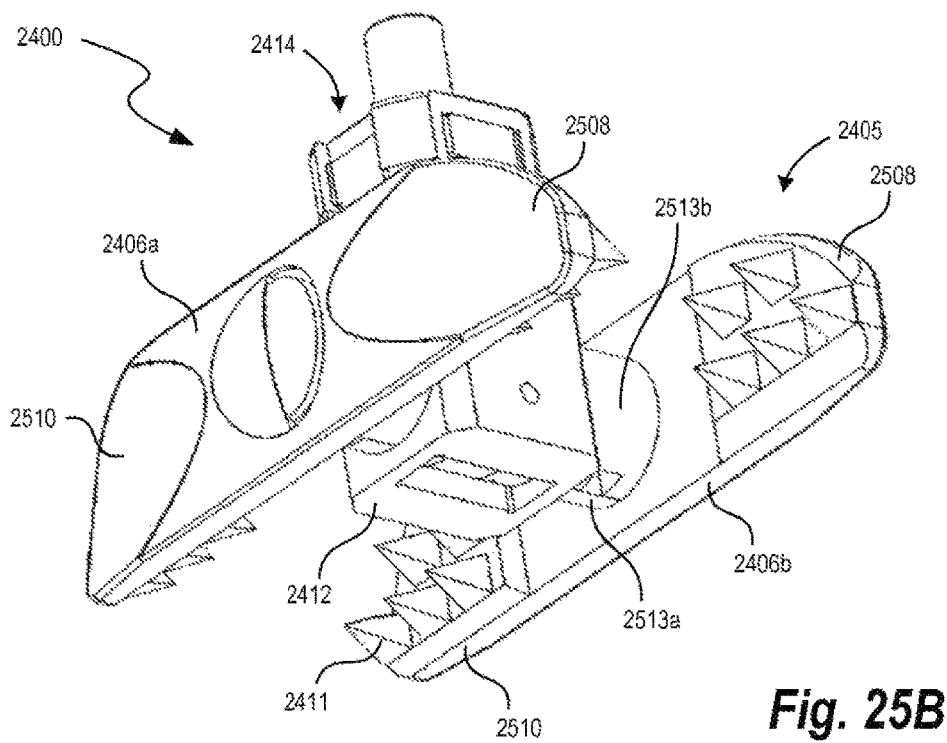
Figure 25C:
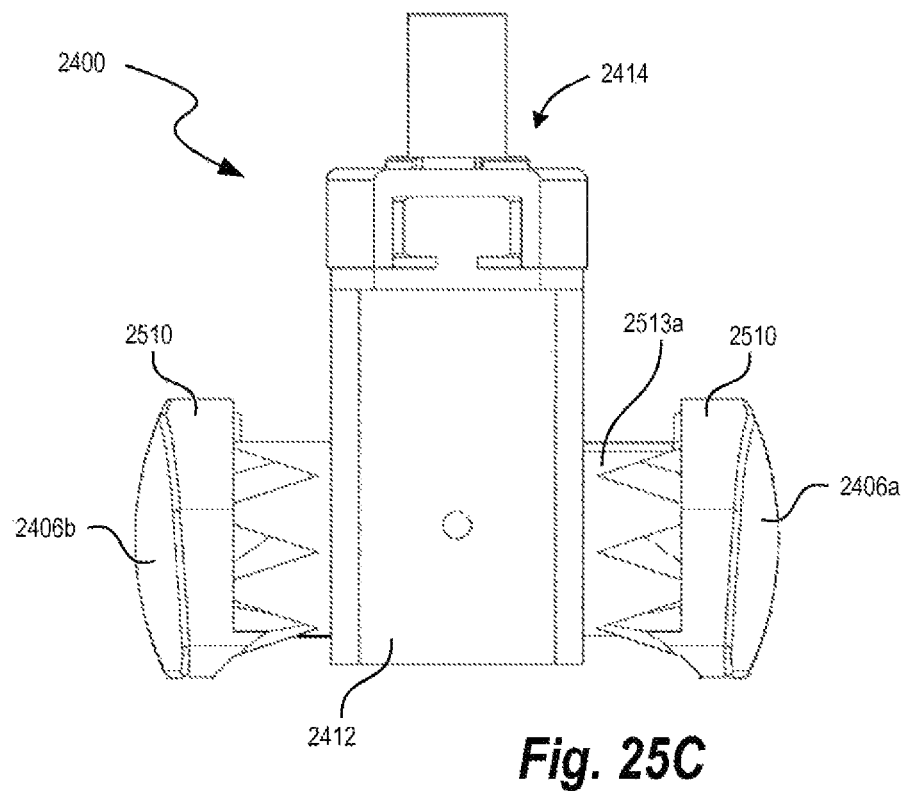
FIG. 25C is an end view.
Figure 25D:
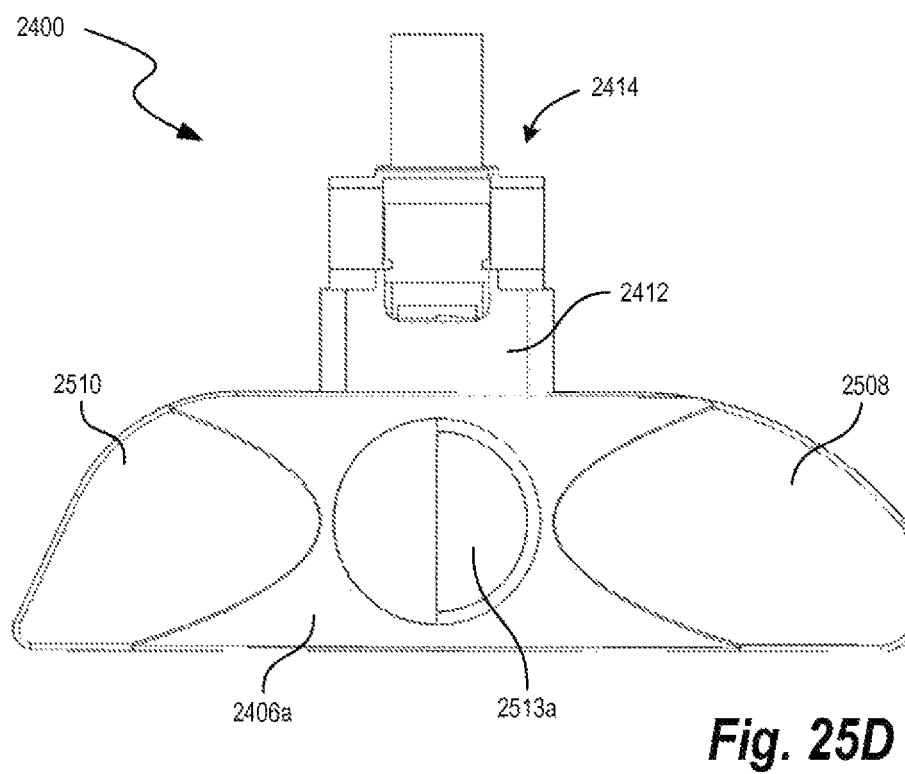
FIG. 25D is a side view.
Figure 25E:
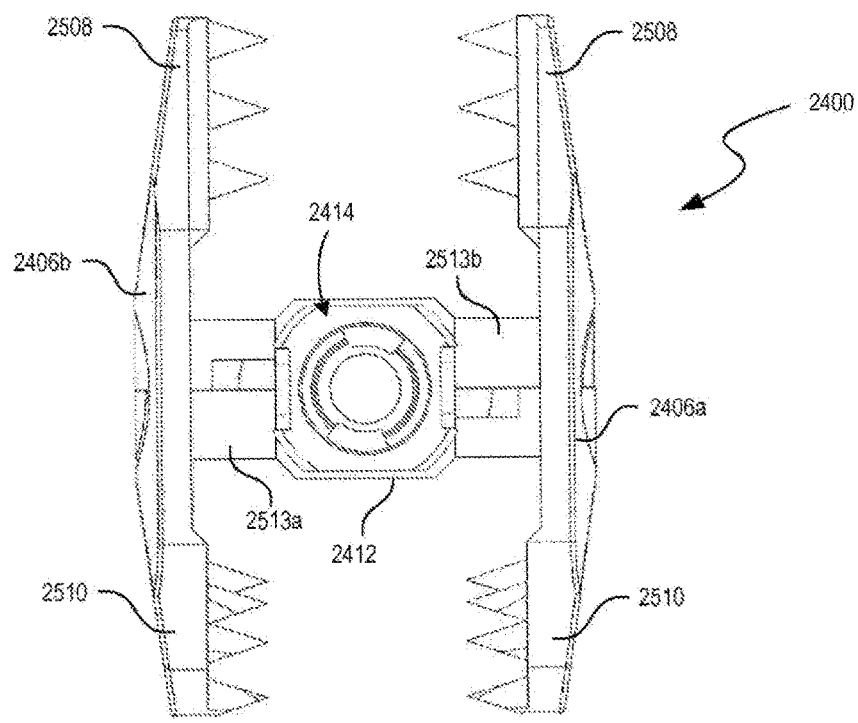
FIG. 25E is a top view.
Figure 25F:
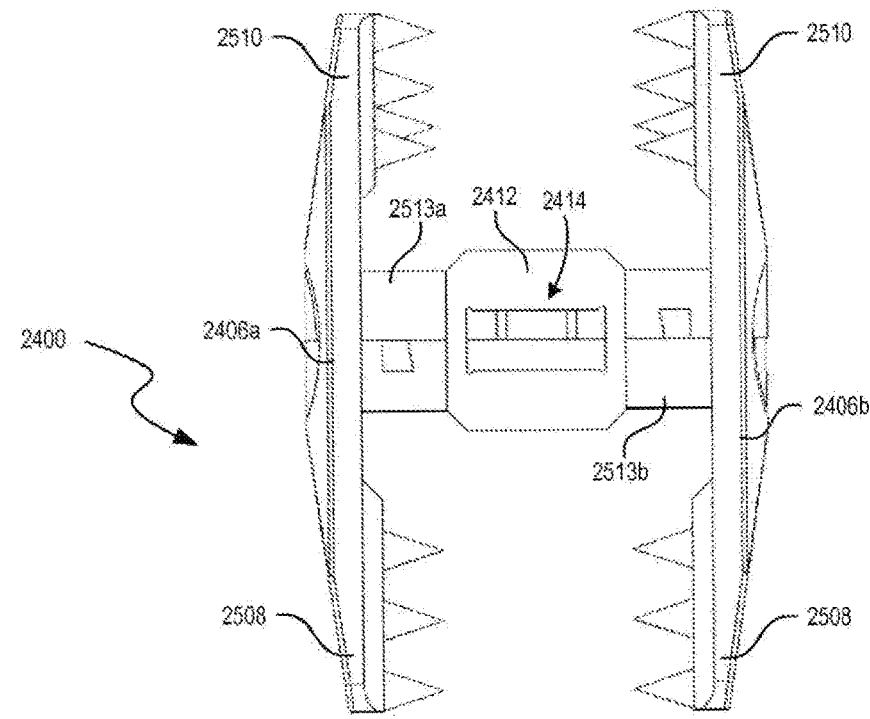
FIG. 25F is a bottom view of a spacer of the assembly illustrated in FIGS. 24A-24E.

FIGS. 25A and 25B are isometric views, FIG. 25C is an end view, FIG. 25D is a side view, FIG. 25E is a top view, and FIG. 25F is a bottom view of the spacer 2400 of FIGS. 24A-24E. Referring to FIGS. 25A-25F together, the spacer 2400 includes the wings 2406 movably coupled to the body 2412, as well as the actuator assembly 2414 operably coupled to the body 2412 and the wings 2406. Each wing 2406 includes a first or proximal end portion 2508 opposite a second or distal end portion 2510. The proximal end portion 2508 of each wing 2406 is configured to contact or engage the plunger 2472 (FIG. 24A) to allow the plunger 2472 to rotate the wings 2406 relative to the body 2412. Each of the first and second end portions 2408, 2410 also includes the multiple engagement features 2411 configured to contact and engage corresponding spinous processes (e.g., spinous processes 102 illustrated in FIG. 1). The spacer 2400 further includes a first wing carrier or guide 2513a (e.g., a pin or a shaft) that couples the first wing 2406a to the body 2412 and the actuator assembly 2414, as well as a second wing carrier or guide 2513b that couples the second wing 2406b to the body 2412 and the actuator assembly 2414.

Figure 25G:
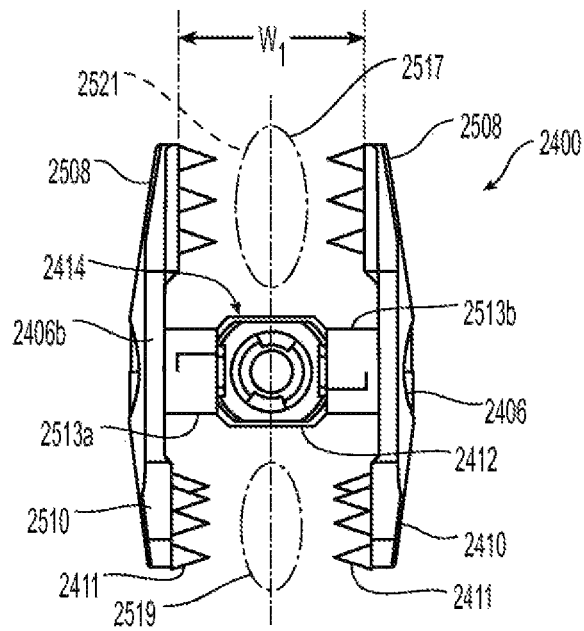
FIG. 25G is a top view of the assembly ready to clamp onto adjacent spinous processes.
Figure 25H:
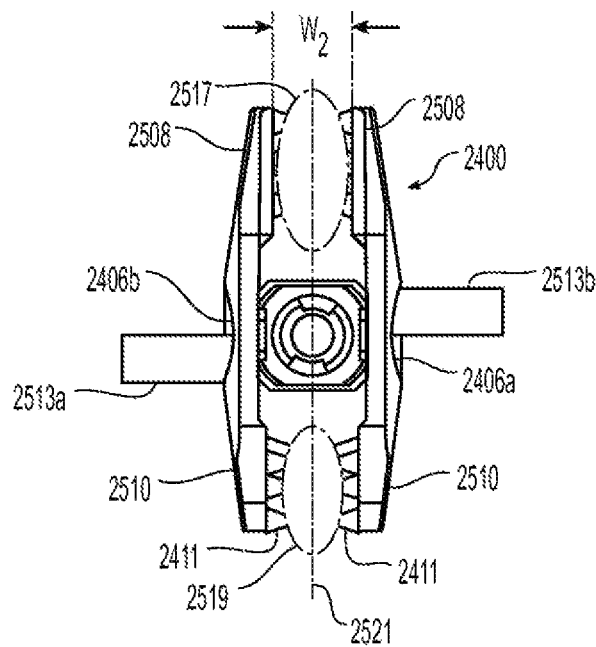
FIG. 25H is a top view of the spacer clamped onto the adjacent spinous processes.

As described in detail below, the guides 2513 interact with the actuator assembly 2414 to urge, drive, clamp, slide, translate or otherwise move the wings 2406 with reference to the body 2412 from the partially deployed configuration (e.g., fully rotated position) to the fully deployed configuration. In FIGS. 25A-25G, the spacer 2400 is shown in the partially deployed configuration with the wings 2406 fully rotated but still spaced apart from the body 2412. More specifically, the body 2412 includes a body longitudinal axis $L_1$ and each wing 2406 includes a wing longitudinal axis $L_2$ (FIG. 25A). In the partially deployed position the wings 2406 are oriented such that their corresponding wing longitudinal axes $L_2$ are at least generally perpendicular to the body longitudinal axis $L_1$. FIG. 25G shows the wings 2406 on opposing sides of a superior spinous process 2517 and an inferior spinous process 2519. Moreover, in the fully deployed position, the wings 2406 are positioned adjacent to the body 212 thereby reducing a width W (FIGS. 25A, 25G, and 25H) between the wings 2406. The width W can be configured to allow the wings 2406 and engagement features 2411 to engage corresponding spinous processes. For example, FIG. 25G shows the width $W_1$. The wings 1406 can be moved towards one another to embed the one or more of the engagement features 2411 of each wing 2406 into the spinous processes 2517, 2519. FIG. 25H shows the width $W_2$ which can be less than about 10%, 20%, 50%, or 90% of the width $W_1$. As shown in FIGS. 25G and 25H, both wings 2406 can be moved towards the sagittal plane 2521. As described in detail below, the wings 2406 can rotate relative to the body 2412, as well as slide or translate relative to the body 2412, between at least the first or undeployed position, the second or partially deployed position, and the third or fully deployed position.

The engagement features 2411 have generally conical shapes to minimize, limit, or substantially eliminate stress concentrations at edges or tips of the engagements features 2411. Stress concentrations can be controlled to inhibit damage (e.g., crack initiation, crack growth, etc.) of the bone tissue of the spinous processes 2517, 2519. In other embodiments, the engagement features 2411 can have pyramidal shapes, tapered shapes, or the like.

Figure 26:
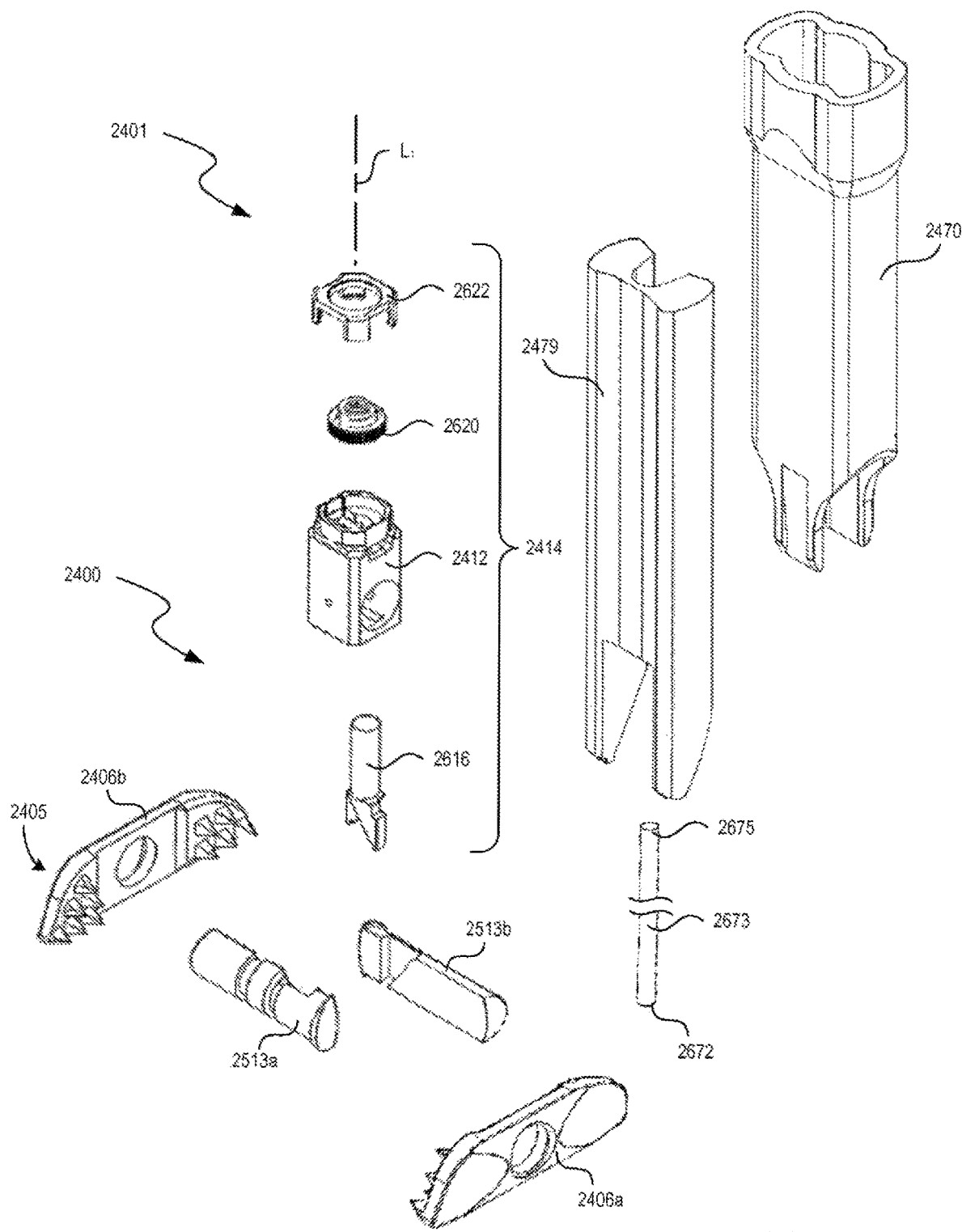
FIG. 26 is an exploded isometric view of the assembly and the spacer illustrated in FIGS. 24A-25H.

FIG. 26 is an exploded isometric view of the assembly 2401 and the spacer 2400 illustrated in FIGS. 25A-25F. As shown in the illustrated embodiment, the actuator assembly 2414 includes the guides 2513, an actuator 2616, an actuator adjuster or wheel 2620, and a cover 2622. The actuator assembly 2414 is operably coupled to, or can include, the body 2412 and the wings 2406 to move the clamp assembly 2405 between the partially deployed and fully deployed configurations. More specifically, rotation of the actuator adjuster 2620 about the body longitudinal axis $L_1$ threadably engages and moves the actuator 2616 within the body 2412 in directions parallel to the body longitudinal axis $L_1$. As the actuator 2616 moves within the body 2412, the actuator 2616 drives or urges the guides 2513 to slide or translate the corresponding wings 2406 relative to the body 212 between the partially deployed (e.g., fully rotated) and deployed configurations to decrease or increase a width between the wings 2406. As such, the actuator 2616 functions as a wing 2406 sliding driver. Further details and features of the individual components illustrated in FIG. 26 are described below with reference to FIGS. 27E-35C.

The assembly 2401 also includes the plunger 2472 configured to be movably received within the cannula 2470, as well as a driver shaft 2673 configured to be movably received within the plunger 2472. The driver shaft 2673 includes a proximate end portion 2675 opposite a distal end portion 2677. The distal end portion 2677 is configured to engage or contact the actuator assembly 2414 to actuate the actuator assembly 2414. The proximal end portion 2675 can be configured to attach to an actuating mechanism or device within the cannula 2470 or positioned outside of the cannula 2470 opposite the spacer 2400. As described in detail below, the plunger 2479 moves relative to the cannula 2470 to contact and rotate the wings 2406 prior to clamping the wings 2406 via the actuator assembly 2414 and corresponding driver shaft 2673.

Figure 27A:
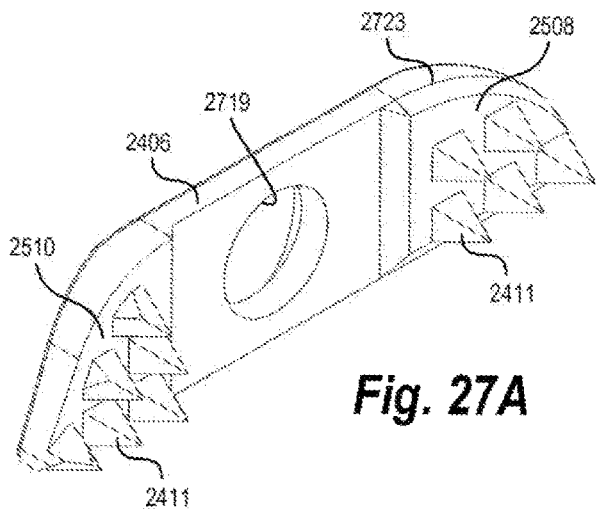
FIG. 27A is an isometric view.
Figure 27B:
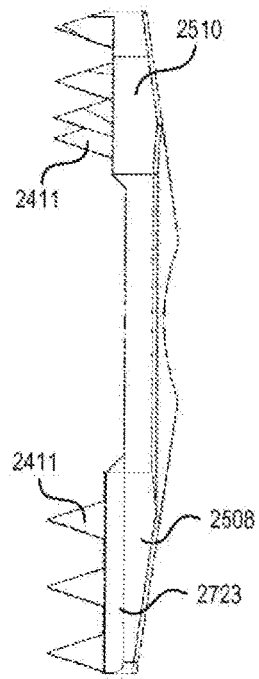
FIG. 27B is a top plan view.
Figure 27D:
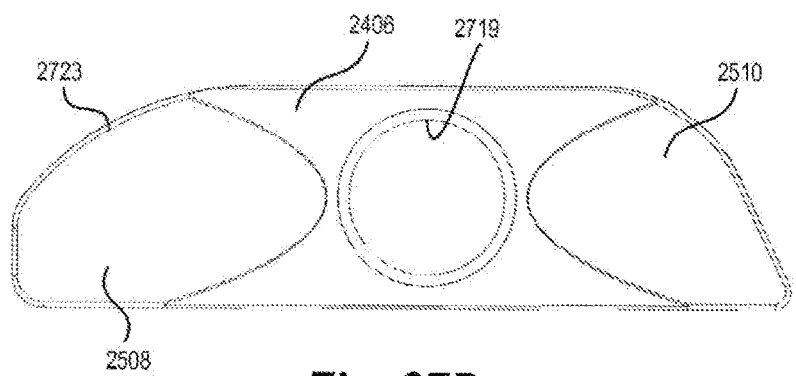
FIGS. 27D and 27E are side views of a wing configured in accordance with an embodiment of the disclosure.
Figure 27C:
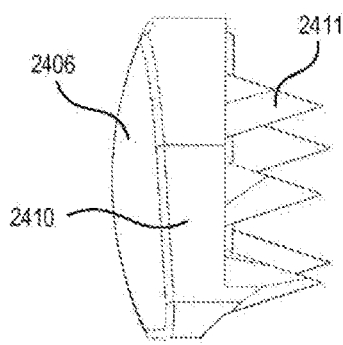
FIG. 27C is an end view.
Figure 27E:
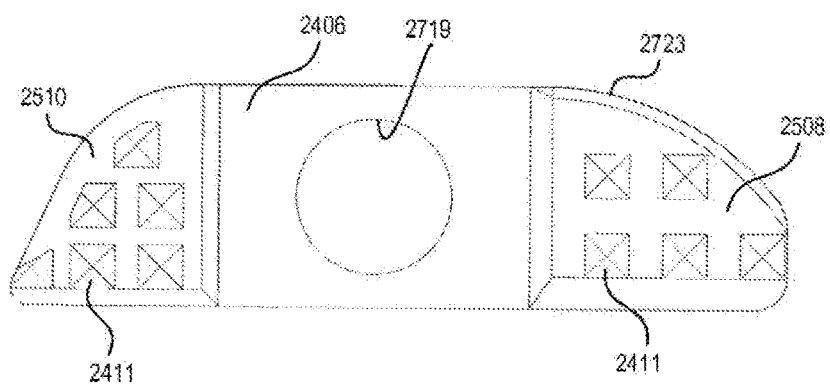

FIG. 27A is an isometric view, FIG. 27B is a top view, FIG. 27C is an end view, and FIGS. 27D and 27E are side views of the wing 2406. The wing 2406 represented in FIGS. 27A-27E is representative of each of the first and second wings 2406a, 2406b illustrated in FIGS. 24A-26. Referring to FIGS. 27A-27E together, the wing 2406 includes the first end portion 2508 and the second end portion 2510, each of which carries the engagement features 2411. As shown in FIGS. 27D and 27E, the first and second end portions 2508, 2510 can have a generally curved outer edge portion. The curvature of the outer edge portion 2723 is a camming surface of the first end portion 2408 that is configured to contact the plunger 2472 to rotate the wing 2406 as the plunger 2472 moves distally or out of the cannula 2470 (FIG. 24A). As such, the outer edge portion 2723 acts as a camming surface or camming feature of the wing 2406 to rotate or pivot the wing 2406 from the undeployed configuration to the partially deployed configuration. The curved outer edge portions of the wing 2406 can further be configured to facilitate or ease rotation of the wing 2406 as the wing 2406 rotates into the partially deployed configuration. For example, the wings 2406 can include chamfers, recesses, or other features that provide clearance with adjacent anatomical structures. The wing 2406 further includes an opening 2719 configured to at least partially receive the corresponding guide 2513 (FIG. 26), which carries the wing 2406 relative to the body 2412 (FIG. 24A) to pivot and slide the wing 2406 relative to the body 2412.

Figure 28A:
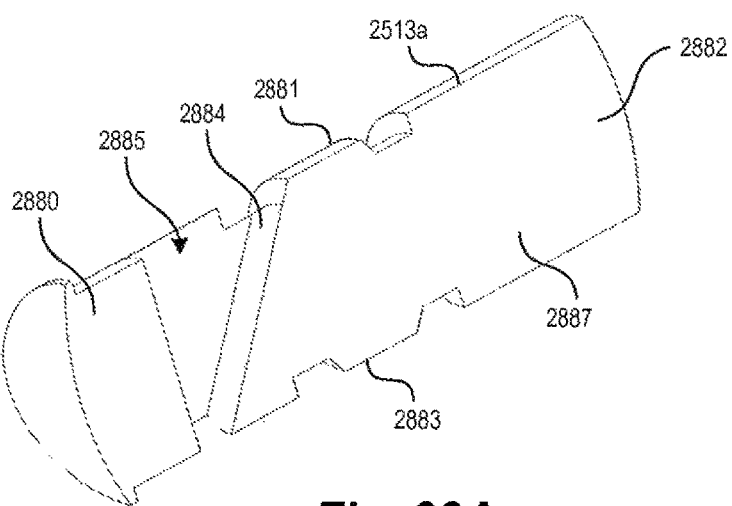
FIG. 28A is an isometric view and FIGS. 28B and 28C are side views of a first guide configured in accordance with an embodiment of the disclosure.
Figure 28B:
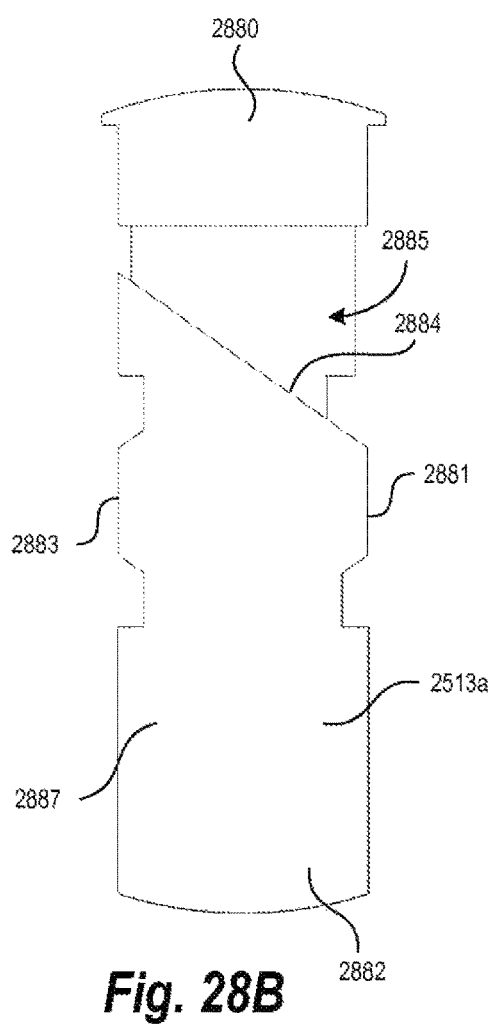
Figure 28C:
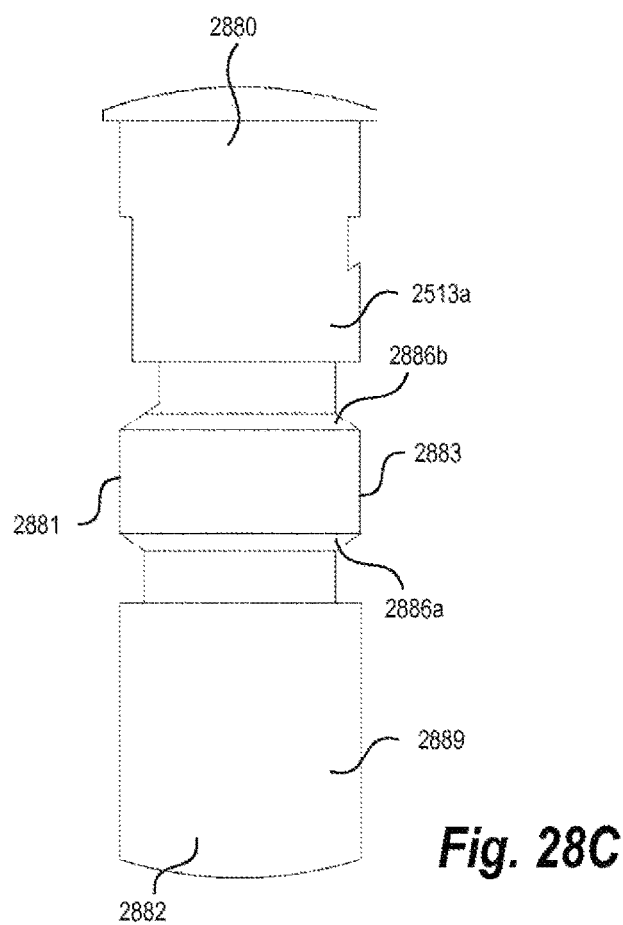

FIG. 28A is an isometric view and FIGS. 28B and 28C are side views of the first guide 2513a. Referring to FIGS. 28A-28C together, the first guide 2513a includes a first end portion 2880 opposite a second end portion 2882. The first end portion 2880 is configured to be coupled to the opening 2719 in the corresponding first wing 2406a, and the second end portion 2882 is configured to extend into the body 2412 (FIG. 25A). The first guide 2513a further includes a generally planar interior surface 2887 opposite a curved exterior surface 2889. The interior surface 2887 is configured to slidingly mate against a corresponding interior surface of the second guide 2513b. The exterior surface 2889 has a generally semi-circular cross-sectional shape such that the mated first and second guides 2513 together have a generally cylindrical shape. The second exterior surface 2889 also includes alignment channels 2886 (identified individually as a first alignment channel 2886a and a second alignment channel 2886b).

According to additional features of the illustrated embodiment, the first guide 2513a also includes a first guide engagement or camming surface 2884. The first guide camming surface 2884 extends at an inclined angle relative to a longitudinal axis of the first guide 2513a. Moreover, the first guide camming surface 2844 tapers from a first or top side 2881 to a second or bottom side 2883 of the first guide 2513a within a channel 2885 extending into the interior surface 2887. As described in detail below, the channel 2885 is configured to at least partially receive a portion of the actuator 2616 (FIG. 26) to allow rotation of guides 2513 and to the first guide camming surface 2884 to engage or mate with a portion of the actuator 2616 to slide or otherwise move the corresponding first wing 2406a via the actuator 2616.

Figure 29A:
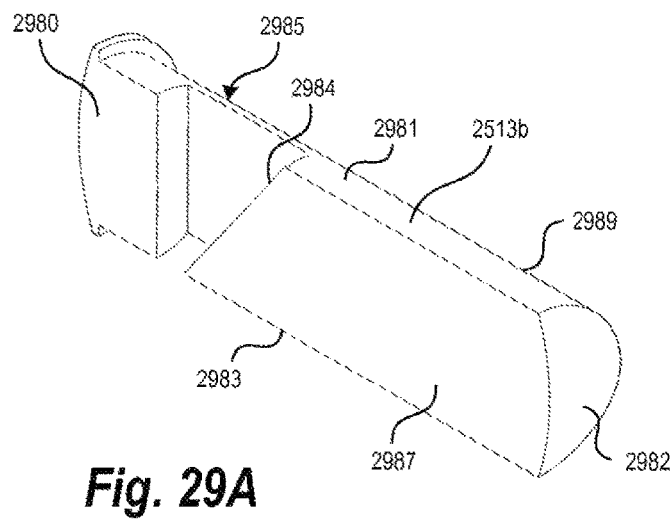
FIG. 29A is an isometric view and FIGS. 29B and 29C are side views of a second guide configured in accordance with an embodiment of the disclosure.
Figure 29B:
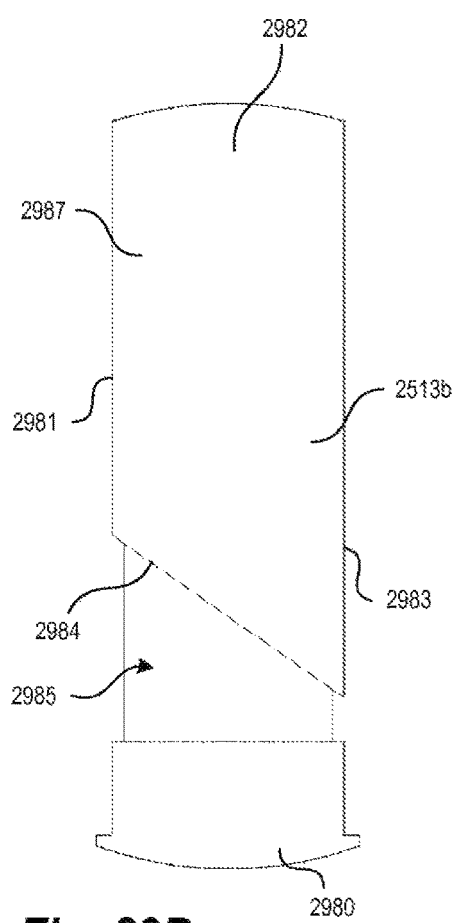
Figure 29C:
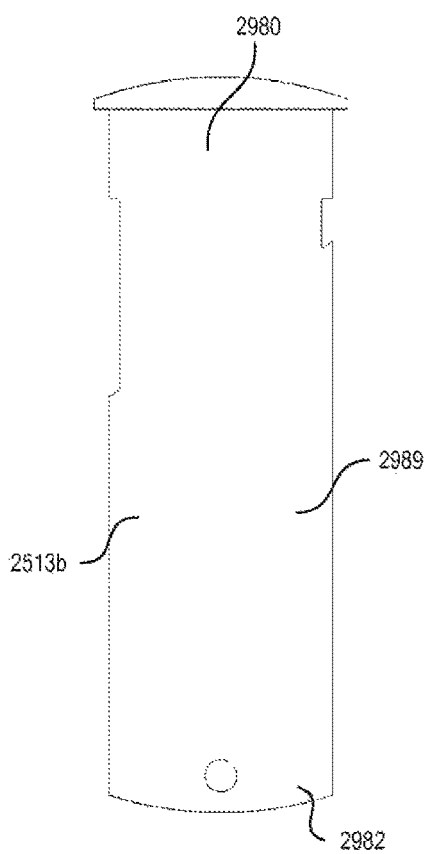

FIG. 29A is an isometric view and FIGS. 29B and 29C are side views of the second guide 2513b. Referring to FIGS. 29A-29C together, the second guide 2513b includes several features that are generally similar in structure and function to the first guide 2513a. For example, the second guide 2513b includes a first end portion 2980 opposite a second end portion 2982. The first end portion 2980 is configured to be coupled to the opening 2719 in the corresponding second wing 2406b, and the second end portion 2982 is configured to extend into the body 2412 adjacent to the first guide 2513a. The second guide 2513b further includes a generally planar interior surface 2987 opposite an exterior surface 2989, as well as a first or top side 2981 opposite a second or bottom side 2983. The second guide 2513b also includes a second guide engagement or camming surface 2984. The second guide camming surface 2984 extends at an inclined angle relative to a longitudinal axis of the second guide 2513b and tapers within a channel 2985 from the first side 2981 to the second side 2983. As described in detail below, the channel 2985 is configured to at least partially receive a portion of the actuator 2616 (FIG. 26) to allow the second guide camming surface 2984 to engage or mate with a portion of the actuator 2616 to slide or otherwise move the corresponding second wing 2406b via the actuator 2616.

Figure 30F:
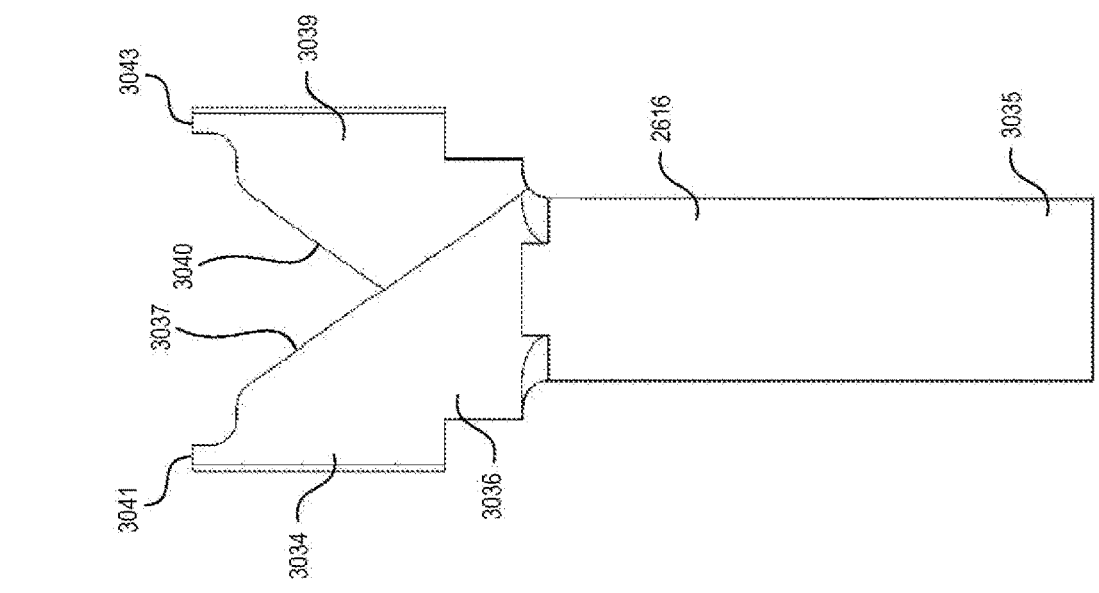
FIG. 30F is a rear view of an actuator configured in accordance with an embodiment of the disclosure.
Figure 30E:
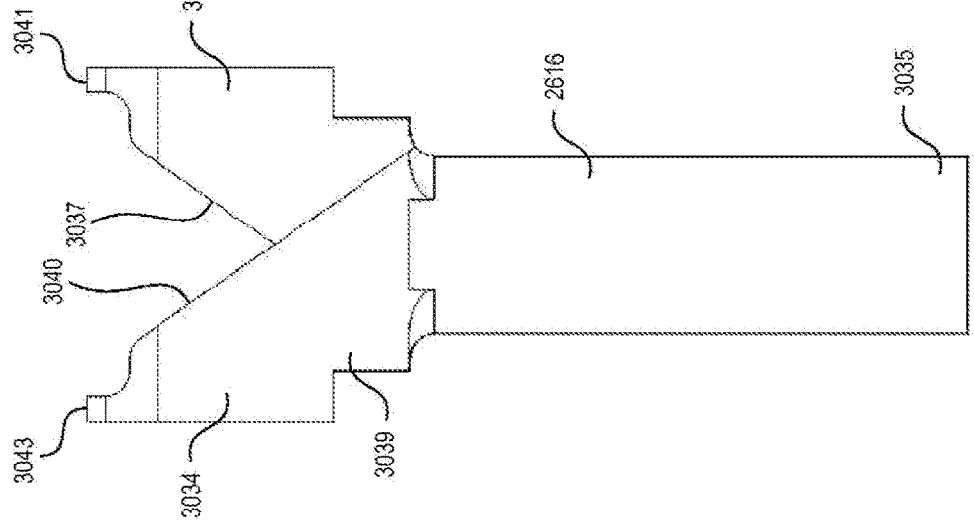
FIG. 30E is a front view.
Figure 30D:
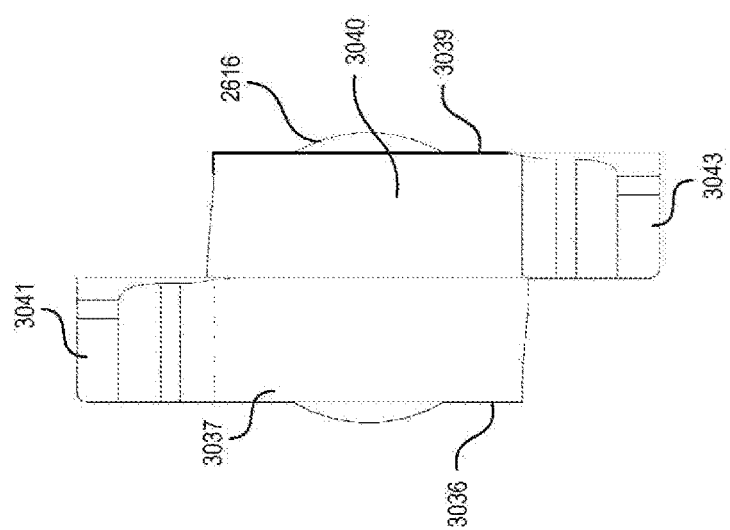
FIG. 30D is an end view.

FIG. 30A is a side view, FIGS. 30B and 30C are isometric views, FIG. 30D is an end view, FIG. 30E is a front view, and FIG. 30F is a rear view of the driver or actuator 2616. Referring to FIGS. 30A-30F together, the actuator 2616 includes a distal end portion 3034 opposite a proximal end portion 3035. The proximal end portion 3035 can be a threaded shaft that threadably engages the actuator adjustor or wheel 2620 (FIG. 26). The distal end portion 3034 includes separate features for moving the corresponding wings 2406 between the partially deployed configuration (e.g., fully rotated but not clamped or drawn together) to the fully deployed configuration (e.g., fully rotated and clamped or drawn together). For example, the distal end portion 3034 includes a first camming feature 3036 and a second camming feature 3039. The first camming features 3036 is generally parallel to and offset from the second camming feature 3039. Moreover, the first camming feature 3036 includes an angled or ramped first camming surface 3037 that is configured to contact the first engagement or camming surface 2884 of the first guide 2513a (FIGS. 28A-28C) to slide or translate the first wing 2406a from the intermediately deployed configuration to the fully deployed configuration. The second camming feature 3039 forms an offset V-shaped intersection with the first camming feature 3036 and includes a converging ramped second camming surface 3040. The second camming surface 540 is configured to contact the second guide engagement surface 2984 of the second guide 2513b to slide or translate the second wing 2406b from the intermediately deployed configuration to the fully deployed configuration. As such, the first camming feature 3036 and/or the first camming surface 3037, as well as the second camming feature 3039 and/or the second camming surface 3040 act as translation or sliding drivers to clamp or otherwise draw the wings 206 together. According to additional features of the illustrated embodiment, the first camming feature 3036 includes a pointed or peaked end portion 3041, and the second camming feature 3039 includes a corresponding pointed or peaked end portion 3043. The end portions 3041, 3043 are configured to facilitate insertion of the first and second camming features 3036, 3039 into the channels 2885, 2985 in the corresponding first and second guides 2513a, 2513b.

Figure 31A:
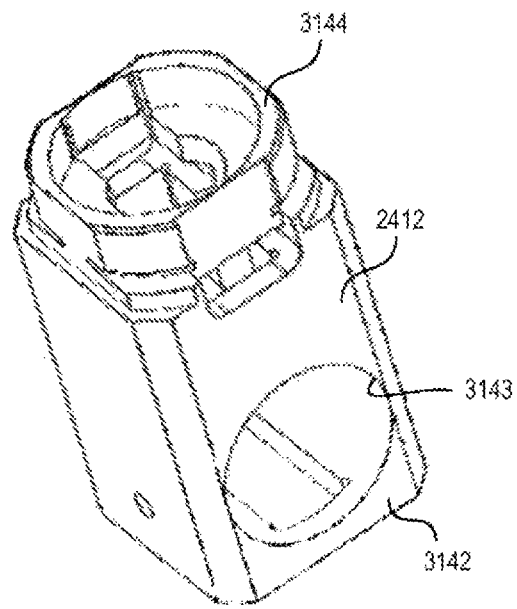
FIG. 31A is an isometric view and FIG. 31B is a side view of a body configured in accordance with an embodiment of the disclosure.
Figure 31B:
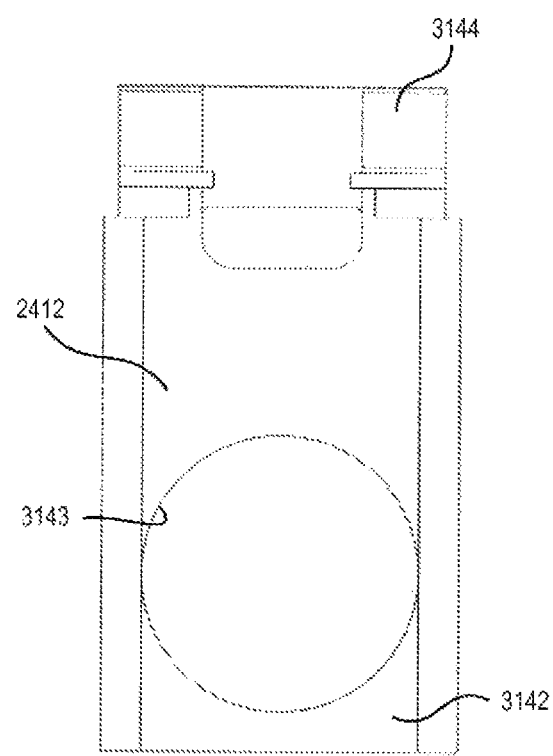

FIG. 31A is an isometric view and FIG. 31B is a side view of the body 2412.

Referring to FIGS. 31A and 31B together, the body 2412 is generally configured to fit between adjacent spinous processes and to at least partially receive portions of the guides 2513, actuator 2616, wheel 2620 and cover 2622 (FIG. 26) in a central portion thereof. The body 2412 includes a proximal end portion 3144 opposite a distal end portion 3142. The proximal end portion 3144 is configured to engage the cover 2622 and at least partially retain and position the wheel 2620 between the cover 2622 and the guide body 2412 (FIG. 26). The distal end portion 3142 includes an opening 3143 extending therethrough that is configured to receive the corresponding guides 2513.

Figure 32A:
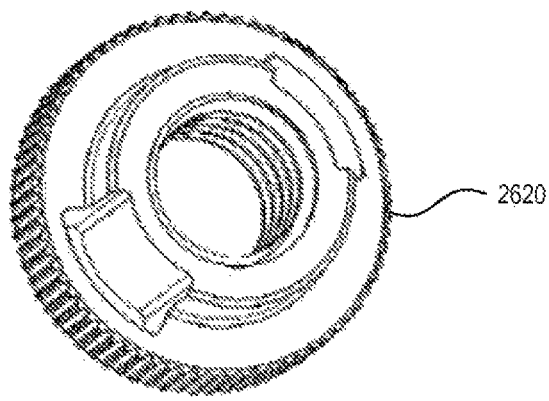
FIGS. 32A and 32B are isometric views and FIG. 32C is a side view of an actuator adjuster or wheel configured in accordance with an embodiment of the disclosure.
Figure 32B:
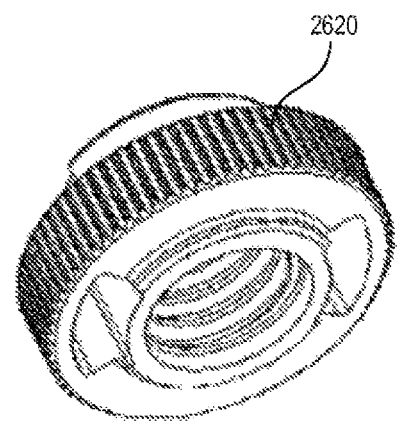
Figure 32C:
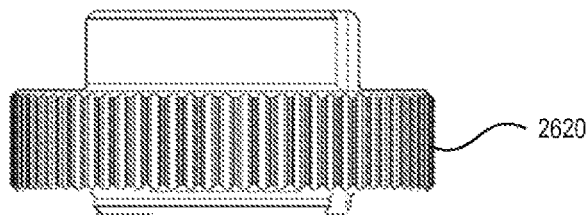

FIGS. 32A and 32B are isometric views and FIG. 32C is a side view of the actuator adjuster or wheel 2620, which is generally similar in structure and function to the actuator adjusters described above with reference to FIGS. 8A and 8B and FIGS. 19A and 19B.

Figure 33A:
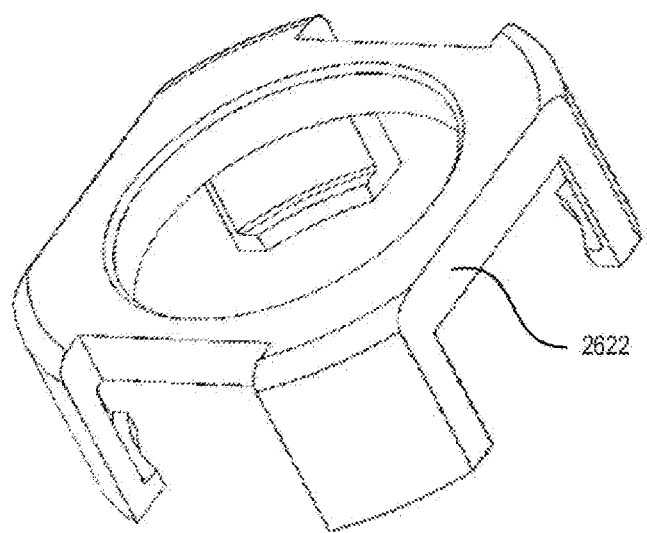
FIGS. 33A and 33B are isometric views of a cover configured in accordance with an embodiment of the disclosure.
Figure 33B:
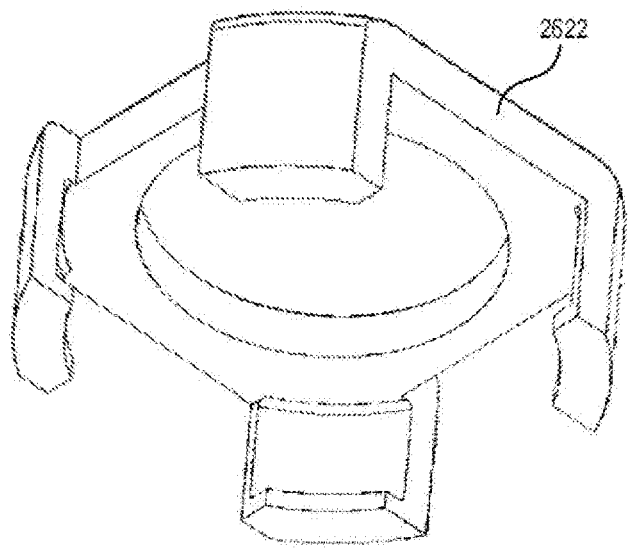

FIGS. 33A and 33B are isometric views of the cap or cover 2622, which is generally similar in structure and function to the cap or covers described above with reference to FIGS. 9A and 9B and FIGS. 20A and 20B.

FIG. 34A is an isometric view, FIGS. 34B and 34C are side views, and FIG. 34D is an end view of the cannula 2470. Referring to FIGS. 34A-34D together, the cannula 2470 is configured and sized to be at least partially inserted into a patient to deliver and deploy the spacer 2400. For example, the cannula 2470 includes a delivery passage 3487 (e.g., an opening) extending from a proximal end portion 3486 to an opposite distal end portion 3488. The delivery passage 3487 is configured to movably receive at least the components described above with reference to FIG. 26 such that these components can move along a longitudinal axis L of the cannula 2470 to at least partially insert and/or withdraw these components from a patient. As shown in the illustrated embodiment, the distal end portion 3488 includes a pair of spaced apart extension portions 3489 (identified individually as a first extension portion 3489a and a second extension portion 3489b).

FIG. 35A is an isometric view and FIGS. 35B and 35C are side views of the actuator or plunger 2472. Referring to FIGS. 35A-35C together, the plunger 2472 is configured to be slidably positioned within the cannula 2470 (FIGS. 34A-34D) to move in directions generally parallel to the longitudinal axis L of the cannula 2470. More specifically, the plunger 2472 is configured to be positioned coaxially within the cannula 2470 and can include a generally complementary cross-sectional shape and/or integral guide features to facilitate axial movement within the cannula 2470. The plunger 2472 includes a receiving feature 3598 (e.g., channel, recess, etc.) extending from a proximal end portion 3590 to an opposite distal end portion 3592. The channel 3598 is configured to at least partially receive or otherwise allow for additional components (e.g., a dialator, a series of dialators, cutting tools, etc.) to move through plunger 2472 and/or the cannula 2470 (e.g., drive shaft 2673 shown in FIG. 26).

According to additional features of the illustrated embodiment, the distal end portion 3592 of the plunger 2472 includes opposed camming features 3594 (identified individually as a first camming feature 3594a and a second camming feature 3594b). Each camming feature 3594 includes a pusher end 3596 with a curved camming or engagement surface 3595. The engagement surface 3595 of each camming feature 3594 is configured to contact the corresponding outer edge portion 2723 of each wing 2406 (FIG. 27A-27E) to slide along the surface of the corresponding outer edge portion 2723 to rotate or pivot the wings 2406 from an undeployed configuration to a partially or intermediately deployed configuration (e.g., to a fully rotated position). In the undeployed or low-profile configuration, each wing 2406 is positioned such that a longitudinal axis of each wing 2406 is generally parallel to a longitudinal axis of the spacer 2400 or the assembly 2401. In the partially deployed configuration, each wing 2406 is rotated or pivoted such that their corresponding longitudinal axes are at least generally perpendicular to the longitudinal axis of the spacer 2400 or the assembly 2401.

Figure 36A:
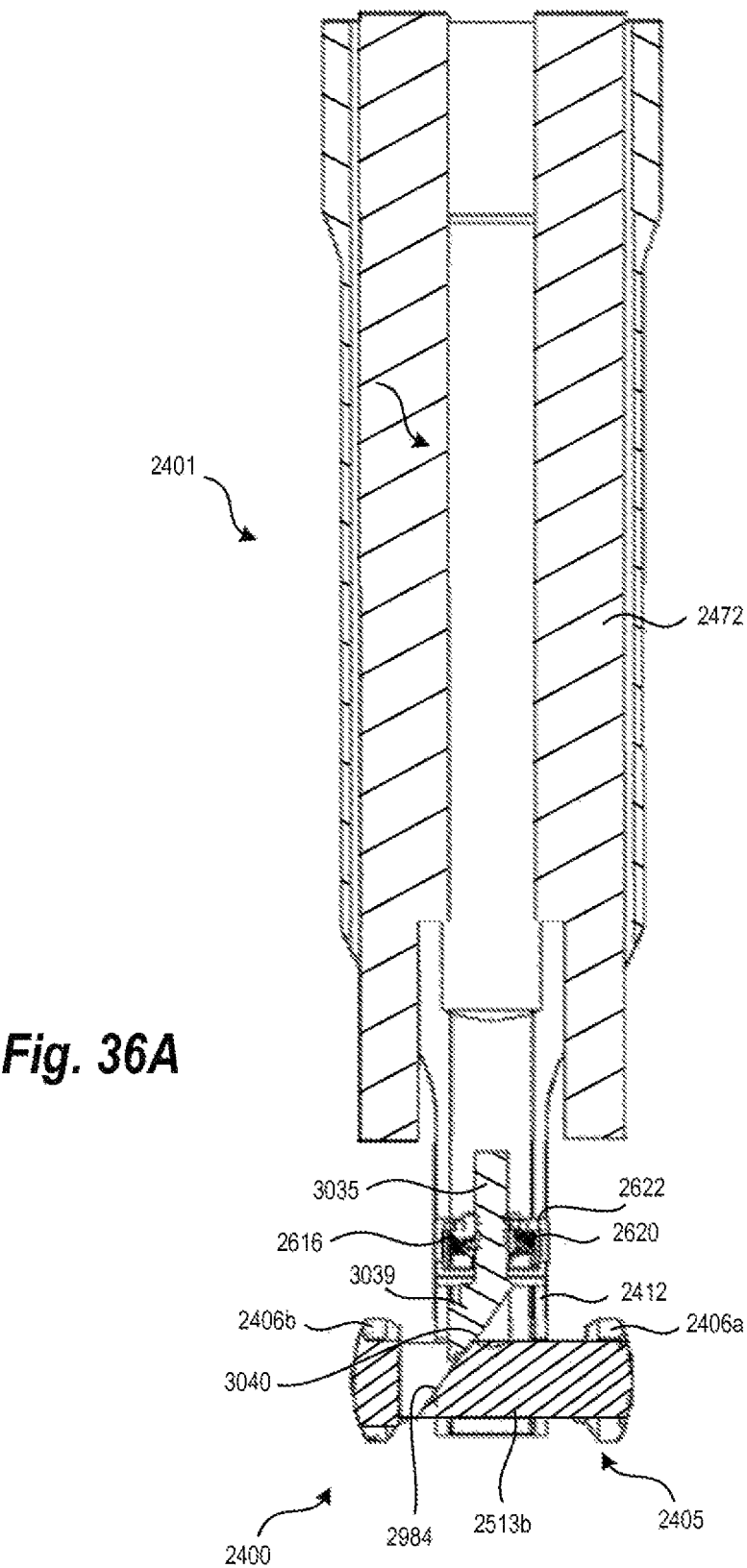
FIG. 36A is a cross-sectional side view of the assembly taken substantially along lines 36A-36A of FIG. 24B.

FIG. 36A is a cross-sectional side view taken substantially along lines 36A-36A of FIG. 24B. The cross-sectional view shown in FIG. 36A illustrates the relative positions of several components of the assembly 2401 and the spacer 2400 when the spacer 2400 is in a partially deployed configuration with the clamp assembly 2405 fully rotated relative to the body 2412 but spaced apart from the body 2412. For example, FIG. 36A illustrates the extension portions or camming features 3594 of the plunger 2472 in a retracted or spaced apart position from the corresponding wings 2406 after the plunger 2472 has contacted and rotated the wings 2406 to the fully rotated position shown in FIG. 36A. FIG. 36A also illustrates the wheel 2620 positioned between the cover 2622 and the body 2412, as well as a threaded bore of the wheel 2620 threadably engaged with the proximal end portion 3035 of the actuator 2616. Moreover, in the partially or intermediately deployed configuration, each wing 2406 is spaced apart from the corresponding sides of the body 212.

According to additional features of the embodiment illustrated in FIG. 36A, the second camming surface 3040 of the second camming feature 3037 of the actuator 2616 is positioned proximate to the second guide camming surface 2984 of the second guide 2513b. As such, when the actuator 2616 moves toward the second guide 2513, the second camming feature 3037 urges or drives the second guide 2513*b* to slide or translate the corresponding second wing 2406*b* toward the body 2412. More specifically, the second guide camming surface 2984 of the second guide 2513*b* slides along the second camming surface 3040 of the second camming feature 3037 of the actuator 2616 as the actuator 2616 moves relative to the body 2412. Although the interaction of the first camming feature 3036 of the actuator 2616 and the first guide 2513*a* are not shown in FIG. 36A, they operate in a manner similar to that described above with reference to the second camming feature 3039 and the second guide 2513*b*.

Figure 36B:
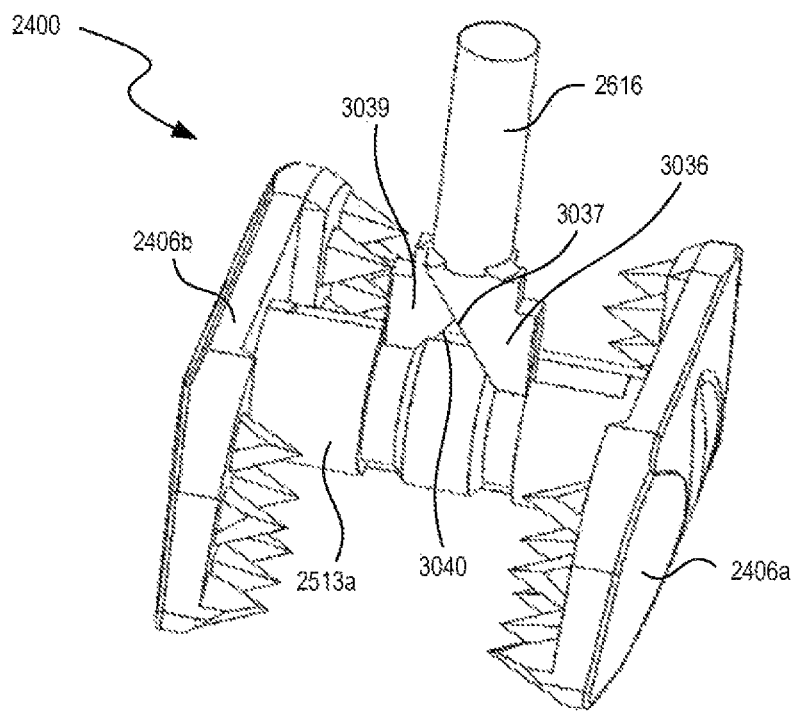
FIG. 36B is an isometric partial view of the spacer.
Figure 36C:
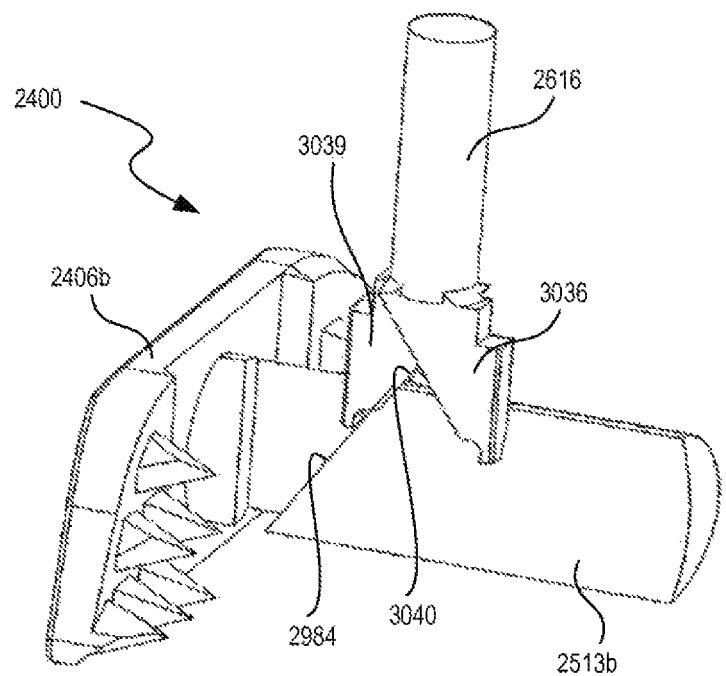
FIG. 36C is an isometric partial view of the spacer.

FIG. 36B is an isometric partial view of the spacer 2400 in the partially deployed position showing only the first and second wings 2406, the first and second guides 2513, and the actuator 2616, and with the remainder of the components of the spacer 2400 removed for purposes of illustration. As shown in FIG. 36B, the camming surfaces 3037, 3040 of the corresponding first and second camming features 3036, 3039 are positioned to contact or engage the corresponding camming surfaces of the first and second guides 2513. FIG. 36C, for example, which is an isometric partial view of the spacer 2400 shown in FIG. 36B with the first guide 2513*a* and the first wing 2406*a* removed for purposes of illustration, illustrates the positional relation of the second camming surface 3040 of the second camming feature 3037 of the actuator 2616 relative to the second guide camming surface 2984 of the second guide 2513*b* prior to the actuator 2616 driving or advancing the second guide 2513*b* and accompanying second wing 2406*b* to the fully deployed configuration.

Figures 37A, 37B, 37C:
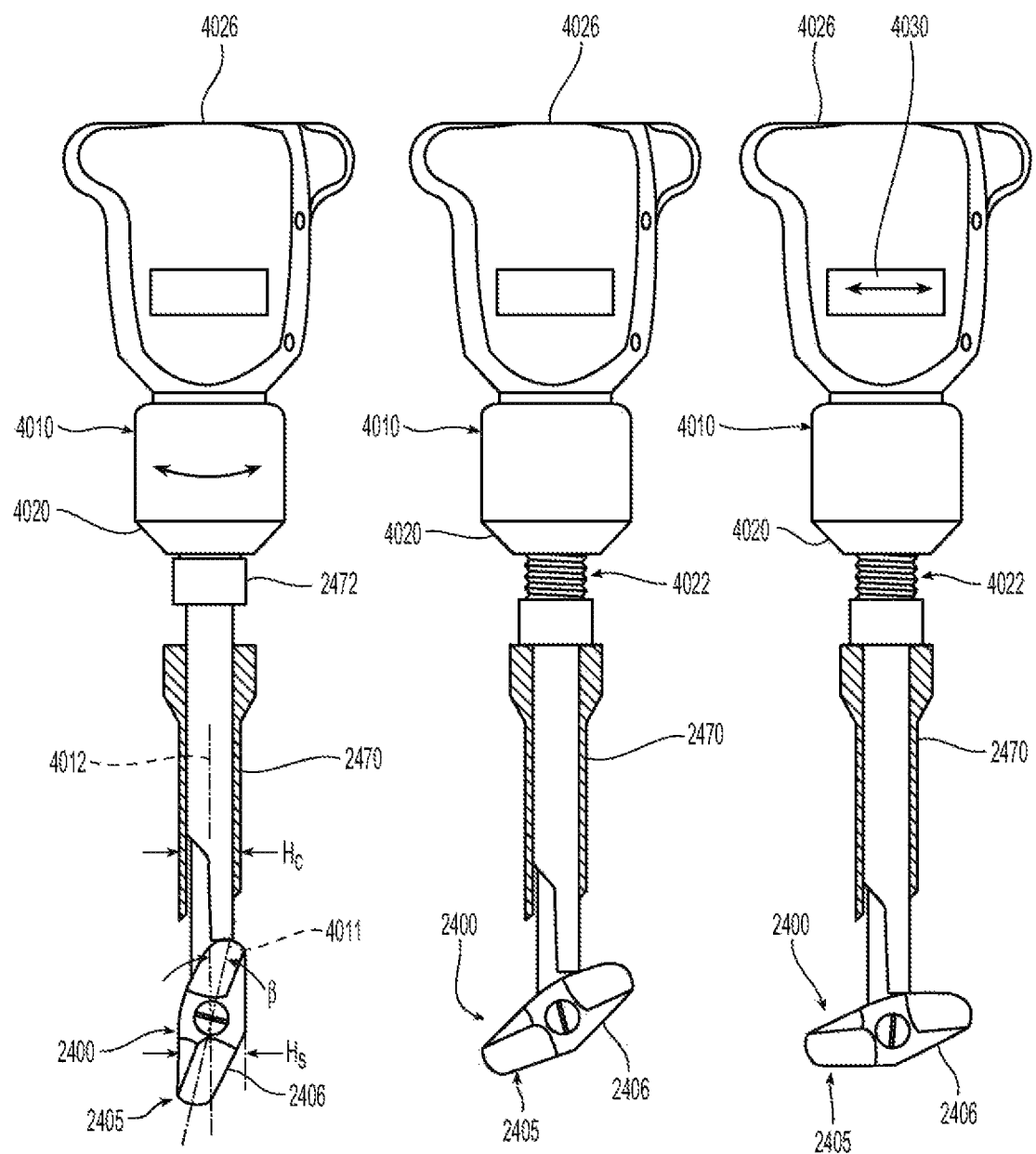
FIG. 37A is a side view of an instrument system coupled to a spacer in an undeployed configuration in accordance with embodiments of the disclosure.
FIG. 37B is a side view of the instrument system coupled to the spacer in an intermediate configuration.
FIG. 37C is a side view of the instrument system coupled to the spacer in a rotated configuration.

FIG. 37A is a side view of an instrument system 4000 coupled to the spacer 2400 in an undeployed configuration in accordance with embodiments of the disclosure. The instrument system 4000 includes the cannula 2470 (shown in cross section), plunger 2472, and a delivery instrument 4010. The wings 2406 can be generally parallel to the longitudinal axis of the main body of the spacer 2400 and/or the longitudinal axis 4012 of the cannula 2470. For example, an angle β can be equal to or less than about 20 degrees, 10 degrees, or 5 degrees. As viewed from the side, the height $H_s$ of the spacer 2400 can be equal to or less than a height $H_C$ of the cannula 2470. Such a low-profile system can be delivered along relatively narrow delivery paths to an interspinous space.

The delivery instrument 4010 can include a drive member 4020 (e.g., a dial, a handle, etc.) that can be rotated about a threaded region 4022 (FIG. 37B) of the plunger 2472 to move the plunger 2472 axially through the cannula 2470. The cannula 2470 and a handle 4026 can be held stationary while the drive member 4020 is rotated. The plunger 2472 can be used to move the wings 2406 to the fully rotated position of FIG. 37C. Another instrument (e.g., a driver, a torquing instrument, or the like) can be used to reconfigure (e.g., move, translate, rotate, etc.) the wings 2406.

After moving the clamping assembly 2405 to the clamping configuration, the delivery instrument 4010 is ready to be separated from the spacer 2400. A dial 4030 of FIG. 37C can be rotated to release the spacer 2400. In some embodiments, the dial 4030 is rotated to drive a push rod distally to push the spacer 2400 from the delivery instrument 4010.

Other types of delivery instruments and delivery techniques can be used to deploy the spacer 2400. U.S. Pat. No. 8,273,108, issued on Nov. 25, 2012, discloses instrument systems (e.g., insertion instruments, drivers, etc.), components, and techniques that can be used with the spacer 2400 and other medical devices disclosed herein. U.S. application Ser. No. 12/338,793, filed on May 28, 2009, discloses instrument systems (e.g., spacer insertion instruments), components, and techniques that can be used with the spacer 2400 and other medical devices disclosed herein. U.S. Pat. No. 8,012,207, issued on Sep. 6, 2011, discloses instruments, tools, and delivery techniques that can be used with embodiments disclosed herein. U.S. Pat. Nos. 8,012,207; 8,273,108 and U.S. application Ser. No. 12/338,793 are incorporated by reference in their entireties.

Figure 38A:
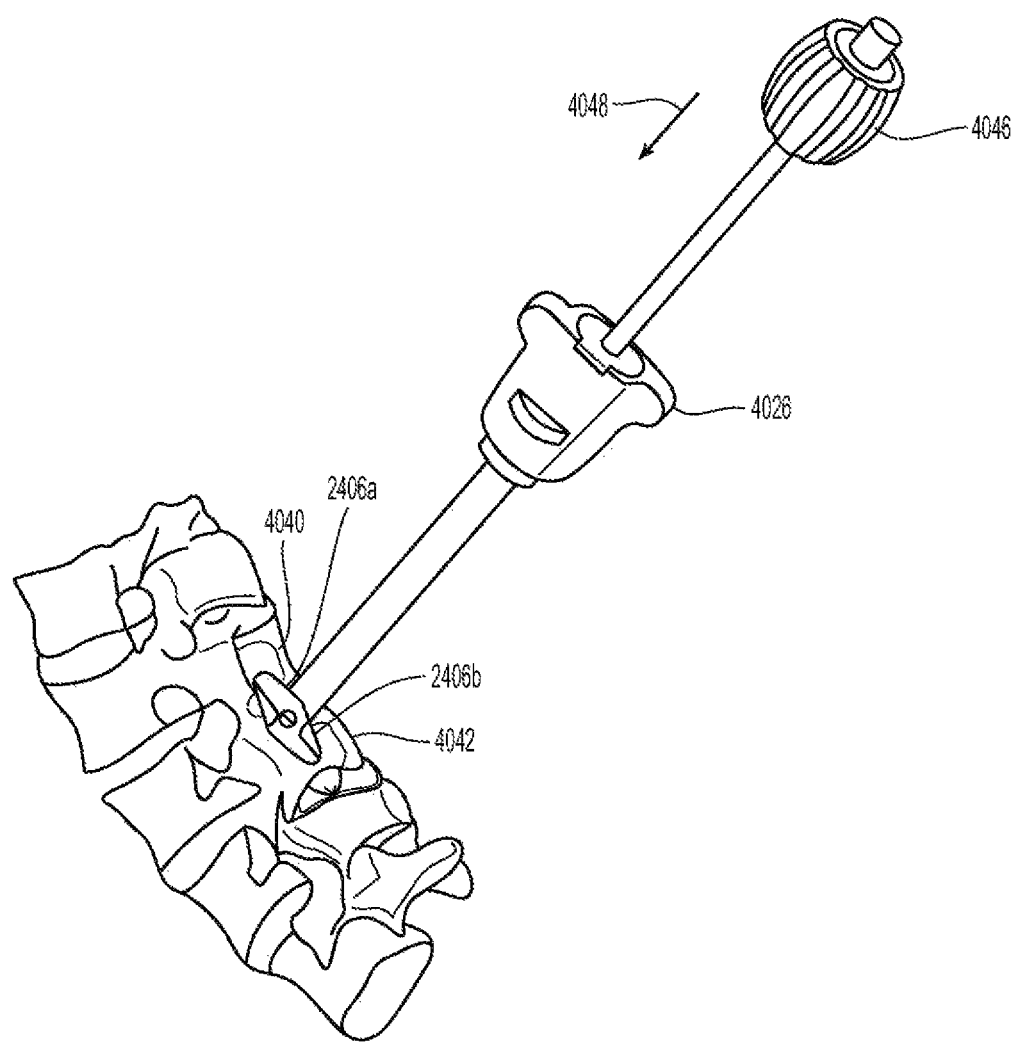
FIGS. 38A and 38B are a series of views of a method of implanting a spacer in accordance with embodiments of the disclosure.
Figure 38B:
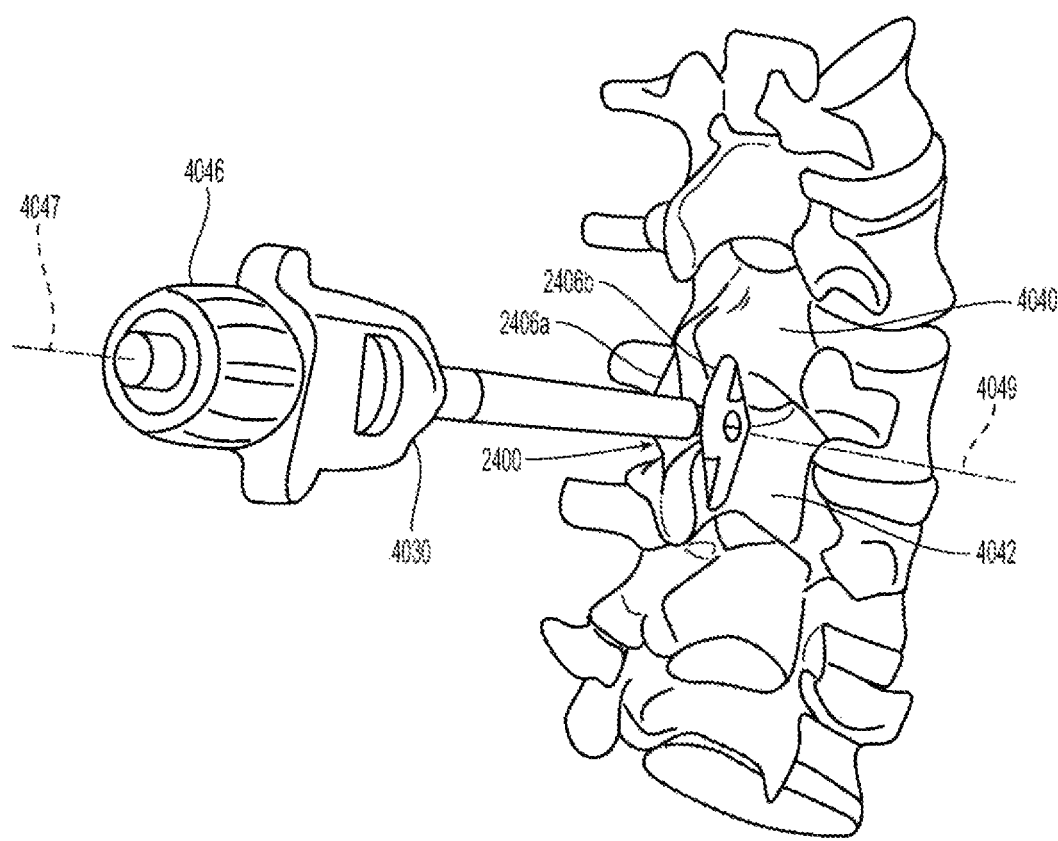
Figure 39:
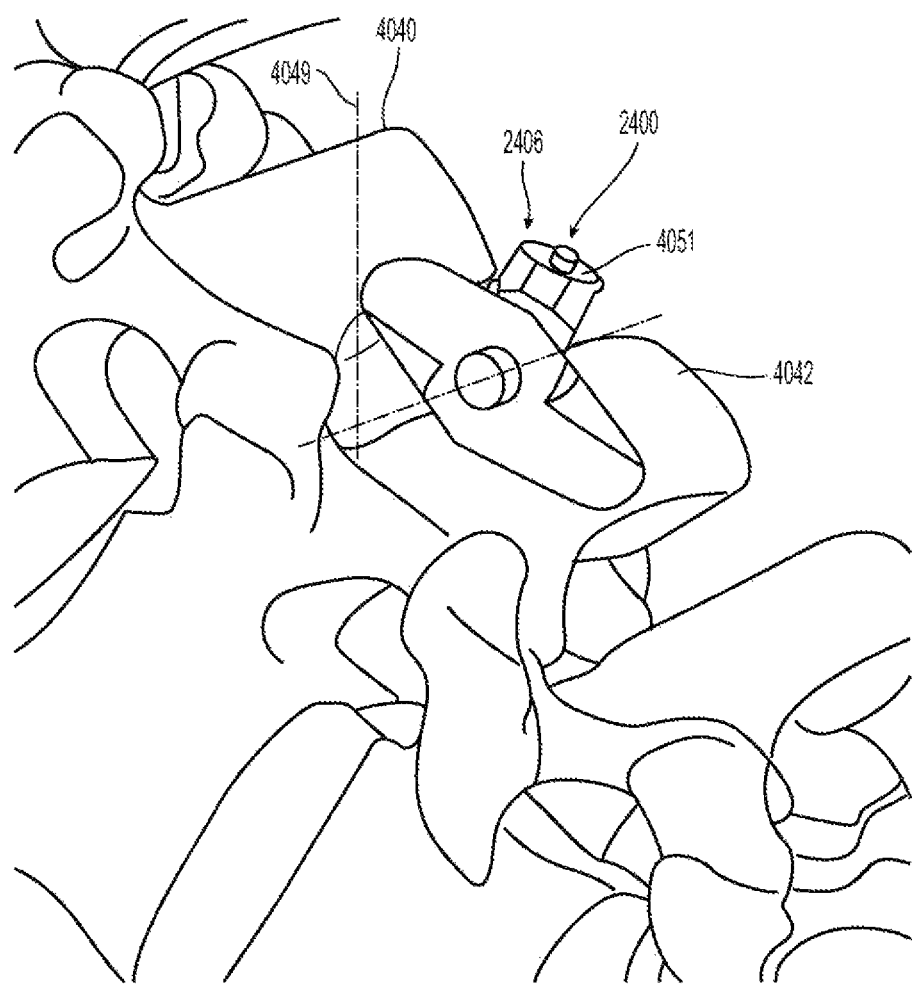
FIG. 39 is a view of a spacer implanted along a spin in accordance with embodiments of the disclosure.

FIGS. 38A, 38B, and 39 are a series of views of a method of implanting the spacer 2400. Generally, an incision can be made at a location posterior of an interspinous space. The spacer 2400 can be inserted anteriorly relative to the incision and into the interspinous space. In some procedures, the spacer 2400 can be moved anteriorly substantially along a midline relative to the superior and inferior spinous processes 4040, 4042. After positioning the spacer 2400, it can be reconfigured to clamp onto the spinous processes 4040, 4042.

Referring to FIG. 39A, the wings 2406*a*, 2406*b* are located on either side of adjacent spinous processes 4040, 4042. Soft tissue can be repositioned or removed to ensure that the wings 2406*a*, 2406*b* can contact the bone tissue. For example, soft tissue can be removed from between the wings 2406*a*, 2406*b* and lateral aspects of the spinous processes 4040, 4042. The position of the spacer 2400 can be evaluated using direct visualization, fluoroscopy (e.g., lateral fluoroscopy), or other suitable visualization techniques.

An instrument in the form of a driver 4046 can be inserted through the handle 4026, as indicated by arrow 4048. FIG. 39B shows the driver 4046 positioned to engage and rotate the adjuster or wheel 2620 (FIG. 26). When the driver 4046 is rotated about an axis of rotation 4047, the wings 2406*a*, 2406*b* can move towards one another to hold onto the spinous processes 4040, 4042. In some procedures, the axis of rotation 4047 can be at an anterior-posterior orientation. Additionally, the axis of rotation 4047 can be generally parallel to or lie within the sagittal plane of the patient. The actuator assembly 2414 of the spacer 2400 can covert rotary motion about the axis 4047 to linear motion of the wings 2406. The linear motion can be along an axis 4049 that is substantially perpendicular to the axis of rotation 4047 and/or the sagittal plane. The axis 4049 can also be at other generally transverse orientations.

After the spacer 2400 is clamped onto the spinous processes, the dial 4030 can be rotated to release an instrument interface of the spacer 2400. FIG. 39 shows the spacer 2400 and instrument interface 4051 after the instruments have been removed from the patient. Additional procedures can be performed. For example, additional spacers can be implanted and fusion procedures can be performed.

Figure 40A:
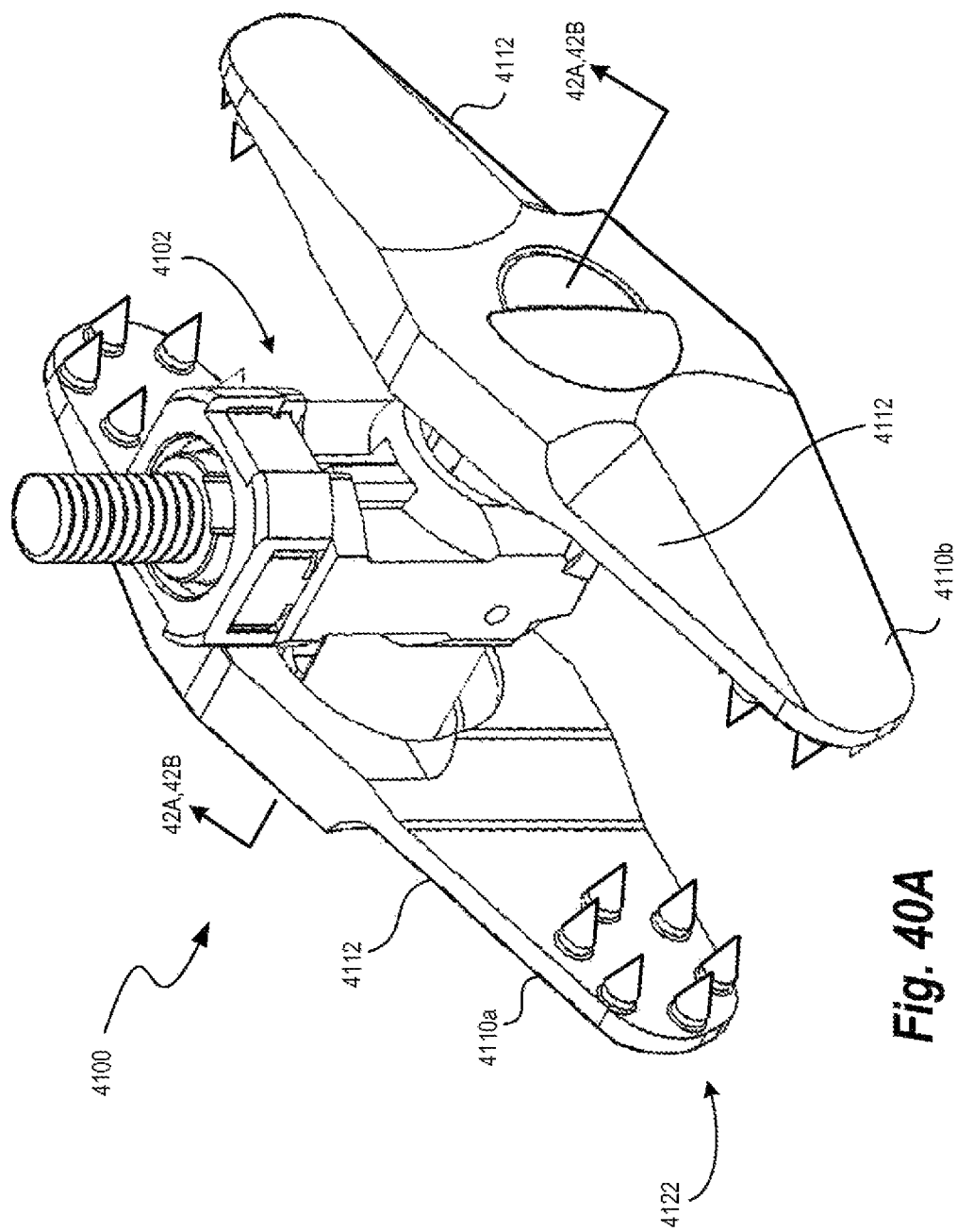
FIGS. 40A and 40B are views of a spacer in accordance with embodiments of the disclosure.
Figure 40B:
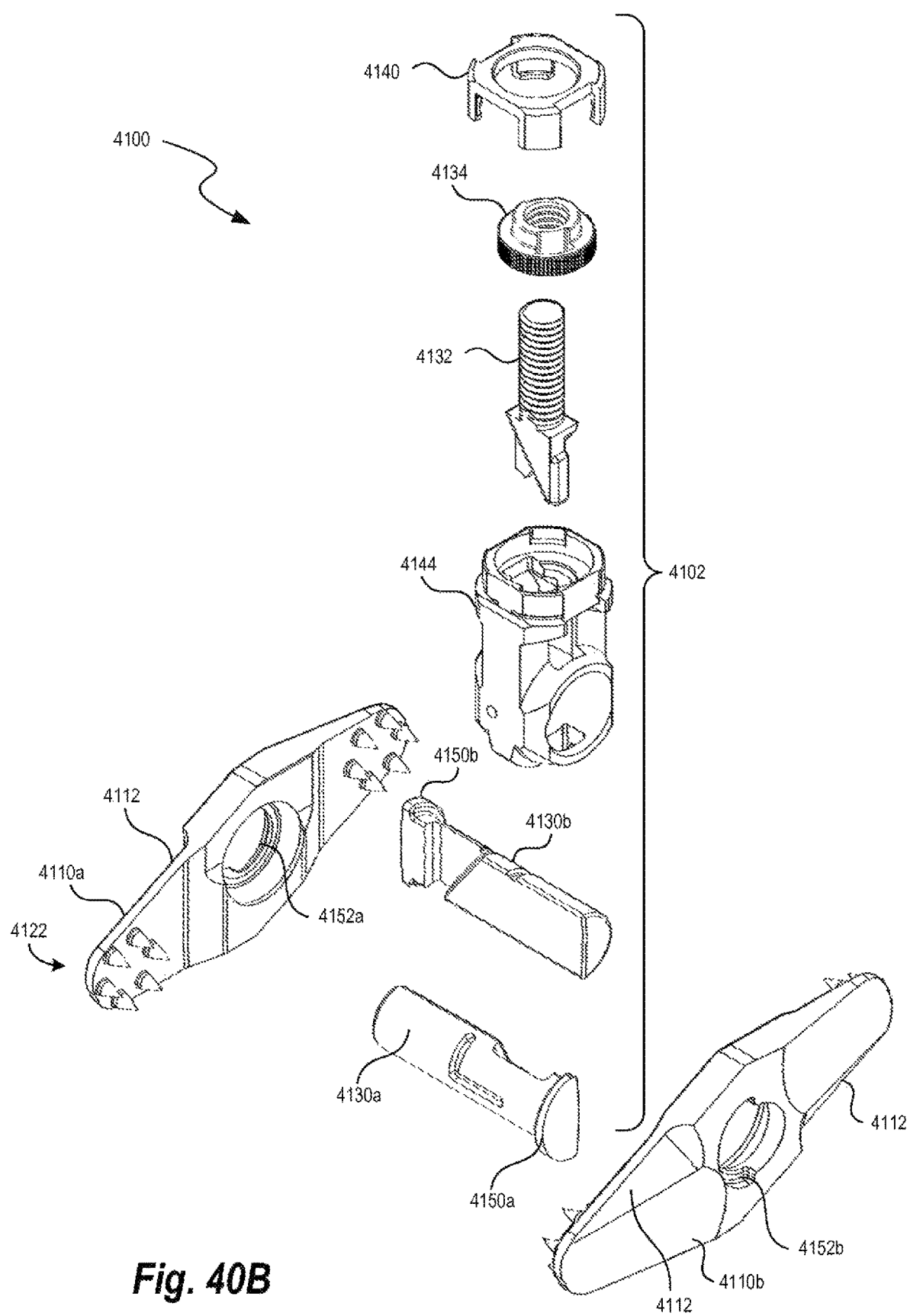

FIG. 40A is an isometric view of a spacer 4100 in accordance with an embodiment of the disclosure. FIG. 40B is an exploded isometric view of the spacer 4100. Referring to FIGS. 40A and 40B together, spacer 4100 is generally similar to the spacer 2400, except as detailed below. The spacer 4100 includes an actuator assembly 4102 and a clamp assembly 4122 with wings 4110 (identified individually as wings 4110*a*, 4110*b*). Each wing 4110 has receiving sections 4112 (three identified in FIG. 40A). The receiving sections 4112 can be chamfered regions that reduce the overall size of the spacer 4100 and facilitate or ease rotation of the wings 4110. The receiving sections 4112 can increase clearance with, for example, the spinous processes and/or delivery instruments. Other spacers disclosed herein can also have receiving sections (e.g., chamfered regions, narrowed regions, depressions, etc.). For example, the spacer 2400 of FIGS. 37A-37 has receiving sections.

The actuator assembly 4102 can include guides 4130 (identified individually as guides 4130a, 4130b), an actuator 4132, an actuator adjuster or wheel 4134, a cover 4140, and a body 4144. The guides 4130a, 4130b can include heads 4150a, 4150b, respectively. The heads 4150a, 4150b (collectively "heads 4150") can be flanges or protrusions received in receiving features 4152a, 4152b (collectively "receiving features 4152") of the wings 4110a, 4110b, respectively. The receiving features 4152 can include, without limitation, slots, recesses, combinations thereof, or other features that receive at least portions of the heads 4150.

Figure 41A:
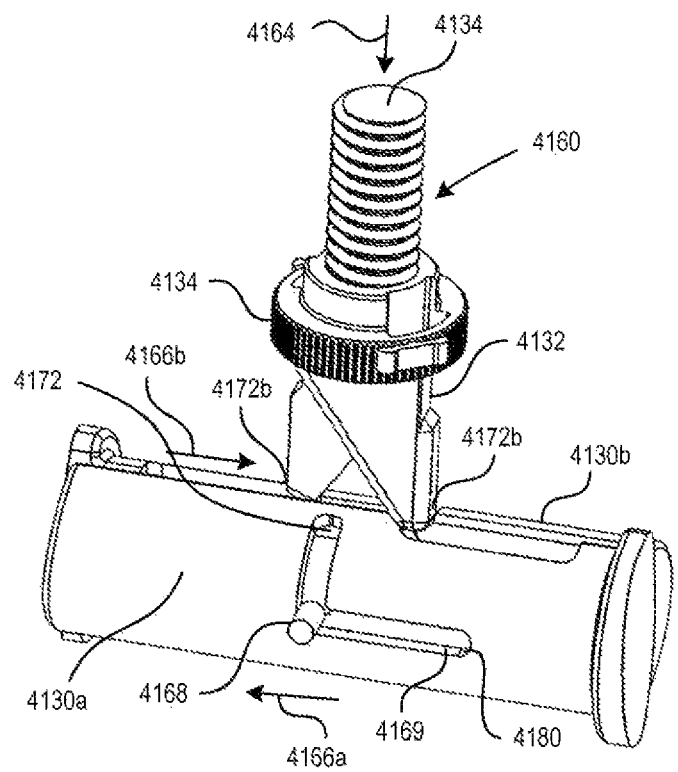
FIGS. 41A and 41B are isometric views of components of an actuator assembly in accordance with embodiments of the disclosure.
Figure 41B:
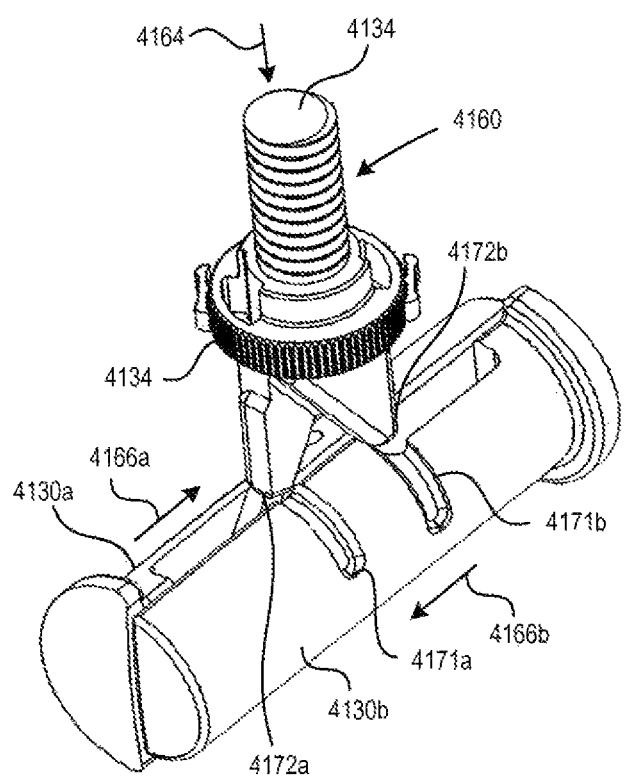

FIGS. 41A and 41B are isometric view of components of the actuator assembly 4102. The actuator adjuster 4134 is positioned along an external threaded shaft 4160 of the actuator 4132. The guide 4130b includes channels 4171 (identified individually as an alignment channel 4171a and a second alignment channel 4171b in FIG. 41B). The guide 4130b can rotate such that the tips 4172 (identified individually as tips 4172a, 4171b) move along the channels 4171. The illustrated actuator 4132 is ready to be translated (as indicated by an arrow 4164) to move the guides 4130 in substantially opposite directions. The guide 4130a can be moved in one direction (indicated by arrow 4166a) and the guide 4130b can be moved another direction (indicated by arrow 4166b).

Referring to FIG. 41A, a pin 4168 can be positioned in slot 4169. The pin 4168 can be moved from a first end 4172 of the slot 4169 to the illustrated position when the wings 4110 move from an undeployed position to an intermediate or rotated position. The pin 4168 can be moved to a second end 4180 of the slot 4169 when the guide 4130a moves, slides or translates, as indicated by arrow 4166a.

Figure 42A:
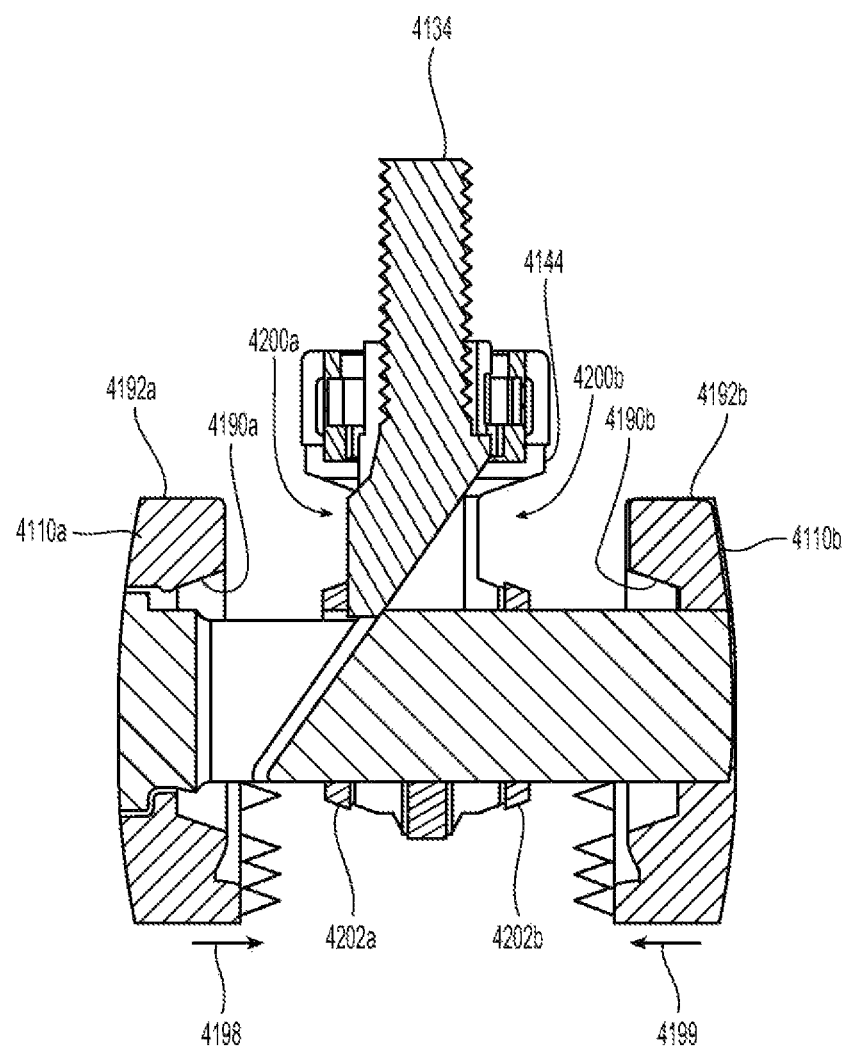
FIG. 42A is a cross-sectional view of a spacer in an intermediate or open position and taken along line 42A-42A of FIG. 40A.
Figure 42B:
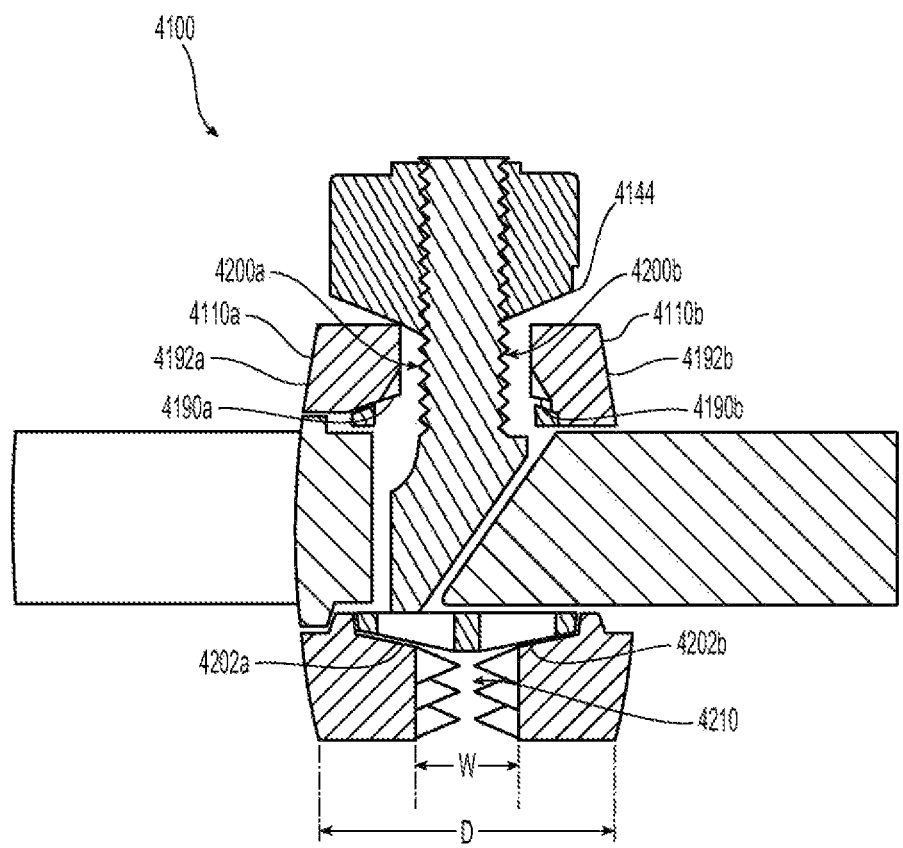
FIG. 42B is a cross-sectional view of the spacer in a fully deployed configuration or a clamping configuration and taken along line 42B-42B of FIG. 40A.

FIG. 42A is a cross-sectional view of the spacer 4100 in an intermediate or open configuration and taken along line 42A-42A of FIG. 40A. FIG. 42B is a cross-sectional view of the spacer 4100 in a deployed or clamping configuration and taken along line 42B-42B of FIG. 40A. Referring to FIG. 42A, the wings 4110 include recessed regions 4190 (identified individually as a recessed region 4190a and a recessed region 4190b) and wing main bodies 4192 (identified individually as a wing main body 4192a and a wing main body 4192b). When the wings 4110 move inwardly (indicated by arrows 4198, 4199), the main bodies 4192a, 4192b can be received by recess regions 4200a, 4200b in the body 4144. FIG. 42B shows the main bodies 4192a, 4192b received by the recess regions 4200a, 4200b. Flanges 4202a, 4202a of the body 4144 are received by the recessed regions 4190a, 4190b, respectively, of the wings 4110 to provide a relative outer dimension D (FIG. 42B) and a relative small width W (FIG. 42B) of a gap 4210.

Figure 43B:
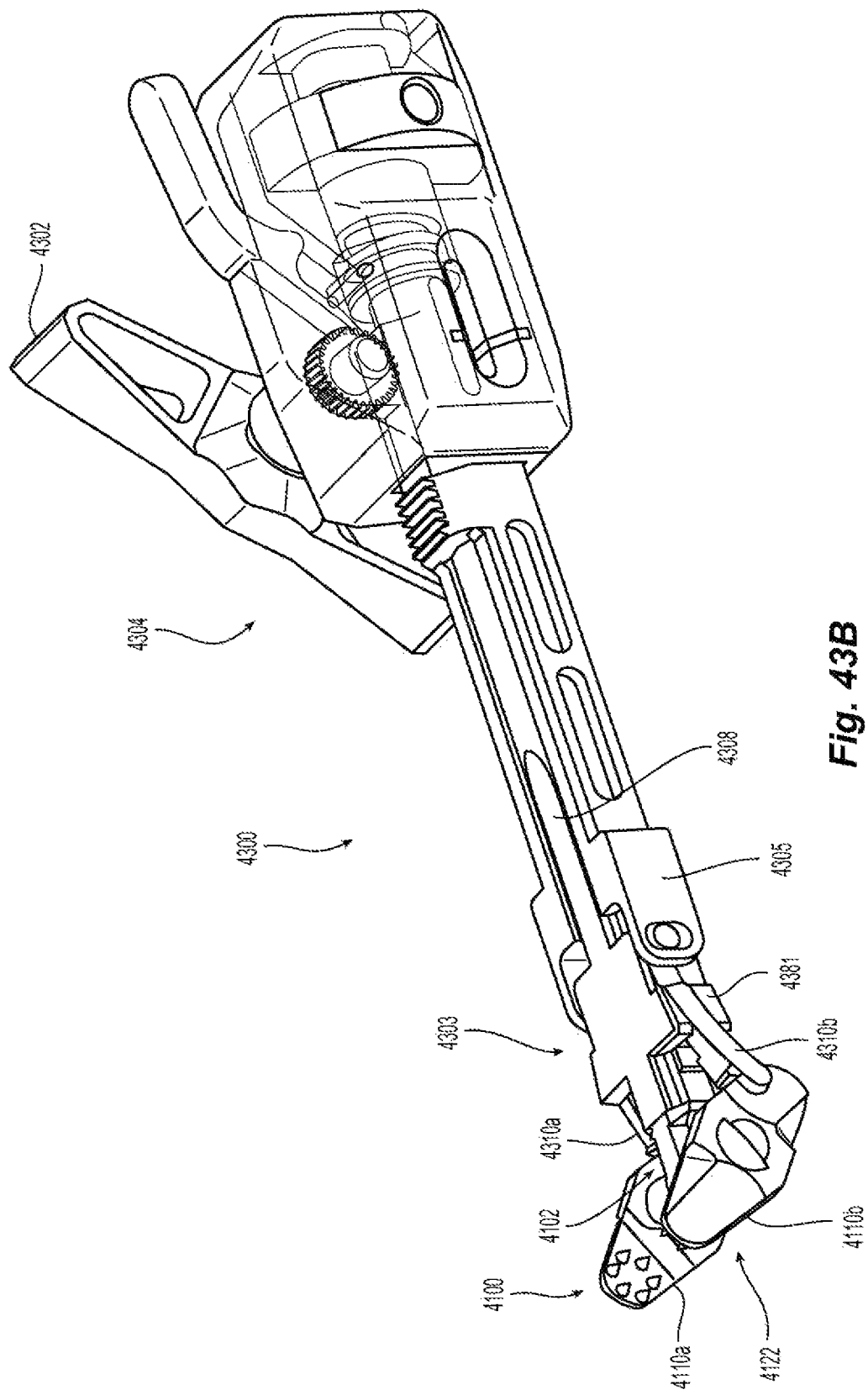

FIG. 43A is an isometric view of a delivery instrument 4300 coupled to the spacer 4100. The delivery instrument 4300 can be used to controllably reconfigure the spacer 4100 and can be used in combination with cannulas or other types of delivery devices. The delivery instrument 4300 can include a holder mechanism 4303 removably coupled to the spacer 4100 and a rotator device 4304 that can reconfigure the clamp assembly 4122.

The holder mechanism 4303 can be comprised of multiple components that cooperate to hold the spacer 4100. In some embodiments, the holder mechanism 4303 can include a guide sheath 4380 with a guide head 4381 matable with the actuator assembly 4102. Other types of holder mechanisms can include, without limitation, one or more jaws, clamps, pins, or other retaining features for detachably coupling to spacers or other medical devices.

The rotator device 4304 can include a handle 4302, a linkage assembly 4305, and arms 4310 (identified individually as an arm 4310a and an arm 4310b). The handle 4302 can be rotated (indicated by arrow 4314) to move the linkage assembly 4305 (indicated by arrow 4316). The arms 4310 can slide along the holder mechanism 4303 to cause rotation of the wings 4110 about an axis of rotation 4322. The delivery instrument 4300 can receive another instrument (e.g., a driver) used to actuate the spacer 4100. After clamping onto spinous processes, the delivery instrument 4300 can release the spacer 4100.

FIG. 44A is a top view of the delivery instrument 4300 coupled to the spacer 4100. FIG. 44B is a cross-sectional view of the delivery instrument 4300 and the spacer 4100 taken along line 44B-44B of FIG. 44A. Referring to FIGS. 44A and 44B together, the linkage assembly 4305 can include a linkage body 4340 and a gear member 4344. In some embodiments, a gear 4346 connected to the handle 4302 is a spur gear with teeth that enmesh with teeth of the gear member 4344. The gear member 4344 can be rack gear coupled to the linkage body 4340. The handle 4302 can rotate about an axis of rotation 4354 (FIG. 44A) to rotate the gear 4346 (indicated by arrow 4364 in FIG. 44B). The gear 4346 can drive the gear member 4344 (indicated by arrow 4366) to move the linkage body 4340. In some embodiments, the linkage body 4340 can slide along a body 4370 of the guide sheath 4380. A lever 4383 can be used to lock and unlock the rotator device 4304.

FIG. 44C is a side view of the delivery instrument 4300 coupled to the spacer 4100, and FIG. 44D is a cross-sectional view of the delivery instrument 4300 and the spacer 4100 taken along line 44D-44D of FIG. 44C. The delivery instrument 4300 can include a removal mechanism 4353 having a dial 4355 and a pusher 4357. The dial 4355 has internal threads 4358 that engage external threads 4359 of the pusher 4357. When the dial 4355 is rotated, the pusher 4357 can be advanced in the distal direction (indicated by arrow 4361) to push on the spacer 4100. When a sufficient force is applied to the spacer 4100, the spacer 4100 is separated from the holder mechanism 4303.

Referring to FIG. 44D, a driver 4341 (shown in dashed line) positioned in a passageway 4343. The driver 4341 can include an end 4342 that can be coupled (e.g., rotationally fixed) to the actuator adjuster 4134. The end 4342 can include, without limitation, one or more teeth, tabs, pins, threads, jaws, sockets, or other features for coupling to the actuator assembly 4102. The driver 4341 can be rotated (e.g., rotated about an axis of rotation 4348) to cause actuation of the clamp assembly 4122. For example, the driver 4341 can be used to close the clamp assembly 4122.

The arms 4310 can be generally similar to one another and, accordingly, the description of one arm 4310 applies generally to the other arm 4310. The features of the arm 4310a are denoted with the letter "a" and the corresponding features of the arm 4310b are denoted with the letter "b." The arm 4310b includes a mounting end 4360b, an engagement end 4362b, and a main body 4363b. The mounting end 4360b includes a pin 4368b positioned in a slot 4370b (FIG. 44C) of the linkage assembly 4305. The engagement end 4362b can include, without limitation, a camming feature 4385b and guide portion 4384b. The guide portion 4384b can inhibit or limit outward movement of the wing 4110b. In some embodiments, the guide portion 4384b can control the angle in which the arms 4301b acuates. The arm movement can also be controlled by its radius of curvature, which can be generally similar to the slot in the guide portion 4384b.

This can allow the arms 4310 to follow a path which slides along the surface of the wings 4110.

FIG. 45A is a detailed isometric view of a portion of the delivery instrument 4300 holding the spacer 4100 in a delivery configuration. FIG. 45B is a detailed isometric view of the delivery instrument 4300 holding the spacer 4100 in a partially rotated configuration. FIG. 45C is a detailed isometric view of the delivery instrument 4300 holding the spacer 4100 in a rotated configuration. Referring to FIG. 45A, the actuator assembly 4102 can be in first mode of operation (e.g., a rotation mode of operation) to allow rotation of the wings 4110. The linkage assembly 4305 can be moved distally (indicated by arrow 4366) towards the guide head 4381. The linkage assembly 4305 can move the arm 4310b along a curved slot 4390b. The camming feature 4285b (FIGS. 45 and 46) can slide along a receiving-feature 4398. The receiving-feature 4398 can be a groove having V-shaped profile, U-shaped profile, or the like. In other embodiments, the receiving-feature 4398 can be in the form of a slot or other suitable feature for guiding the camming feature 4285b. As the linkage assembly 4305 advances distally, the arm 4310b slides along the slot 4390b and pushes on the wing 4110b of FIG. 45A. The wing 4110b rotates about an axis of rotation 4395, as indicated by an arrow 4397 (FIG. 45A). As the wing 4110b rotates, the pin 4368b moves across the slot 4370b.

Referring to FIG. 45B, the wing 4110b is at a partially rotated position. The pin 4368b is positioned at the middle of the slot 4370b. The camming feature 4385b is positioned midway along the length of the receiving-feature 4398. The arm 4310b moves distally to continue to cause rotation of the wing 4110b until the arm 4310b is in the fully rotated position.

FIG. 45C shows the clamp assembly 4122 in a rotated configuration. The wings 4110 are in the fully rotated position. The pin 4368b is positioned at the end of the slot 4370b. The actuator assembly 4102 has a second mode of operation (e.g., a translation mode of operation) to move the wings 4110 together using a driver (e.g., drive 4341 of FIG. 44D).

FIG. 46 is an isometric view of a spacer 4400 in accordance with some embodiments of the disclosure. The spacer 4400 has an actuator assembly 4402 and a clamp assembly 4406. The clamp assembly 4406 is configured to accommodate different sized spinous processes and can include wings 4410 (identified individually as a wing 4410a and a wing 4410b) each rotatable about a plurality of axes. This allows the wings 4410 to seat against spinous process of different shapes and geometries. The wings 4410 can have any number of different planes of rotation based on the procedure to be performed. In some embodiments, the wings 4410 are rotatable about an axis of rotation 4414. The wing 4410a is also rotatable about an axis of rotation 4418a, and the wing 4410b is also rotatable about an axis of rotation 4418b. In some embodiments, the axis of rotation 4414 can be angled (e.g., substantially perpendicular) to one or both axes of rotation 4418a, 4418b. The axes of rotation 4418a, 4418b can be generally parallel to one another.

Figure 47A:
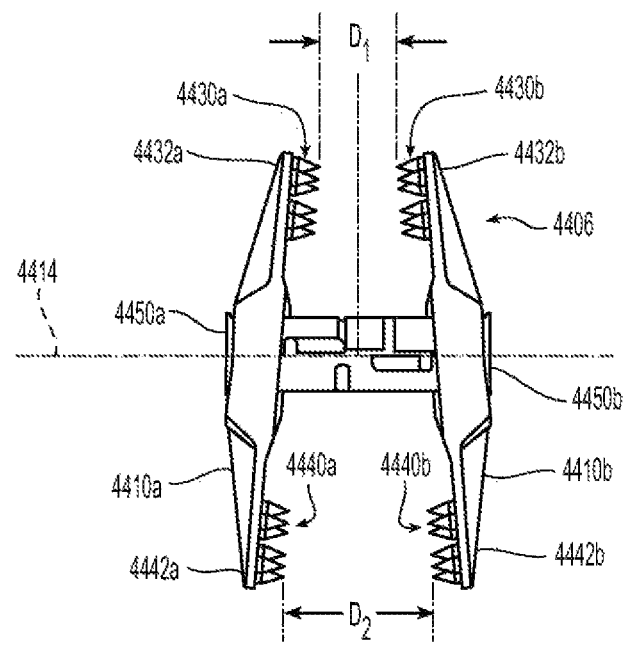
FIG. 47A is a top view of a pair of guides and a clamp assembly in an open configuration in accordance with an embodiment of the disclosure.
Figure 47B:
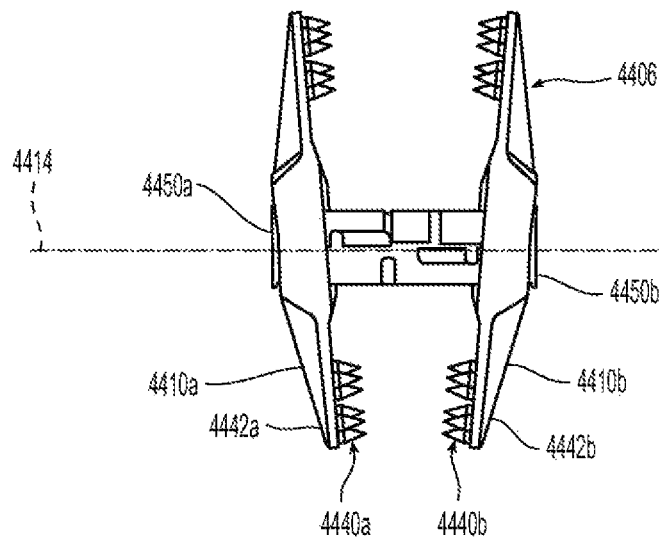
FIG. 47B is a top view of the pair of guides and the clamp assembly in another configuration.
Figure 47C:
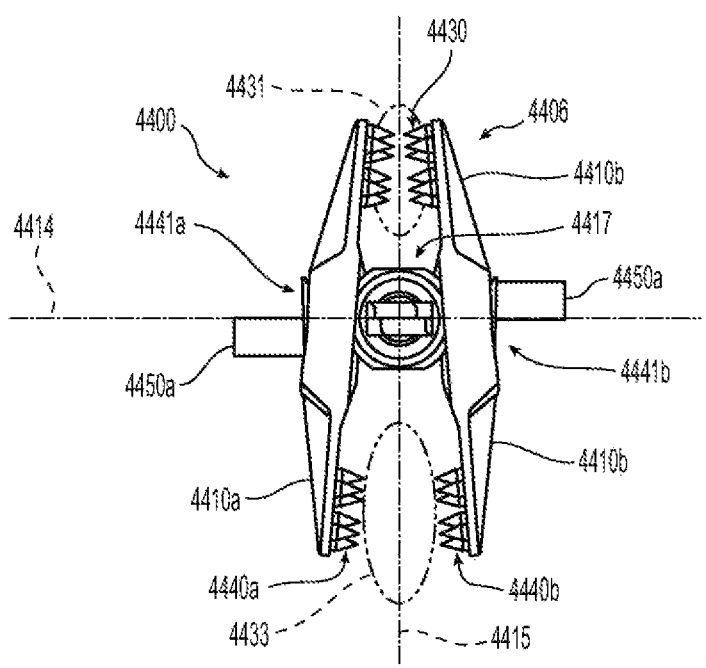
FIG. 47C is a top view of a spacer in a clamping configuration.

FIGS. 47A-47C are top views of the clamp assembly 4406 in different configurations. Referring to FIG. 47A, guides 4450 (identified individually as a guide 4450a and a guide 4450b) are coupled to the wings 4410a, 4410b. The wings 4410a, 4410b are rotatable about axes of rotation 4418a, 4418b (FIG. 46), respectively, to adjust (e.g., increase or decrease) the distance $D_1$ and the distance $D_2$. The distance $D_1$ is between engagement features 4430a of a wing end portion 4432a and engagement features 4430b of a wing end portion 4432b. The distance $D_1$ is between engagement features 4440a of a wing end portion 4442a and engagement features 4440b of a wing end portion 4442b.

FIG. 47A shows the end portions 4432a, 4432b close together and the end portions 4442a, 4442b spaced far apart. FIG. 47B shows the end portions 4432a, 4432b spaced far apart and the ends portions 4442a, 4442b close together. In some embodiments, the wings 4410 can be moved to define a distance $D_1$, $D_2$ in a range of about 5 cm and 13 cm. Other ranges are also possible. The wings 4410 can be rotated about the axes of rotation angles less than about 20 degrees. In one embodiment, the wings 4410 can be rotated about the axes of rotation 4418 (FIG. 46) an angle within a range about 2 to 6 degrees. In some embodiments, the wings 4410 can be rotated a maximum angle of about 10 degrees, 4 degrees, or 2 degrees. In some embodiments, the wings 4410 can be rotated+/−8 degrees. In some embodiments, the wings 4410 can be rotated an angle in a range of about 75 degrees to 105 degrees (e.g., when rotated from a delivery position or undeployed position to a rotated position) and the angle of rotation is less than about 20 degrees (e.g., when rotated from the rotated position to the clamped position). Other angles are also possible.

FIG. 47C shows the clamp assembly 4406 in a clamping configuration. The wings 4410 have been moved (e.g., translated) along the axis 4414 from open positions (FIG. 47B) to clamped positions (FIG. 47C). The engagement features 4430 are embedded in a spinous process 4431, and the engagement features 4440 are embedded in a spinous process 4433. When the spacer 4400 is positioned at an interspinous space 4417, the axis of rotation 4414 can extend transversely to the sagittal plane 4415. The axis of rotation 4418 (FIG. 46) can be generally parallel to the sagittal plane 4415. For example, an angle formed between one or both of the axes of rotation 4418 and the sagittal plane 4415 can be less than about 10 degrees or 5 degrees. A joint 4441a can be formed by the wing 4410a and the guide 4450a and near the interspinous space 4417. In some procedures, the joint 4441a is near (e.g., laterally adjacent to) the interspinous space 4417. A joint 4441b can be formed by the wing 4410b and the guide 4450b and near (e.g., laterally adjacent to) the interspinous space 4417. The joints 4441a, 4441b can define the axes of rotation 4418a, 4418b, respectively, (FIG. 46) and can be partially spherical joints, ball joints, revolution joints, or the like. The joints 4441 allow rotation of the wings 4110 to equilibrate the applied forces. For example, the forces applied to the spinous processes 4431, 4433 can be equilibrated (e.g., substantially equal). Additionally, the spacer 4400 can be used to clamp onto a wide range of different sized spinous processes.

Figure 48:
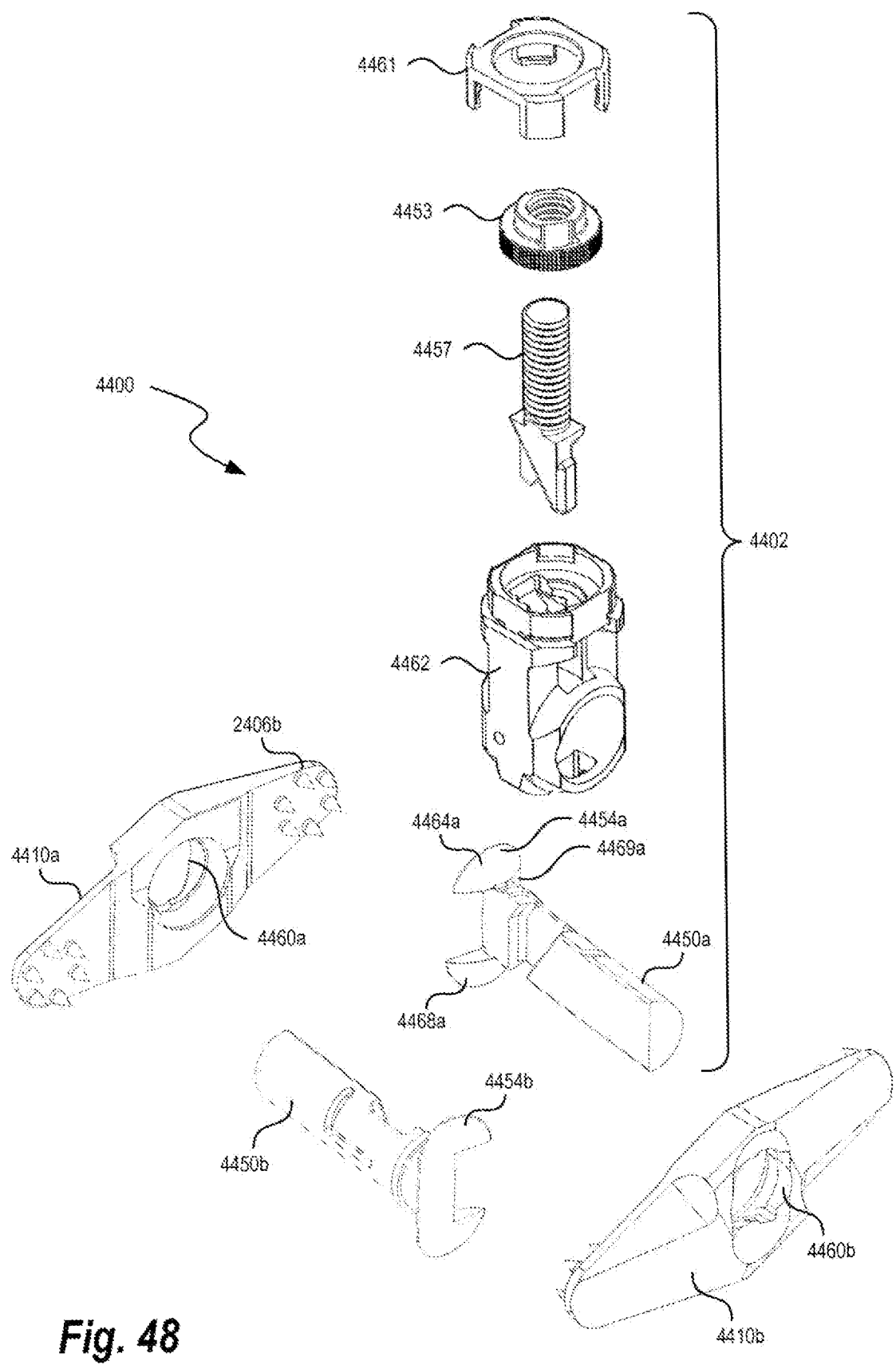
FIG. 48 is an exploded isometric view of the spacer of FIG. 46 in accordance with an embodiment of the disclosure.

FIG. 48 is an exploded isometric view of the spacer 4400. The actuator assembly 4402 can include the guides 4450 (identified individually as guides 4450a, 4450b), an actuator 4453, a cover 4461, and a body 4462. The guides 4450a, 4450b includes heads 4454a, 4454b, respectively. The heads 4454a, 4454b (collectively "heads 4454") can be received by receiving features 4460a, 4460b (collectively "receiving features 4460") of the wings 4410a, 4410b, respectively. The receiving features 4460 can include, without limitation, one or more slots, recesses, or other features with a complementary shape to the heads 4454.

Figure 49A:
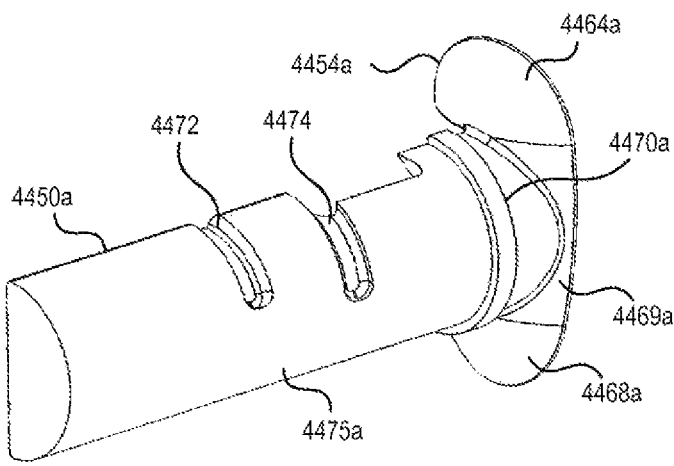
FIG. 49A is an isometric view.
Figure 49B:
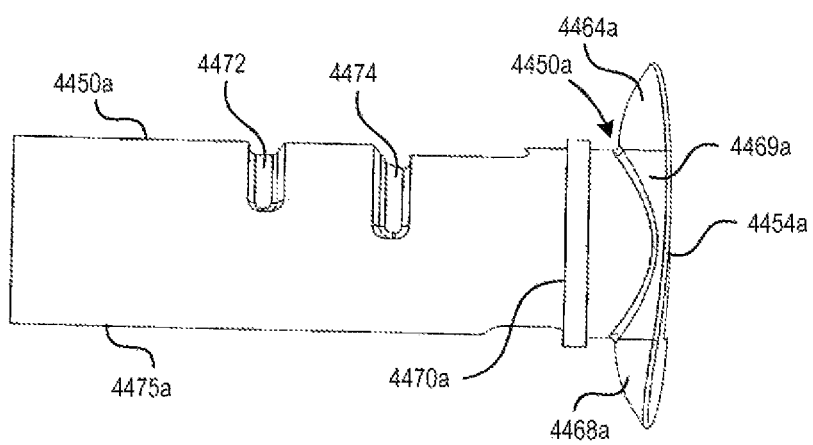
FIG. 49B is a front view.
Figure 49C:
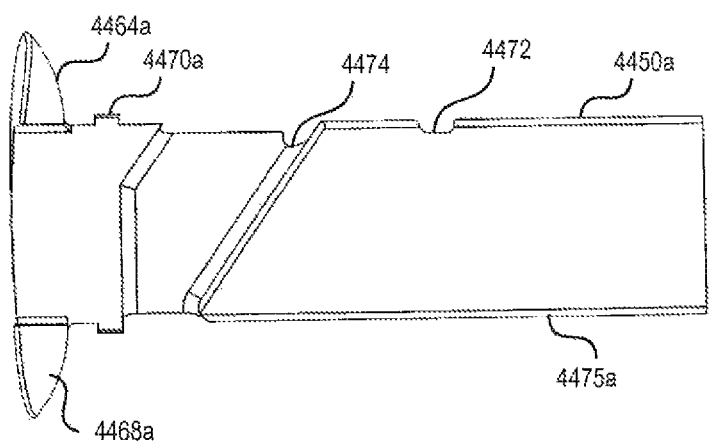
FIG. 49C is a back view.
Figure 49D:
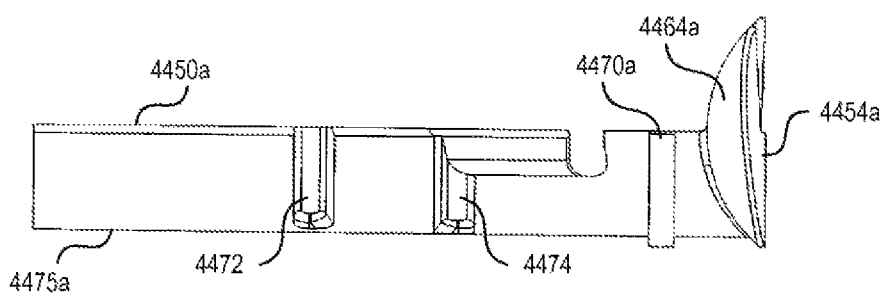
FIG. 49D is a top view of a guide in accordance with an embodiment of the disclosure.

FIG. 49A is an isometric view, FIG. 49B is a front view, FIG. 49C is a back view, and FIG. 49D is a top view of the guide 4450a in accordance with an embodiment of the disclosure. The guide 4450a includes several features that are generally similar in structure and function to other guides disclosed herein. The guide 4450a can include channels 4472, 4474 configured to receive the tips of the actuator 4457 (FIG. 48). The channels 4472, 4474 can extend circumferentially about a main body 4475a of the guide 4450a. The head 4454a is coupled to the main body 4475a and includes curved surfaces 4464a, 4468a, 4469a. The curved surfaces 4464a, 4468a can have partially spherical configurations. The surface 4469a can have a partially cylindrical configuration. The surfaces 4464a, 4468a, 4469a can have other shapes and configurations. A retaining feature 4470a is positioned along the main body 4475a and is spaced apart from the head 4454a.

Figure 50A:
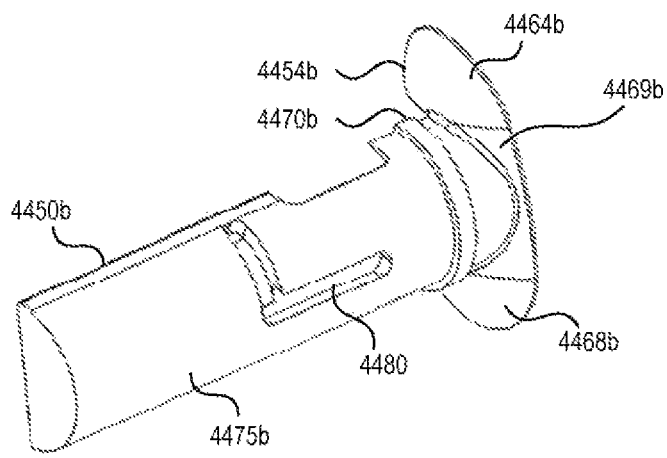
FIG. 50A is an isometric view.
Figure 50B:
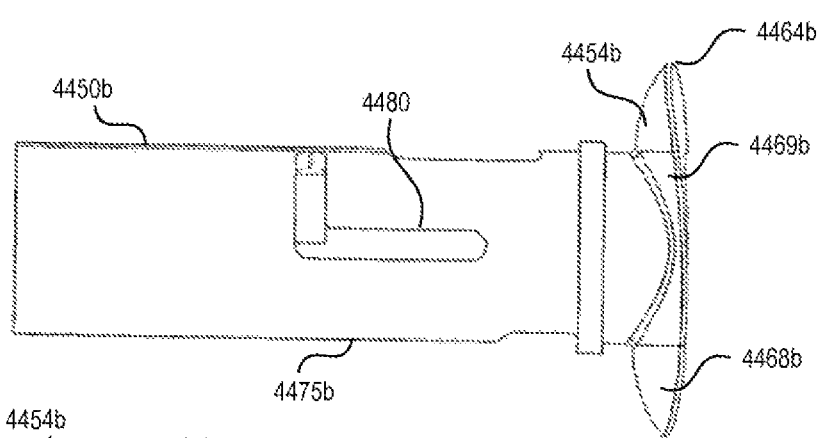
FIG. 50B is a front view.
Figure 50C:
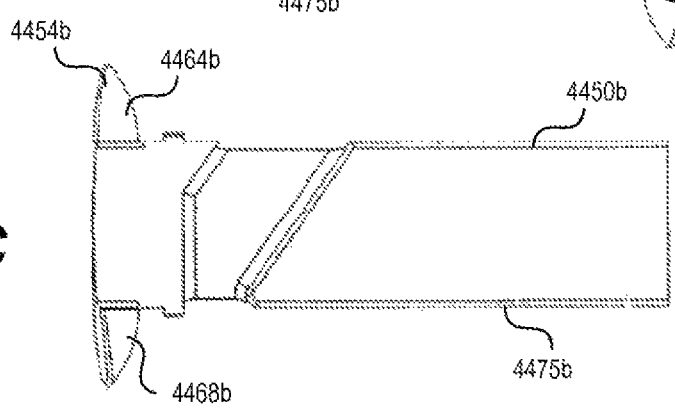
FIG. 50C is a back view.
Figure 50D:
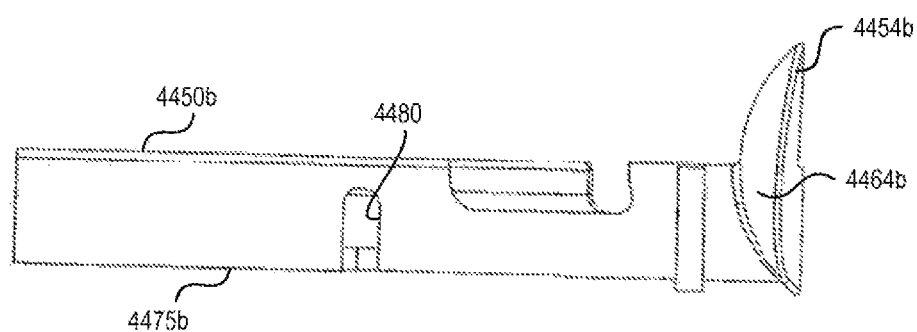
FIG. 50D is a top view of a guide in accordance with an embodiment of the disclosure.

FIG. 50A is an isometric view, FIG. 50B is a front view, FIG. 50C is a back view, and FIG. 50D is a top view of the guide 4450b in accordance with an embodiment of the disclosure. The guide 4450b includes several features that are generally similar in structure and function to other guides disclosed herein. The guide 4450b can include a slot 4480 configured to receive a pin of the body 4462 (FIG. 48). The head 4454b is coupled to a main body 4475b and includes curved surfaces 4464b, 4468b, 4469b. A retaining feature 4470b is positioned along the main body 4475b and is spaced apart from the head 4454b.

FIGS. 51A and 51B are isometric views, FIG. 51C is a side view, and FIG. 51D is a back view of the wing 4410a. The wing 4410a can include an interior surface 4500 surrounding an opening 4501 and can be configured to slidingly mate against the head 4454a (FIG. 48). In some embodiments, the interior surface 4500 can include curved surfaces 4510, 4512, 4514 that can slidingly mate with corresponding surfaces 4464a, 4468a, 4469a (FIG. 48) of the guide 4450a. The engagement features 4430a, 4440a can be in a generally circular pattern, an elliptical pattern, a polygonal pattern, or other suitable pattern.

Figure 52A:
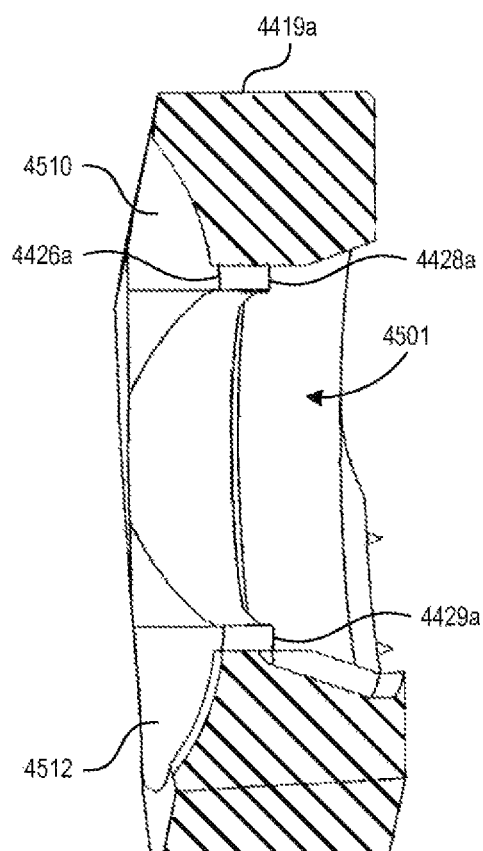
FIG. 52A is a cross-sectional view of the wing taken along line 52A-52A of FIG. 51D.
Figure 52B:
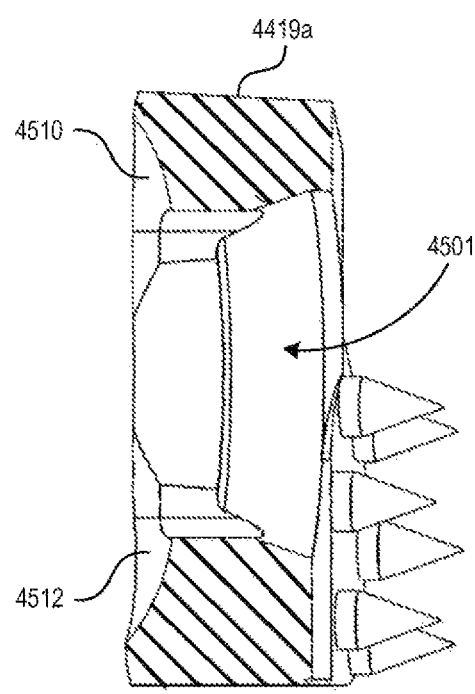
FIG. 52B is a cross-sectional view of the wing taken along line 52B-52B of FIG. 51D.

FIG. 52A is a cross-sectional view of the wing 4410a taken along line 52A-52A of FIG. 51D. FIG. 52B is a cross-sectional view of the wing 4410a taken along line 52B-52B of FIG. 51D. Referring to FIG. 52A, the wing 4410a can include a flange 4426a. Ends 4428a, 4429a of the flange 4426a are positioned adjacent to keying features 4429a, 4429b (FIG. 51D). The keying features 4429a, 4429b (e.g., recessed regions, cutouts, etc.) allow insertion of the guide 4450a.

Figure 53A:
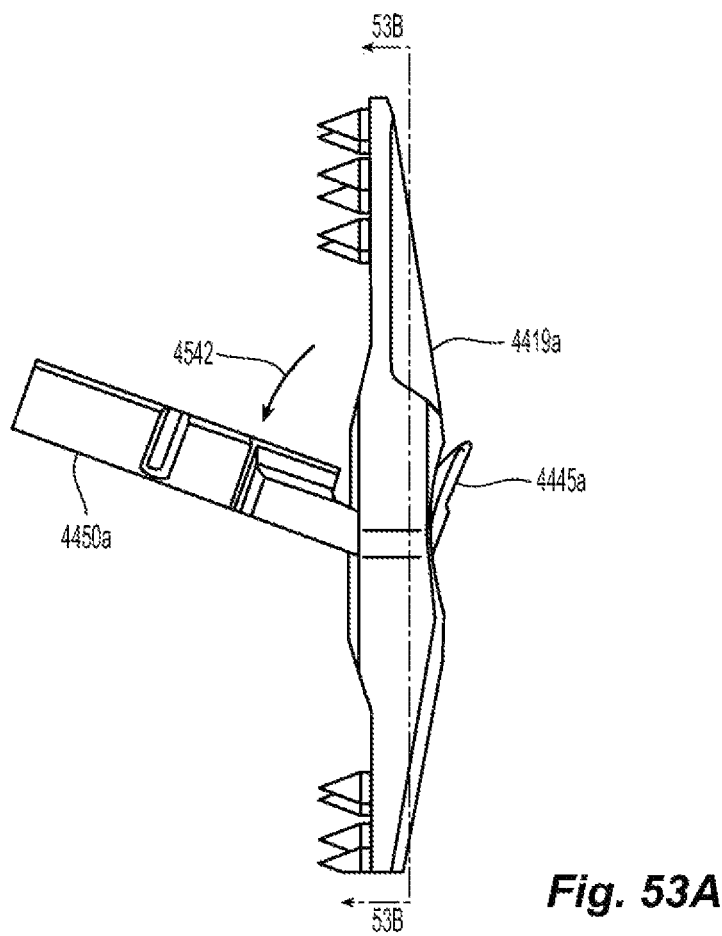
FIG. 53A is a top view and FIG. 53B is a cross-sectional view of a guide inserted into a wing.
Figure 53B:
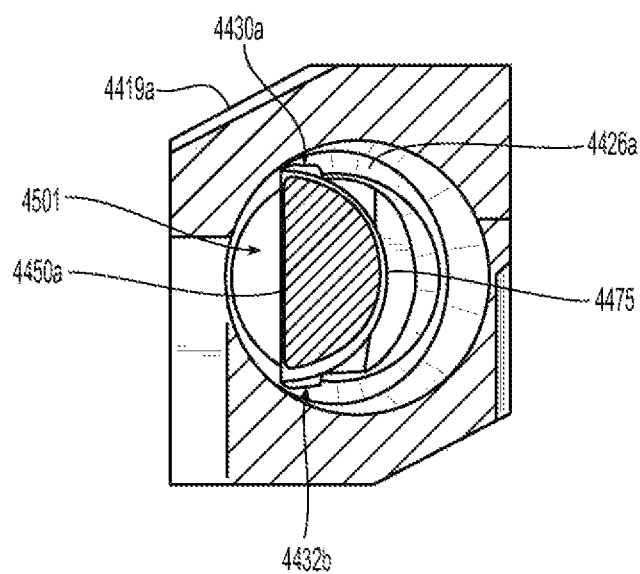

FIG. 53A is a plan view and FIG. 53B is a cross-sectional view of the guide 4450a inserted into the wing 4410a. The guide 4450a can be rotated (indicated by arrow 4542) to position the flange 4426a in a gap 4550a (FIG. 49B).

Figure 54A:
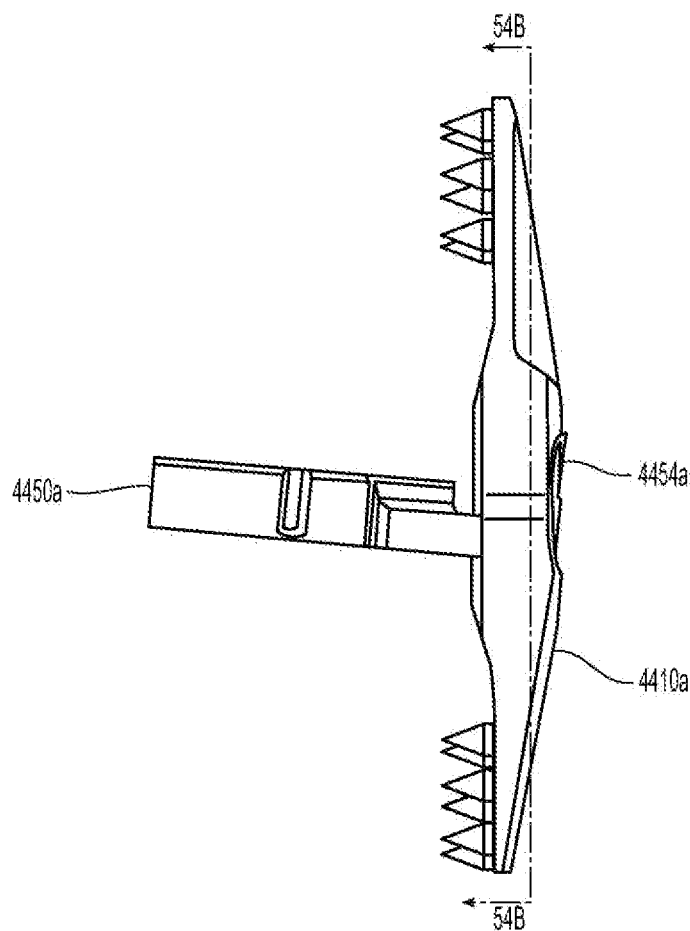
FIG. 54A is a top view and FIG. 54B is a cross-sectional view of the guide inserted into the wing.
Figure 54B:
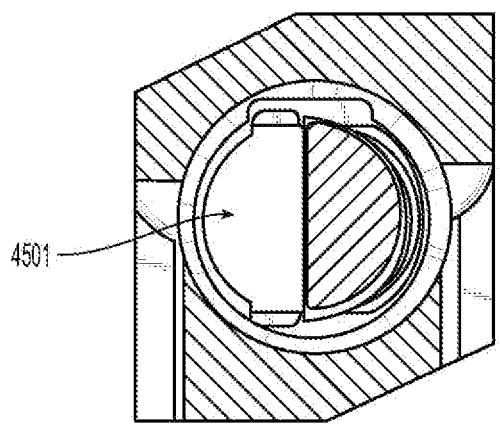
Figure 54C:
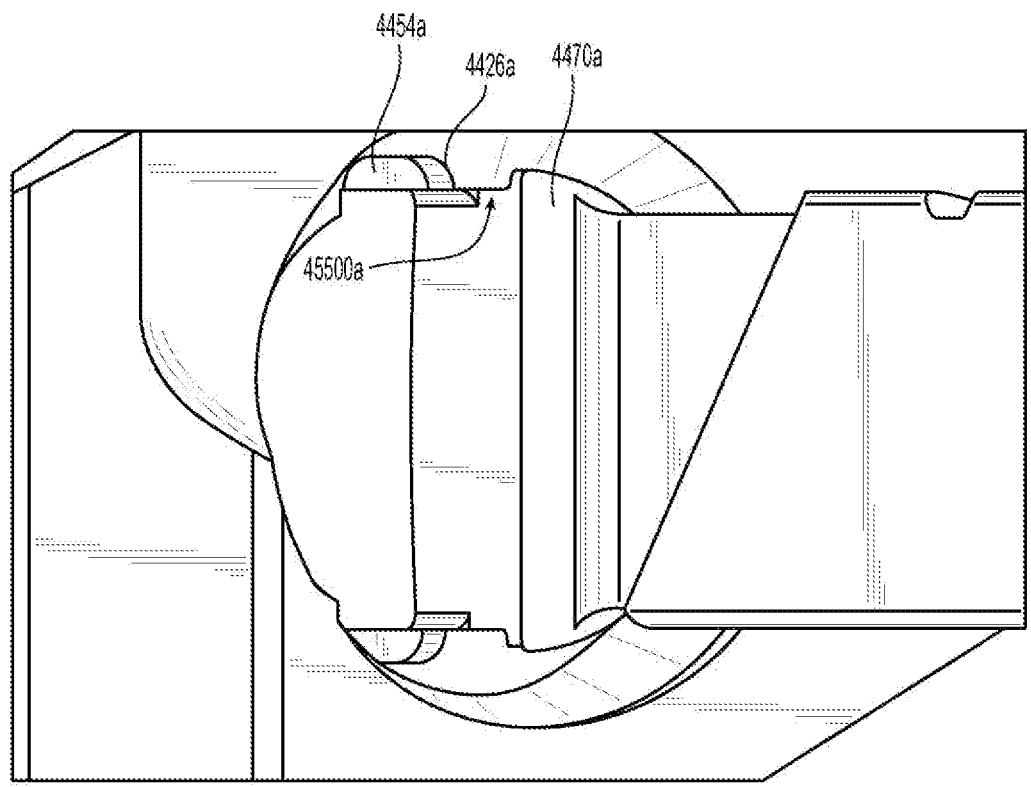
FIG. 54C is an oblique view of the connection between the guide and the wing.

FIGS. 54A and 54B show the guide 4450a locked in the wing 4410a. FIG. 54C shows the flange 4426a positioned in the gap 4550a such that side-to-side movement (e.g., lateral movement, medial movement, etc.) is prevent or limited.

Figure 55A:
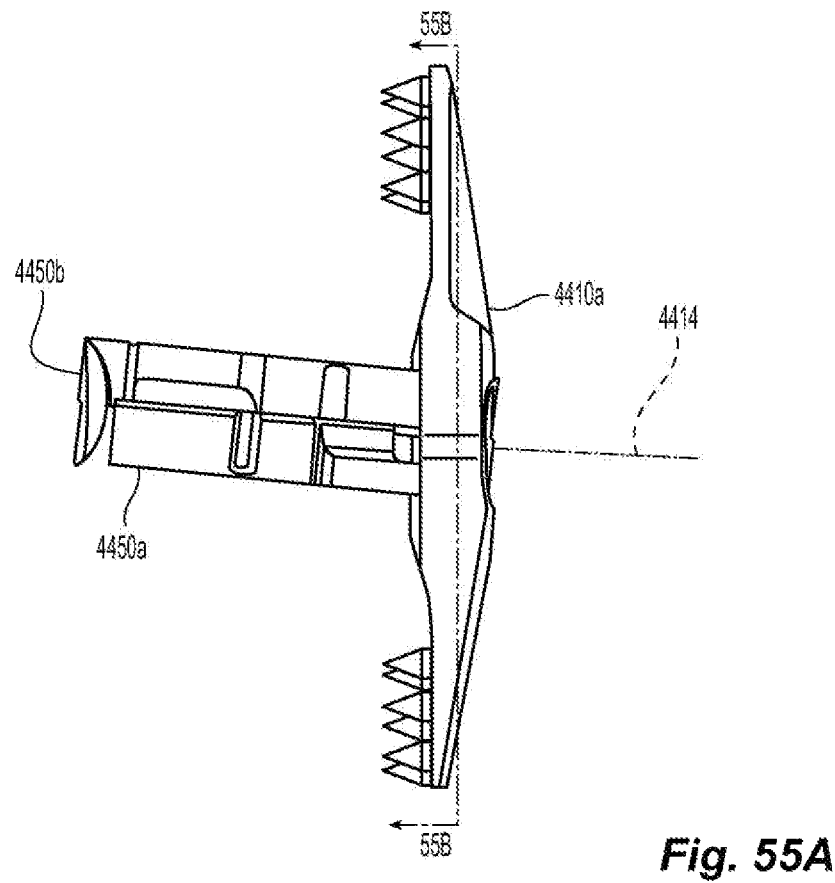
FIG. 55A is a top view and FIG. 55B is a cross-sectional view of the guide locked to the wing.
Figure 55B:
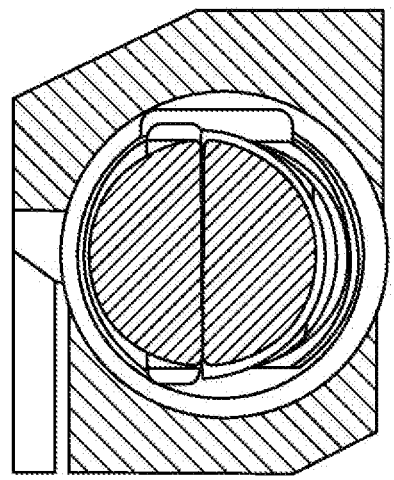

FIGS. 55A and 55B show both guides 4450a, 4450b coupled to the wings 4410. The guides 4450 are rotationally locked to the wing 4110 relative to the axis of rotation 4414.

Figure 56B:
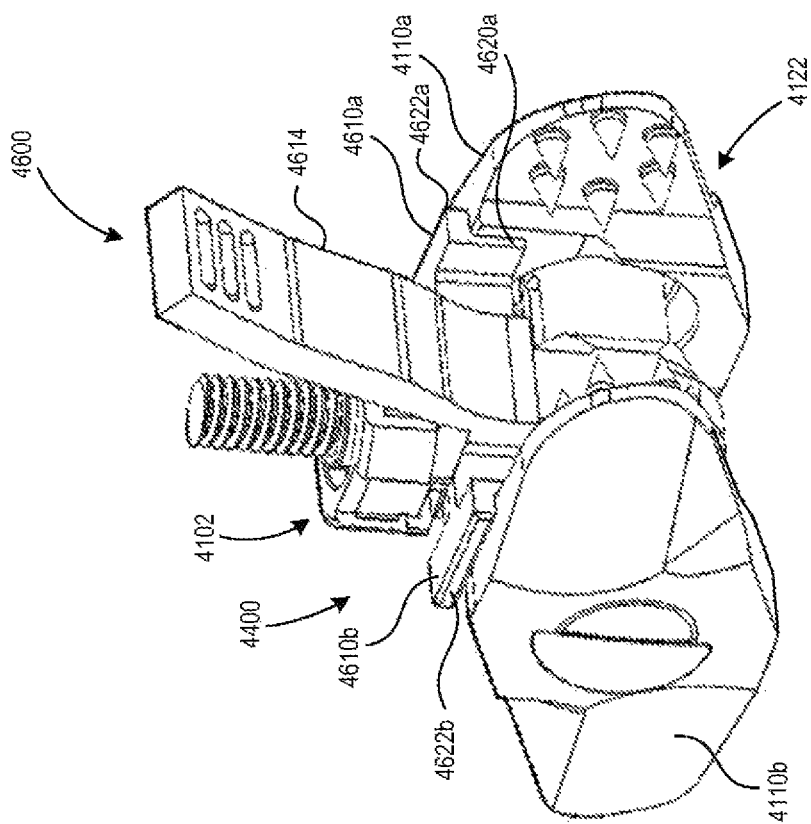
FIGS. 56A and 56B are isometric views of a spacer and a retainer in accordance with some embodiments of the disclosure.
Figure 56A:
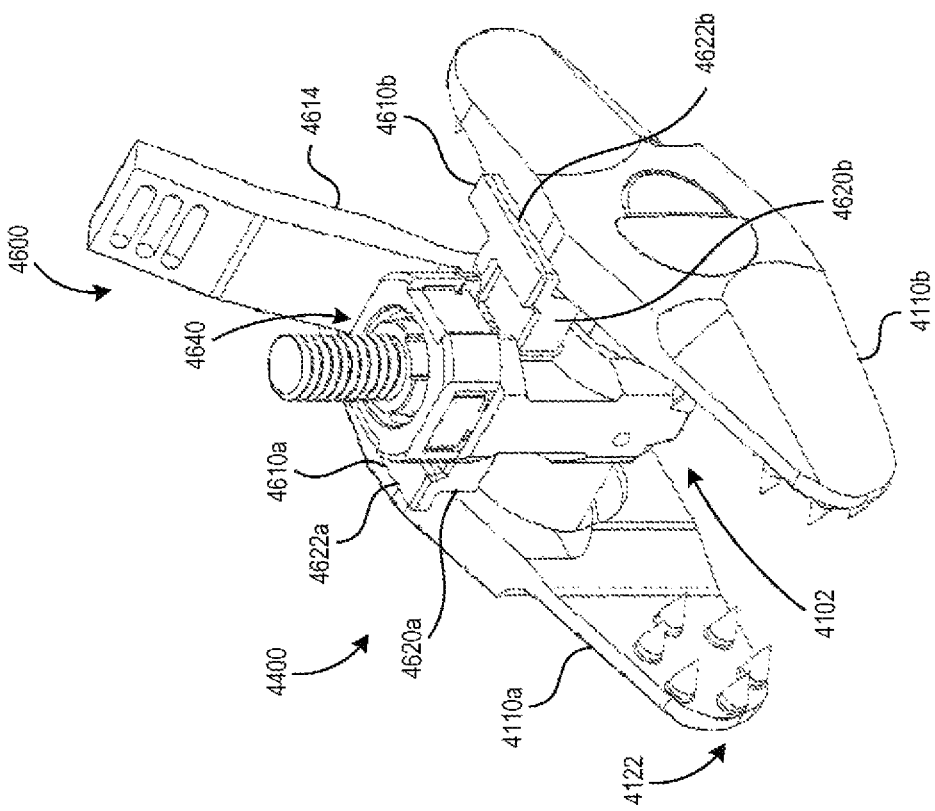
Figure 57:
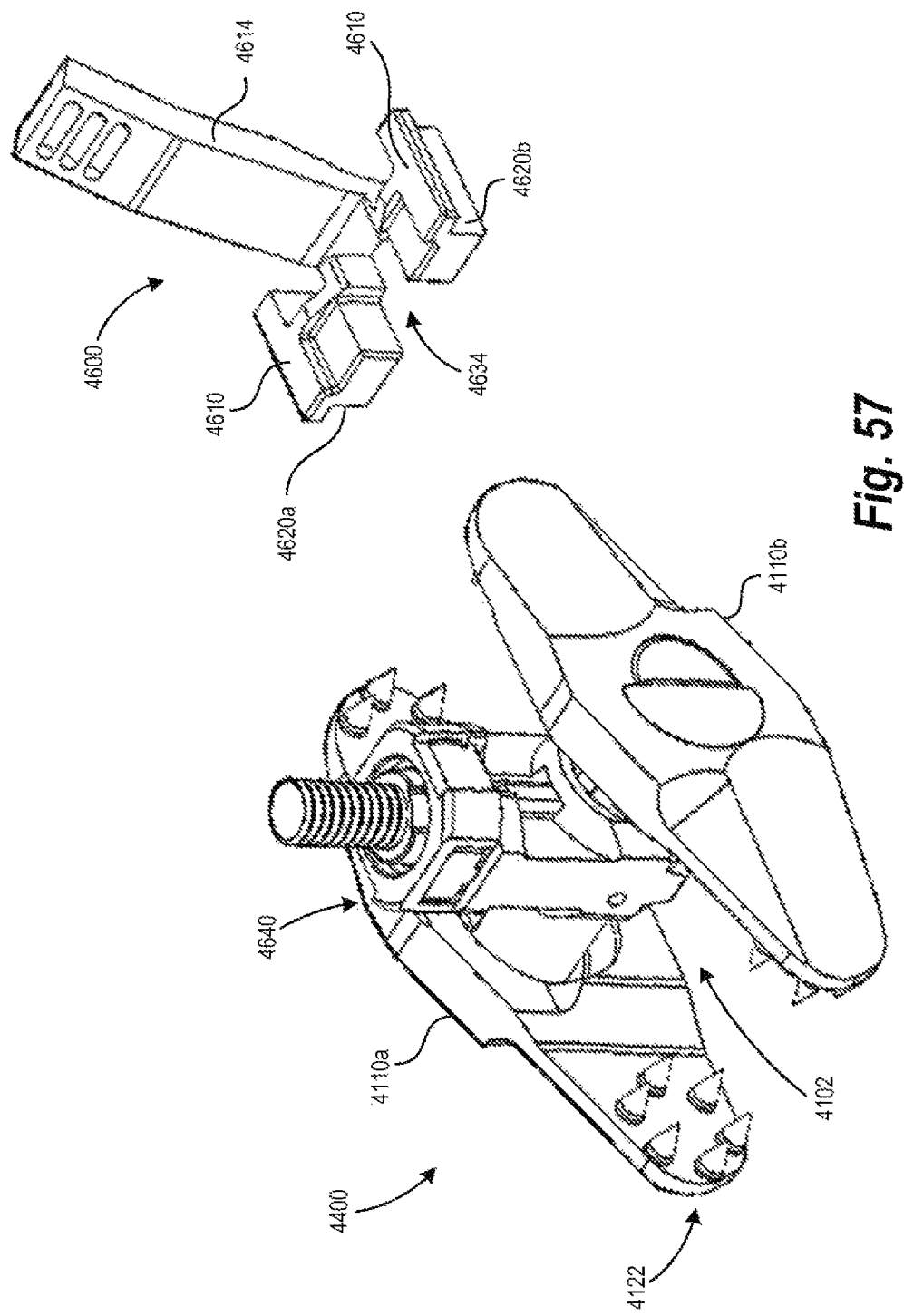
FIG. 57 is an isometric view of a spacer and a retainer spaced apart from one another in accordance with some embodiments of the disclosure.

FIGS. 56A and 56B are isometric views of the spacer 4400 and a retainer 4600 in accordance with some embodiments of the disclosure. The retainer 4600 can hold the spacer 4400 to facilitate handling and can be separated from the spacer 4400. FIG. 57 shows the retainer 4600 spaced apart from the spacer 4400.

The retainer 4600 can include wing holders 4610a, 4610b (identified individually as a wing holder 4610a and a wing holder 4610b) and a main body 4614. The wing holders 4610a, 4610b can engage the corresponding wings 4110a, 4110b. Each wing holder 4610 can include a wall 4620 (identified individually as a wall 4620a and a wall 4620b) and a ledge of shelf structure 4622 (identified individually as a ledge structure 4622a and a ledge structure 4622b). The walls 4620 can keep the wings 4110 spaced apart and the ledge structures 4622 can rest on the corresponding wings 4110.

The actuator assembly 4102 can be received in opening 4634 (FIG. 57) between the wing holders 4610. FIGS. 56A and 56B show instrument connection region 4640 of the spacer 4600 exposed and ready to engage an instrument. The instrument connection region 4640 can include, without limitation, a portion of the actuator 4457, wheel 4453, etc. or other feature suitable for engaging an instrument.

The retainer 4600 can be separated from the spacer 4400 before, during, and/or after an instrument is coupled to the spacer 4400. In open procedures, the retainer 4600 can hold the clamp assembly 4122 in the open configuration. An instrument can be coupled to the actuator assembly 4102 while a user manually holds the clamp assembly 4122. The retainer 4600 can prevent closing of the clamp assembly 4122 on the user's fingers. Once the spacer 4400 is ready for insertion into the interspinous space, the retainer 4600 can be removed, and the spacer 4400 can then be inserted at an interspinous space.

Figure 58:
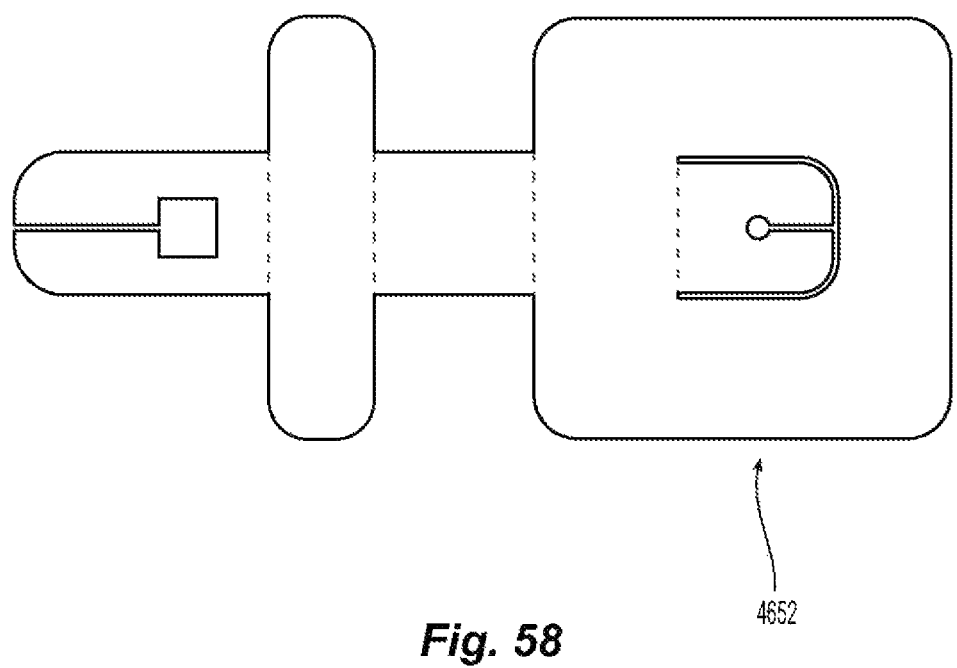
FIG. 58 illustrates a foldable retainer in accordance with some embodiments of the disclosure.

Other types of retainers can also be used to hold spacers. FIG. 58 shows a retainer 4652 ready to be installed on a spacer. The retainer 4652 can be folded along the dashed lines to surround a spacer. FIG. 58 shows the spacer 4400 held by the retainer 4652. The retainer 4652 can overlay the wings 4110a, 4410b, such that a user can conveniently handle the spacer 4400 without directly contacting the wings 4110.

The disclosed medical devices, instruments, or any of their components can be made of a wide range of materials, including any biologically adaptable or compatible materials. Materials considered acceptable for biological implantation include, but are not limited to, stainless steel, titanium, tantalum, combination metallic alloys, various plastics, polymers, resins, ceramics, biologically absorbable materials and the like. Any component may be also coated/made with osteo-conductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, a surface of any of the implants may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone ingrowth or establish a mineralized connection between the bone and the implant, and reduce the likelihood of implant loosening. Any assembly or its components can also be entirely or partially made of a shape memory material or other deformable material.

From the foregoing, it will be appreciated that specific embodiments of the disclosure have been described herein for purposes of illustration, but that various modifications may be made without deviating from the spirit and scope of the various embodiments of the disclosure. The medical devices (e.g., spacers) can be implanted at various sites in a body and can be delivered using lateral approaches. Further, while various advantages associated with certain embodiments of the disclosure have been described above in the context of those embodiments, other embodiments may also exhibit such advantages, and not all embodiments need necessarily exhibit such advantages to fall within the scope of the disclosure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spacer, comprising:
an actuator assembly including an actuator body having a longitudinal axis and an actuator rotatable about the longitudinal axis, a portion of the actuator assembly arranged to be inserted between a superior spinous process and an inferior spinous process of a subject such that the longitudinal axis is generally parallel to a sagittal plane of the subject; and
a clamp assembly including:
a first wing having a first surface and a first engagement feature extending from the first surface; and
a second wing having a second surface and a second engagement feature extending from the second surface,
wherein at least one of the first or second wings is moveable relative to the actuator body within a first plane to transition the clamp assembly between a first configuration and a second configuration, and wherein the at least one of the first or second wings is further moveable relative to the actuator body within a second plane transverse to the first plane to transition the clamp assembly between the second configuration and a third configuration in which the first and second engagement features engage the superior and inferior spinous processes.

2. The spacer of claim 1, wherein rotation of the actuator about the longitudinal axis moves the clamp assembly from the first configuration to the second configuration to position the at least one of the first or second wings relative to the superior spinous process and the inferior spinous process.

3. The spacer of claim 1, wherein the first and second planes are perpendicular to one another.

4. The spacer of claim 1, wherein the at least one of the first or second wings moves towards the actuator body when the clamp assembly moves from the second configuration to the third configuration.

5. The spacer of claim 1, wherein, with the clamp assembly in the third configuration, the first and second wings clamp onto the superior spinous process and the inferior spinous process and fix the superior spinous process and the inferior spinous process relative to one another.

6. A system, comprising:
a delivery instrument including a working end; and
a spacer, comprising:
an actuator assembly including an actuator body having a longitudinal axis and an actuator, the actuator body arranged to be inserted between a superior spinous process and an inferior spinous process of a subject such that the longitudinal axis is generally parallel to a sagittal plane of the subject, the actuator configured to engage a portion of the working end of the delivery instrument and arranged to rotate about the longitudinal axis of the actuator body; and
a clamp assembly including:
a first wing having a first surface and a first engagement feature extending from the first surface; and
a second wing having a second surface and a second engagement feature extending from the second surface,
wherein at least one of the first or second wings is moveable relative to the actuator body within a first plane to transition the clamp assembly between a first configuration and a second configuration, and wherein the at least one of the first or second wings is further moveable relative to the actuator body within a second plane transverse to the first plane to transition the clamp assembly between the second configuration and a third configuration in which the first and second engagement features engage the superior and inferior spinous processes.

7. The system of claim 6, wherein rotation of the actuator about the longitudinal axis moves the clamp assembly from the first configuration to the second configuration to position the at least one of the first or second wings relative to the superior spinous process and the inferior spinous process.

8. The system of claim 6, wherein the first and second planes are perpendicular to one another.

9. The system of claim 6, wherein the at least one of the first or second wings moves towards the sagittal plane of the subject when the clamp assembly moves from the second configuration to the third configuration.

10. The system of claim 6, wherein, with the clamp assembly in the third configuration, the first and second wings clamp onto the superior spinous process and the inferior spinous process and fix the superior spinous process and the inferior spinous process relative to one another.

11. The system of claim 6, wherein the actuator assembly convers rotational motion of the actuator into linear motion of the at least one of the first or second wings.

12. A method for delivering a spacer including an actuator assembly and a clamp assembly into a subject comprising the steps of:
inserting a portion of the actuator assembly between a superior spinous process and an inferior spinous process of the subject, the actuator assembly having a rotatable actuator;
rotating the actuator about a sagittal axis of the subject to move at least one of a first wing or a second wing of the clamp assembly relative to the actuator assembly and within a first plane to transition the clamp assembly from a first configuration to a second configuration; and
moving the at least one of the first wing or the second wing relative to the actuator assembly within a second plane transverse to the first plane to transition the clamp assembly from the second configuration to a third configuration such that the first and second wings engage the superior spinous process and the inferior spinous and fix the superior and inferior spinous processes relative to one another.

13. The method of claim 12, wherein the rotating step includes positioning the first wing of the clamp assembly along a first side of the superior spinous process and a first side of the inferior spinous process and positioning the second wing of the clamp assembly along a second side of the superior spinous process and a second side of the inferior spinous process.

14. The method of claim 12, wherein the first wing and the second wing are provided with at least one protrusion that engages with at least one of the superior and inferior spinous processes when the clamp assembly is in the third configuration.

15. The method of claim 12, wherein the rotating step is performed after the inserting step.

16. The method of claim 12, wherein the rotating step is performed with a delivery instrument oriented in an anterior-posterior direction.

17. The method of claim 12, wherein each of the first and second wings include a planar surface and the planar surfaces have the same angulation relative to one another in both the second configuration and the third configuration.

18. The method of claim 12, wherein the at least one of the first wing or the second wing translates relative to the actuator assembly during the moving step.

\* \* \* \* \*